US011040028B2

(12) United States Patent
Shao et al.

(10) Patent No.: US 11,040,028 B2
(45) Date of Patent: Jun. 22, 2021

(54) PENICINOTAM DERIVATIVE, PREPARATION METHOD AND USE THEREOF

(71) Applicant: OCEAN UNIVERSITY OF CHINA, Qingdao (CN)

(72) Inventors: Changlun Shao, Qingdao (CN); Meiyan Wei, Qingdao (CN); Yaoyao Jiang, Qingdao (CN)

(73) Assignee: OCEAN UNIVERSITY OF CHINA, Shandong (CN)

( * ) Notice: Subject to any disclaimer, the term of this patent is extended or adjusted under 35 U.S.C. 154(b) by 0 days.

(21) Appl. No.: 16/580,521

(22) Filed: Sep. 24, 2019

(65) Prior Publication Data
US 2021/0008045 A1 Jan. 14, 2021

Related U.S. Application Data

(63) Continuation-in-part of application No. PCT/CN2018/080287, filed on Mar. 23, 2018.

(30) Foreign Application Priority Data

Mar. 24, 2017 (CN) .......................... 201710180851.2

(51) Int. Cl.
*A61K 31/437* (2006.01)
*A61P 29/00* (2006.01)
*A61K 45/06* (2006.01)
*C07D 471/14* (2006.01)

(52) U.S. Cl.
CPC ............ *A61K 31/437* (2013.01); *A61K 45/06* (2013.01); *A61P 29/00* (2018.01); *C07D 471/14* (2013.01)

(58) Field of Classification Search
CPC ....... A61K 31/437; A61K 45/06; A61P 29/00; C07D 471/14
See application file for complete search history.

(56) References Cited

PUBLICATIONS

El-Neketi et al., 76(6) J. Natural Products 1099-1104 (2013) (Year: 2013).*

* cited by examiner

*Primary Examiner* — Timothy R Rozof
(74) *Attorney, Agent, or Firm* — FisherBroyles, LLP

(57) ABSTRACT

Provided are penicinotam derivatives, a tautomer, a stereoisomer, a racemate, a nonequal mixture of enantiomers, a geometric isomer, a solvate, a pharmaceutically acceptable salt or a prodrug thereof, and a pharmaceutical composition comprising the derivatives. Also provided herein is use of the derivatives and the pharmaceutical compositions in treating diseases caused by inflammation, immune system disorders.

16 Claims, No Drawings

PENICINOTAM DERIVATIVE, PREPARATION METHOD AND USE THEREOF

CROSS-REFERENCE TO RELATED APPLICATIONS

The present application is a continuation-in-part of International Patent Application No. PCT/CN2018/080287, filed 23 Mar. 2018 and published as WO 2018/171740 on 27 Sep. 2018, which claims priority to Chinese Patent Application No. 201710180851.2, filed 24 Mar. 2017, all of which are incorporated herein by reference in their entireties.

TECHNICAL FIELD

The present application relates to the field of medicine, and specifically to penicinotam derivatives and a pharmaceutical composition thereof. The present application also relates to use of the penicinotam derivatives and the pharmaceutical composition thereof in treating diseases caused by inflammation, immune system disorders.

BACKGROUND ART

NF-κB reactive gene is a gene encoding inflammatory molecules. The regulation of the transcription of these inflammatory molecules is the most important function of NF-κB, which has been extensively studied. A good number of factors can activate the nucleus transcription factor NF-κB, which shifts from the cytoplasm to the nucleus, causing a series of inflammatory responses. Therefore, the inhibition of excessive activation of NF-κB is likely to be a better approach for treating inflammation. A variety of factors have been found to induce NF-κB activation, including tumor necrosis factor-α (TNF-α), interleukin-β, lipopolysaccharide (LPS), oxidants, radiation, ultraviolet light, viruses and their metabolites, etc. Factors related to cell division and proliferation, such as antigen receptor cross-linking, calcium ionophore, protein kinase PKC, antigen, plant lectin PHA, and concanavalin CON A, can also promote the activation of NF-κB.

Inflammation is a defensive response of the body to infection. Under normal physiological conditions, inflammation is beneficial to the body. Under pathological conditions, inflammation can also lead to a series of pathological changes causing body injury, such as arthritis, sepsis, tissue and organ fibrosis, and atherosclerosis. When body injury occurs, macrophages, as the first line of defense, release a series of cellular inflammatory factors, including tumor necrosis factor (TNF), interleukin (IL), and prostaglandin E2 (PGE2) and Nitricoxide (NO), etc., these inflammatory factors have an important impact on the body repairing processes. Inflammation leads to necrosis of organ parenchymal cells, abnormal pathogenesis of extracellular matrix in the tissue and excessive deposition. The slight becomes fibrosis, and the severe tissue structure is destroyed and organ hardening occurs.

Slight fibrosis of organ or tissue is called fibrosis, and severe fibrosis can cause damage of tissues leading to organ scarring. Tissue fibrosis can occur not only in lung and liver, but in all the organs and systems of the human body. A variety of factors (such as inflammation, immune response, poison, ischemia and changes of hemodynamics, and so on) cause parenchymal cellular damage. This leads to parenchymal cells inflammation, deformation, necrosis, and activates the corresponding macrophages to release cytokines and growth factors, which in turn activate the resting extracellular martrix (ECM) to produce cells, and then transform the cells into myofibroblasts. Myofibroblasts proliferate and secrete cytokines which act on macrophages through paracrine. Myofibroblasts are able to synthesize a lot of ECM such as collagen, and ECM degradation is decreased at the same time, which leads to organ or tissue fibrosis as a result.

SUMMARY OF THE DISCLOSURE

Provided herein is a compound, or a tautomer thereof, or a stereoisomer thereof, or a racemate thereof, or a nonequal mixture of enantiomers thereof, or a geometric isomer thereof, or a solvate thereof, or a pharmaceutically acceptable salt thereof, or a solvate of the salt of the compound, wherein the compound has a structure of Formula I or II

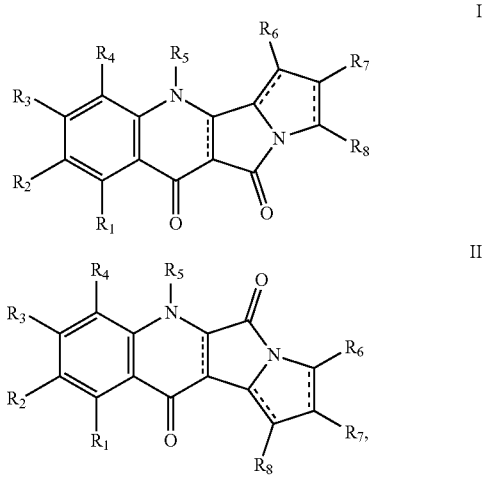

wherein "- - -" is a single bond or absent;

$R_1$, $R_2$, $R_3$ and $R_4$ are each independently selected from the group consisting of hydrogen, deuterium, halogen, hydroxy, amino, nitro, cyano, alkyl, haloalkyl, alkoxy, alkylamino, alkanoyl, hydroxyalkoxy, hydroxyalkylamino, hydroxyalkanoyl, haloalkoxy, haloalkylamino, haloalkanoyl, aminoalkoxy, cycloalkyl, cycloalkyloxy, cycloalkylamino, cycloalkanoyl, alkenyl, alkenylalkoxy, alkenylalkylamino, alkenylalkanoyl, alkynyl, alkynylalkoxy, alkynylalkylamino, alkynylalkanoyl, aryl, aryloxy, aroyl, arylamino, arylalkoxy, arylalkylamino, heteroaryl, heteroaryloxy, heteroaroyl, heteroarylamino, heteroarylalkoxy, heteroarylalkylamino, heteroarylalkanoyl, heterocycloalkyl, heterocyclyloxy, heterocyclylamino, heterocyclylanoyl, heterocyclylalkoxy, heterocyclylalkylamino, heterocyclylalkanoyl, azidoalkoxy, fused bicyclyl, fused heterobicyclyl, fused bicyclyl aliphatic, fused heterobicyclyl aliphatic, fused bicycloxy, fused heterobicycloxy, fused bicyclylamino, fused heterobicyclylamino, fused bicyclylalkoxy, fused heterobicyclylalkoxy, fused bicyclylalkylamino, fused heterobicyclylalkylamino, fused bicycloxyalkoxy, fused heterobicycloxyalkoxy, fused bicyclylaminoalkoxy, fused heterobicyclylaminoalkoxy, fused bicyclyl-C(O)—, fused bicyclyl-C(=O)O—, fused heterobicyclyl-C(=O)—, fused heterobicyclyl-C(=O)O—, fused bicyclylamino-C(=O)—, fused heterobicyclylamino-C(=O)—, fused bicyclyl-C(=O)N($R_9$)—, fused heterobicyclyl-C(=O)N($R_9$)—, spiro bicyclyl, spiro heterobicyclyl, spiro bicyclyl aliphatic, spiro heterobicyclyl aliphatic, spiro bicycloxy, spiro heterobicycloxy, spiro bicyclylamino, spiro heterobicyclylamino, spiro bicyclylalkoxy, spiro heterobicyclylalkoxy, spiro bicyclylalkylamino, spiro heterobicyclylalkylamino, spiro bicycloxyalkoxy, spiro heterobicycloxyalkoxy, spiro bicyclylaminoalkoxy, spiro heterobicyclylaminoalkoxy, spiro bicyclyl-C(=O)—, spiro bicyclyl-C(=O)O—, spiro heterobicyclyl-C(=O)—, spiro heterobicyclyl-C(=O)O—, spiro bicyclylamino-C(=O)—, spiro heterobicyclylamino-C(=O)—, spiro bicyclyl-C(=O)N($R_9$)—, spiro heterobicyclyl-C(=O)N($R_9$)—, $R_{10}R_9N$—, —C(=O)N$R_9R_{10}$, —OC(=O)N$R_9R_{10}$, —OC(=O)O$R_9$, —N($R_9$)C(=O)N$R_9R_{10}$, —N($R_9$)C(=O)O$R_{10}$, —N($R_9$)C(=O)—$R_{10}$, $R_9R_{10}N$—S(=O)$_t$—, $R_9S(=O)_t$—, $R_9S(=O)_tN(R_{10})$—, $R_{10}R_9N$-alkyl, $R_9S(=O)_t$-alkyl, $R_{10}R_9N$—C(=O)-alkyl, $R_{10}R_9N$-alkoxy, $R_9S(=O)_t$-alkoxy, $R_9R_{10}N$—C(=O)-alkoxy, aryl-$(CH_2)_p$-G-$(CH_2)_m$—, heteroaryl-$(CH_2)_p$-G-$(CH_2)_m$—, heterocyclyl-$(CH_2)_p$-G-$(CH_2)_m$—, and cycloalkyl-$(CH_2)_p$-G-$(CH_2)_m$—, wherein G is selected from the group consisting of O, S, N$R_{11}$, S(=O), S(=O)$_2$, C(=O), —C(=O)N($R_9$)—, —OC(=O)N($R_9$)—, —OC(=O)—, —N($R_9$)C(=O)N($R_9$)—, —($R_9$)N—S(=O)—, —OS(=O)$_t$—, and —OS(=O)$_tN(R_9)$—, wherein each t is 1 or 2, p and m are each independently 0, 1, 2, 3 or 4, wherein each of the aryl-$(CH_2)_p$-G-$(CH_2)_m$—, heteroaryl-$(CH_2)_p$-G-$(CH_2)_m$—, heterocyclyl-$(CH_2)_p$-G-$(CH_2)_m$—, and cycloalkyl-$(CH_2)_p$-G-$(CH_2)_m$— is optionally substituted by one or more substituents selected from the group consisting of F, Cl, Br, I, alkyl, alkenyl, alkynyl, alkoxy and cyano;

$R_5$ is selected from the group consisting of hydrogen, alkyl, haloalkyl, alkanoyl, hydroxyalkanoyl, haloalkanoyl, cycloalkyl, cycloalkanoyl, alkenyl, alkenylalkanoyl, alkynyl, alkynylalkanoyl, aryl, aroyl, heteroaryl, heteroaroyl, heteroarylalkanoyl, heterocycloalkyl, heterocyclylanoyl, heterocyclylalkanoyl, azidoalkyl, fused bicyclyl, fused heterobicyclyl, fused bicyclyl-C(=O)—, fused heterobicyclyl-C(=O)—, fused bicyclylamino-C(=O)—, fused heterobicyclylamino-C(=O)—, spiro bicyclyl, spiro heterobicyclyl, spiro bicyclyl aliphatic, spiro heterobicyclyl aliphatic, spiro bicyclyl-C(=O)—, spiro heterobicyclyl-C(=O)—, spiro bicyclylamino-C(=O)—, spiro heterobicyclylamino-C(=O)—, —C(=O)N$R_9R_{10}$, —OC(=O)N$R_9R_{10}$, —OC(=O)O$R_9$, $R_9R_{10}N$—S(=O)$_t$—, $R_9S(=O)_t$—, $R_9S(=O)_tN(R_{10})$—, $R_{10}R_9N$-alkyl, $R_9S(=O)_t$-alkyl, $R_{10}R_9N$—C(=O)-alkyl, $R_{10}R_9N$-alkoxy, $R_9S(=O)_t$-alkoxy, $R_9R_{10}N$—C(=O)-alkoxy, aryl-$(CH_2)_p$-G-$(CH_2)_m$—, heteroaryl-$(CH_2)_p$-G-$(CH_2)_m$—, heterocyclyl-$(CH_2)_p$-G-$(CH_2)_m$—, and cycloalkyl-$(CH_2)_p$-G-$(CH_2)_m$—, wherein G is O, S, N$R_{11}$, S(=O), S(=O)$_2$, C(=O), —C(=O)N($R_9$)—, —OC(=O)N($R_9$)—, —OC(=O)—, —($R_9$)N—S(=O)$_t$—, —OS(=O)$_t$—, or —OS(=O)$_tN(R_9)$—, each t is 1 or 2, p and m are each independently 0, 1, 2, 3 or 4, wherein each of the aryl-$(CH_2)_p$-G-$(CH_2)_m$—, heteroaryl-$(CH_2)_p$-G-$(CH_2)_m$—, heterocyclyl-$(CH_2)_p$-G-$(CH_2)_m$—, and cycloalkyl-$(CH_2)_p$-G-$(CH_2)_m$— is optionally substituted by one or more substituents selected from the group consisting of F, Cl, Br, I, alkyl, alkenyl, alkynyl, alkoxy and cyano;

$R_6$, $R_7$ and $R_8$ are each independently selected from the group consisting of hydrogen, deuterium, halogen, hydroxy, amino, nitro, cyano, alkyl, haloalkyl, alkoxy, alkylamino, alkanoyl, hydroxyalkoxy, hydroxyalkylamino, hydroxyalkanoyl, haloalkoxy, haloalkylamino, haloalkanoyl, aminoalkoxy, cycloalkyl, cycloalkyloxy, cycloalkylamino, cycloalkanoyl, alkenyl, alkenylalkoxy, alkenylalkylamino, alkenylalkanoyl, alkynyl, alkynylalkoxy, alkynylalkylamino, alkynylalkanoyl, aryl, aryloxy, aroyl, arylamino, arylalkoxy, arylalkylamino, heteroaryl, heteroaryloxy, heteroaroyl, heteroarylamino, heteroarylalkoxy, heteroarylalkylamino, heteroarylalkanoyl, heterocycloalkyl, heterocyclyloxy, heterocyclylamino, heterocyclylanoyl, heterocyclylalkoxy, heterocyclylalkylamino, heterocyclylalkanoyl, azidoalkoxy, fused bicyclyl, fused heterobicyclyl, fused bicyclyl aliphatic, fused heterobicyclyl aliphatic, fused bicycloxy, fused heterobicycloxy, fused bicyclylamino, fused heterobicyclylamino, fused bicyclylalkoxy, fused heterobicyclylalkoxy, fused bicyclylalkylamino, fused heterobicyclylalkylamino, fused bicycloxyalkoxy, fused heterobicycloxyalkoxy, fused bicyclylaminoalkoxy, fused heterobicyclylaminoalkoxy, fused bicyclyl-C(=O)—, fused bicyclyl-C(=O)O—, fused heterobicyclyl-C(=O)—, fused heterobicyclyl-C(=O)O—, fused bicyclylamino-C(=O)—, fused heterobicyclylamino-C(=O)—, fused bicyclyl-C(=O)N($R_9$)—, fused heterobicyclyl-C(=O)N($R_9$)—, spiro bicyclyl, spiro heterobicyclyl, spiro bicyclyl aliphatic, spiro heterobicyclyl aliphatic, spiro bicycloxy, spiro heterobicycloxy, spiro bicyclylamino, spiro heterobicyclylamino, spiro bicyclylalkoxy, spiro heterobicyclylalkoxy, spiro bicyclylalkylamino, spiro heterobicyclylalkylamino, spiro bicycloxyalkoxy, spiro heterobicycloxyalkoxy, spiro bicyclylaminoalkoxy, spiro heterobicyclylaminoalkoxy, spiro bicyclyl-C(=O)—, spiro bicyclyl-C(=O)O—, spiro heterobicyclyl-C(=O)—, spiro heterobicyclyl-C(O)O—, spiro bicyclylamino-C(=O)—, spiro heterobicyclylamino-C(=O)—, spiro bicyclyl-C(=O)N($R_9$)—, spiro heterobicyclyl-C(=O)N($R_9$)—, $R_{10}R_9N$—, —C(=O)N$R_9R_{10}$, —OC(=O)N$R_9R_{10}$, —OC(=O)O$R_9$, —N($R_9$)C(=O)N$R_9R_{10}$, —N($R_9$)C(=O)O$R_{10}$, —N($R_9$)C(=O)—$R_{10}$, $R_9R_{10}N$—S(=O))$_t$—, $R_9S(=O)_t$—, $R_9S(=O)_tN(R_{10})$—, $R_{10}R_9N$-alkyl, $R_9S(=O)_t$-alkyl, $R_{10}R_9N$—C(=O)-alkyl, $R_{10}R_9N$-alkoxy, $R_9S(=O)_t$-alkoxy, $R_9R_{10}N$—C(=O)-alkoxy, aryl-$(CH_2)_p$-G-$(CH_2)_m$—, heteroaryl-$(CH_2)_p$-G-$(CH_2)_m$—, heterocyclyl-$(CH_2)_p$-G-$(CH_2)_m$—, and cycloalkyl-$(CH_2)_p$-G-$(CH_2)_m$—, wherein G is selected from the group consisting of O, S, N$R_{11}$, S(=O), S(=O)$_2$, C(=O), —C(=O)N($R_9$)—, —OC(=O)N($R_9$)—, —OC(=O)—, —N($R_9$)C(=O)N($R_9$)—, —($R_9$)N—S(=O)—, —OS(=O)$_t$—, and —OS(=O)$_tN(R_9)$—, wherein each t is 1 or 2, p and m are each independently 0, 1, 2, 3 or 4, wherein each of the aryl-$(CH_2)_p$-G-$(CH_2)_m$—, heteroaryl-$(CH_2)_p$-G-$(CH_2)_m$—, heterocyclyl-$(CH_2)_p$-G-$(CH_2)_m$—, and cycloalkyl-$(CH_2)_p$-G-$(CH_2)_m$— is optionally substituted by one or more substituents selected from the group consisting of F, Cl, Br, I, alkyl, alkenyl, alkynyl, alkoxy and cyano;

$R_{10}$ and $R_9$ are each independently selected from the group consisting of hydrogen, aliphatic, haloaliphatic, hydroxyaliphatic, aminoaliphatic, alkoxyaliphatic, alkylaminoaliphatic, alkylthioaliphatic, arylaliphatic, heteroarylaliphatic, heterocyclylaliphatic, cycloalkylaliphatic, aryloxyaliphatic, heterocyclyloxyaliphatic, cycloalkyloxyaliphatic, arylaminoaliphatic, heterocyclylaminoaliphatic, cycloalkylaminoaliphatic, aryl, heteroaryl, heterocyclyl and cycloalkyl; with the proviso that where $R_{10}$ and $R_9$ are bonded to a same nitrogen atom, $R_{10}$ and $R_9$ together with the nitrogen atom they are attached to, optionally form a substituted or unsubstituted 3-8 membered ring, a substituted or unsubstituted fused bicyclic ring or a substituted or unsubstituted spiro bicyclic ring, wherein hetero atoms in the heterocyclyl, heteroaryl, fused heterobicyclyl or spiro heterocyclyl are independently selected from the group consisting of N, O, S, and Se, and the number of the hetero atoms is 1-5;

$R_{11}$ is selected from the group consisting of hydrogen, $R_{10}R_9NC(=O)$—, $R_{10}OC(=O)$—, $R_{10}C(=O)$—, $R_{10}R_9NS(=O)$—, $R_{10}OS(=O)$—, $R_{10}S(=O)$—, $R_{10}R_9NS(=O)_2$—, $R_{10}OS(=O)_2$—, $R_{10}S(=O)$—, aliphatic, haloaliphatic, hydroxyaliphatic, aminoaliphatic, alkoxyaliphatic, alkylaminoaliphatic, alkylthioaliphatic, arylaliphatic, heteroarylaliphatic, heterocyclylaliphatic, cycloalkylaliphatic, aryloxyaliphatic, heterocyclyloxyaliphatic, cycloalkyloxyaliphatic, arylaminoaliphatic, heterocyclylaminoaliphatic, cycloalkylaminoaliphatic, aryl, heteroaryl, heterocyclyl and carbocyclyl;

$R_1$, $R_2$, $R_3$, $R_4$, $R_5$, $R_6$, $R_7$, $R_8$, $R_9$, $R_{10}$, $R_{11}$ are optionally substituted by one or more substituents selected from the group consisting of hydroxyl, hydroxymethyl, carboxyl, acetylamino, alkyl, alkoxy, alkylamino, cycloalkyl, alkenyl, alkynyl, trifluoromethyl, trifluoroacetyl, thiol, halogen, nitro, amino, azido (—$N_3$), guanidyl, cyano, tert-butoxycarbonyl (-Boc), carbonyl (—C=O), oxo (=O), thio (=S), sulfonyl, aryl, heteroaryl, and heterocyclyl; wherein in Formula I, when $R_1$, $R_2$, $R_3$, $R_4$, $R_6$, $R_7$, $R_8$ are H, $R_5$ is not H or $CH_3$; and in Formula I, when $R_1$, $R_2$, $R_3$, $R_4$, $R_5$, $R_6$ and $R_7$ are H, $R_8$ is not

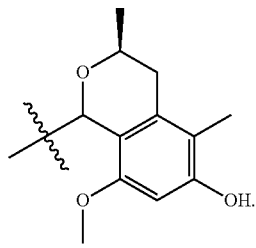

In some embodiments, $R_1$, $R_2$, $R_3$ and $R_4$ are each independently selected from the group consisting of H, D, F, Cl, Br, I, hydroxy, amino, nitro, cyano, C1-C20 alkyl, C1-C20 haloalkyl, C1-C20 alkoxy, C1-C20 alkylamino, C1-C20 alkanoyl, hydroxy-substituted C1-C20 alkoxy, hydroxy-substituted C1-C20 alkylamino, hydroxy-substituted C1-C20 alkanoyl, C1-C20 haloalkoxy, C1-C20 haloalkylamino, C1-C20 haloalkanoyl, C1-C20 aminoalkoxy, C3-C10 cycloalkyl, C3-C10 cycloalkyloxy, C3-C10 cycloalkylamino, C3-C10 cycloalkanoyl, C2-C8 alkenyl, C2-C8 alkynyl, C6-C10 aryl, C6-C10 aryloxy, C6-C10 aroyl, C6-C10 arylamino, C6-C10 aryl C1-C6 alkoxy, C6-C10 arylalkylamino, C5-C12 heteroaryl, C5-C12 heteroaryloxy, C5-C12 heteroaroyl, C5-C12 heteroarylamino, C5-C12 heteroaryl C1-C6 alkoxy, C5-C12 heteroaryl C1-C6 alkylamino, C4-C12 heterocyclyl C1-C6 alkanoyl, C4-C12 heterocycloalkyl, C4-C12 heterocyclyloxy, C4-C12 heterocyclylamino, C4-C12 heterocyclylanoyl, C4-C12 heterocyclyl C1-C6 alkoxy, C4-C12 heterocyclyl C1-C6 alkylamino, C4-C12 heterocyclyl C1-C6 alkanoyl, $R_{10}R_9N$—, —C(=O)$NR_9R_{10}$, —OC(=O)$NR_9R_{10}$, —OC(=O)$OR_9$, —N($R_9$)C(=O)$NR_9R_{10}$, —N($R_9$)C(=O)$OR_{10}$, —N($R_9$)C(=O)—$R_{10}$, $R_9R_{10}N$—S(=O)$_t$—, $R_9S(=O)_t$—, $R_9S(O)_t$—$NR_{10}$—, $R_{10}R_9N$—C1-C6 alkyl, $R_9S(=O)_t$—C1-C6 alkyl, $R_9R_{10}N$—C(=O)—C1-C6 alkyl, $R_{10}R_9N$—C1-C6 alkoxy, $R_9S(=O)_t$—C1-C6 alkoxy, $R_9R_{10}N$—C(=O)—C1-C6 alkoxy, C6-C10 aryl-$(CH_2)_p$-G-$(CH_2)_m$—, C5-C12 heteroaryl-$(CH_2)_p$-G-$(CH_2)_m$—, C4-C12 heterocyclyl-$(CH_2)_p$-G-$(CH_2)_m$—, or C3-C10 cycloalkyl-$(CH_2)_p$-G-$(CH_2)_m$—, wherein G is selected from the group consisting of O, S, $NR_{11}$, S(=O), S(=O)$_2$, C(=O), —C(=O)N($R_9$)—, —OC(=O)N($R_9$)—, —OC(=O)—, —N($R_9$)C(=O)N($R_9$)—, —($R_9$)N—S(=O)$_t$—, —OS(=O)$_t$—, and —OS(=O)$_t$N($R_9$)—, wherein each t is 1 or 2, p and m are each independently 0, 1, 2, 3 or 4, wherein the C6-C10 aryl-$(CH_2)_p$-G-$(CH_2)_m$—, C5-C12 heteroaryl-$(CH_2)_p$-G-$(CH_2)_m$—, C4-C12 heterocyclyl-$(CH_2)_p$-G-$(CH_2)_m$—, and C3-C10 cycloalkyl-$(CH_2)_p$-G-$(CH_2)_m$— are each optionally substituted by one or more substituents selected from the group consisting of F, Cl, Br, I, alkyl, alkenyl, alkynyl, alkoxy and cyano;

$R_5$ is selected from the group consisting of H, C1-C20 alkyl, C1-C20 haloalkyl, C1-C20 alkanoyl, C1-C20 hydroxyalkanoyl, C1-C20 haloalkanoyl, C3-C10 cycloalkyl, C3-C10 cycloalkanoyl, C2-C8 alkenyl, C2-C8 alkenylalkanoyl, C2-C8 alkynyl, C2-C8 alkynylalkanoyl, C6-C10 aryl, C6-C10 aroyl, C5-C12 heteroaryl, C5-C12 heteroaroyl, C4-C12 heterocyclylalkanoyl, C4-C12 heterocycloalkyl, C4-C12 heterocyclylanoyl, C4-C12 heterocyclyl C1-C6 alkanoyl, C5-C12 fused bicyclyl, C5-C12 fused heterobicyclyl, —C(=O)$NR_9R_{10}$, $R_9R_{10}N$—S(=O)$_t$—, $R_9S(=O)_t$—, $R_9S(=O)_t$—$NR_{10}$—, $R_{10}R_9N$—C1-C6 alkyl, $R_9S(=O)_t$—C1-C6 alkyl, $R_9R_{10}N$—C(=O)—C1-C6 alkyl, $R_{10}R_9N$—C1-C6 alkoxy, $R_9S(=O)_t$—C1-C6 alkoxy, $R_9R_{10}N$—C(=O)—C1-C6 alkoxy, C6-C10 aryl-$(CH_2)_p$-G-$(CH_2)_m$—, C5-C12 heteroaryl-$(CH_2)_p$-G-$(CH_2)_m$—, C4-C12 heterocyclyl-$(CH_2)_p$-G-$(CH_2)_m$—, and C3-C10 cycloalkyl-$(CH_2)_p$-G-$(CH_2)_m$—, wherein G is selected from the group consisting of O, S, $NR_{11}$, S(=O), S(=O)$_2$, C(=O), —C(=O)N($R_9$)—, —OC(=O)N($R_9$)—, —OC(=O)—, —($R_9$)N—S(=O)$_t$—, —OS(=O)$_t$—, and —OS(=O)$_t$N($R_9$)—, wherein each t is 1 or 2, p and m are each independently 0, 1, 2, 3 or 4, wherein the C6-C10 aryl-$(CH_2)_p$-G-$(CH_2)_m$—, C5-C12 heteroaryl-$(CH_2)_p$-G-$(CH_2)_m$—, C4-C12 heterocyclyl-$(CH_2)_p$-G-$(CH_2)_m$—, and C3-C10 cycloalkyl-$(CH_2)_p$-G-$(CH_2)_m$— are each optionally substituted by one or more substituents selected from the group consisting of F, Cl, Br, I, alkyl, alkenyl, alkynyl, alkoxy and cyano;

$R_6$, $R_7$ and $R_8$ are each independently selected from the group consisting of H, D, F, Cl, Br, I, hydroxy, amino, nitro, cyano, C1-C20 alkyl, C1-C20 haloalkyl, C1-C20 alkoxy, C1-C20 alkylamino, C1-C20 alkanoyl, hydroxy-substituted C1-C20 alkoxy, hydroxy-substituted C1-C20 alkylamino, hydroxy-substituted C1-C20 alkanoyl, C1-C20 haloalkoxy, C1-C20 haloalkylamino, C1-C20 haloalkanoyl, C1-C20 aminoalkoxy, C3-C10 cycloalkyl, C3-C10 cycloalkyloxy, C3-C10 cycloalkylamino, C3-C10 cycloalkanoyl, C2-C8 alkenyl, C2-C8 alkynyl, C6-C10 aryl, C6-C10 aryloxy, C6-C10 aroyl, C6-C10 arylamino, C6-C10 aryl C1-C6 alkoxy, C6-C10 arylalkylamino, C5-C12 heteroaryl, C5-C12 heteroaryloxy, C5-C12 heteroaroyl, C5-C12 heteroarylamino, C5-C12 heteroaryl C1-C6 alkoxy, C5-C12 heteroaryl C1-C6 alkylamino, C4-C12 heterocyclyl C1-C6 alkanoyl, C4-C12 heterocycloalkyl, C4-C12 heterocyclyloxy, C4-C12 heterocyclylamino, C4-C12 heterocyclylanoyl, C4-C12 heterocyclyl C1-C6 alkoxy, C4-C12 heterocyclyl C1-C6 alkylamino, C4-C12 heterocyclyl C1-C6 alkanoyl, $R_{10}R_9N$—, —C(=O)$NR_9R_{10}$, —OC(=O)$NR_9R_{10}$, —OC(=O)$OR_9$, —N($R_9$)C(=O)$NR_9R_{10}$, —N($R_9$)C(=O)$OR_{10}$, —N($R_9$)C(=O)—$R_{10}$, $R_9R_{10}N$—S(=O)$_t$—, $R_9S(=O)_t$—, $R_9S(=O)_t$—$NR_{10}$—, $R_{10}R_9N$—C1-C6 alkyl, $R_9S(=O)_t$—C1-C6 alkyl, $R_9R_{10}N$—C(=O)—C1-C6 alkyl, $R_{10}R_9N$—C1-C6 alkoxy, $R_9S(=O)_t$—C1-C6 alkoxy, $R_9R_{10}N$—C(=O)—C1-C6 alkoxy, C6-C10 aryl-$(CH_2)_p$-G-$(CH_2)_m$—, C5-C12 heteroaryl-$(CH_2)_p$-G-$(CH_2)_m$—, C4-C12 heterocyclyl-$(CH_2)_p$-G-$(CH_2)_m$—, and C3-C10 cycloalkyl-$(CH_2)_p$-G-$(CH_2)_m$—, wherein G is selected from the group consisting of O, S, $NR_{11}$, S(=O), S(=O)$_2$, C(=O), —C(=O)N($R_9$)—, —OC(=O)N($R_9$)—, —OC(=O)—, —N($R_9$)C(=O)N($R_9$)—, —($R_9$)N—S(=O)$_t$—, —OS(=O)$_t$—, and —OS(=O)$_t$N($R_9$)—, wherein each t is 1 or 2, p and m are each independently 0, 1, 2, 3 or 4, wherein the C6-C10 aryl- (CH₂)$_p$-G-(CH₂)$_m$—, C5-C12 heteroaryl-(CH₂)$_p$-G-(CH₂)$_m$—, C4-C12 heterocyclyl-(CH₂)$_p$-G-(CH₂)$_m$—, and C3-C10 cycloalkyl-(CH₂)$_p$-G-(CH₂)$_m$— are each optionally substituted by one or more substituents selected from the group consisting of F, Cl, Br, I, alkyl, alkenyl, alkynyl, alkoxy and cyano;

$R_{10}$ and $R_9$ are each independently selected from the group consisting of H, D, C1-C3 aliphatic, C1-C3 haloaliphatic, C1-C3 hydroxyaliphatic, C1-C3 aminoaliphatic, C1-C3 alkoxy C1-C3 aliphatic, C1-C3 alkylamino C1-C3 aliphatic, C1-C3 alkylthio C1-C3 aliphatic, C6-C10 aryl C1-C3 aliphatic, C5-C9 heteroaryl C1-C3 aliphatic, C4-C10 heterocyclyl C1-C3 aliphatic, C3-C10 cycloalkyl C1-C3 aliphatic, C6-C10 aryloxy C1-C3 aliphatic, C4-C10 heterocyclyloxy C1-C3 aliphatic, C3-C10 cycloalkyloxy C1-C3 aliphatic, C6-C10 arylamino C1-C3 aliphatic, C4-C10 heterocyclylamino C1-C3 aliphatic, C3-C10 cycloalkylamino C1-C3 aliphatic, C6-C10 aryl, C5-C10 heteroaryl, C4-C10 heterocyclyl and C3-C10 cycloalkyl; with the proviso that where $R_{10}$ and $R_9$ are bonded to a same nitrogen atom, $R_{10}$ and $R_9$, together with the nitrogen atom they are attached to, optionally form a substituted or unsubstituted 3-8 membered ring, a substituted or unsubstituted fused bicyclic ring or a substituted or unsubstituted spiro bicyclic ring, wherein hetero atoms in the heterocyclyl, heteroaryl, fused heterobicyclyl or spiro heterocyclyl are independently selected from the group consisting of N, O, S, and Se, and the number of the hetero atoms is 1-5;

$R_{11}$ is selected from the group consisting of H, D, $R_{10}R_9NC(=O)$—, $R_{10}OC(=O)$—, $R_{10}C(=O)$—, $R_{10}R_9NS(=O)$—, $R_{10}OS(=O)$—, $R_{10}S(=O)$—, $R_{10}R_9NS(=O)_2$—, $R_{10}OS(=O)_2$—, $R_{10}S(=O)_2$—, C1-C3 aliphatic, C1-C3 haloaliphatic, C1-C3 hydroxyaliphatic, C1-C3 aminoaliphatic, C1-C3 alkoxy C1-C3 aliphatic, C1-C3 alkylamino C1-C3 aliphatic, C1-C3 alkylthio C1-C3 aliphatic, C6-C10 aryl C1-C3 aliphatic, C5-C9 heteroaryl C1-C3 aliphatic, C4-C10 heterocyclyl C1-C3 aliphatic, C3-C10 cycloalkyl C1-C3 aliphatic, C6-C10 aryloxy C1-C3 aliphatic, C4-C10 heterocyclyloxy C1-C3 aliphatic, C3-C10 cycloalkyloxy C1-C3 aliphatic, C6-C10 arylamino C1-C3 aliphatic, C4-C10 heterocyclylamino C1-C3 aliphatic, C3-C10 cycloalkylamino C1-C3 aliphatic, C6-C10 aryl, C5-C10 heteroaryl, C4-C10 heterocyclyl and C3-C10 cycloalkyl;

wherein $R_1$, $R_2$, $R_3$, $R_4$, $R_5$, $R_6$, $R_7$, $R_8$, $R_9$, $R_{10}$, $R_{11}$ are optionally substituted by one or more substituents selected from the group consisting of hydroxyl, hydroxymethyl, carboxyl, acetylamino, alkyl, alkoxy, alkylamino, cycloalkyl, alkenyl, alkynyl, trifluoromethyl, trifluoroacetyl, thiol, halogen, nitro, amino, azido (—N₃), guanidyl, cyano, tert-butoxycarbonyl (-Boc), carbonyl (—C=O), oxo (=O), thio (=S), sulfonyl, aryl, heteroaryl, and heterocyclyl; and in Formula 1, when $R_1$, $R_2$, $R_3$, $R_4$, $R_5$, $R_6$ and $R_7$ are H, $R_8$ is not

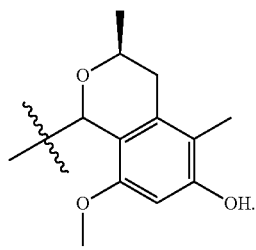

In some other embodiments, $R_1$, $R_2$, $R_3$ and $R_4$ are each independently selected from the group consisting of H, D, F, Cl, Br, I, hydroxy, amino, nitro, cyano, methyl, ethyl, propyl, isopropyl, butyl, tert-butyl, $C_5H_{11}$, $C_6H_{13}$, $C_8H_{17}$, trifluoromethyl, hydroxymethyl, aminomethyl, methoxy, ethoxy, tert-butoxy, methylamino, ethylamino, isopropylamino, 3-hydroxy-propyl, acetyl, trifluoroacetyl, cyanoacetyl, methylaminoacetyl, propionyl, isopropionyl, 2-hydroxypropanoyl, 2-aminopropanoyl, 2-chloropropanoyl, 2-bromopropanoyl, pentanoyl, hexanoyl, heptanoyl, methacryloyl, phenyl, benzoyl, p-nitrophenyl, p-methylbenzoyl, m-fluorobenzoyl, p-aminobenzoyl, p-methoxybenzoyl, 2,4-dimethylbenzoyl, m-azidobenzoyl, benzyl, p-chlorobenzyl, vinyl, propenyl, allyl, n-butenyl, isobutenyl, n-pentenyl, isopentenyl, cyclopropyl, cyclopropanoyl, cyclopentanoyl, cyclohexanoyl, 3-pyridinecarbonyl, naphthyl, phenethylimidazolyl, pyridyl, pyrrolyl, oxazolyl, isoxazolyl, triazolyl, tetrazolyl, furyl, thienyl, thiazolyl, piperidinyl, piperazinyl, indolyl, carbazolyl, benzofuranyl, tetrahydrofuranyl, tetrahydropyranyl, pyrimidine, purine, —N(CH₃)₂, —C(C=O)NH—C1-C4 alkyl, —OC(C=O)—NH—C1-C4 alkyl, —OC(O=O)O—C1-C4 alkyl, —NHC(=O)NH—C1-C4 alkyl, —NHC(=O)O—C1-C4 alkyl, —NHC(=O)—C1-C4 alkyl, C1-C4 alkyl-NH—S(=O)₂—, C1-C4 alkyl-S(=O)₂—, C1-C4 alkyl-S(=O)₂NH—, phenyl-(CH₂)$_P$-G-(CH₂)$_m$—, fluorophenyl-(CH₂)$_P$-G-(CH₂)$_m$—, thiazolyl-(CH₂)$_p$-G-(CH₂)$_m$—, pyridyl-(CH₂)$_p$-G-(CH₂)$_m$—, phenylethyl, and cyclohexyl-(CH₂)$_p$-G-(CH₂)$_m$—, wherein G is selected from the group consisting of O, S, S(=O), S(=O)₂, and C(=O), p and m are each independently 0, 1, 2 or 3, wherein the C6-C10 aryl-(CH₂)$_P$-G-(CH₂)$_m$— is optionally substituted by one or more substituents selected from the group consisting of F, Cl, Br, I, methyl, ethyl, propyl, ethynyl, propynyl, butynyl, methoxy, ethoxy and cyano, wherein $R_1$, $R_2$, $R_3$, $R_4$ are each optionally substituted by one or more substituents selected from the group consisting of F, Cl, Br, I, hydroxy, hydroxymethyl, carboxy, acetylamino, C1-C6 alkyl, C1-C6 alkoxy, C1-C6 alkylamino, trifluoromethyl, trifluoroacetyl, thiol, nitro, amino, azido (—N3), guanidyl, cyano, tert-butoxycarbonyl (-Boc), carbonyl (—C=O), oxo (=O), thio (=S), sulfonyl and phenyl;

$R_5$ is selected from the group consisting of H, methyl, ethyl, propyl, isopropyl, butyl, tert-butyl, $C_5H_{11}$, $C_6H_{13}$, $C_8H_{17}$, trifluoromethyl, hydroxymethyl, aminomethyl, 3-hydroxy-propyl, acetyl, trifluoroacetyl, cyanoacetyl, methylaminoacetyl, propionyl, isopropionyl, 2-hydroxypropanoyl, 2-aminopropanoyl, 2-chloropropanoyl, 2-bromopropanoyl, pentanoyl, hexanoyl, heptanoyl, methacryloyl, phenyl, benzoyl, p-nitrophenyl, p-methylbenzoyl, m-fluorobenzoyl, p-aminobenzoyl, p-methoxybenzoyl, 2,4-dimethylbenzoyl, m-azidobenzoyl, benzyl, p-chlorobenzyl, vinyl, propenyl, allyl, n-butenyl, isobutenyl, n-pentenyl, isopentenyl, cyclopropyl, cyclopropanoyl, cyclopentanoyl, cyclohexanoyl, 3-pyridinecarbonyl, naphthyl, phenethylimidazolyl, pyridyl, pyrrolyl, oxazolyl, isoxazolyl, triazolyl, tetrazolyl, furyl, pyranyl, thienyl, thiazolyl, piperidinyl, piperazinyl, indolyl, carbazolyl, benzofuranyl, tetrahydrofuranyl, tetrahydropyranyl, pyrimidine, purine, pentose, hexose, —(C=O)NH—C1-C4 alkyl, C1-C4 alkyl-NH—S(=O)₂—, C1-C4 alkyl-S(=O)₂—, phenyl-(CH₂)$_p$-G-(CH₂)$_m$—, fluorophenyl-(CH₂)$_p$-G-(CH₂)$_m$—, thiazolyl-(CH₂)$_p$-G-(CH₂)$_m$—, pyridyl-(CH₂)$_p$-G-(CH₂)$_m$—, phenylethyl, and cyclohexyl-(CH₂)$_p$-G-(CH₂)$_m$—, wherein G is selected from the group consisting of O, S, S(=O), S(=O)₂, and C(=O), p and m are each independently 0, 1, 2 or 3, wherein the C6-C10 aryl-(CH₂)$_p$-G-(CH₂)$_m$— is optionally substituted by one or more substituents selected from the group consisting of F, Cl, Br, I, methyl, ethyl, propyl, ethynyl, propynyl, butynyl, methoxy, ethoxy and cyano, wherein $R_5$ is optionally substituted by one or more substituents selected from the group consisting of D, F, Cl, Br, I, hydroxy, hydroxymethyl, carboxy, acetylamino, C1-C6 alkyl, C1-C6 alkoxy, C1-C6 alkylamino, trifluoromethyl, trifluoroacetyl, thiol, nitro, amino, azido (—N3), guanidyl, cyano, tert-butoxycarbonyl (-Boc), carbonyl (—C=O), oxo (=O), thio (=S), sulfonyl and phenyl;

$R_6$, $R_7$ and $R_8$ are each independently selected from the group consisting of H, D, F, Cl, Br, I, hydroxy, amino, nitro, cyano, methyl, ethyl, propyl, isopropyl, butyl, ter-butyl, $C_5H_{11}$, $C_6H_{13}$, $C_8H_{17}$, trifluoromethyl, hydroxymethyl, aminomethyl, methoxy, ethoxy, tert-butoxy, methylamino, ethylamino, isopropylamino, 3-hydroxy-propyl, acetyl, trifluoroacetyl, cyanoacetyl, methylaminoacetyl, propionyl, isopropionyl, 2-hydroxypropanoyl, 2-aminopropanoyl, 2-chloropropanoyl, 2-bromopropanoyl, pentanoyl, hexanoyl, heptanoyl, methacryloyl, phenyl, benzoyl, p-nitrophenyl, p-methylbenzoyl, m-fluorobenzoyl, p-aminobenzoyl, p-methoxybenzoyl, 2,4-dimethylbenzoyl, m-azidobenzoyl, benzyl, p-chlorobenzyl, vinyl, propenyl, allyl, n-butenyl, isobutenyl, n-pentenyl, isopentenyl, cyclopropyl, cyclopropanoyl, cyclopentanoyl, cyclohexanoyl, 3-pyridinecarbonyl, naphthyl, phenethylimidazolyl, pyridyl, pyrrolyl, oxazolyl, isoxazolyl, triazolyl, tetrazolyl, furyl, thienyl, thiazolyl, piperidinyl, piperazinyl, indolyl, carbazolyl, benzofuranyl, tetrahydrofuranyl, tetrahydropyranyl, pyrimidine, purine, —N(CH$_3$)$_2$, —C(C=O)NH—C1-C4 alkyl, —OC(C=O)—NH—C1-C4 alkyl, —OC(O=O)O—C1-C4 alkyl, —NHC(=O)NH—C1-C4 alkyl, —NHC(=O)O—C1-C4 alkyl, —NHC(=O)—C1-C4 alkyl, C1-C4 alkyl-NH—S(=O)$_2$—, C1-C4 alkyl-S(=O)$_2$—, C1-C4 alkyl-S(=O)$_2$NH—, phenyl-(CH$_2$)$_p$-G-(CH$_2$)$_m$—, fluorophenyl-(CH$_2$)$_p$-G-(CH$_2$)$_m$—, thiazolyl-(CH$_2$)$_p$-G-(CH$_2$)$_m$—, pyridyl-(CH$_2$)$_p$-G-(CH$_2$)$_m$—, phenylethyl, and cyclohexyl-(CH$_2$)$_p$-G-(CH$_2$)$_m$—, wherein G is selected from the group consisting of O, S, S(=O), S(=O)$_2$, and C(=O), p and m are each independently 0, 1, 2 or 3, wherein the C6-C10 aryl-(CH$_2$)$_p$-G-(CH$_2$)— is optionally substituted by one or more substituents selected from the group consisting of F, Cl, Br, I, methyl, ethyl, propyl, ethynyl, propynyl, butynyl, methoxy, ethoxy and cyano, wherein $R_6$, $R_7$, $R_8$ are each optionally substituted by one or more substituents selected from the group consisting of F, Cl, Br, I, hydroxy, hydroxymethyl, carboxy, acetylamino, C1-C6 alkyl, C1-C6 alkoxy, C1-C6 alkylamino, trifluoromethyl, trifluoroacetyl, thiol, nitro, amino, azido (—N3), guanidyl, cyano, tert-butoxycarbonyl (-Boc), carbonyl (—C=O), oxo (=O), thio (=S), sulfonyl and phenyl.

In some embodiments, the compound has a structure of Formula III or IV,

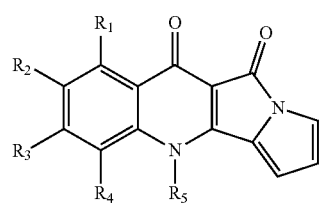

III

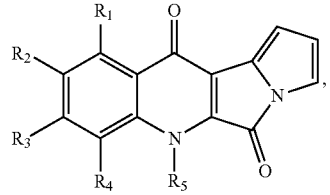

IV wherein $R_1$, $R_2$, $R_3$, $R_4$, $R_6$, $R_7$ and $R_8$ are each independently selected from following substituents

| |
|---|
| H |
| F |
| Cl |
| Br |
| I |
| OCH$_3$ |
| OH |
| C$_3$H$_7$ |
| C$_2$H$_5$ |
| CH$_3$ |
| CN |
| CF$_3$ |
| OCF$_3$ |
| CHF$_2$ |
| NO$_2$ |
| SO$_2$CH$_3$ |
| NH$_2$ |
| COOH |
| NHOCH$_3$ |
| COOCH$_3$ |
| COOC$_2$H$_5$ |
| NHOC$_2$H$_5$ |
| CONH$_2$ |
| CONHCH$_3$ |
| CONH(CH$_3$)$_2$ |
| SCH$_3$ |
| CH(CH$_3$)OH |
| CH$_2$CH$_2$OH |
| CH$_2$CH$_2$NH |
| CH(CH$_2$NH)OH |
| 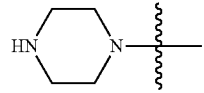 |
| 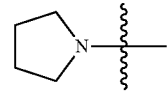 |
| 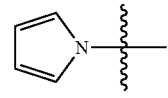 |
| 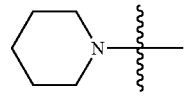 |
| 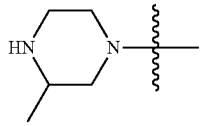 |

$R_5$ is selected from:
C$_2$H$_5$
n-C$_3$H$_7$
n-C$_4$H$_9$
n-C$_5$H$_{11}$
CH(CH$_3$)$_2$
H$_2$CHC=CH$_2$
H$_2$CCCH
CH$_2$CH$_2$CH(CH$_3$)$_2$
H$_2$CHC=C(CH$_3$)$_2$
CH$_2$OH
C$_2$H$_4$OH
C$_2$H$_4$N(CH$_3$)$_2$
CH$_2$NH$_2$
C$_2$H$_4$NH$_2$
C$_2$H$_4$N(C$_2$H$_5$)$_2$
C$_3$H$_6$OH
CH$_2$N(CH$_3$)$_2$
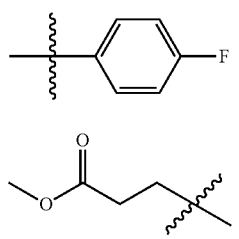
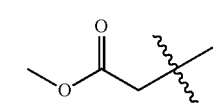
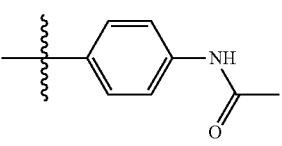
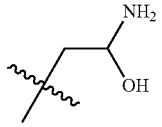
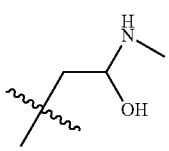
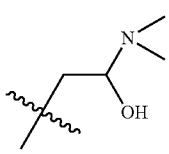
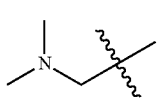
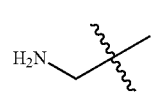
-continued
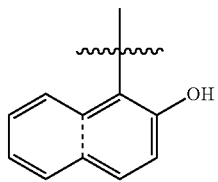
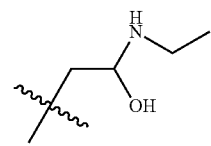
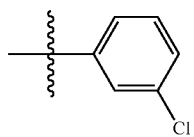
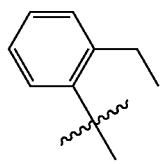
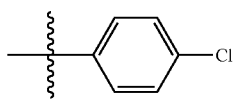
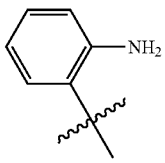
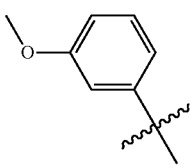
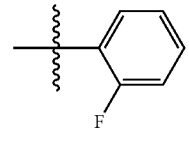
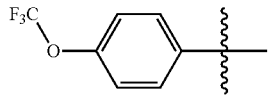

-continued
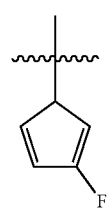
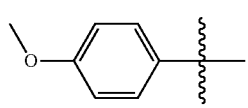
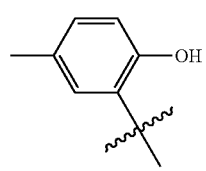
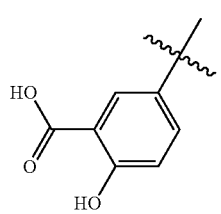
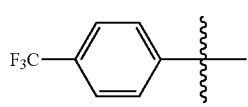
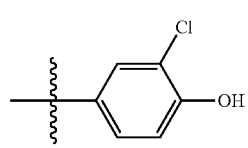
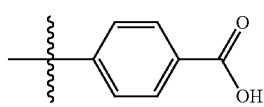
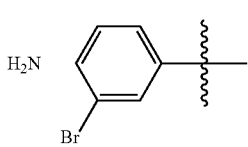
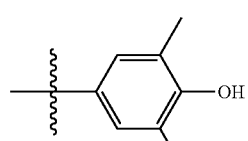
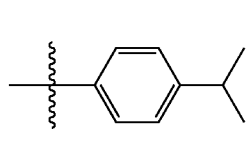
-continued
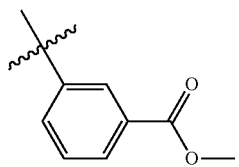
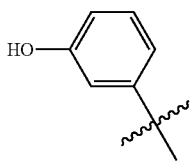
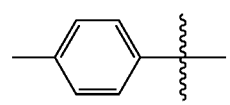
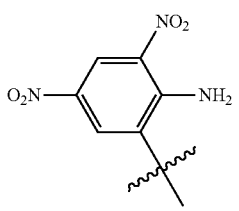
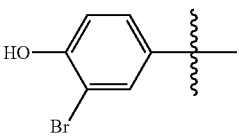
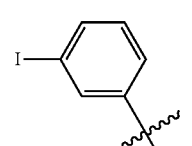
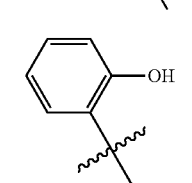
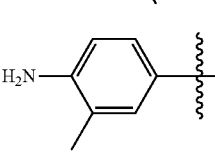
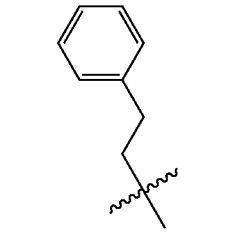
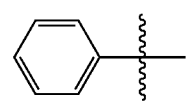

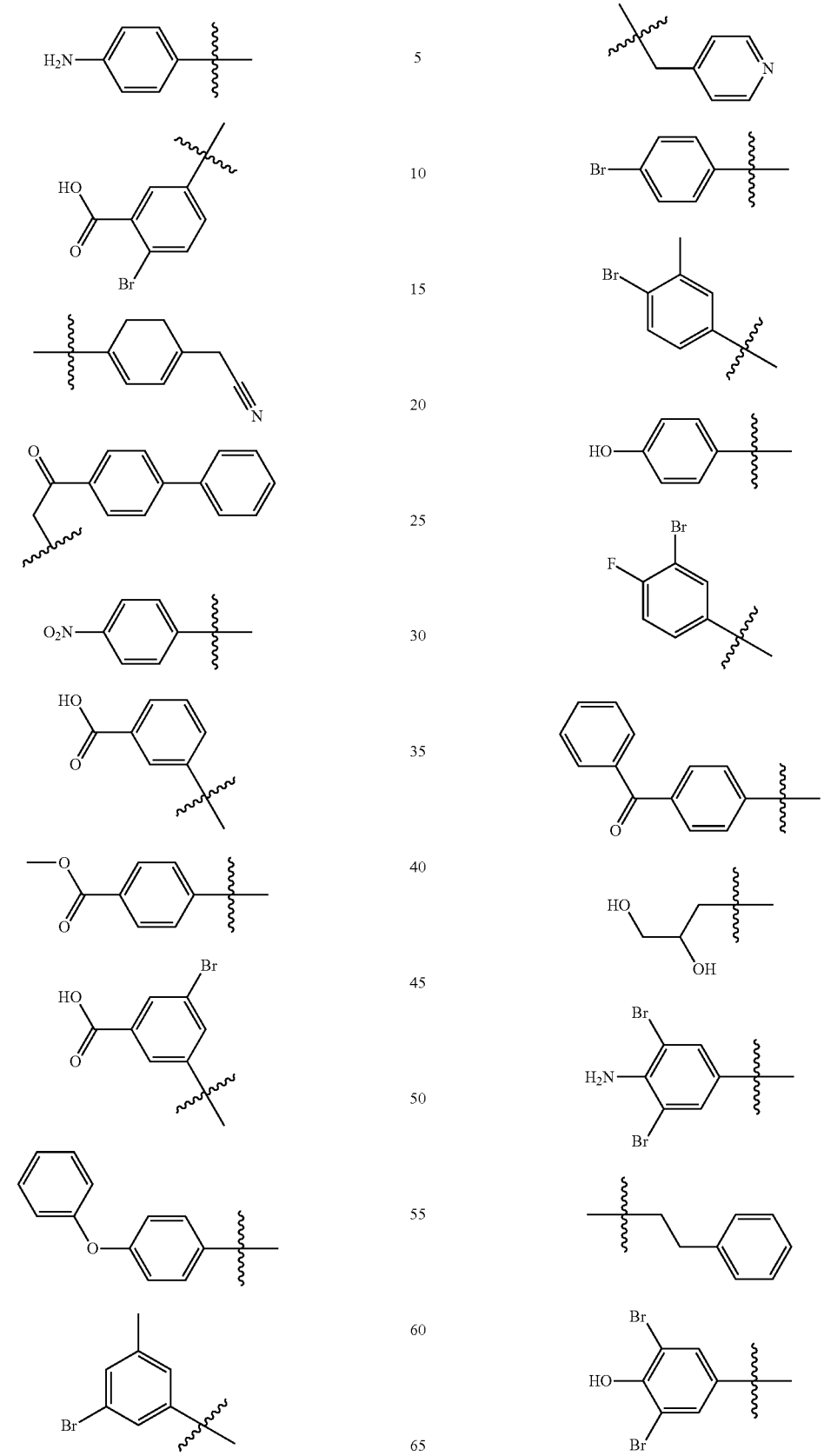

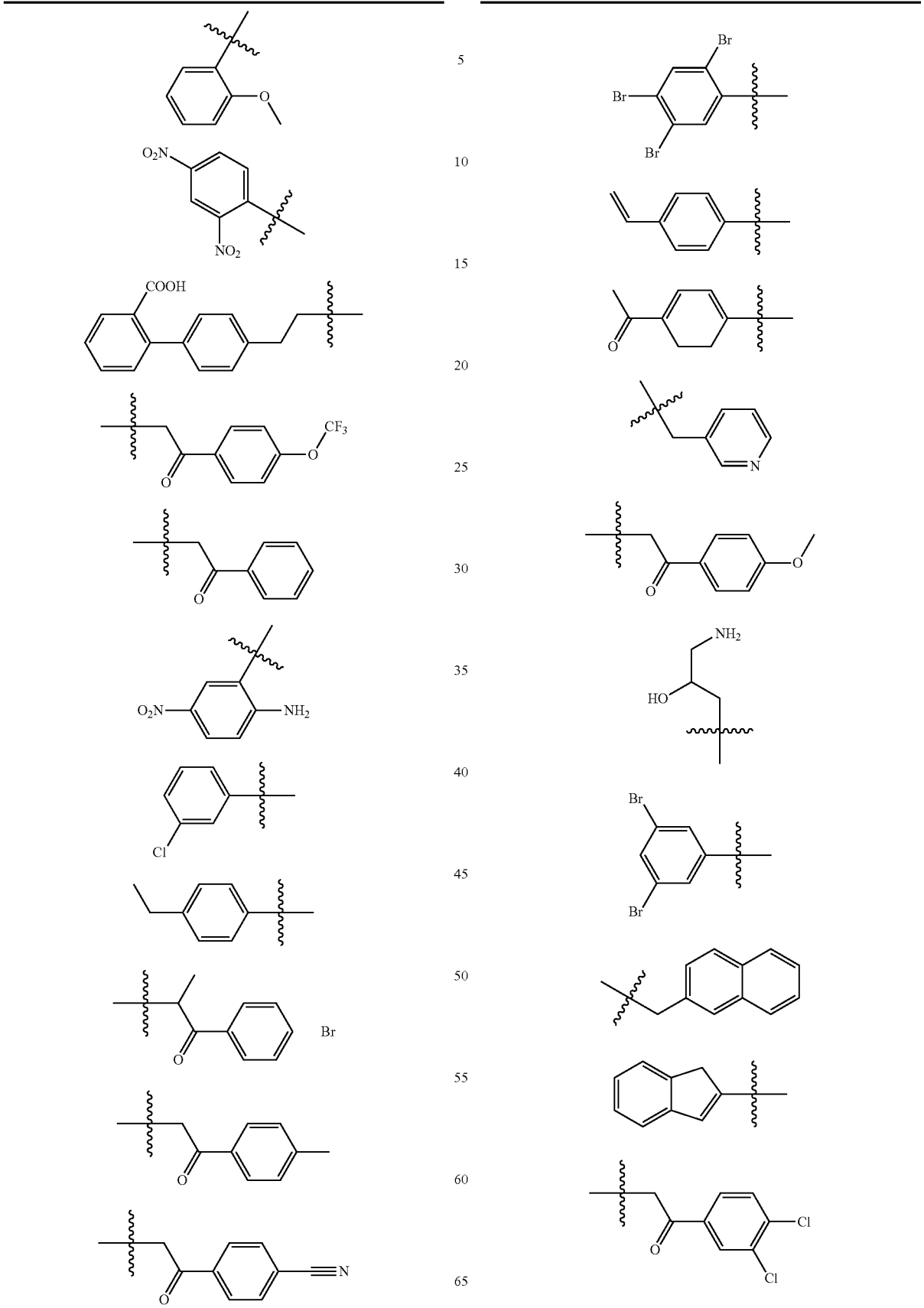

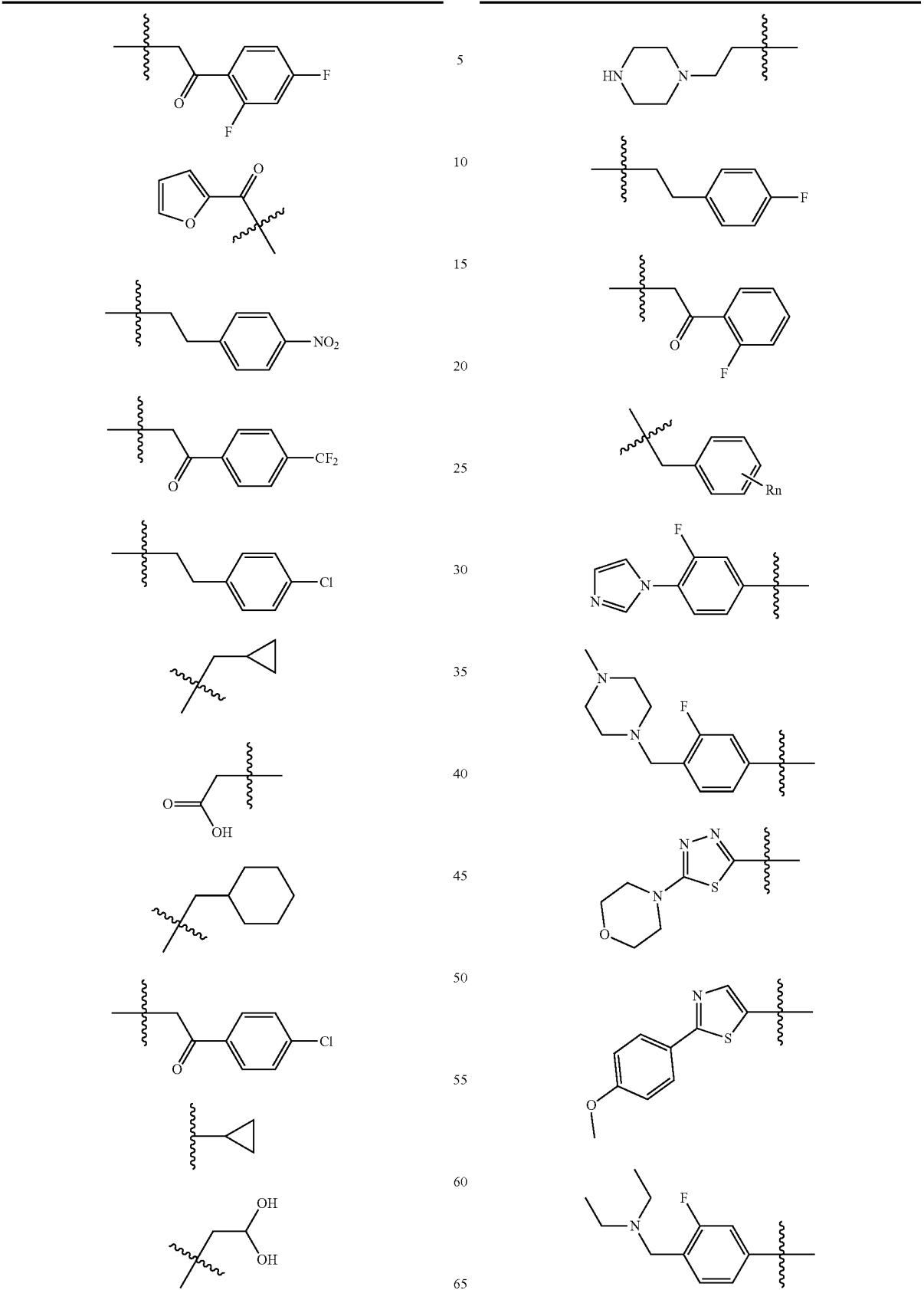

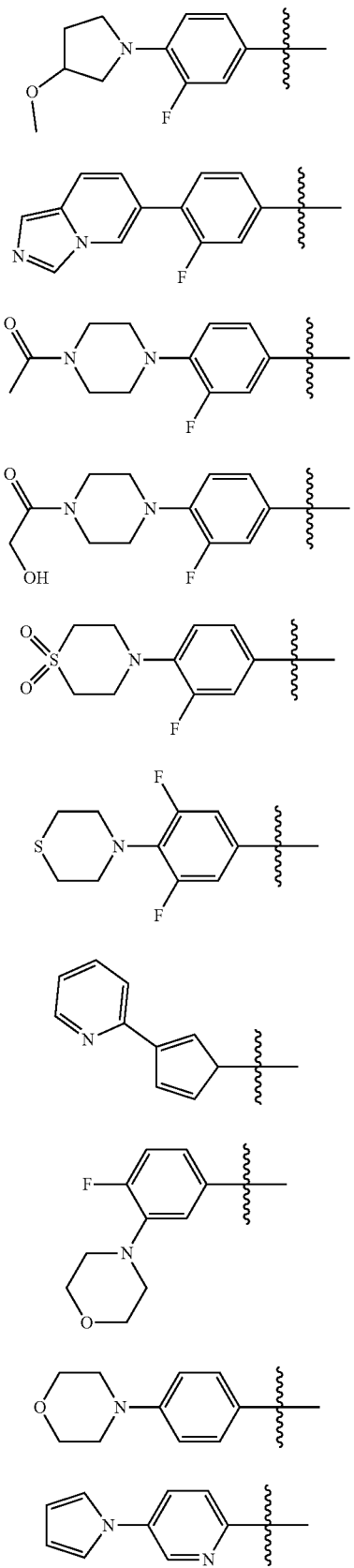
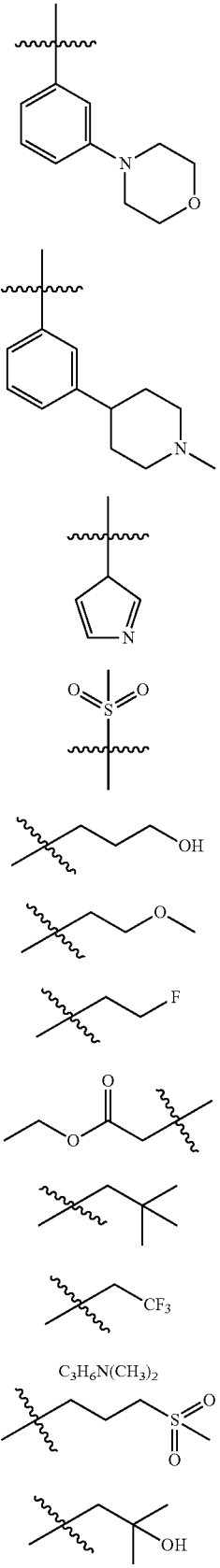

-continued

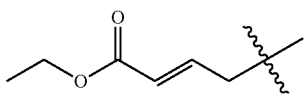
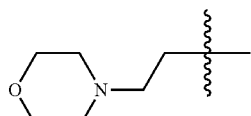
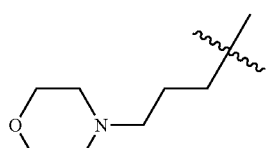
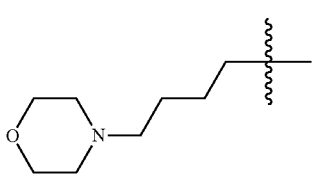
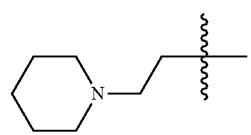
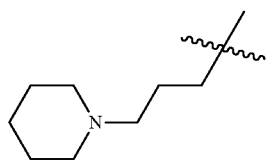
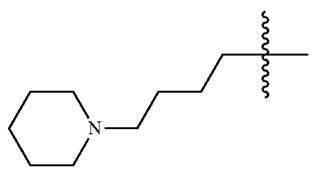

-continued

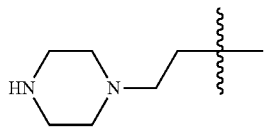
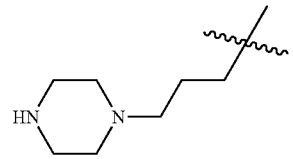
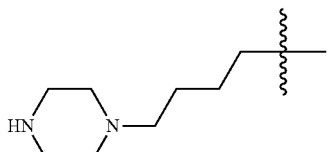
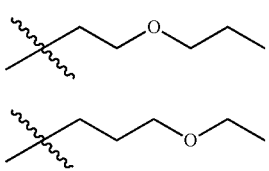
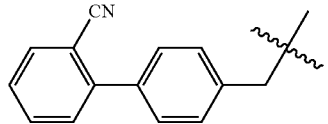
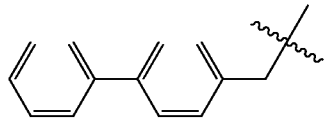

when $R_5$ is

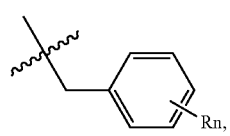

$R_n$ is:

| | | | | | |
|---|---|---|---|---|---|
| H | 3-OCF$_3$ | 2,3-2F | 2,3-2OCH$_3$ | 2-OCF$_3$ | 3-C(CH$_3$)$_3$ |
| 2-CH$_3$ | 3-NO$_2$ | 2,4-2F | 2,4-2OCH$_3$ | 2,3-2F | 2,5-2OCH$_3$ |
| 2-F | 3-COOH | 2,4-2F | 2,6-2OCH$_3$ | 3-CH$_3$ | 4-OCF$_3$ |
| 2-Cl | 3-COOCH$_3$ | 2,5-2F | 3,4-2CH$_3$ | 3-OCF$_3$ | 4-NO$_2$ |
| 2-Br | 3-COOC$_3$H$_5$ | 2,6-2F | 3,5-2CH$_3$ | 3-F | 4-C(CH$_3$)$_3$ |
| 2-I | 3-SO$_2$CH$_3$ | 3,4-2F | 2,3-2Cl | 3-Cl | 4-COOH |
| 2-CN | 3-CH$_2$Br | 3,5-2F | 2,4-2Cl | 3-Br | 4-COOCH$_3$ |
| 2-CF$_3$ | 4-CH$_3$ | 2,3,4-3F | 2,5-2Cl | 3-I | 4-COOC$_2$H$_3$ |
| 2-OCF$_3$ | 4-OCF$_3$ | 2,4,5-3F | 2,6-2Cl | 3-CN | 4-SO$_2$CH$_3$ |
| 2-NO$_2$ | 4-F | 2,3,5-3F | 3,4-2Cl | 3-CF$_3$ | 4-CH$_2$Br |
| 2-C(CH$_3$)$_3$ | 4-Cl | 2,3,6-3F | 3,5-2Cl | 2,3,5,6-4F | 2-F-3-Cl |
| 2-COOH | 4-Br | 2,4,6-3F | 2-F-3-Cl | 2,3,4,5,6-5F | 2-Cl-4-F |
| 2-COOCH$_3$ | 4-I | 2,3,4,5-4F | 2-F-3-Br | 2,3-2CF$_3$ | 3-F-4-OCH$_3$ |
| 2-COOC$_2$H$_5$ | 4-CN | 3,4,5-3F | 3-CF$_3$-5-CF$_3$ | 2,4-2CF$_3$ | 3-Cl-5-F |
| 2-SO$_2$CH$_3$ | 4-CF$_3$ | 2,4,5,6-4F | 3-Cl-4-F | 2,5-2CF$_3$ | 2-Br-5-F |
| 2,6-2CF$_3$ | 2-CN-5-F | 3,4-2CF$_3$ | 2-Cl-5-CF$_3$ | 3,5-2CF$_3$ | 2-OCH$_3$ |
| 3-OCH$_3$ | 4-OCH$_3$ | | | | | wherein in the Formula I, when $R_1=R_2=R_3=R_4=H$, $R_5$ is not H or $CH_3$.

Some of the compounds of the present disclosure can be illustrated by the specific compounds listed in Tables 1-26, but are not limited to these compounds.

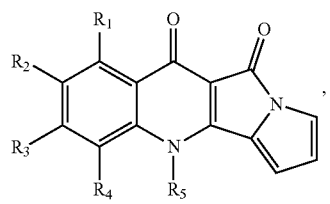

$R_1=R_2=R_3=R_4=H$,

TABLE 1

| Compd. | $R_5$ |
|---|---|
| 1 | $C_2H_5$ |
| 2 | $n\text{-}C_3H_7$ |
| 3 | $n\text{-}C_4H_9$ |
| 4 | $n\text{-}C_5H_{11}$ |
| 5 | $CH(CH_3)_2$ |
| 6 | $H_2CHC\!=\!CH_2$ |
| 7 | $H_2CC\!\equiv\!CH$ |
| 8 | $CH_2CH_2CH(CH_3)_2$ |
| 9 | $H_2CHC\!=\!C(CH_3)_2$ |
| 10 | $CH_2OH$ |
| 11 | $C_2H_4OH$ |
| 12 | $C_2H_4N(CH_3)_2$ |
| 13 | $CH_2NH_2$ |
| 14 | $C_2H_4NH_2$ |
| 15 | $C_2H_4N(C_2H_5)_2$ |
| 16 | $C_3H_6OH$ |
| 17 | $CH_2N(CH_3)_2$ |
| 18 | 4-fluorophenyl group |
| 19 | methyl ester chain (methyl 4-oxobutanoate substituent) |
| 20 | methyl ester chain (methyl 3-oxopropanoate substituent) |
| 21 | 4-acetamidophenyl group |
| 22 | 2-amino-1-hydroxyethyl group |
| 23 | 1-hydroxy-2-(methylamino) group |

TABLE 1-continued

| Compd. | $R_5$ |
|---|---|
| 24 | 2-(dimethylamino)-1-hydroxy group |
| 25 | 2-(methylamino) group |
| 26 | 2-aminoethyl group |
| 27 | 2-hydroxynaphthalen-1-yl group |
| 28 | 2-(ethylamino)-1-hydroxy group |
| 29 | 2-aminophenyl group |
| 30 | 3-methoxyphenyl group |
| 31 | oxiran-2-ylmethyl group |
| 32 | 3-chlorophenyl group |
| 33 | 2-ethylphenyl group |
| 34 | 4-chlorophenyl group |

TABLE 1-continued

| Compd. | R₅ |
|---|---|
| 35 | 4-methyl-2-hydroxyphenyl (attached at position with wavy bond) |
| 36 | 2-hydroxy-5-(attachment)-benzoic acid |
| 37 | 2-fluorophenyl |
| 38 | 4-(trifluoromethoxy)phenyl |
| 39 | 6-hydroxynaphthalen-2-yl |
| 40 | 4-methoxyphenyl |
| 41 | 4-hydroxy-3,5-dimethylphenyl |
| 42 | 4-isopropylphenyl |
| 43 | 4-(trifluoromethyl)phenyl |
| 44 | 3-hydroxyphenyl |
| 45 | 4-carboxyphenyl |
| 46 | 4-amino-3-bromophenyl |
| 47 | 3-bromo-4-hydroxyphenyl |
| 48 | 3-iodophenyl |
| 49 | 4-(cyanomethyl)phenyl |
| 50 | 2-(biphenyl-4-yl)-2-oxoethyl |
| 51 | 4-methylphenyl |
| 52 | phenyl |
| 53 | 4-aminophenyl |
| 54 | 2-bromo-5-(attachment)-benzoic acid |
| 55 | 4-phenoxyphenyl |

TABLE 1-continued

| Compd. | R₅ |
|---|---|
| 56 | 3-bromo-5-methylphenyl |
| 57 | 3-aminophenyl |
| 58 | 3-carboxyphenyl |
| 59 | 4-(methoxycarbonyl)phenyl |
| 60 | 4-hydroxyphenyl |
| 61 | 3-bromo-4-fluorophenyl |
| 62 | 4-benzoylphenyl |
| 63 | 4-nitrophenyl |
| 64 | 4-bromophenyl |
| 65 | 4-bromo-3-methylphenyl |
| 66 | 3,5-dibromo-4-hydroxyphenyl |
| 67 | 2-methoxyphenyl |
| 68 | 4-acetylphenyl |
| 69 | pyridin-4-ylmethyl |
| 70 | 4-amino-3,5-dibromophenyl |
| 71 | 2-phenylethyl (gem-dimethyl) |
| 72 | 2-amino-5-nitrophenyl |
| 73 | dibenzofuran-2-yl |
| 74 | 1H-inden-2-yl |
| 75 | 3,4-dihydroxy-2-methylbutyl |

TABLE 1-continued
| Compd. | R5 |
|---|---|
| 76 | 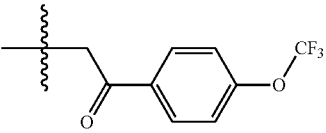 |
| 77 | 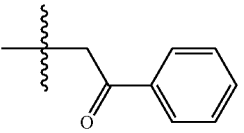 |
| 78 | 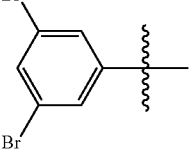 |
| 79 | 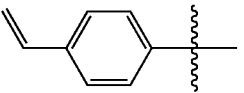 |
| 80 | 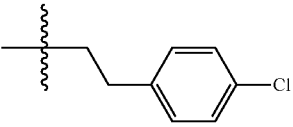 |
| 81 | 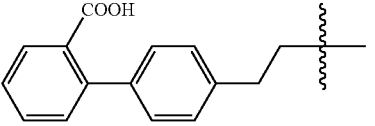 |
| 82 | 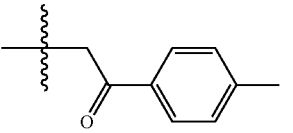 |
| 83 | 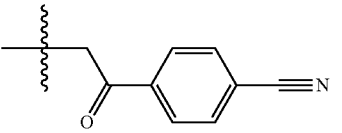 |
| 84 | 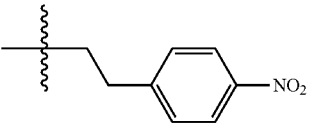 |
| 85 | 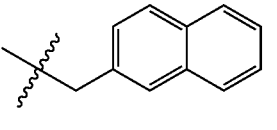 |
| 86 | 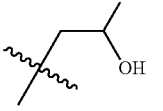 |
| 87 | 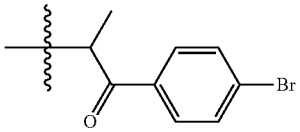 |
| 88 | 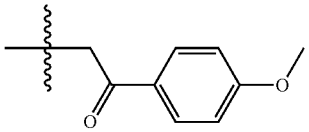 |
| 89 | 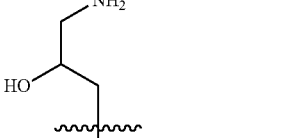 |
| 90 | 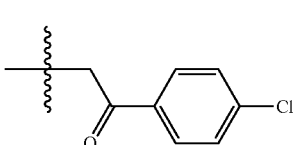 |
| 91 | 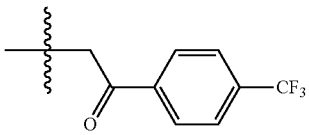 |
| 92 | 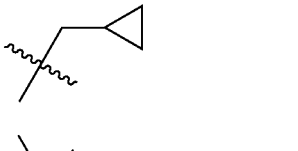 |
| 93 | 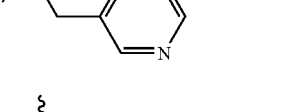 |
| 94 | 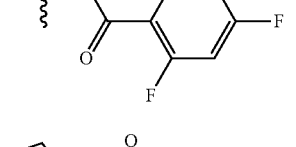 |
| 95 | 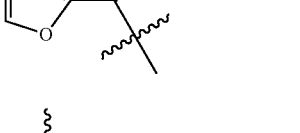 |
| 96 | 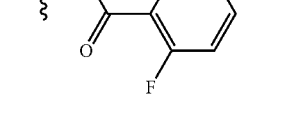 |

TABLE 1-continued
| Compd. | R5 |
|---|---|
| 97 | 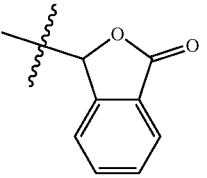 |
| 98 | 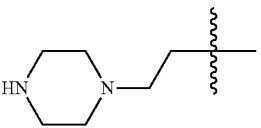 |
| 99 | 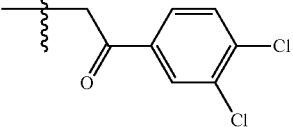 |
| 100 | 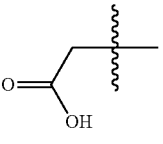 |
| 101 | 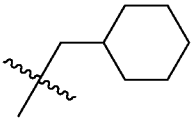 |
| 102 | 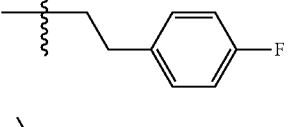 |
| 103 | 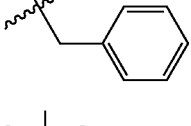 |
| 650 | 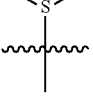 |
| 651 | 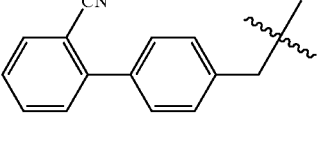 |
| 652 | 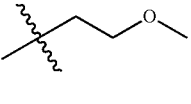 |
| 653 |  |
| 654 | 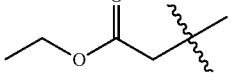 |
| 655 | 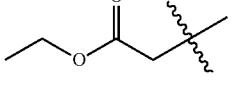 |
| 656 |  |
| 657 | 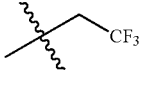 |
| 658 | $C_3H_6N(CH_3)_2$ |
| 659 | 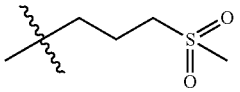 |
| 660 | 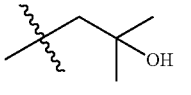 |
| 661 | 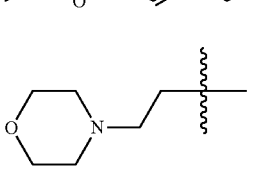 |
| 662 | 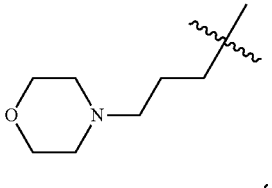 |
| 663 | 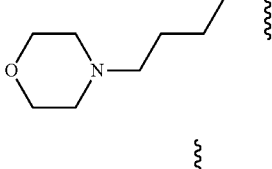 |
| 664 | 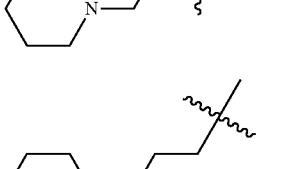 |
| 665 |  |
| 666 | 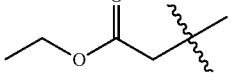 |

TABLE 1-continued
| Compd. | R₅ |
|---|---|
| 667 | 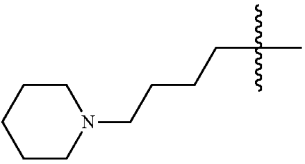 |
| 668 | 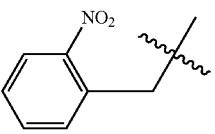 |
| 669 | 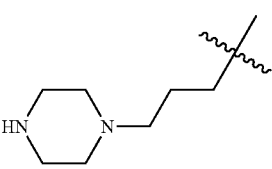 |
| 670 | 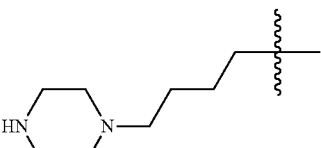 |
| 671 | 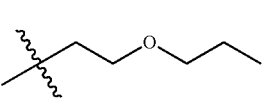 |
| 672 | 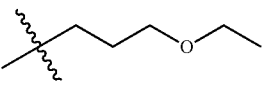 |
| 673 | 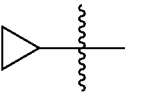 |
| 674 | 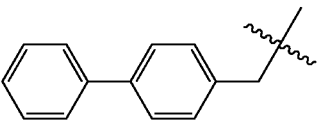 |
$R_1=R_3=R_4=H, R_2=F,$
TABLE 2
| Compd. | R₅ |
|---|---|
| 104 | $C_2H_5$ |
| 105 | $CH_2CH_2CH(CH_3)_2$ |
| 106 | $n\text{-}C_4H_9$ |
| 107 | $CH_2OH$ |
| 108 | $CH(CH_3)_2$ |
| 109 | $H_2CHC\!=\!CH_2$ |
| 110 | $H_2CC\!\equiv\!CH$ |
| 111 | $C_2H_4NH_2$ |
| 112 | $H_2CHC\!=\!C(CH_3)_2$ |
| 113 | $C_3H_6OH$ |
| 114 | $C_2H_4OH$ |
| 115 | $C_2H_4N(CH_3)_2$ |
| 116 | $CH_2NH_2$ |
TABLE 2-continued
| Compd. | R₅ |
|---|---|
| 117 | 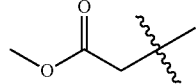 |
| 118 | $C_2H_4N(C_2H_5)_3$ |
| 119 |  |
| 120 | $CH_2N(CH_3)_2$ |
| 121 | 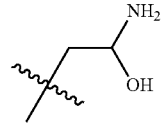 |
| 122 |  |
| 123 | 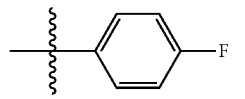 |
| 124 | 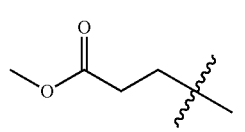 |
| 125 | 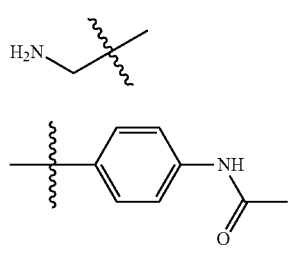 |
| 126 | 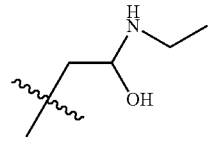 |
| 127 | 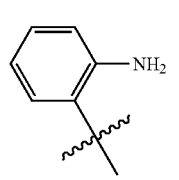 |
| 128 | 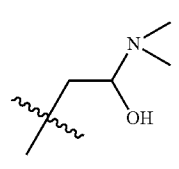 |
| 129 | 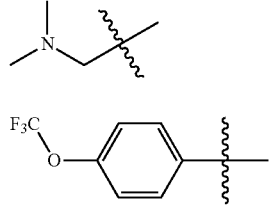 |

TABLE 2-continued

| Compd. | R₅ |
|---|---|
| 130 | 6-hydroxynaphthalen-2-yl-methyl |
| 131 | (4-methoxyphenyl)methyl |
| 132 | 4-hydroxy-3,5-dimethylphenyl |
| 133 | 4-chlorophenyl |
| 134 | 2-fluorophenyl |
| 135 | 2-(4-chlorophenyl)ethyl |
| 136 | 2'-acetyl-[1,1'-biphenyl]-4-yl methyl |
| 137 | 2-(4-methylphenyl)-2-oxoethyl |
| 138 | 2-(4-cyanophenyl)-2-oxoethyl |
| 139 | 2-(4-nitrophenyl)ethyl |
| 140 | (4-vinylphenyl)methyl |
| 141 | 2-phenylethyl |
| 142 | 2-(piperazin-1-yl)ethyl |
| 143 | 2-(4-methoxyphenyl)-2-oxoethyl |
| 144 | 3-amino-2-hydroxypropyl |
| 145 | 2-(4-chlorophenyl)-2-oxoethyl |
| 146 | naphthalen-2-ylmethyl |
| 147 | cyclopropylmethyl |
| 148 | pyridin-3-ylmethyl |
| 149 | 2-(2,4-difluorophenyl)-2-oxoethyl |
| 150 | 2-(furan-2-yl)-2-oxoethyl |

TABLE 2-continued

| Compd. | R₅ |
|---|---|
| 151 | 2-fluorophenyl ketone (–CH₂–C(=O)–C₆H₄–F (ortho)) |
| 152 | 4-(trifluoromethyl)phenyl ketone (–CH₂–C(=O)–C₆H₄–CF₃) |
| 153 | –CH₂–C(=O)–OH (with methyl branch) |
| 154 | –CH₂–cyclohexyl (with methyl branch) |
| 155 | –CH₂–CH₂–C₆H₄–F (para) |
| 156 | H |
| 157 | CH₃ |

$R_1 = R_3 = R_4 = H$, $R_2 = Cl$,

TABLE 3

| Compd. | R₅ |
|---|---|
| 158 | C₂H₅ |
| 159 | CH₂CH₂CH(CH₃)₂ |
| 160 | n-C₄H₉ |
| 161 | CH₂OH |
| 162 | CH(CH₃)₂ |
| 163 | H₂CHC=CH₂ |
| 164 | 2-fluorophenyl |
| 165 | –CH₂–CH₂–C₆H₄–Cl (para) |
| 166 | 2'-acetyl-biphenyl-4-yl-ethyl |

TABLE 3-continued

| Compd. | R₅ |
|---|---|
| 167 | 4-methylphenyl ketone (–CH₂–C(=O)–C₆H₄–CH₃) |
| 168 | 4-cyanophenyl ketone (–CH₂–C(=O)–C₆H₄–C≡N) |
| 169 | –CH₂–CH₂–C₆H₄–NO₂ (para) |
| 170 | 4-vinylphenyl (with methyl branch) |
| 171 | –CH₂–CH(OH)–OH (gem-diol, with methyl branch) |
| 172 | –CH₂–CH₂–N(piperazinyl)–NH (with methyl branch) |
| 173 | 4-methoxyphenyl ketone (–CH₂–C(=O)–C₆H₄–OCH₃) |
| 174 | –CH₂–CH(OH)–CH₂–NH₂ (with methyl branch) |
| 175 | 4-chlorophenyl ketone (–CH₂–C(=O)–C₆H₄–Cl) |
| 176 | 4-(trifluoromethyl)phenyl ketone (–CH₂–C(=O)–C₆H₄–CF₃) |
| 177 | –CH₂–C(=O)–OH (with methyl branch) |

TABLE 3-continued
| Compd. | R$_5$ |
|---|---|
| 178 | 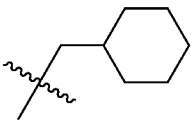 |
| 179 | 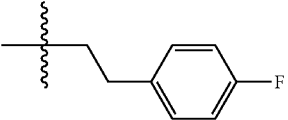 |
| 180 | H |
| 181 | CH$_3$ |
$R_1=R_3=R_4=H$, $R_2=CN$,
TABLE 4
| Compd. | R$_5$ |
|---|---|
| 182 | C$_2$H$_5$ |
| 183 | CH$_2$CH$_2$CH(CH$_3$)$_2$ |
| 184 | n-C$_4$H$_9$ |
| 185 | CH$_2$OH |
| 186 | CH(CH$_3$)$_2$ |
| 187 | H$_2$CHC=CH$_2$ |
| 188 | H$_2$CC≡CH |
| 189 | C$_2$H$_4$NH$_2$ |
| 190 | H$_2$CHC=C(CH$_3$)$_2$ |
| 191 | C$_3$H$_6$OH |
| 192 | C$_2$H$_4$OH |
| 193 | C$_2$H$_4$N(CH$_3$)$_2$ |
| 194 | CH$_2$NH$_2$ |
| 195 | 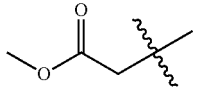 |
| 196 | C$_2$H$_4$N(C$_2$H$_5$)$_3$ |
| 197 | 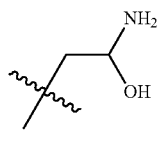 |
| 198 | CH$_2$N(CH$_3$)$_2$ |
| 199 | 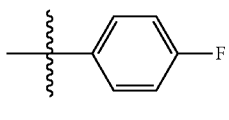 |
| 200 | 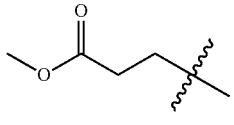 |
| 201 | 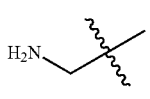 |
TABLE 4-continued
| Compd. | R$_5$ |
|---|---|
| 202 | 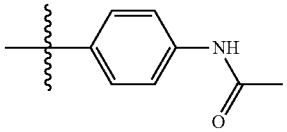 |
| 203 | 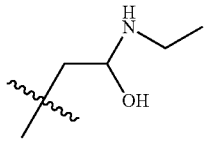 |
| 204 | 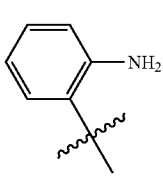 |
| 205 | 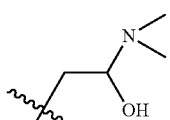 |
| 206 | 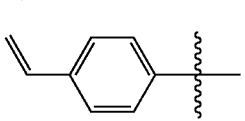 |
| 207 | 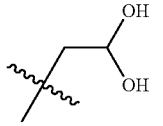 |
| 208 | 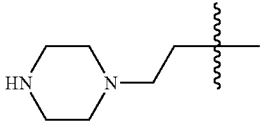 |
| 209 | 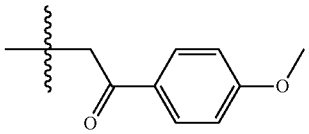 |
| 210 | 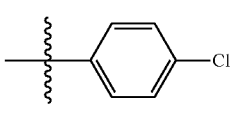 |
| 211 | 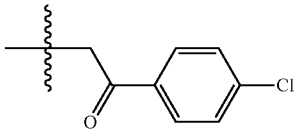 |
| 212 | 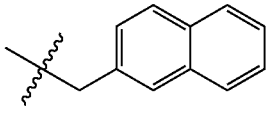 |

TABLE 4-continued
| Compd. | R₅ |
|---|---|
| 213 | 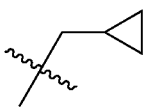 |
| 214 | 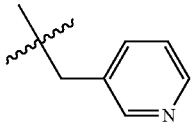 |
| 215 | 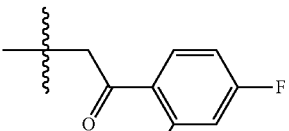 |
| 216 | 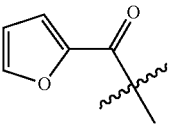 |
| 217 | 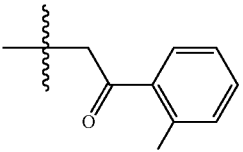 |
| 218 | 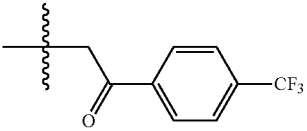 |
| 219 | 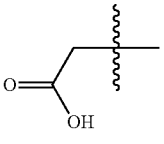 |
| 220 | 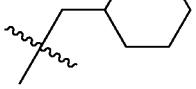 |
| 221 | 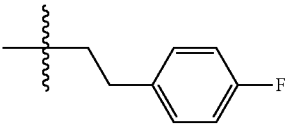 |
| 222 | H |
| 223 | CH₃ |
$R_1=R_3=R_4=H, R_2=Br,$
TABLE 5
| Compd. | R₅ |
|---|---|
| 224 | C₂H₅ |
| 225 | CH₂CH₂CH(CH₃)₂ |
| 226 | n-C₄H₉ |
| 227 | CH₂OH |
| 228 | CH(CH₃)₂ |
| 229 | H₂CHC═CH₂ |
| 230 |  |
| 231 |  |
| 232 | 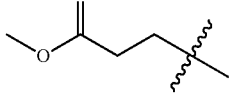 |
| 233 | 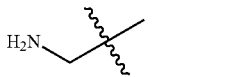 |
| 234 |  |
| 235 | 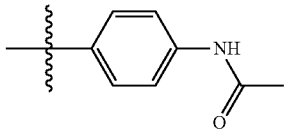 |
| 236 | 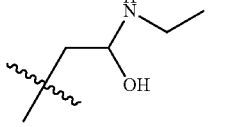 |
| 237 | 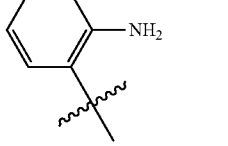 |
| 238 | 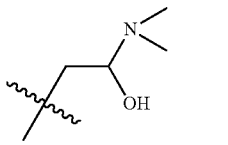 |
| 239 | 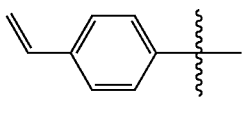 |

TABLE 5-continued

| Compd. | R₅ |
|---|---|
| 240 | (structure: CH₂NH₂-CH(OH)-CH₂-C with wavy bond, methyl) |
| 241 | (structure: -CH₂-C(=O)-C₆H₄-Cl (para)) |
| 242 | (structure: -CH₂-C(=O)-C₆H₄-CF₃ (para)) |
| 243 | (structure: -CH₂-COOH with methyl branch) |
| 244 | (structure: -CH₂-cyclohexyl) |
| 245 | (structure: -CH₂-CH₂-C₆H₄-F (para)) |
| 246 | H |
| 247 | CH₃ |

$R_1=R_3=R_4=H$, $R_2=CF_3$,

TABLE 6

| Compd. | R₅ |
|---|---|
| 248 | H₂CC≡CH |
| 249 | C₂H₄NH₂ |
| 250 | H₂CHC=C(CH₃)₂ |
| 251 | C₃H₆OH |
| 252 | C₂H₄OH |
| 253 | C₂H₄N(CH₃)₂ |
| 254 | CH₂NH₂ |
| 255 | (structure: methyl ester -CH₂-C(=O)-O-CH₃) |
| 256 | C₂H₄N(C₂H₅)₂ |
| 257 | (structure: -CH(OH)-CH₂-NH₂) |

TABLE 6-continued

| Compd. | R₅ |
|---|---|
| 258 | CH₂N(CH₃)₂ |
| 259 | (structure: -C₆H₄-F (para)) |
| 260 | (structure: methyl ester -CH₂CH₂-C(=O)-O-CH₃) |
| 261 | (structure: -C(CH₃)₂-CH₂-NH₂) |
| 262 | (structure: -C₆H₄-NHC(=O)CH₃ (para)) |
| 263 | (structure: -CH(OH)-CH₂-NH-C₂H₅) |
| 264 | (structure: -C₆H₄-NH₂ (ortho)) |
| 265 | (structure: -CH(OH)-CH₂-N(CH₃)₂) |
| 266 | (structure: -C₆H₄-F (ortho)) |
| 267 | (structure: -CH₂-CH₂-C₆H₄-Cl (para)) |
| 268 | (structure: biphenyl with COCH and CH₂CH₂ linker) |
| 269 | (structure: -CH₂-C(=O)-C₆H₄-CH₃ (para)) |

TABLE 6-continued

| Compd. | R₅ |
|---|---|
| 270 | 4-cyanophenyl ketone (–C(O)–C₆H₄–CN) |
| 271 | 4-nitrophenethyl (–CH₂CH₂–C₆H₄–NO₂) |
| 272 | 4-vinylphenyl |
| 273 | –CH₂CH(OH)(OH) |
| 274 | –CH₂CH₂–N(piperazinyl)–NH |
| 275 | –C(O)CH₂–C₆H₄–OCH₃ (4-methoxy) |
| 276 | 4-chlorophenyl |
| 277 | –C(O)CH₂–C₆H₄–Cl (4-chloro) |
| 278 | –C(O)CH₂–C₆H₄–CF₃ (4-CF₃) |
| 279 | –CH₂C(O)OH (with methyl) |
| 280 | –CH₂-cyclohexyl |
| 281 | –CH₂CH₂–C₆H₄–F (4-fluoro) |
| 282 | H |
| 283 | CH₃ |

$R_1=R_3=R_4=H$, $R_2=OCF_3$,

TABLE 7

| Compd. | R₅ |
|---|---|
| 284 | C₂H₅ |
| 285 | CH₂CH₂CH(CH₃)₂ |
| 286 | n-C₄H₉ |
| 287 | CH₂OH |
| 288 | CH(CH₃)₂ |
| 289 | H₂CHC=CH₂ |
| 290 | methyl ester –C(CH₃)(CH₂C(O)OCH₃) |
| 291 | H₂N–CH₂–C(CH₃) |
| 292 | 4-acetamidophenyl (–C₆H₄–NHC(O)CH₃) |
| 293 | –C(CH₃)(CH(OH)–NH–C₂H₅) |
| 294 | 2-aminophenyl |
| 295 | –C(CH₃)(CH(OH)–N(CH₃)₂) |
| 296 | 4-vinylphenyl |
| 297 | –C(CH₃)(CH(OH)(OH)) |

TABLE 7-continued
| Compd. | R5 |
|---|---|
| 298 | 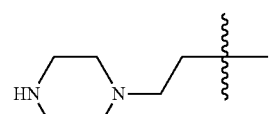 |
| 299 | 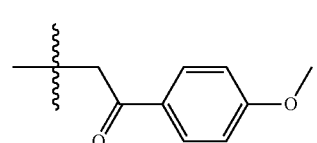 |
| 300 | 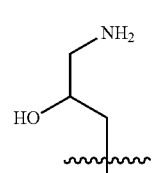 |
| 301 | 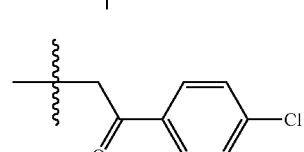 |
| 302 | 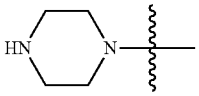 |
| 303 | 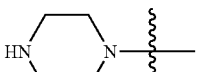 |
| 304 | 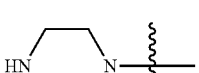 |
| 305 | 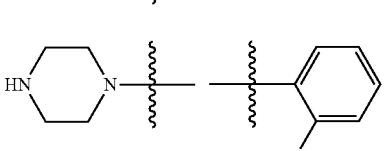 |
| 306 | H |
| 307 | CH$_3$ |
$R_1 = R_4 = H$,
TABLE 8
| Compd. | R$_2$ | R$_3$ | R$_5$ |
|---|---|---|---|
| 308 | H | 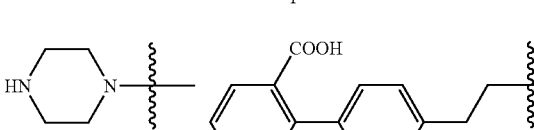 | H$_2$CC≡CH |
| 309 | H | 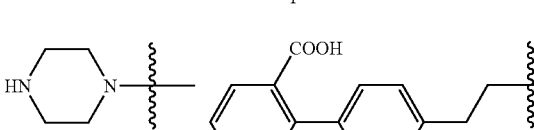 | H$_2$CHC═C(CH$_3$)$_2$ |
| 310 | H | 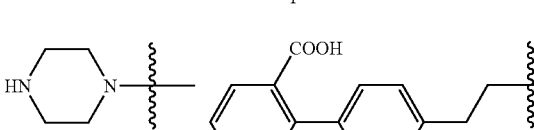 | C$_2$H$_4$OH |
| 311 | H | 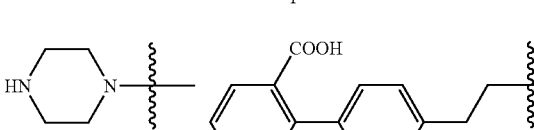 | 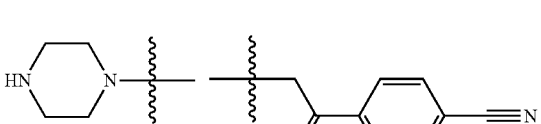 |
| 312 | H | 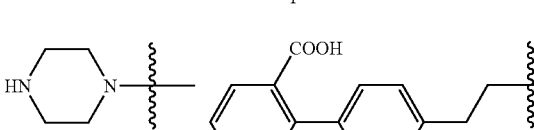 | 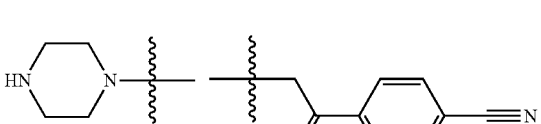 |
| 313 | H | 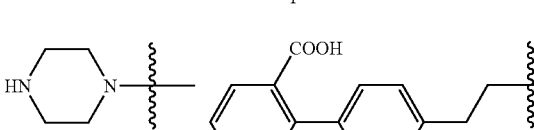 | 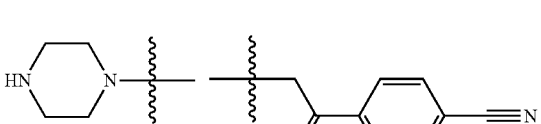 |

TABLE 8-continued

| Compd. | R$_2$ | R$_3$ | R$_5$ |
|---|---|---|---|
| 314 | H | piperazinyl-CH$_2$- | -CH$_2$-(naphthalen-2-yl) |
| 315 | H | piperazinyl-CH$_2$- | -CH$_2$-(pyridin-3-yl) |
| 316 | H | piperazinyl-CH$_2$- | -C(=O)-(furan-2-yl) |
| 317 | H | piperazinyl-CH$_2$- | -CH$_2$-C(=O)-C$_6$H$_4$-4-CF$_3$ |
| 318 | H | piperazinyl-CH$_2$- | -CH$_2$-cyclohexyl |
| 319 | H | piperazinyl-CH$_2$- | H |
| 320 | H | piperazinyl-CH$_2$- | -C$_6$H$_4$-4-OCF$_3$ |
| 321 | H | piperazinyl-CH$_2$- | -C$_6$H$_4$-4-OCH$_3$ |
| 322 | H | piperazinyl-CH$_2$- | -C$_6$H$_4$-4-iPr |
| 323 | H | piperazinyl-CH$_2$- | -CH$_2$-CH(OH)$_2$ |
| 324 | H | piperazinyl-CH$_2$- | -CH$_2$-C(=O)-C$_6$H$_4$-4-OCH$_3$ |
| 325 | H | piperazinyl-CH$_2$- | -CH$_2$-C(=O)-C$_6$H$_4$-4-Cl |

TABLE 8-continued

| Compd. | R₂ | R₃ | R₅ |
|---|---|---|---|
| 326 | H | piperazinyl (HN-piperazine-N–) | –CH(CH₃)–CH₂–C(=O)OH |
| 327 | H | piperazinyl | –CH₂–CH₂–C₆H₄–F (4-F) |
| 328 | H | piperazinyl | CH₃ |
| 329 | F | piperazinyl | C₂H₅ |
| 330 | F | piperazinyl | n-C₄H₉ |
| 331 | F | piperazinyl | CH(CH₃)₂ |
| 332 | F | piperazinyl | CH₂NH₂ |
| 333 | F | piperazinyl | C₂H₄N(C₂H₅)₂ |
| 334 | F | piperazinyl | CH₂N(CH₃)₂ |
| 335 | F | piperazinyl | –CH₂–C₆H₄–F (2-F) |
| 336 | F | piperazinyl | 2-COOH-biphenyl-4'-yl-CH₂CH₂– |
| 337 | F | piperazinyl | –CH₂–C(=O)–C₆H₄–CN (4-CN) |

TABLE 8-continued

| Compd. | R₂ | R₃ | R₅ |
|---|---|---|---|
| 338 | F | piperazinyl | 4-vinylphenyl |
| 339 | F | piperazinyl | 2-(piperazin-1-yl)ethyl |
| 340 | F | piperazinyl | cyclopropyl |
| 341 | F | piperazinyl | naphthalen-2-ylmethyl |
| 342 | F | piperazinyl | pyridin-3-ylmethyl |
| 343 | F | piperazinyl | 1-(furan-2-yl)-1-oxomethyl |
| 344 | F | piperazinyl | 3-oxo-3-(4-(trifluoromethyl)phenyl)propyl |
| 345 | F | piperazinyl | cyclohexylmethyl |
| 346 | F | piperazinyl | H |
| 347 | F | piperazinyl | CH₂CH₂CH(CH₃)₂ |
| 348 | F | piperazinyl | CH₂OH |
| 349 | F | piperazinyl | H₂CHC=CH₂ |
| 350 | F | piperazinyl | C₂H₄NH₂ |

TABLE 8-continued

| Compd. | R₂ | R₃ | R₅ |
|---|---|---|---|
| 351 | F | piperazinyl (HN-piperazine-N-) | $C_3H_6OH$ |
| 352 | F | piperazinyl | $C_2H_4N(CH_3)_2$ |
| 353 | F | piperazinyl | $-CH(CH_3)CH_2C(O)OCH_3$ |
| 354 | F | piperazinyl | $H_2CCH=C(CH_3)_2$ |
| 355 | F | piperazinyl | $-CH(-)-C_6H_4-4-F$ |
| 356 | F | piperazinyl | $-CH(-)CH_2$-cyclopropyl |
| 357 | F | piperazinyl | $-CH(-)CH_2C(O)-C_6H_3-2,4-F_2$ |
| 358 | F | piperazinyl | $-CH(-)CH_2C(O)-C_6H_4-2-F$ |
| 359 | F | piperazinyl | $-C(CH_3)(-)CH_2C(O)OH$ |
| 360 | F | piperazinyl | $-CH(-)CH_2CH_2-C_6H_4-4-F$ |
| 361 | F | piperazinyl | $CH_3$ |
| 362 | Cl | piperazinyl | $C_2H_5$ |

TABLE 8-continued

| Compd. | R₂ | R₃ | R₅ |
|---|---|---|---|
| 363 | Cl | piperazinyl | n-C₄H₉ |
| 364 | Cl | piperazinyl | CH(CH₃)₂ |
| 365 | Cl | piperazinyl | 2-fluorophenyl |
| 366 | Cl | piperazinyl | 2'-carboxybiphenyl-4-ylethyl |
| 367 | Cl | piperazinyl | 3-(4-cyanophenyl)-3-oxopropyl |
| 368 | Cl | piperazinyl | 4-vinylbenzyl |
| 369 | Cl | piperazinyl | 2-(piperazin-1-yl)ethyl |
| 370 | Cl | piperazinyl | 4-amino-3-hydroxybutyl |
| 371 | Cl | piperazinyl | 3-oxo-3-(4-trifluoromethylphenyl)propyl |
| 372 | Cl | piperazinyl | cyclohexylmethyl |
| 373 | Cl | piperazinyl | H |
| 374 | Cl | piperazinyl | 4-(trifluoromethoxy)phenyl |

TABLE 8-continued

| Compd. | R₂ | R₃ | R₅ |
|---|---|---|---|
| 375 | Cl | piperazinyl | 4-methoxyphenyl |
| 376 | Cl | piperazinyl | 4-isopropylphenyl |
| 377 | Cl | piperazinyl | cyclopropylmethyl |
| 378 | Cl | piperazinyl | -CH₂-C(=O)-(2,4-difluorophenyl) |
| 379 | Cl | piperazinyl | -CH₂-C(=O)-(2-fluorophenyl) |
| 380 | Cl | piperazinyl | -CH₂-C(=O)OH |
| 381 | Cl | piperazinyl | -CH₂-CH₂-(4-fluorophenyl) |
| 382 | Cl | piperazinyl | CH₃ |
| 383 | CN | piperazinyl | 2-fluorophenyl |
| 384 | CN | piperazinyl | 2'-carboxy-biphenyl-4-ylethyl |
| 385 | CN | piperazinyl | -CH₂-C(=O)-(4-cyanophenyl) |

TABLE 8-continued

| Compd. | R₂ | R₃ | R₅ |
|---|---|---|---|
| 386 | CN | piperazinyl | cyclopropylmethyl |
| 387 | CN | piperazinyl | -CH₂-C(O)-(2,4-difluorophenyl) |
| 388 | CN | piperazinyl | -CH₂-C(O)-(2-fluorophenyl) |
| 389 | CN | piperazinyl | -C(CH₃)(CH₂C(O)OH)- |
| 390 | CN | piperazinyl | -CH₂-CH₂-(4-fluorophenyl) |
| 391 | CN | piperazinyl | CH₃ |
| 392 | CF₃ | piperazinyl | -(4-vinylphenyl)- |
| 393 | CF₃ | piperazinyl | -CH₂-CH₂-(piperazin-1-yl) |
| 394 | CF₃ | piperazinyl | -CH(CH₃)-CH₂-CH(OH)-CH₂-NH₂ |
| 395 | CF₃ | piperazinyl | -CH₂-C(O)-(4-trifluoromethylphenyl) |
| 396 | CF₃ | piperazinyl | cyclohexylmethyl |

TABLE 8-continued

| Compd. | R₂ | R₃ | R₅ |
|---|---|---|---|
| 397 | CF₃ | 4-piperazinyl (HN-piperazine-N-) | H |
| 398 | CF₃ | 4-piperazinyl | 4-(trifluoromethoxy)phenyl |
| 399 | CF₃ | 4-piperazinyl | 4-methoxyphenyl |
| 400 | CF₃ | 4-piperazinyl | 4-isopropylphenyl |
| 401 | CF₃ | 4-piperazinyl | -CH(CH₂COOH)- |
| 402 | CF₃ | 4-piperazinyl | -CH(CH₂-(4-fluorophenyl))- |
| 403 | CF₃ | 4-piperazinyl | CH₃ |
| 404 | OCF₃ | 4-piperazinyl | 4-vinylphenyl |
| 405 | OCF₃ | 4-piperazinyl | -CH(CH₂-(4-piperazinyl))- |
| 406 | OCF₃ | 4-piperazinyl | -C(CH₃)(CH₂CH(OH)CH₂NH₂)- |
| 407 | OCF₃ | 4-piperazinyl | -CH(CH₂C(O)-(4-trifluoromethylphenyl))- |
| 408 | OCF₃ | 4-piperazinyl | -C(CH₃)(CH₂-cyclohexyl)- |

TABLE 8-continued
| Compd. | R₂ | R₃ | R₅ |
|---|---|---|---|
| 409 | OCF₃ | 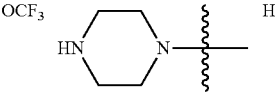 | H |
| 410 | OCF₃ | 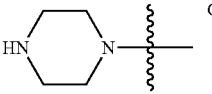 | C₂H₄NH₂ |
| 411 | OCF₃ | 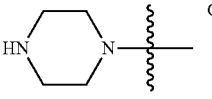 | C₃H₆OH |
| 412 | OCF₃ | 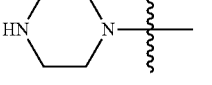 | C₂H₄N(CH₃)₂ |
| 413 | NO₂ | 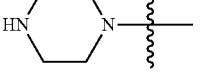 | CH₂NH₂ |
| 414 | NO₂ | 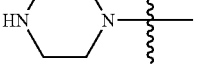 | C₂H₄N(C₂H₅)₂ |
| 415 | NO₂ | 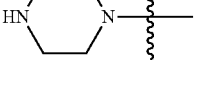 | CH₂N(CH₃)₂ |
| 416 | Br | 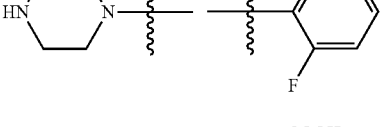 | 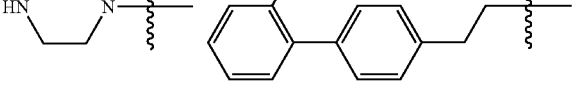 |
| 417 | Br | 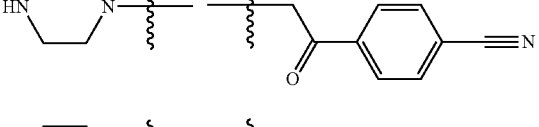 | |
| 418 | Br |  | |
| 419 | Br | 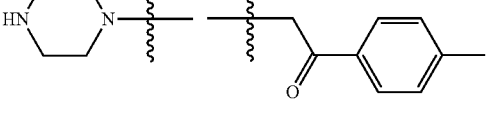 | |
| 420 | Br | | |

TABLE 8-continued
| Compd. | R₂ | R₃ | R₅ |
|---|---|---|---|
| 421 | Br | 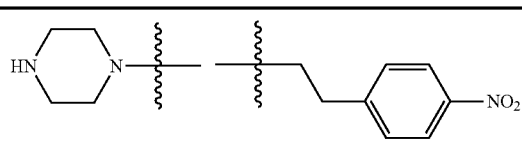 | 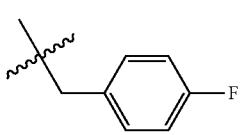 |
| 422 | H | CF₃ | H |
| 423 | H | CF₃ | CH₃ |
| 424 | H | CF₃ | H₂CHC=C(CH₃)₂ |
| 425 | H | CF₃ | 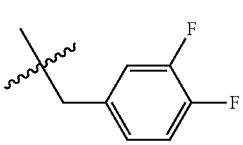 |
| 426 | H | CF₃ | 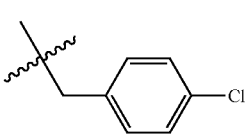 |
| 427 | H | CF₃ | 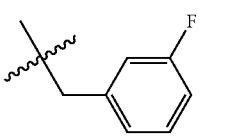 |
| 428 | H | CF₃ | 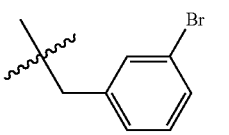 |
| 429 | H | CF₃ | 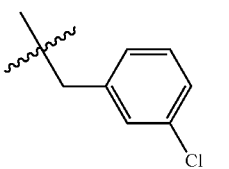 |
| 430 | H | CF₃ | 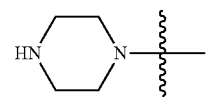 |
R₂=R₃=H,
TABLE 9
| Compd. | R₁ | R₄ | R₅ |
|---|---|---|---|
| 431 | H | 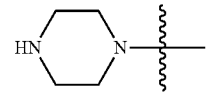 | C₂H₅ |
| 432 | H | 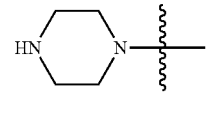 | n-C₄H₉ |
| 433 | H | | CH(CH₃)₂ |

TABLE 9-continued
| Compd. | R₁ | R₄ | R₅ |
|---|---|---|---|
| 434 | H | 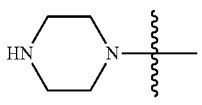 | 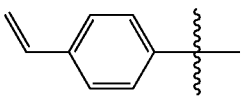 |
| 435 | H | 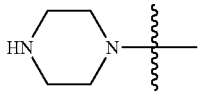 | 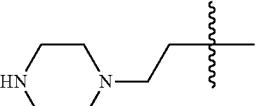 |
| 436 | H | 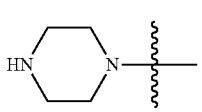 | 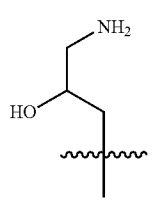 |
| 437 | H | 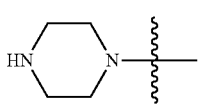 | CH₂CH₂CH(CH₃)₂ |
| 438 | H | 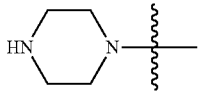 | CH₂OH |
| 439 | H | 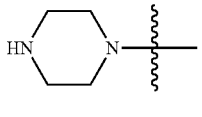 | H₂CHC=CH₂ |
| 440 | H | 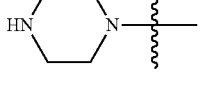 | 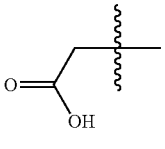 |
| 441 | H | 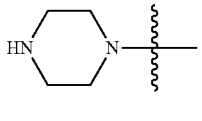 | 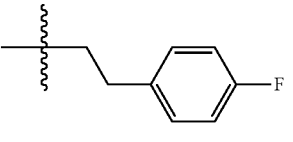 |
| 442 | H | 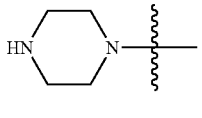 | CH₃ |
| 443 | H | Cl | H |
| 444 | H | F | H |
| 445 | H | OH | H |
| 446 | H | OCH₃ | H |
| 447 | H | CN | H |
| 448 | H | CF₃ | H |
| 449 | H | CN | 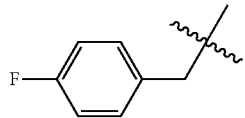 |
| 450 | H | CF₃ | 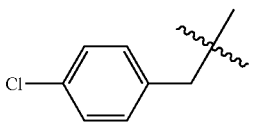 |

TABLE 9-continued
| Compd. | R1 | R4 | R5 |
|---|---|---|---|
| 451 | H | Cl | 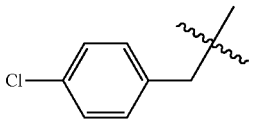 |
| 452 | H | F | 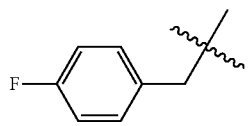 |
| 453 | H | F | 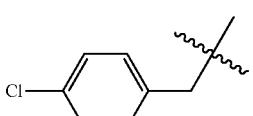 |
| 454 | H | CN | 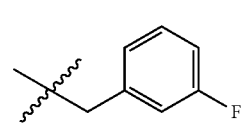 |
| 455 | H | CF3 | 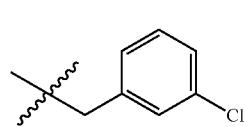 |
| 456 | H | CN | 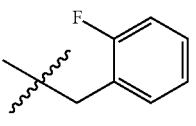 |
| 457 | H | CF3 | 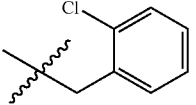 |
| 458 | H | F | 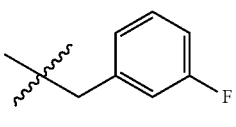 |
| 459 | H | Cl | 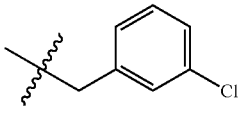 |
| 460 | H | Cl | 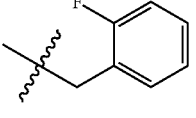 |
| 461 | H | Cl | 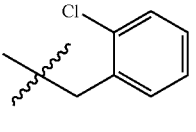 |
| 462 | CN | H | 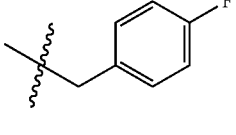 |

TABLE 9-continued
| Compd. | R₁ | R₄ | R₅ |
| --- | --- | --- | --- |
| 463 | CN | H | 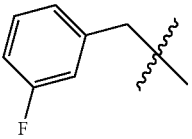 |
| 464 | Cl | H | H |
| 465 | CF₃ | H | 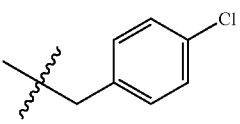 |
| 466 | CF₃ | H | 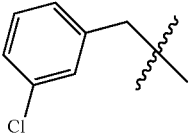 |
| 467 | F | H | H |
| 468 | F | H | 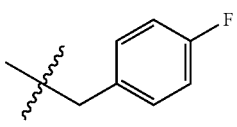 |
| 469 | CN | H | 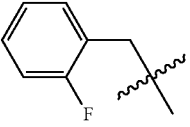 |
| 470 | OH | H | H |
| 471 | F | H | 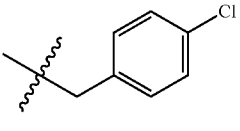 |
| 472 | CF₃ | H | 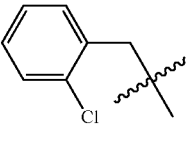 |
| 473 | OCH₃ | H | H |
| 474 | Cl | H | 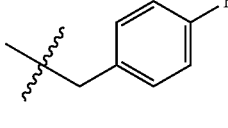 |
| 475 | F | H | 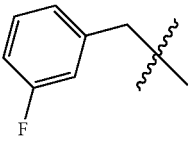 |
| 476 | CN | H | H |
| 477 | Cl | H | 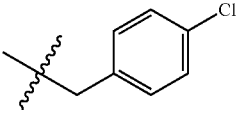 |

TABLE 9-continued

| Compd. | R1 | R4 | R5 |
|---|---|---|---|
| 478 | Cl | H | 3-chlorobenzyl |
| 479 | CF3 | H | H |
| 480 | Cl | H | 2-fluorobenzyl |
| 481 | H | Cl | 4-fluorobenzyl |

$R_1 = R_2 = H$,

| Compd. | R3 | R4 | R5 |
|---|---|---|---|
| 482 | piperazinyl | CN | 4-fluorobenzyl |
| 483 | piperazinyl | CF3 | 4-chlorobenzyl |
| 484 | piperazinyl | F | 4-chlorobenzyl |
| 485 | piperazinyl | F | 4-fluorobenzyl |
| 486 | piperazinyl | CN | 4-fluorobenzyl |
| 487 | piperazinyl | CF3 | 4-chlorobenzyl |

$R_1 = R_2 = R_4 = H, R_3 = F$,

TABLE 11

| Compd. | R5 |
|---|---|
| 488 | H |
| 489 | CH3 |
| 490 | 4-fluorobenzyl |
| 491 | 3-fluorobenzyl |
| 492 | 2-fluorobenzyl |
| 493 | 4-bromobenzyl |
| 494 | C2H5 |
| 495 | 2-bromobenzyl |
| 496 | 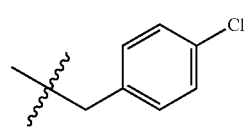 |

TABLE 11-continued

| Compd. | R₅ |
|---|---|
| 497 | 3-chlorobenzyl |
| 498 | 2-chlorobenzyl |
| 499 | 3-bromobenzyl |

$R_1=R_2=R_4=H$, $R_3=Cl$,

TABLE 12

| Compd. | R₅ |
|---|---|
| 500 | H |
| 501 | CH₃ |
| 502 | 4-fluorobenzyl |
| 503 | 3-fluorobenzyl |
| 504 | 2-fluorobenzyl |
| 505 | 4-bromobenzyl |
| 506 | C₂H₅ |
| 507 | 2-bromobenzyl |
| 508 | 4-chlorobenzyl |

TABLE 12-continued

| Compd. | R₅ |
|---|---|
| 509 | 3-chlorobenzyl |
| 510 | 2-chlorobenzyl |
| 511 | 3-bromobenzyl |

$R_1=R_2=R_4=H$, $R_3=CN$,

TABLE 13

| Compd. | R₅ |
|---|---|
| 512 | H |
| 513 | CH₃ |
| 514 | 4-fluorobenzyl |
| 515 | 3-fluorobenzyl |
| 516 | 2-fluorobenzyl |
| 517 | 4-bromobenzyl |
| 518 | C₂H₅ |
| 519 | 2-bromobenzyl |
| 520 | 4-chlorobenzyl |

TABLE 13-continued

| Compd. | R₅ |
|---|---|
| 521 | 3-chlorobenzyl |
| 522 | 2-chlorobenzyl |
| 523 | 3-bromobenzyl |

$R_1=R_2=R_4=H, R_3=OH,$

TABLE 14

| Compd. | R₅ |
|---|---|
| 524 | H |
| 525 | CH₃ |
| 526 | 4-fluorobenzyl |
| 527 | 3-fluorobenzyl |
| 528 | 2-fluorobenzyl |
| 529 | 4-bromobenzyl |
| 530 | C₂H₅ |
| 531 | 2-bromobenzyl |
| 532 | 4-chlorobenzyl |

TABLE 14-continued

| Compd. | R₅ |
|---|---|
| 533 | 3-chlorobenzyl |
| 534 | 2-chlorobenzyl |
| 535 | 3-bromobenzyl |

$R_1=R_2=R_4=H, R_3=CF,$

TABLE 15

| Compd. | R₅ |
|---|---|
| 536 | H |
| 537 | CH₃ |
| 538 | 4-fluorobenzyl |
| 539 | 3-fluorobenzyl |
| 540 | 2-fluorobenzyl |
| 541 | 4-bromobenzyl |
| 542 | C₂H₅ |
| 543 | 2-bromobenzyl |
| 544 | 4-chlorobenzyl |

TABLE 15-continued

| Compd. | R<sub>5</sub> |
|---|---|
| 545 | 3-chlorobenzyl |
| 546 | 2-chlorobenzyl |
| 547 | 3-bromobenzyl |

$R_1=R_2=R_4=H$, $R_3=OCF_3$,

TABLE 16

| Compd. | R$_5$ |
|---|---|
| 548 | H |
| 549 | CH$_3$ |
| 550 | 4-fluorobenzyl |
| 551 | 3-fluorobenzyl |
| 552 | 2-fluorobenzyl |
| 553 | 4-bromobenzyl |
| 554 | C$_2$H$_5$ |
| 555 | 2-bromobenzyl |
| 556 | 4-chlorobenzyl |

TABLE 16-continued

| Compd. | R$_5$ |
|---|---|
| 557 | 3-chlorobenzyl |
| 558 | 2-chlorobenzyl |
| 559 | 3-bromobenzyl |

$R_1=R_2=R_4=H$, $R_3=OCH_3$,

TABLE 17

| Compd. | R$_5$ |
|---|---|
| 560 | H |
| 561 | CH$_3$ |
| 562 | 4-fluorobenzyl |
| 563 | 3-fluorobenzyl |
| 564 | 2-fluorobenzyl |
| 565 | 4-bromobenzyl |
| 566 | C$_2$H$_5$ |
| 567 | 2-bromobenzyl |
| 568 | 4-chlorobenzyl |

TABLE 17-continued

| Compd. | R5 |
|---|---|
| 569 | 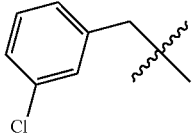 3-Cl-benzyl |
| 570 | 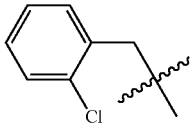 2-Cl-benzyl |
| 571 | 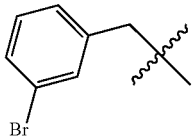 3-Br-benzyl |

$R_4$=H, when $R_5$ is

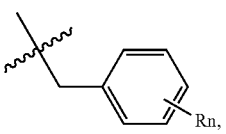

| Compd. | $R_1$ | $R_2$ | $R_3$ | $R_n$ |
|---|---|---|---|---|
| 572 | H | H | H | 2-Cl-4-F |
| 573 | H | H | H | 2,5-2F |
| 574 | H | H | H | 2-CH$_3$ |
| 575 | H | H | H | 4-I |
| 576 | H | H | H | 2-I |
| 577 | H | H | H | 2-CN |
| 578 | H | H | H | 2,4-2F |
| 579 | H | H | H | 3,5-2F |
| 580 | H | H | H | 3,5-2OCH$_3$ |
| 581 | H | H | H | 2-CF$_3$ |
| 582 | H | H | H | 2-F-3-Cl |
| 583 | H | H | H | 3-NO$_2$ |
| 584 | H | H | H | 2,3,4-3F |
| 585 | H | H | H | 2,4,5-3F |
| 586 | H | H | H | 2,3,4,5,6-5F |
| 587 | H | H | H | 2,3,4,5-4F |
| 588 | H | H | H | 4-F |
| 589 | H | H | H | 4-Cl |
| 590 | H | H | H | 4-CN |
| 591 | H | H | H | 4-CF$_3$ |
| 592 | H | H | H | 4-OCF$_3$ |
| 593 | H | H | H | 4-NO$_2$ |
| 594 | H | H | H | 4-Br |
| 595 | H | H | H | 3-F |
| 596 | H | H | H | 3-Cl |
| 597 | H | H | H | 3-CN |
| 598 | H | H | H | 3-CF$_3$ |
| 599 | H | H | H | 2-F |
| 600 | H | H | H | 2-Cl |
| 601 | H | H | H | 3,4-2F |
| 602 | H | H | H | 2-F-4-Cl |
| 603 | H | H | H | 3-Cl-4-F |
| 604 | H | H | H | 4-CH$_3$ |
| 605 | H | H | H | 4-C(CH$_3$)$_3$ |
| 606 | H | H | H | 2-F-4-Br |
| 607 | H | H | H | 3,5-2CF$_3$ |
| 608 | H | H | H | 3-I |
| 609 | H | H | H | 3-CH$_3$ |
| 610 | H | H | H | 3-OCH$_3$ |
| 611 | H | H | H | 2-Cl-5-CF$_3$ |
| 612 | H | H | H | 2-Br |
| 613 | H | H | H | 3,4,-2Cl |
| 614 | H | H | H | 2,6-2Cl |
| 615 | H | H | H | 2,6-2F |
| 616 | H | H | H | 2-CN-5-F |
| 617 | H | F | H | 4-F |
| 618 | H | F | H | 4-Cl |
| 619 | H | F | H | 4-CN |
| 620 | H | F | H | 4-CF$_3$ |
| 621 | H | F | H | 2-F-4-Cl |
| 622 | H | H | piperazinyl | 2,4-2F |
| 623 | H | F | H | 3,5-2CF$_3$ |
| 624 | H | CN | H | 4-F |
| 625 | H | CN | H | 4-Cl |
| 626 | H | CN | H | 4-CN |
| 627 | H | CN | H | 4-CF$_3$ |
| 628 | H | CN | H | 4-phenyl |
| 629 | H | CN | H | 4-(2-cyanobiphenyl) |
| 630 | H | H | piperazinyl | 2,4-2F |
| 631 | H | H | piperazinyl | 3,5-2CF$_3$ |
| 632 | H | F | piperazinyl | 4-Cl |
| 633 | H | F | piperazinyl | 4-Br |
| 634 | H | F | piperazinyl | 4-F |
| 635 | H | F | piperazinyl | 4-CN |
| 636 | H | F | piperazinyl | 4-CF$_3$ |
| 637 | H | F | piperazinyl | 4-phenyl |
| 638 | H | F | piperazinyl | 4-(2-cyanobiphenyl) |
| 639 | H | F | piperazinyl | 3,5-2CF$_3$ |
| 640 | H | CN | piperazinyl | 4-Cl |
| 641 | H | CN | piperazinyl | 4-CN |
| 642 | H | ON | piperazinyl | 4-CF$_3$ |
| 643 | H | CN | piperazinyl | 4-phenyl |
| 644 | H | CN | piperazinyl | 4-(2-cyanobiphenyl) |
| 645 | Cl | H | H | 2-Cl |
| 646 | F | H | piperazinyl | 4-F |
| 647 | F | H | piperazinyl | 4-Cl |
| 648 | H | H | H | 4-(2-cyanobiphenyl) |
| 649 | H | H | H | 4-phenyl |

$R_2$=$R_3$=$R_4$=H, $R_1$=CH$_3$,

TABLE 19

| Compd. | R$_5$ |
|---|---|
| 675 | 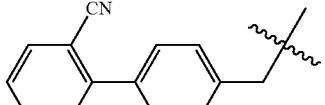 |
| 676 |  |
| 677 | 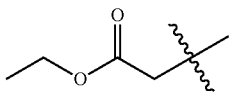 |
| 678 | H |
| 679 | 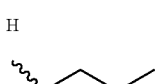 |
| 680 | 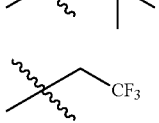 |
| 681 | C$_3$H$_6$N(CH$_3$)$_2$ |

TABLE 19-continued

| Compd. | R₅ |
|---|---|
| 682 | propyl-SO₂-CH₃ |
| 683 | -C(CH₃)₂-OH (2-methyl-2-hydroxypropyl) |
| 684 | morpholine-N-CH₂CH₂-C(CH₃)- |
| 685 | -CH₂CH₂-O-CH₂CH₂CH₃ |
| 686 | morpholine-N-(CH₂)₃-C(CH₃)- |
| 687 | -CH₂CH₂-O-CH₂CH₂CH₃ |
| 688 | piperidine-N-CH₂CH₂-C(CH₃)- |
| 689 | Rn-phenyl-CH₂- |
| 690 | piperazine-N-CH₂CH₂-C(CH₃)- |
| 691 | CH₃-SO₂- |

R₁=R₃=R₄=H, R₂=CH₃,

TABLE 20

| Compd. | R₅ |
|---|---|
| 692 | 2-cyano-biphenyl-4-CH₂- |
| 693 | -CH₂CH₂-O-CH₃ |
| 694 | -CH₂CH₂CH₂-F |
| 695 | ethyl-O-C(=O)-CH₂CH₂- |
| 696 | H |
| 697 | -C(CH₃)₃ (neopentyl) |
| 698 | -CH₂-CF₃ |
| 699 | C₃H₆N(CH₃)₂ |
| 700 | propyl-SO₂-CH₃ |
| 701 | -C(CH₃)₂-OH |
| 702 | morpholine-N-CH₂CH₂-C(CH₃)- |
| 703 | -CH₂CH₂-O-CH₂CH₂CH₃ |
| 704 | morpholine-N-(CH₂)₃- |
| 705 | -CH₂CH₂-O-CH₂CH₂CH₃ |
| 706 | piperidine-N-CH₂CH₂-C(CH₃)- |
| 707 | Rn-phenyl-CH₂- |

TABLE 20-continued
| Compd. | R₅ |
|---|---|
| 708 |  |
| 709 |  |
$R_1=R_2=R_4=H$, $R_3=CH_3$,
TABLE 21
| Compd. | R₅ |
|---|---|
| 710 | 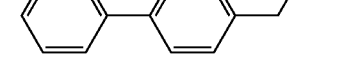 |
| 711 |  |
| 712 |  |
| 713 | 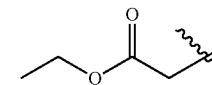 |
| 714 | H |
| 715 | 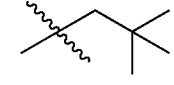 |
| 716 |  |
| 717 | C₃H₆N(CH₃)₂ |
| 718 | 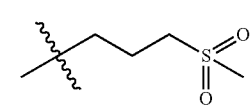 |
| 719 |  |
| 720 | 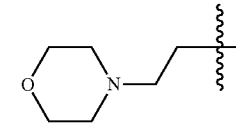 |
| 721 | 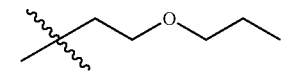 |
TABLE 21-continued
| Compd. | R₅ |
|---|---|
| 722 | 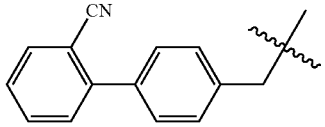 |
| 723 | 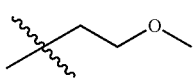 |
| 724 |  |
| 725 | 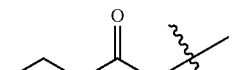 |
| 726 |  |
| 727 | |
$R_1=R_2=R_3=H$, $R_4=CH_3$,
TABLE 22
| Compd. | R₅ |
|---|---|
| 728 | |
| 729 | |
| 730 | |
| 731 | |
| 732 | H |
| 733 | |

TABLE 22-continued
| Compd. | R5 |
|---|---|
| 734 |  |
| 735 | C3H6N(CH3)2 |
| 736 | 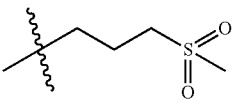 |
| 737 |  |
| 738 | 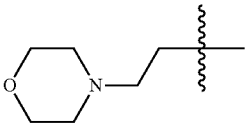 |
| 739 | 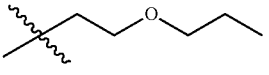 |
| 740 | 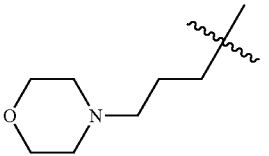 |
| 741 | 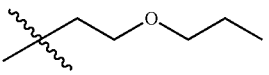 |
| 742 | 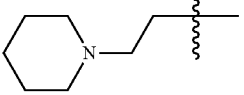 |
| 743 | 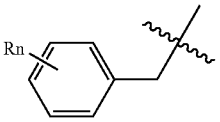 |
| 744 | 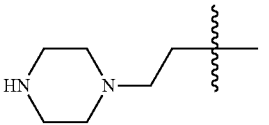 |
TABLE 22-continued
| Compd. | R5 |
|---|---|
| 745 | 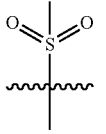 |
$R_1=R_3=H, R_4=R_2=CH_3,$
TABLE 23
| Compd. | R5 |
|---|---|
| 746 | 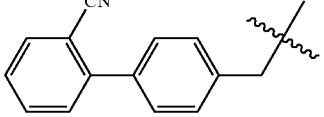 |
| 747 | 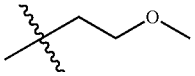 |
| 748 | 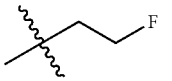 |
| 749 | 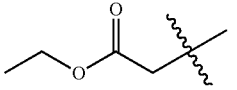 |
| 750 | H |
| 751 | 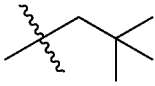 |
$R_1=R_4=H, R_3=R_2=CH_3,$
TABLE 24
| Compd. | R5 |
|---|---|
| 752 |  |
| 753 | C3H6N(CH3)2 |
| 754 | 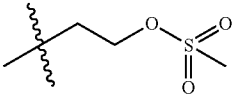 |
| 755 | 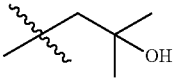 |
| 756 | H |
| 757 | 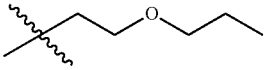 |

TABLE 24-continued

| Compd. | R$_5$ |
|---|---|
| 758 |  |
| 759 |  |
| 760 |  |
| 761 |  |
| 762 |  |
| 763 |  |

$R_1=R_3=CH_3, R_4=R_2=H,$

TABLE 25

| Compd. | R$_5$ |
|---|---|
| 764 |  |
| 765 | $C_3H_6N(CH_3)_2$ |
| 766 |  |
| 767 |  |
| 768 | H |

TABLE 25-continued

| Compd. | R$_5$ |
|---|---|
| 769 | 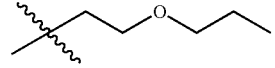 |

$R_1=R_4=CH_3, R_3=R_2=H,$

TABLE 26

| Compd. | R$_5$ |
|---|---|
| 770 |  |
| 771 | 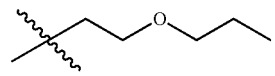 |
| 772 | H |
| 773 | 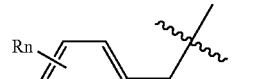 |
| 774 | 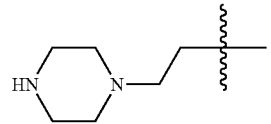 |
| 775 |  |

In some embodiments, the pharmaceutically acceptable salt is selected from the group consisting of hydrochloride, sulfate, phosphate, oxalate, maleate, methanesulfonate, succinate, citrate, fumarate, glucuronide, formate, and acetate; wherein the solvate of the salt of the compound is selected from the group consisting of monohydrate, dihydrate, trihydrate, monomethanol, dimethanol, monoacetonitrile, diacetonitrile, monoacetone, diacetone, hemi-fumarate monohydrate, fumarate dihydrate, and fumarate monoethanol.

In some embodiments, the compound, the tautomer, the stereoisomer, the racemate, the nonequal mixture of enantiomers, the geometric isomer, the solvate, the pharmaceutically acceptable salt thereof, or the solvate of the salt of the compound possesses immunomodulatory activity, anti-inflammatory activity, or anti-fibrotic activity.

In some embodiments, the compound, the tautomer, the stereoisomer, the racemate, the nonequal mixture of enantiomers, the geometric isomer, the solvate, the pharmaceutically acceptable salt thereof, or the solvate of the salt of the compound possesses inhibitory activity against NF-κB.

Embodiments of the present disclosure provide a pharmaceutical composition comprising the compound, or the tautomer, or the stereoisomer, or the racemate, or the nonequal mixture of enantiomers, or the geometric isomer, or the solvate, or the pharmaceutically acceptable salt, or the solvate of the salt of the compound and a pharmaceutically acceptable carrier, diluent, excipient, adjuvant, vehicle or a combination thereof.

In some embodiments, the pharmaceutical composition further comprises at least one drug having immunomodulatory activity, anti-inflammatory activity or anti-fibrosis activity, comprising azathioprine, cyclophosphamide, prednisone, prednisolone, aspirin, acetaminophen, indomethacin, naproxen, nabumetone, diclofenac, ibuprofen, nimesulide, rofecoxib, celecoxib, levamisole, interleukin, interferon, transfer factor, thymosin, anti-lymphocyte globulin, cyclosporine, mycophenolate mofetil.

In some embodiments, the pharmaceutical composition possesses immunomodulatory activity, anti-inflammatory activity, or anti-fibrotic activity.

In some embodiments, the pharmaceutical composition possesses inhibitory activity against NF-κB.

Embodiments of the present disclosure provide a method of preventing, treating or ameliorating a variety of diseases caused by inflammation, disorders of the immune system, etc., comprising administering to a patient therapeutically effective amount of the compound, or the tautomer, or the stereoisomer, or the racemate, or the nonequal mixture of enantiomers, or the geometric isomer, or the solvate, or the pharmaceutically acceptable salt, or the solvate of the salt of the compound or the pharmaceutical composition of the present disclosure.

In some embodiments, the disease is caused by inflammation, immune system disorders, and the like, wherein the disease is selected from the group consisting of renal interstitial fibrosis, glomerulosclerosis, liver fibrosis, pulmonary fibrosis, peritoneum fibrosis, myocardial fibrosis, dermatofibrosis, post-surgery adhesions, benign prostatic hypertrophy, skeletal muscle fibrosis, dermatosclerosis, multiple sclerosis, pancreatic fibrosis, liver cirrhosis, myosarcoma, neurofibroma, pulmonary interstitial fibrosis, diabetic nephropathy, alzheimer disease, vascular fibrosis, serous inflammation, fibrinitis, suppurative inflammation, hemorrhagic inflammation, necrotizing inflammation, catarrhal inflammation, tuberculosis, syphilis, leprosy, lymphogranuloma, allergies, rheumatoid arthritis, rheumatoid heart disease, AIDS, delayed-type immune disease, cytotoxic immune disease, and neurodegenerative diseases.

In some embodiments, the disease is organ or tissue fibrosis.

In some embodiments, the disease is an immune disorder disease caused by activating NF-κB reactive gene.

In some embodiments, the disease is an immune disorder disease caused by activating NF-κB reactive gene by factors comprising tumor necrosis factor-α (TNF-α), interleukin-β, lipopolysaccharide (LPS), oxidant, radiation, ultraviolet light, virus or metabolites thereof.

The present disclosure also provides a method for preparation of the compounds of the present application, which follows the synthetic schemes below:

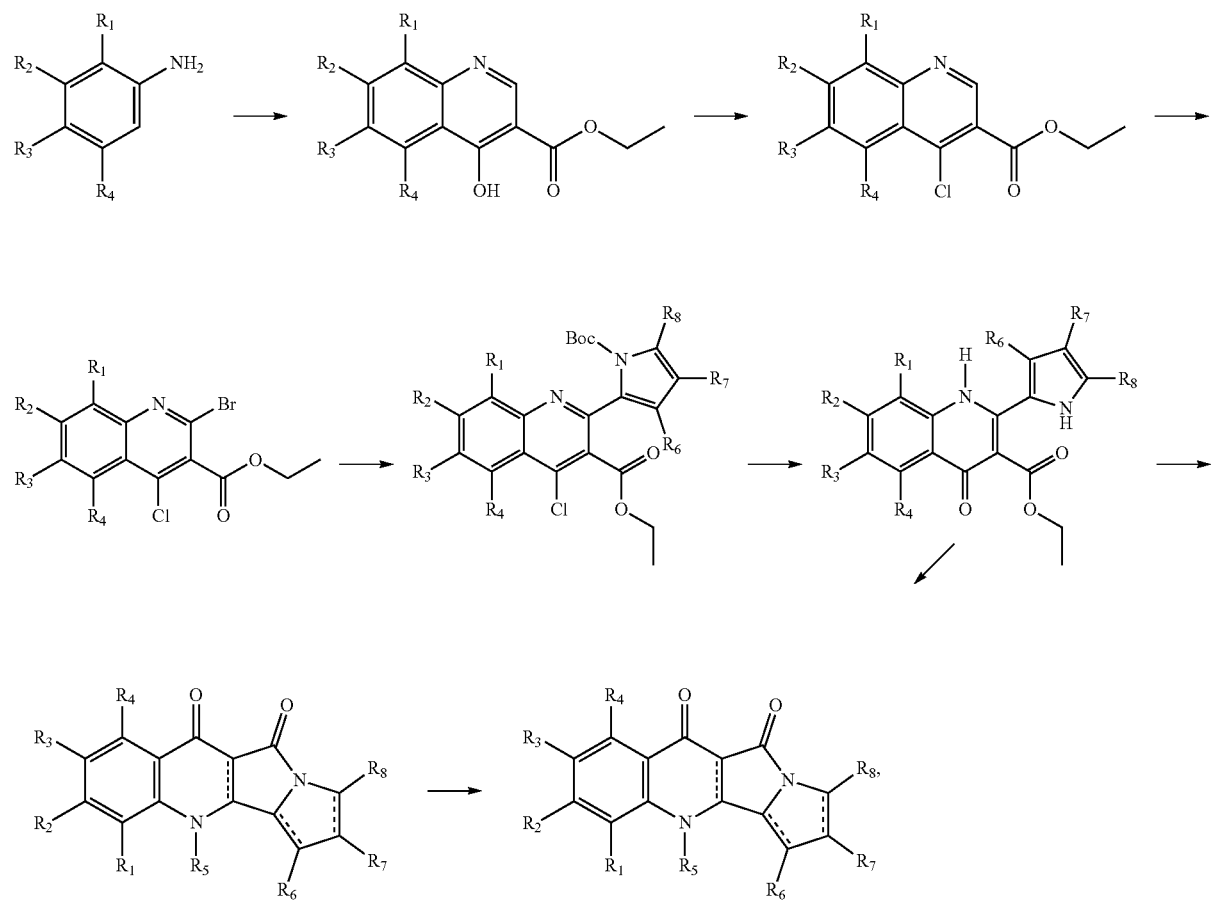

I

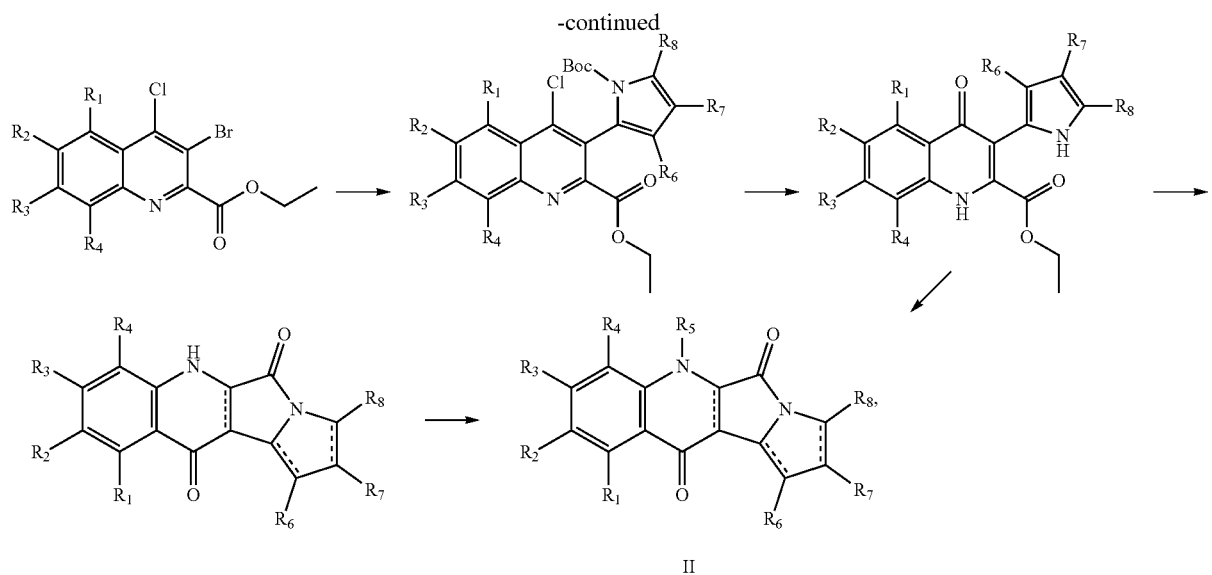

wherein $R_1$, $R_2$, $R_3$, $R_4$, $R_5$, $R_6$, $R_7$, $R_8$, and "- - -" have the abovementioned definition.

The foregoing description merely summarizes certain aspects of the disclosure, but is not limited to these aspects. These and other aspects will be described in more detail below.

Definitions and General Terms

Reference will be made in detail corresponding to certain embodiments disclosed herein, examples of which are illustrated by the accompanying structures and formulas. The disclosure is intended to cover all alternatives, modifications, and equivalents that may be included within the scope disclosed herein as defined by the claims. One skilled in the art will recognize many methods and materials similar or equivalent to those described herein, which could be used in the practice disclosed herein. Described herein is in no way limited to the methods and materials. In the event that one or more of the incorporated literature, patents, and similar materials differ from or contradict this application, including but not limited to the term definition, term usage, described techniques, or like the scope the present application controls.

As used herein, the following definitions shall be used unless otherwise indicated. For purposes disclosed herein, the chemical elements are identified in accordance with the Periodic Table of the Elements, CAS version, and the *Handbook of Chemistry and Physics*, 75h Ed. 1994. Additionally, general principles of organic chemistry are described in Sorrell et al., "*Organic Chemistry*", University Science Books, Sausalito: 1999, and Smith et al., "*March's Advanced Organic Chemistry*", John Wiley & Sons, Inc., New York: 2007, all of which are incorporated herein by reference in their entireties.

As described herein, compounds may be optionally substituted with one or more substituents, such as those illustrated above, or as exemplified by particular classes, subclasses, and species disclosed herein. It will be appreciated that the term "optionally substituted" is used interchangeably with the term "substituted or unsubstituted". In general, the term "substituted" whether preceded by the term "optionally" or not, refers to the replacement of one or more hydrogen radicals in a given structure with the radical of a specified substituent. Unless otherwise indicated, an optionally substituted group may have a substituent at each substitutable position of the group. When more than one position in a given structure may be substituted with more than one substituent selected from a specified group, the substituent may be either the same or different at each position. Wherein the substituents comprise, but are not limited to, hydroxyl, amino, halo, cyano, aryl, heteroaryl, alkoxy, alkylamino, alkylthio, alkyl, haloalkyl, alkenyl, alkynyl, heterocyclyl, thiol, nitro, aryloxy, heteroaryloxy, oxo (O=), carboxy, hydroxyl-substituted alkoxy, hydroxyl-substituted alkyl-C(=O)—, alkyl-C(=O)—, alkyl-S(=O)—, alkyl-S(=O)—, hydroxy-substituted alkyl-S(=O)—, hydroxy-substituted alkyl-S(=O)$_2$—, carboxyalkoxy, and the like.

The term "aliphatic" or "aliphatic group" refers to a straight-chain (i.e., unbranched) or branched, substituted or unsubstituted hydrocarbon chain that is completely saturated or that contains one or more units of unsaturation. Unless otherwise specified, aliphatic groups contain 1-20 carbon atoms. In some embodiments, aliphatic groups contain 1-10 carbon atoms. In other embodiments, aliphatic groups contain 1-8 carbon atoms. In still other embodiments, aliphatic groups contain 1-6 carbon atoms. In yet other embodiments, aliphatic groups contain 1-4 carbon atoms and in yet other embodiments, aliphatic groups contain 1-3 carbon atoms. Suitable aliphatic groups comprise, but are not limited to, linear or branched, substituted or unsubstituted alkyl, alkenyl, or alkynyl groups, such as methyl, ethyl, propyl, isopropyl, butyl, tert-butyl, hexyl, isobutyl, sec-butyl, vinyl, and the like.

The term "haloaliphatic" refers to an aliphatic group substituted by one or more of the same or different halogen atoms, wherein the aliphatic group is as defined herein, halogen atoms refer to F, Cl, Br or I. Some non-limiting examples comprise trifluoromethyl, trifluoroethyl, chloromethyl, 2-chloroethylene, and the like.

The term "hydroxyaliphatic" refers to an aliphatic group substituted by one or more hydroxy groups, wherein the aliphatic group is as defined herein. Some non-limiting examples comprise hydroxyethyl, 2-hydroxypropyl, hydroxymethyl, and the like.

The term "aminoaliphatic" refers to an aliphatic group substituted by one or more amino groups, wherein the aliphatic group is as defined herein. Some non-limiting examples comprise aminomethyl, 2-aminoethyl, 2-aminoisopropyl, and the like.

The term "alkyl" refers to a saturated linear or branched-chain monovalent hydrocarbon radical of 1-20 carbon atoms, 1-10 carbon atoms, 1-6 carbon atoms, 1-4 carbon atoms, or 1-3 carbon atoms, wherein the alkyl radical may be optionally substituted independently with one or more substituents described below. Further examples of alkyl groups comprise, but are not limited to, methyl (Me, —CH$_3$), ethyl (Et, —CH$_2$CH$_3$), 1-propyl (n-Pr, n-propyl, —CH$_2$CH$_2$CH$_3$), 2-propyl (i-Pr, i-propyl, —CH(CH$_3$)$_2$), 1-butyl (n-Bu, n-butyl, —CH$_2$CH$_2$CH$_2$CH$_3$), 2-methyl-1-propyl (i-Bu, i-butyl, —CH$_2$CH(CH$_3$)$_2$), 2-butyl (s-Bu, s-butyl, —CH(CH$_3$)CH$_2$CH$_3$), 2-methyl-2-propyl (t-Bu, t-butyl, —C(CH$_3$)$_3$, 1-pentyl (n-pentyl, —CH$_2$CH$_2$CH$_2$CH$_2$CH$_3$), 2-pentyl (—CH(CH$_3$)CH$_2$CH$_2$CH$_3$), 3-pentyl (—CH(CH$_2$CH$_3$)$_2$, 2-methyl-2-butyl (—C(CH$_3$)$_2$CH$_2$CH$_3$), 3-methyl-2-butyl (—CH(CH$_3$)CH(CH$_3$)$_2$), 3-methyl-1-butyl (—CH$_2$CH$_2$CH(CH$_3$)$_2$), 2-methyl-1-butyl (—CH$_2$CH(CH$_3$)CH$_2$CH$_3$), 1-hexyl (—CH$_2$CH$_2$CH$_2$CH$_2$CH$_2$CH$_3$), 2-hexyl (—CH(CH$_3$)CH$_2$CH$_2$CH$_2$CH$_3$), 3-hexyl (—CH(CH$_2$CH$_3$)(CH$_2$CH$_2$CH$_3$)), 2-methyl-2-pentyl (—C(CH$_3$)$_2$CH$_2$CH$_2$CH$_3$), 3-methyl-2-pentyl (—CH(CH$_3$)CH(CH$_3$)CH$_2$CH$_3$), 4-methyl-2-pentyl (—CH(CH$_3$)CH$_2$CH(CH$_3$)$_2$), 3-methyl-3-pentyl (—C(CH$_3$)(CH$_2$CH$_3$)$_2$), 2-methyl-3-pentyl (—CH(CH$_2$CH$_3$)CH(CH$_3$)$_2$). 2,3-dimety-2-butyl (—C(CH$_3$)$_2$CH(CH$_3$)$_2$), 3,3-dimethyl-2-buty (—CH(CH$_3$)C(CH$_3$)$_3$, 1-heptyl, 1-octyl, and the like. The terms "alkyl" and the prefix "alk-" are inclusive of both straight chain and branched saturated carbon chain.

The term "alkenyl" refers to a linear or branched-chain monovalent hydrocarbon radical of 2-12 carbon atoms, 2-8 carbon atoms, 2-6 carbon atoms, or 2-4 carbon atoms, with at least one site of unsaturation, i.e., a carbon-carbon, sp$^2$ double bond, wherein the alkenyl radical may be optionally substituted independently with one or more substituents described herein, and comprises radicals having "cis" and "rans" orientations, or alternatively, "E" and "Z" orientations. Some non-limiting examples comprise ethenyl or vinyl (—CH=CH$_2$), allyl (—CH$_2$CH=CH$_2$), and the like.

The term "alkynyl" refers to a linear or branched-chain monovalent hydrocarbon radical of 2-12 carbon atoms, 2-8 carbon atoms, 2-6 carbon atoms, or 2-4 carbon atoms, with at least one site of unsaturation, i.e., a carbon-carbon, sp triple bond, wherein the alkynyl radical may be optionally substituted independently with one or more substituents described herein. Some non-limiting examples comprise ethynyl(-C≡CH), 2-propynyl (—CH$_2$C≡CH), and the like.

The term "hydroxy-substituted alkyl" refers to an alkyl group substituted with one or more hydroxy groups, wherein the alkyl group is as defined herein. Some non-limiting examples comprise hydroxymethyl, hydroxyethyl, 1,2-dihydroxyethyl, and the like.

The term "carbocycle", "carbocyclyl", "cycloalkyl" refers to a monovalent or multivalent, non-aromatic, saturated or partially unsaturated ring, and not containing heteroatoms, having 3 to 12 carbon atoms as a monocyclic ring or 7 to 12 carbon atoms as a bicyclic ring or a tricyclic ring. Bicyclic carbocycles having 7 to 12 atoms can be arranged, for example, as a bicyclo [4,5], [5,5], [5,6] or [6,6] system, and bicyclic carbocycles having 9 or 10 ring atoms can be arranged as a bicyclo [5,6] or [6,6] system. Some non-limiting examples of cycloaliphatic groups comprise cycloalkyl, cycloalkenyl, and cycloalkynyl. Further examples of cycloaliphatic groups comprise cyclopropyl, cyclobutyl, cyclopentyl, 1-cyclopent-enyl, 1-cyclopent-2-enyl, 1-cyclopent-3-enyl, cyclohexyl, 1-cyclohex-1-enyl, 1-cyclohex-2-enyl, 1-cyclohex-3-enyl, cyclohexadienyl, cycloheptyl, cyclooctyl, cyclononyl, cyclodecyl, cycloundecyl, cyclododecyl, adamantly, and the like. The "cycloaliphatic", "carbocycle", "carbocyclyl", or "cycloalkyl" may be substituted or unsubstituted, wherein the substituent may be, but is not limited to, hydroxy, amino, halo, cyano, aryl, heteroaryl, alkoxy, alkylamino, alkyl, haloalkyl, alkenyl, alkynyl, heterocyclyl, thiol, nitro, arloxy, hydroxy-substituted alkoxy, hydroxy-substituted —C(=O)—, alkyl-C(=O)—, alkyl-S(=O)—, alkyl-S(=O)$_2$—, hydroxy-substituted alkyl-S(=O)—, hydroxy-substituted alkyl-S(=O)$_2$—, carboxyalkoxy, and the like.

The term "cycloalkyloxy" or "carbocyclyloxy" refers to an optionally substituted cycloalkyl radical or carbocyclyl radical, as defined herein, attached to an oxygen atom, which is connected to the rest of the molecule. Some non-limiting examples comprise cyclopropyloxy, cyclopentyloxy, cyclohexyloxy, hydroxy-substituted cyclopropyloxy, and the like.

The term "cycloalkylamino" refers to an amino group substituted with one or two cycloalkyl groups, wherein the cycloalkyl group is as defined herein. Some non-limiting examples comprise cyclopropylamino, cyclopentylamino, cyclohexylamino, hydroxy-substituted cyclopropylamino, dicyclohexylamino, dicyclopropylamino, and the like.

The term "cycloalkyloxyaliphatic" refers to an aliphatic group substituted with one or more cycloalkyloxy groups, wherein the aliphatic group and cycloalkyloxy group are as defined herein. Some non-limiting examples comprise cyclopropyloxymethyl, cyclopropyloxyethyl, cyclopentyloxymethyl, cyclopentyloxyethyl, cyclohexyloxyethyl, halocyclopropyloxyethyl, and the like.

The term "cycloalkylaminoaliphatic" refers to an aliphatic group substituted with one or more cycloalkylamino groups, wherein the aliphatic group and cycloalkylamino group are as defined herein. Some non-limiting examples comprise cyclopropylaminomethyl, cyclopropylaminethyl, cyclopentylaminomethyl, cyclopentylaminoethyl, cyclohexylaminoethyl, halocyclopropylaminoethyl, and the like.

The term "cycloalkylaliphatic" or "carbocyclylaliphatic" refers to an aliphatic group substituted with one or more cycloalkyl groups or carbocyclyl groups, wherein the carbocyclyl, cycloalkyl group and aliphatic group are as defined herein. Some non-limiting examples comprise cyclopropylmethyl, cyclopropylethyl, cyclopropylpropyl, The term "heterocycle", "heterocyclyl", "heterocycloaliphatic" or "heterocyclic" as used interchangeably herein refers to a monocyclic, bicyclic, or tricyclic ring system in which one or more ring members are an independently selected heteroatom and that is completely saturated or that contains one or more units of unsaturation, but not aromatic having a single point of attachment to the rest of the molecule. One or more ring atoms are optionally substituted independently with one or more substituents described herein. In some embodiments, the "heterocycle", "heterocyclyl", "heterocycloaliphatic" or "heterocyclic" group is a monocycle having 3 to 7 ring members (e.g., 1 to 6 carbon atoms and 1 to 3 heteroatoms selected from N, O, P or S, wherein the S or P is optionally substituted with one or more oxo to provide the group SO or SO$_2$, PO or PO$_2$, with the proviso that when the ring is a 3-membered ring, there is only one heteroatom) or a bicycle having 7 to 10 ring members (e.g., 4 to 9 carbon atoms and 1 to 3 heteroatoms selected from N, O, P or S, wherein the S or P is optionally substituted with one or more oxo to provide the group SO or SO$_2$, PO or PO$_2$).

The heterocyclyl may be a carbon radical or heteroatom radical. "Hetetocyclyl" also comprises radicals where heterocycle radicals are fused with a saturated, partially unsaturated ring, or heterocyclic ring. Some non-limiting examples of heterocyclic rings comprise pyrrolidinyl, tetrahydrofuranyl, dihydrofuranyl, tetrahydrothienyl, tetrahydropyranyl, dihydropyranyl, tetrahydrothiopyranyl, piperidino, morpholino, thiomorpholino, thioxanyl, piperazinyl, homopiperazinyl, azetidinyl, oxetanyl, thietanyl, piperidino, homopiperidinyl, epoxypropyl, azepanyl, oxepanyl, thiepanyl, 4-methoxy-piperidin-1-yl, 1,2,3,6-tetrahydropyridin-1-yl, oxazepinyl, diazepinyl, thiazepinyl, pyrrolin-1-yl, 2-pyrrolinyl, 3-pyrrolinyl, indolinyl, 2H-pyranyl, 4H-pyranyl, dioxanyl, 1,3-dioxolanyl, pyrazolinyl, dithianyl, dithiolanyl, dihydrothienyl, pyrazolidinylimidazolinyl, imidazolidinyl, 1,2,3,4-tetrahydroisoquinolinyl, 1,2,6-thiadiazine-1,1-dioxo-2-yl, 4-hydroxy-1,4-azaphosphinan-4-oxide-1-yl, 2-hydroxy-1-(piperazin-1-yl)ethanone-4-yl, 2-hydroxy-1-(5,6-dihydro-1,2,4-triazin-1(4H)-yl)ethanone-4-yl, 5,6-dihydro-4H-1,2,4-oxadiazin-4-yl, 2-hydroxy-1-(5,6-dihydropyridin-1(2H)-yl) ethanone-4-yl, 3-azabicyclo[3.1.0]hexanyl, 3-azabicyclo [4.1.0]heptanyl, azabicyclo[2.2.2]hexanyl, 2-methyl-5,6,7,8-tetrahydro-[1,2,4]triazolo[1,5-c]pyrimidin-6-yl, 4,5,6,7-tetrahydroisoxazole[4,3-c]pyridin-5-yl, 3H-indolyl-2-oxo-5-azabicyclo[2.2.1]heptan-5-yl, 2-oxo-5-azabicyclo[2.2.2] octan-5-yl, quinolizinyl and N-pyridyl urea. Some non-limiting examples of a heterocyclic ring comprise 1,1-dioxothiomorpholinyl and heterocyclic group wherein two carbon atoms on the ring are substituted with oxo (=O) moieties are pyrimidindionyl. The heterocyclic group herein may be substituted or unsubstituted, wherein the substituent may be, but is not limited to, oxo (=O), hydroxy, amino, halo, cyano, heteroaryl, alkoxy, alkylamino, alkyl, haloalkyl, alkenyl, alkynyl, heterocyclyl, thiol, nitro, aryloxy, hydroxyl-substituted alkoxy, hydroxyl-substituted alkyl-C(=O)—, alkyl-C(=O)—, alkyl-S(=O)—, hydroxyl-substituted alkyl-S(=O)—, hydroxyl-substituted alkyl-S(=O)$_2$—, carboxyalkoxy, and the like.

The term "heterocyclylaliphatic" refers to heterocyclic-substituted aliphatic group, wherein the heterocyclic radical and aliphatic group are as defined herein. Some non-limiting examples comprise pyrrol-2-ylmethyl, piperidin-2-ylethyl, piperazin-2-ylethyl, piperidin-2-ylmethyl, and the like.

The ten "heterocyclyloxy" refers to optionally substituted heterocyclyl radical, as defined herein, connected to an oxygen atom, and the oxygen atom serves as the attaching point to the rest of the molecule. Some non-limiting examples comprise pyrrol-2-yloxy, pyrrol-3-yloxy, piperidin-2-yloxy, piperidin-3-yloxy, piperazin-2-yloxy, piperidin-4-yloxy, and the like.

The term "heterocyclylamino" refers to an amino group substituted with one or two heterocyclyl groups, wherein the heterocyclyl group is as defined herein. Some non-limiting examples comprise pyrrol-2-ylamino, pyrrol-3-ylamino, piperidin-2-ylamino, piperidin-3-ylamino, piperidin-4-ylamino, piperazin-2-ylamino, dipyrrol-2-ylamino, and the like.

The term "heterocyclyloxyaliphatic" refers to an aliphatic group substituted with one or more heterocyclyloxy groups, wherein the aliphatic group and heterocyclyloxy group are as defined herein. Some non-limiting examples comprise pyrrol-2-yloxymethyl, piperazin-3-yloxyethyl, piperazin-2-yloxyethyl, morpholin-2-yloxymethyl, piperidin-2-yloxyethyl, and the like. The term "heterocyclylaminoaliphatic" refers to an aliphatic group substituted with one or more heterocyclylamino groups, wherein the aliphatic group and heterocyclylamino group are as defined herein. Some non-limiting examples comprise pyrrol-2-ylaminomethyl, piperazin-3-lyaminoethyl, piperazin-2-lyaminoethyl, piperidin-2-lyaminoethyl, morpholin-2-lyaminomethyl, and the like.

The term "heteroatom" refers to one or more of oxygen, sulfur, nitrogen, phosphorus, or silicon, including any oxidized form of nitrogen, sulfur, or phosphorus; the quatemized form of any basic nitrogen; or a substitutable nitrogen of a heterocyclic ring, for example, N (as in 3,4-dihydro-2H-pyrrolyl), NH (as in pyrrolidinyl) or NR (as in N-substituted pyrrolidinyl).

The term "halogen" refers to F, Cl, Br or I.

The term "unsaturated" refers to a moiety having one or more degrees of unsaturation.

The term "alkoxy" refers to an alkyl group, as previously defined, attached to the principal carbon chain through an oxygen ("alkoxy") atom. Some non-limiting examples comprise methoxy, ethoxy, propoxy, butoxy, and the like. The alkoxy defined above may be substituted or unsubstituted, wherein the substituent may be, but is not limited to, hydroxy, amino, halo, cyano, alkoxy, alkyl, alkenyl, alkynyl, thiol, nitro, and the like.

The term "hydroxy-substituted alkoxy" or "hydroxyalkoxy" refers to an alkoxy group substituted with one or more hydroxy groups, wherein the alkoxy group is as defined above. Some non-limiting examples comprise hydroxymethoxy, 2-hydroxyethoxy, 2-hydroxypropoxy, 2-hydroxyisopropoxy, and the like.

The term "aminoalkoxy" refers to an alkoxy group substituted with one or more amino groups, wherein the alkoxy group is as defined above. Some non-limiting examples comprise aminomethoxy, 2-aminoethoxy, 2-aminopropoxy, 2-aminoisopropoxy, and the like.

The term "haloalkyl", "haloalkenyl" or "haloalkoxy" refers to an alkyl group, alkenyl group or alkoxy group substituted with one or more halogen atoms. Some non-limiting examples comprise trifluoromethyl, 2-chloro-ethenyl, trifluoromethoxy, and the like.

The term "aryl" refers to monocyclic, bicyclic, and tricyclic carbocyclic ring systems having a total of six to fourteen ring members, wherein at least one ring in the system is aromatic, wherein each ring in the system contains 3 to 7 ring members and that has a single point of attachment to the rest of the molecule. The term "aryl" may be used interchangeably with the term "aryl ring". Some non-limiting examples of aryl rings comprise phenyl, naphthyl, and anthracene. The aryl defined herein may be substituted or unsubstituted, wherein the substituent may be, but is not limited to, hydroxy, amino, halogen, cyano, aryl, heteroaryl, alkoxy, alkylamino, alkyl, haloalkyl, alkenyl, alkynyl, heterocyclyl, thiol, nitro, aryloxy, hydroxy-substituted alkoxy, hydroxy-substituted alkyl-C(=O)—, alkyl-C(=O)—, alkyl-S(=O)—, alkyl-S(=O)$_2$—, hydroxy-substituted alkyl-S(=O)—, hydroxy-substituted alkyl-S(=O)$_2$—, carboxyalkoxy, and the like.

The term "fluoro-substituted phenyl" refers to a phenyl group substituted with one or more fluorine atoms.

The term "arylaliphatic" refers to an aliphatic group substituted with one or more aryl groups, wherein the aliphatic group and the aryl group are as defined herein. Some non-limiting examples comprise phenylethyl, phenylmethyl, (p-tolyl)ethyl, styryl, and the like.

The term "aryloxy" refers to optionally substituted aryl radicals, as defined herein, attached to an oxygen atom, wherein the oxygen atom serves as the attaching point to the rest of the molecule. Wherein the aryl radical is as defined herein. Some non-limiting examples comprise phenyloxy, methylphenyloxy, ethylphenyloxy, and the like.

The term "arylamino" refers to an amino group substituted with one or two aryl groups, wherein the aryl group is as defined herein. Some non-limiting examples comprise phenylamino, (p-fluorophenyl)amino, diphenylamino, ditolylamino, (di-p-tolyl)amino, and the like.

The term "aryloxyaliphatic" refers to an aliphatic group substituted with one or more aryloxy groups, wherein the alkoxy group and the aliphatic group are as defined herein. Some no-limiting examples comprise phenyloxymethoxy, phenyloxyethyl, tolyloxyethyl, phenyloxypropoxy, and the like.

The term "heteroaryloxyaliphatic" refers to an aliphatic group may be substituted with one or more heteroaryloxy groups, wherein the heteroaryloxy group and the aliphatic group are as defined herein. Some non-limiting examples comprise furanyloxymethyl, pyrimidinyloxyethyl, and the like.

The term "arylaminoaliphatic" refers to an aliphatic group substituted with one or more arylamino groups, wherein the arylamino group and the aliphatic group are as defined herein. Some non-limiting examples comprise phenylaminomethyl, phenylaminoethyl, tolylaminoethyl, phenylaminopropyl, phenylaminoallyl, and the like.

The term "arylalkoxy" refers to an alkoxy group substituted with one or more aryl groups, wherein the aryl group and the alkoxy group are as defined herein. Some non-limiting examples, comprise phenylmethoxy, phenylethoxy, (p-tolyl)methoxy, phenylpropoxy, and the like. The aryl defined herein may be substituted or unsubstituted, wherein the substituent may be, but is not limited to, hydroxy, amino, halogen, cyano, aryl, heteroaryl, alkoxy, alkylamino, alkyl, haloalkyl, alkenyl, alkynyl, heterocyclyl, thiol, nitro, aryloxy, hydroxy-substituted alkoxy, hydroxy-substituted alkyl-C(=O)—, alkyl-C(=O)—, alkyl-S(=O)—, alkyl-S(=O)$_2$—, hydroxy-substituted alkyl-S(=O)—, hydroxy-substituted alkyl-S(=O)$_2$—, carboxyalkoxy, and the like.

The term "arylalkylamino" refers to an alkylamino group substituted with one or more aryl groups, wherein the aryl group and the alkylamino group are as defined herein. Some non-limiting examples comprise phenylmethylamino, phenylethylamino, phenylpropylamino, (p-tolyl)methylamino, and the like.

The term "heteroaryl" used alone or as part of a larger moiety as in "heteroaralkyl" or "heteroarylalkoxy" refers to monocyclic, bicyclic, and tricyclic ring systems having a total of five to fourteen ring members, wherein at least one ring in the system is aromatic, at least one ring in the system contains one or more heteroatoms, wherein each ring in the system contains 3 to 7 ring members and that has a single point of attachment to the rest of the molecule. The term "heteroaryl" may be used interchangeably with the term "heteroaryl ring" or the term "heteroaromatic". The heteroaryl defined herein may be substituted or unsubstituted, wherein the substituent may be, but is not limited to, hydroxy, amino, halogen, cyano, aryl, heteroaryl, alkoxy, alkylamino, alkyl, haloalkyl, alkenyl, alkynyl, heterocyclyl, thiol, nitro, aryloxy, hydroxy-substituted alkoxy, hydroxy-substituted alkyl-C(=O)—, alkyl-C(=O), alkyl-S(=O)—, alkyl-S(≡O)—, hydroxy-substituted alkyl-S(=O)—, hydroxy-substituted alkyl-S(=O)$_2$—, carboxyalkoxy, and the like.

In other embodiments, some non-limiting examples of suitable heteroaryl rings comprise the following monocycles: 2-furanyl, 3-furanyl, N-imidazolyl, 2-imidazolyl, 4-imidazolyl, 5-imidazolyl, 3-isoxazolyl, 4-isoxazolyl, 5-isoxazolyl, 2-oxazolyl, 4-oxazolyl, 5-oxazolyl, 4-methylisoxazol-5-yl, N-pyrrolyl, 2-pyrrolyl, 3-pyrrolyl, 2-pyridyl, 3-pyridyl, 4-pyridyl, 2-pyrimidinyl, 4-pyrimidinyl, 5-pyrimidinyl, pyridazinyl (e.g., 3-pyridazinyl), 2-thiazolyl, 4-thiazolyl, 5-thiazolyl, tetrazolyl (e.g., 5-tetrazolyl), triazolyl (e.g., 2-triazolyl and 5-triazolyl), 2-thienyl, 3-thienyl, pyrazolyl (e.g., 2-pyrazolyl), isothiazolyl, 1,2,3-oxadiazolyl, 1,2,5-oxadiazolyl, 1,2,4-oxadiazolyl, 1,2,3-triazolyl, 1,2,3-thiadiazolyl, 1,3,4-thiadiazolyl, 1,2,5-thiadiazolyl, 1,3,4-thiadiazol-2-yl, pyrazinyl, 2-pyrazinyl, 1,3,5-triazinyl, benzo[d]thiazol-2-yl, imidazo[1,5-a]pyridyl and also comprise the following bicycles: benzimidazolyl, benzofuryl, benzothiophenyl, benzothiazolyl, indolyl (e.g., 2-indolyl), purinyl, quinolinyl (e.g., 2-quinolinyl, 3-quinolinyl, 4-quinolinyl), or isoquinolinyl (e.g., 1-isoquinolinyl, 3-isoquinolinyl, or 4-isoquinolinyl).

The term "heteroaryloxy" refers to optionally substituted aryl radicals, as defined herein, attached to an oxygen atom, wherein the oxygen atom serves as the attaching point to the rest of the molecule. Some non-limiting examples comprise pyrid-2-yloxy, thiazol-2-yloxy, imidazol-2-yloxy, pyrimidin-2-yloxy, and the like.

The term "carboxyalkoxy" refers to an alkoxy group substituted with one or more carboxy groups, wherein the alkoxy group and the carboxy group are as defined herein Some non-limiting examples comprise carboxymethoxy, carboxyethoxy, and the like.

The term "alkylthio" refers to radicals containing a linear or branched alkyl radical, of one to ten carbon atoms, attached to a divalent sulfur atom. In other embodiments, alkylthio radicals are lower alkylthio radicals having one to three carbon atoms. Some non-limiting examples of "alkylthio" comprise methylthio ($CH_3S$—). The term "haloalkylthio" refers to radicals containing a haloalkyl radical, of one to ten carbon atoms, attached to a divalent sulfur atom. In other embodiments, haloalkylthio radicals are lower haloalkylthio radicals having one to three carbon atoms. Some non-limiting examples of "haloalkylthio" comprise trifluoromethylthio.

The term "alkylamino" refers to N-alkylamino" and "N,N-dialkylamino" where amino groups are independently substituted with one alkyl radical or with two alkyl radicals, respectively. In other embodiments, alkylamino radicals are "lower alkylamino" radicals having one or two alkyl radicals of one to six carbon atoms, attached to a nitrogen atom. In still other embodiments, alkylamino radicals are lower alkylamino radicals having one to three carbon atoms. Some non-limiting examples of suitable alkylamino radicals comprise mono or dialkylamino such as N-methylamino, N-ethylamino, N,N-dimethylamino, N,N-diethylamino, and the like.

The term "heteroarylamino" refers to amino groups substituted with one or two heteroaryl radicals, wherein the heteroaryl radical is as defined herein. Some non-limiting examples of heteroarylamino comprise N-thienylamino, and the like. In other embodiments, the "heteroarylamino" radicals comprise substituted on the heteroaryl ring portion of the radical.

The term "heteroarylaliphatic" refers to aliphatic groups substituted with one or more heteroaryl radicals, wherein the heteroaryl radical and the aliphatic group are as defined herein. Some non-limiting examples of heteroarylaliphatic comprise thiophen-2-ylpropenyl, pyridin-4-ylethyl, imidazol-2-methyl, furan-2-ethyl, indole-3-methyl, and the like.

The term "heteroarylalkyl" refers to alkyl groups substituted with one or more heteroaryl radicals, wherein the heteroaryl radical and the alkyl group are as defined herein.

Some non-limiting examples of heteroarylalkyl comprise imidazol-2-methyl, furan-2-ethyl, indole-3-methyl, and the like.

The term "heteroarylalkylamino" refers to nitrogen-containing heteroarylalkyl radicals attached through a nitrogen atom to other radicals, wherein the heteroarylalkyl radicals is as defined herein. Some non-limiting examples of heteroarylalkylamino comprise pyridin-2-methylamino, thiazol-2-ethylamino, imidazol-2-ethylamino, pyrimidin-2-propylamino, pyrimidin-2-methylamino, and the like.

The term "heteroarylalkoxy" refers to oxy-containing heteroarylalkyl radicals attached through an oxygen atom to other radicals, wherein the heteroarylalkyl radical is as defined herein. Some non-limiting examples of such radicals comprise pyridin-2-ylmethoxy, thiazol-2-ylethoxy, imidazol-2-ylethoxy, pyrimidin-2-ylpropoxy, pyrimidin-2-ylmethoxy, and the like.

The term "fused bicyclic", "fused cyclic", "fused bicyclyl" or "fused cyclyl" refers to saturated or unsaturated fused ring system, which involves a bicyclic ring system that is not aromatic. Such a system may contain isolated or conjugated unsaturated moiety, but does not contain aromatic or heteroaromatic rings in its core structure (but may have aromatic substitution thereon). Each cyclic ring in the fused bicyclyl can be either a carbocyclic or a heteroalicyclic. Some non-limiting examples of fused bicyclic ring system comprise hexahydro-furo[3,2-b]furan, 2,3,3a,4,7,7a-hexahydro-1H-indene, 7-azabicyclo[2.3.0]heptane, fused bicyclo[3.3.0]octane, fused bicyclo[3.1.0]hexane, 1,2,3,4,4a,5,8,8a-octahydro naphthalene, and the like. The fused bicyclyl defined herein may be substituted or unsubstituted, wherein the substituents comprise, but are not limited to, oxo (=O), hydroxy, amino, halogen, cyano, aryl, heteroaryl, alkoxy, alkylamino, alkyl, haloalkyl, alkenyl, alkynyl, heterocyclyl, thiol, nitro, aryloxy, hydroxy-substituted alkoxy, hydroxy-substituted alkyl-C(=O)—, alkyl-C(=O)—, alkyl-S(=O)—, alkyl-S(=O)$_2$—, hydroxy-substituted alkyl-S(=O)—, hydroxy-substituted alkyl-S(=O)$_2$—, carboxy alkoxy, and the like.

The term "fused heterobicyclyl" refers to saturated or unsaturated bridged ring system, which refers to a bicyclic ring system that is not aromatic. Such a system may contain isolated or conjugated unsaturation, but not aromatic or heteroaromatic rings in its core structure (but may have aromatic substitution thereon). Wherein at least one ring in the system contains one or more heteroatoms, wherein each ring in the system contains 3 to 7 ring members and that contains one to six carbon atoms and one to three heteroatoms selected from N, O, P, S, wherein the S or P is optionally substituted with one or more oxo to provide the group SO, SO$_2$, PO or PO$_2$, Some non-limiting examples of fused heterobicyclic ring system comprise hexahydro-furo[3,2-b]furan, 7-azabicyclo[2.3.0]heptane, and the like. The fused heterobicyclyl defined herein may be substituted or unsubstituted, wherein the substituents comprise, but are not limited to, oxo (=O), hydroxy, amino, halogen, cyano, aryl, heteroaryl, alkoxy, alkylamino, alkyl, haloalkyl, alkenyl, alkynyl, heterocyclyl, thiol, nitro, aryloxy, hydroxy-substituted alkoxy, hydroxy-substituted alkyl-C(=O)—, alkyl-C(=O)—, alkyl-S(=O)—, alkyl-S(=O)$_2$, hydroxy-substituted alkyl-S(=O)—, hydroxy-substituted alkyl-S(=O)$_2$—, carboxyalkoxy, and the like.

The term "fused bicyclylaliphatic" refers to aliphatic groups substituted with one or more fused bicyclyl groups, wherein the aliphatic group and the fused bicyclyl group are as defined herein. Some non-limiting examples comprise 1,2,3,4,4a,5,8,8a-octahydro-naphthylethyl, 1,23,4,4a5,8,8a-octahydro-naphthylmethyl, 1,2,3,4,4a,5,8,8a-octahydro-naphthylpropyl, fused bicyclo[3.3.0]octylmethyl, fused bicyclo[3.1.0]hexylethyl, and the like.

The term "fused heterobicyclylaliphatic" refers to aliphatic groups substituted with one or more fused heterobicyclyl groups, wherein the aliphatic group and the fused heterobicyclyl group are as defined herein. Some non-limiting examples comprise hexahydro-furo[3,2-b]furan-2-ylethyl, hexahydro-furo[3,2-b]furan-2-ylmethyl, 7-azabicyclo[2.3.0]hept-2-ylmethyl, 7-azabicyclo[2.3.0]hept-2-yethyl, 7-azabicyclo[2.3.0]hept-4-ylmethyl, and the like.

The term"fused bicycloxy" refers to optionally substituted fused bicyclyl radicals, as defined herein, oxy-containing fused bicyclyl radicals attached through an oxygen atom to other radicals, wherein the fused bicyclyl radical is as defined herein. Some non-limiting examples comprise 1,2,3,4,4a,5,8,8a-octahydro-naphthyloxy, fused bicyclo[3.3.0]oct-2-yloxy, fused bicyclo[3. 1.0]hex-2-yloxy, and the like.

The term "fused heterobicycloxy" refers to optionally substituted fused heterobicyclyl radicals, as defined herein, oxy-containing fused heterobicyclyl radicals attached through an oxygen atom to other radicals. Some non-limiting examples comprise hexahydro-furo[3,2-b]furan-2-yloxy, 7-azabicyclo[2.3.0]hept-2-yloxy, 7-azabicyclo[2.3.0]hept-4-yloxy, and the like.

The term "fused bicyclylamino" refers to an amino group substituted with one or two fused bicyclyl groups, wherein the fused bicyclyl group is as defined herein. Some non-limiting examples comprise 1,2,3,4,4a,5,8,8a-octahydro-naphthylamino, di(1,2,3,4a,5,8,8a-octahydro-naphthyl)amino, fused bicyclo[3.3.0]octylamino, fused bicyclo[3.1.0]hexylamino, and the like.

The term "fused bicyclylamino" refers to an amino group substituted with one or two fused bicyclyl groups, wherein the fused bicyclyl group is as defined herein. Some non-limiting examples comprise 1,2,3,4,4a,5,8,8a-octahydro-naphthylamino, di(1,2,3,4a,5,8,8a-octahydro-naphthyl)amino, fused bicyclo[3.3.0]octylamino, fused bicyclo[3.1.0]hexylamino, and the like.

The term "fused bicyclylamino" refers to an amino group substituted with one or two fused bicyclyl groups, wherein the fused bicyclyl group is as defined herein. Some non-limiting examples comprise 1,2,3,4,4a,5,8,8a-octahydro-naphthylamino, di(1,2,3,4a,5,8,8a-octahydro-naphthyl)amino, fused bicyclo[3.3.0]octylamino, fused bicyclo[3.1.0]hexylamino, and the like.

The term "fused heterobicyclylalkylamino" refers to alkylamino groups substituted with one or more fused heterobicyclyl groups, wherein the fused heterobicyclyl group as defined herein. Some non-limiting examples comprise hexahydro-furo[3,2-b]furan-2-ylmethylamino, 7-azabicyclo[2.3.0]hept-2-ylmethylamino, 7-azabicyclo[2.3.0]hept-4-yl-methylamino, and the like.

The term "fused bicyclylalkoxy" refers to alkoxy groups substituted with one or more fused bicyclyl groups, wherein the fused bicyclyl group is as defined herein. Some non-limiting examples comprise 1,2,3,4,4a,5,8,8a-octahydro-naphthylmethoxy, 1,2,3,4,4,5,8,8a-octahydro-naphthylethoxy, fused bicyclo[3.3.0]octylethoxy, fused bicyclo[3.1.0]hexylpropoxy, and the like.

The term "fused heterobicyclylalkoxy" refers to alkoxy groups substituted with one or more fused heterobicyclyl groups, wherein the fused heterobicyclyl group is as defined herein. Some non-limiting examples comprise hexahydro-furo[3,2-b]furan 2-ylpropoxy, 7-azabicyclo[2.2.1]hept-2-ylethoxy, 7-azabicyclo[2.3.0]hept-4-ylpropoxy, hexahydro-furo[3,2-b]furan-2-ylethoxy, 7-azabicyclo[2.3.0]hept-4-ylpropoxy, 7-azabicyclo[2.3.0]hept-4-ylethoxy, and the like.

The term "fused bicycloxyalkoxy" refers to alkoxy groups substituted with one or more fused bicycloxy groups, wherein the alkoxy group and the fused bicycloxy group are as defined herein. Some non-limiting examples comprise 1,2,3,4,4a,5,8,8a-octahydro-naphthyloxymethoxy, 1,2,3,4,4a,5,8,8a-octahydro-naphthyloxymethoxy, 1,2,3,4,4a.5,8,8a-octahydro-naphthyloxyethoxy, fused bicyclo[3.3.0]oct-2-yloxyethoxy, fused bicyclo[3.1.0]hex-2-yloxypropoxy, and the like.

The term "fused heterobicycloxyalkoxy" refers to alkoxy groups substituted with one or more fused heterobicycloxy groups, wherein the alkoxy group and the fused heterobicyclyl group are as defined herein. Some non-limiting examples comprise hexahydro-furo[3,2-b]furan-2-yloxypropoxy, 7-azabicyclo[2.2.1]hept-2-yloxyethoxy, 7-azabicyclo[2.3.0]hept-4-yloxypropoxy, hexahydro-furo[3,2-b]furan-2-yloxyethoxy, 7-azabicyclo[2.3.0]hept-2-yloxypropoxy, 7-azabicyclo[2.3.0]hept-4-yloxyethoxy, and the like.

The term "fused bicyclylaminoalkoxy" refers to alkoxy groups substituted with one or more fused bicyclylamino groups, wherein the alkoxy group and the fused bicyclylamino group are as defined herein. Some non-limiting examples comprise 1,2,3,4,4a,5,8,8a-octahydro-naphthylaminoethoxy, 1,2,3,4,4a,5,8,8a-octahydro-naphthylaminopropoxy, di(1,2,3,4,4a,5,8,8a-octahydro naphthylaminopropoxy, fused bicyclo[3.3.0]oct-2-ylaminoethoxy, fused bicyclo[3.1.0]hex-2-ylaminopropoxy, and the like.

The term "fused heterobicyclylaminoalkoxy" refers to alkoxy groups substituted with one or more fused heterobicyclylamino groups, wherein the alkoxy group and the fused heterobicyclylamino group are as defined herein. Some non-limiting examples comprise 7-azabicyclo[2.2.1]hept-2-ylaminoethoxy, 7-azabicyclo[2.3.0]hept-4-ylaminopropoxy, hexahydro-furo[3,2-b]furan-2-ylaminoethoxy, hexahydro-furo[3,2-b]furan-2-ylaminopropoxy, hexahydro-furo[3,2-b]furan-2-ylaminomethoxy, and the like.

The term "spirocyclyl", "spirocyclic", "spiro bicyclyl" or "spiro bicyclic" refers to a ring originating from a particular annular carbon of another ring. For example, as depicted below, a saturated bridged ring system (ring B and B') is termed as "fused bicyclic", whereas ring A and ring B share an atom between the two saturated ring system, which terms as a "spirocyclyl" or "spiro bicyclyl".

Each cyclic ring in the spirocyclyl or spiro bicyclyl can be either a carbocyclic or a heteroalicyclic. Some non-limiting examples comprise 2,7-diaza-spiro[4.4]non-2-yl,7-oxo-2-azaspiro[4.5]dec-2-yl, 4-azaspiro[2.4]hept-5-yl, 4-oxaspiro[2.4]hept-5-yl, 5-azaspiro[2.4]hept5-yl, spiro[2.4]heptyl, spiro[4.4]nonyl, 7-hydroxy-5-azaspiro[2.4]hept-5-yl, and the like. The spirocyclyl or spiro bicyclyl can be optionally substituted, wherein the substituents can be, but are not limited to, oxo (=O), hydroxy, amino, halogen, cyano, aryl, heteroaryl, alkoxy, alkylamino, alkyl, haloalkyl, alkenyl, alkynyl, heterocyclyl, thiol, nitro, aryloxy, hydroxysubstitute alkoxy, hydroxy-substituted alkyl-C(=O), alkyl-C(=O)—, alkyl-S(=O)—, alkyl-S(=O)$_2$—, hydroxy-substituted alkyl-S(=O)—, hydroxy-substituted alkyl-S(=O)$_2$—, carboxy alkoxy, and the like.

The term "spiro heterobicyclyl" refers to a ring originating from a particular annular carbon of another ring. For example, as depicted above, a saturated bridged ring system (ring B and B') is termed as "fused bicyclic", whereas ring A and ring B share an carbon atom between the two saturated ring system, which terms as a "spirocyclyl" or "spiro bicyclyl". In addition, at least one ring in the system contains one or more heteroatoms, wherein each ring in the system contains 3 to 7 ring members and that contains one to six carbon atoms and one to three heteroatoms selected from N, O, P, S, wherein the S or P is optionally substituted with one or more oxo to provide the group SO, SO$_2$, PO or PO$_2$. Some non-limiting examples of spiro heterobicyclic ring system comprise 4-azaspiro[2.4]hept-5-yl, 4-oxaspiro[2.4]hept-5-yl, 5-azaspiro[2.4]hept-5-yl, 7-hydroxy-5-azaspiro[2.4]hept-5-yl, and the like. The spiro heterobicyclyl defined herein may be substituted or unsubstituted, wherein the substituents comprise, but are not limited to, oxo (=O), hydroxy, amino, halogen, cyano, aryl, heteroaryl, alkoxy, alkylamino, alkyl, haloalkyl, alkenyl, alkynyl, heterocyclyl, thiol, nitro, aryloxy, hydroxy-substituted alkoxy, hydroxy-substituted alkyl-C(=O)—, alkyl-C(=O)—, alkyl-S(=O), alkyl-S(=O)$_2$—, hydroxy-substituted alkyl-S(=O)—, hydroxy-substituted alkyl-S(=O)$_2$—, carboxyalkoxy, and the like.

The term "spiro bicyclylaliphatic" refers to aliphatic groups substituted with one or more spiro bicyclyl groups, wherein the aliphatic group and the spiro bicyclyl group are as defined herein. Some non-limiting examples comprise spiro[2.4]heptylmethyl, spiro[2.4]heptylethyl, spiro[2.4]heptylpropyl, spiro[4.4]nonylmethyl, spiro[4.4]nonylethyl, 4-azaspiro[2.4]hept-5-yl-methyl, 4-azaspiro[2.4]hept-5-yl-ethyl, 4-oxaspiro[2.4]hept-5-yl-ethyl, 5-azaspiro[2.4]hept-5-yl-propyl, 7-hydroxy-5-azaspiro[2.4]hept-5-yl-propyl, and the like.

The term "spiro heterobicyclylaliphatic" refers to aliphatic groups substituted with one or more spiro heterobicyclyl groups, wherein the aliphatic group and the fused heterobicyclyl group are as defined herein. Some non-limiting examples comprise 4-azaspiro[2.4]hept-5-yl-methyl, 4-azaspiro[2.4]hept-5-yl-ethyl, 4-oxaspiro[2.4]hept-5-yl-ethyl, 5-azaspiro[2.4]hept-5-yl-propyl, 7-hydroxy-5-azaspiro[2.4]hept-5-yl-propyl, and the like.

The term "spiro bicycloxy" comprises optionally substituted spiro bicyclyl radicals, as defined herein, attached to an oxygen atom, and the spiro bicycloxy is attached to other radicals through the oxygen atom. Some non-limiting examples comprise spiro[2.4]heptyl-2-oxy, spiro[2.4]heptyl-3-oxy, spiro[2.4]heptyl-4-oxy, spiro[4.4]nonyl-2-oxy, spiro[4.4]nonyl-4-oxy, 4-azaspiro[2 4]hept-5-oxy, and the like.

The term "spiro heterobicycloxy" comprises optionally substituted spiro heterobicyclyl radicals, as defined herein, attached to an oxygen atom, and the spiro heterobicycloxy is attached to other radicals through the oxygen atom. Some non-limiting examples comprise 4-azaspiro[2.4]hept-5-yloxy, 4-oxaspiro[2.4]hept-5-yloxy, 5-azaspiro[2.4]hept-5-yloxy, and the like.

The term "spiro bicyclylamino" refers to an amino group substituted with one or two spiro bicyclyl groups, wherein the spiro bicyclyl group is as defined herein. Some non-limiting examples comprise spiro[2.4]heptyl-2-amino, spiro[2.4]heptyl-3-amino, spiro[2.4]heptyl-4-amino, spiro[4.4]nonyl-2-amino, spiro[4.4]nonyl-4-amino, 4-azaspiro[2.4]hept-5-amino, and the like.

The term "spiro heterobicyclylamino" refers to an amino group substituted with one or two spiro heterobicyclyl groups, wherein the spiro heterobicyclyl group is as defined herein. Some non-limiting examples comprise 4-azaspiro[2.4]hept-5-ylamino, 4-oxaspiro[2.4]hept-2-ylamino, 4-oxaspiro[2.4]hept-5-ylamino, 5-azaspiro[2.4]hept-5-ylamino, and the like.

The term "spiro bicyclylalkoxy" refers to alkoxy groups substituted with one or more spiro bicyclyl groups, wherein the spiro bicyclyl group is as defined herein. Some non-limiting examples comprise spiro[2.4]heptyl-2-methoxy, spiro[2.4]heptyl-3-ethoxy, spiro[2.4]heptyl-4-ethoxy, spiro[4.4]nonyl-2-methoxy, spiro[4.4]nonyl-4-propoxy, 4-azaspiro[2.4]hept-5-methoxy, and the like.

The term "spiro heterobicyclylalkoxy" refers to alkoxy groups substituted with one or more spiro heterobicyclyl groups, wherein the spiro heterobicyclyl group is as defined herein. Some non-limiting examples comprise 4-azaspiro[2.4]hept-5-yl-methoxy, 4-azaspiro[2.4]hept-2-yl-ethoxy, 4-oxaspiro[2.4]hept-5-yl-ethoxy, 5-azaspiro[2.4]hept-5-yl-propoxy, and the like.

The term "spiro bicyclylalkyamino" refers to alkylamino groups substituted with one or more spiro bicyclyl groups, wherein the spiro bicyclyl group is as defined herein. Some non-limiting examples comprise spiro[2.4]heptyl-2-methylamino, spiro[2.4]heptyl-3-ethylamino, spiro[2.4]heptyl-4-ethylamino, spiro[4.4]nonyl-2-methylamino, spiro[4.4]nonyl-4-propylamino, 4-azaspiro[2.4]hept-5-methylamino, and the like.

The term "spiro heterobicyclylalkyamino" refers to alkylamino groups substituted with one or more spiro heterobicyclyl groups, wherein the spiro heterobicyclyl group is as defined herein. Some non-limiting examples comprise 4-azaspiro[2.4]hept-5-yl-methylamino, 4-azaspiro[2.4]hept-2-yl-ethylamino, 4-oxaspiro[2.4]hept-5-yl-ethylamino, 5-azaspiro[2.4]hept-5-yl-propylamino, and the like.

The term "spiro bicycloxyalkoxy" refers to alkoxy groups substituted with one or more spiro bicycloxy groups, wherein the alkoxy group and the spiro bicyclyl group are as defined herein Some non-limiting examples comprise spiro[2.4]heptyl-2-oxyethoxy, spiro[2.4]heptyl-3-oxypropoxy, spiro[2.4]heptyl-4-oxypropoxy, spiro[4.4]nonyl-2-oxyethoxy, spiro[4.4]nonyl-4-oxypropoxy, 4-azaspiro[2.4]hept-5-oxypropoxy, and the like.

The term "spiro heterobicycloxyalkoxy" refers to alkoxy groups substituted with one or more spiro heterobicycloxy groups, wherein the alkoxy group and the spiro heterobicyclyl group are as defined herein. Some non-limiting examples comprise 4-azaspiro[2.4]hept-5-yloxyethoxy, 4-oxaspiro[2.4]hept-5-yloxyethoxy, 5-azaspiro[2.4]hept-5-yloxyethoxy, 4-azaspiro[2.4]hept-5-yloxypropoxy, 4-oxaspiro[2.4]hept-5-yloxypropoxy, 5-azaspiro[2.4]hept-5-yloxypropoxy, and the like.

The term "spiro bicyclylaminoalkoxy" refers to alkoxy groups substituted with one or more spiro bicyclylamino groups, wherein the alkoxy group and the spiro bicyclylamino group are as defined herein. Some non-limiting examples comprise spiro[2.4]heptyl-2-aminoethoxy, spiro[2.4]heptyl-3-aminopropoxy, spiro[2.4]heptyl-4-aminoethoxy, spiro[4.4]nonyl-2-aminoethoxy, spiro[4.4]nonyl-4-aminopropoxy, 4-azaspiro[2.4]hept-5-aminopropoxy, and the like.

The term "spiro heterobicyclylaminoalkoxy" refers to alkoxy groups substituted with one or more spiro heterobicyclylamino groups, wherein the alkoxy group and the spiro heterobicyclylamino group are as defined herein. Some non-limiting examples comprise 4-azaspiro[2.4]hept-5-ylaminoethoxy, 4-oxaspiro[2.4]hept-2-ylaminopropoxy, 4-oxaspiro[2.4]hept-5-ylaminoethoxy, 5-azaspiro[2.4]hept-5-ylaminopropoxy, and the like.

Unless otherwise stated, structures depicted herein are also meant to comprise all isomeric (e.g, enantiomeric, diastereomeric, and geometric (or conformational)) forms of the structure, for example, the R and S configurations for each asymmetric center, (Z) and (E) double bond isomers, and (Z) and (E) conformational isomers. Therefore, single stereochemical isomers as well as enantiomeric, diastereomeric, or geometric (or conformational) mixtures of the present compounds are within the scope disclosed herein.

The term "prodrug" refers to a compound that is transformed in vivo into a compound of Formula I or II. Such a transformation can be affected, for example, by hydrolysis in blood or enzymatic transformation of the prodrug form to the parent form in blood or tissue. Prodrugs of the compounds disclosed herein may be, for example, esters. Esters that may be utilized as prodrugs in the present disclosure are phenyl esters, aliphatic (C1-C24) esters, acyloxymethyl esters, carbonates, carbamates, and amino acid esters. For example, a compound disclosed herein that contains an OH group may be acylated at this position in its prodrug form. Other prodrug forms comprise phosphates, such as, for example those phosphates resulting from the phosphonation of an OH group on the parent compound. A thorough discussion of prodrugs is provided in T. Higuchi and V. Stella, Pro-drugs as Novel Delivery Systems, Vol. 14 of the A.C.S. Symposium Series, Edward B. Roche, ed., Bioreversible Carriers in Drug Design, American Pharmaceutical Association and Pergamon Press, 1987, J. Rautio et al, Prodrugs: Design and Clinical Applications, *Nature Review Drug Discovery*, 2008, 7, 255-270, and S. J. Hecker et al, Prodrugs of Phosphates and Phosphonates, *Journal of Medicinal Chemistry*, 2008, 51, 2328-2345, all of which are incorporated herein by reference. Unless otherwise stated, all tautomeric forms of the compounds disclosed herein are within the scope of the disclosure. Additionally, unless otherwise stated, structures depicted herein are also meant to comprise compounds that differ only in the presence of one or more isotopically enriched atoms.

A "metabolite" is a product produced through metabolism in the body of a specified compound or salt thereof. Metabolites of a compound may be identified using routine techniques known in the art and their activities determined using tests such as those described herein. Such products may result for example from the oxidation, reduction, hydrolysis, amidation, deamidation, esterification, deesterification, enzymatic cleavage, and the like, of the administered compound. Accordingly, the disclosure comprises metabolites of compounds disclosed herein, including compounds produced by a process comprising contacting a compound disclosed herein with a mammal for a period of time sufficient to yield a metabolic product thereof.

The compounds disclosed herein may contain asymmetric or chiral centers, and therefore exist in different stereoisomeric forms. It is intended that all stereoisomeric forms of the compounds disclosed herein, including but not limited to, diastereomers, enantiomers and atropisomers, as well as mixtures thereof such as racemic mixtures, form part of the present disclosure. Many organic compounds exist in optically active forms, i.e, they have the ability to rotate the plane of plane-polarized light. In describing an optically active compound, the prefixes D and L, or R and S, are used to denote the absolute configuration of the molecule about its chiral center(s). The prefixes D and L or (+) and (−) are employed to designate the sign of rotation of plane polarized light by the compound, with (−) or L meaning that the compound is levorotatory. A compound prefixed with (+) or D is dextrorotatory. For a given chemical structure, these stereoisomers are identical except that they are mirror images of one another. A specific stereoisomer may be also referred to as an enantiomer, and a mixture of such isomers is often called an enantiomeric mixture. A 50:50 mixture of enantiomers is referred to as a racemic mixture or a racemate, which may occur where there has been no stereoselection or stereospecificity in a chemical reaction or process. The term "racemic mixture" or "racemate" refers to an equimolar mixture of two enantiomeric species, devoid of optical activity.

The term "tautomer" or "tautomeric form" refers to structural isomers of different energies which are interconvertible via a low energy barrier. Some non-limiting examples of proton tautomers (also known as prototropic tautomers) comprise interconversions via migration of a proton, such as keto-enol and imine-enamine isomerizations. Valence tautomers comprise interconversions by reorganization of some of the bonding electrons.

A "Pharmaceutically acceptable salts" used in the present disclosure refer to organic or inorganic salts of a compound disclosed herein. Pharmaceutically acceptable salts are well known in the art. For example, S. M. Berge et al. describe pharmaceutically acceptable salts in detail in J. Pharmaceutical Sciences, 66: 1-19, 1977, which is incorporated herein by reference. Some non-limiting examples of pharmaceutically acceptable salts comprise salts formed by an amino group with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts comprise adipate, malic acid salts, 2-hydracrylic acid salt, alginate, ascorbate, aspartate, benzenesulfonate, benzoate, bisulfate, borate, butyrate, camphorate, camphorsulfonate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, malonate, methanesulfonate, 2-naphthalenesulfonate, nicotinate, nitrate, oleate, palmitate, pamoate, pectinate, persulfate, 3-phenylpropionate, picrate, pivalate, propionate, stearate, thiocyanate, p-toluenesulfonate, undecanoate, valerate salts, and the like. Salts derived from appropriate bases comprise alkali metal, alkaline earth metal, ammonium and N*(C1-C4 alkyl)$_4$ salts. This disclosure also envisions the quaternization of any basic nitrogen-containing groups of the compounds disclosed herein. Water or oil soluble or dispersable products may be obtained by such quaternization. Representative alkali or alkaline earth metal salts comprise sodium, lithium, potassium, calcium, magnesium, and the like. Pharmaceutically acceptable salts further comprise, appropriate and nontoxic ammonium, quaternary ammonium, and ammonium cations formed using counterions such as halide, hydroxide, carboxylate, sulfate, phosphate, nitrate, C1-C8 sulfonate or aryl sulfonate.

Salts of some of the compounds depicted herein can be illustrated by the salts of the specific compounds listed below, but does not limit the present application:

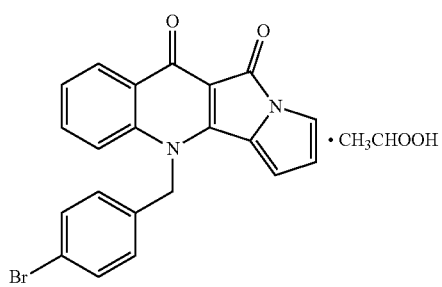

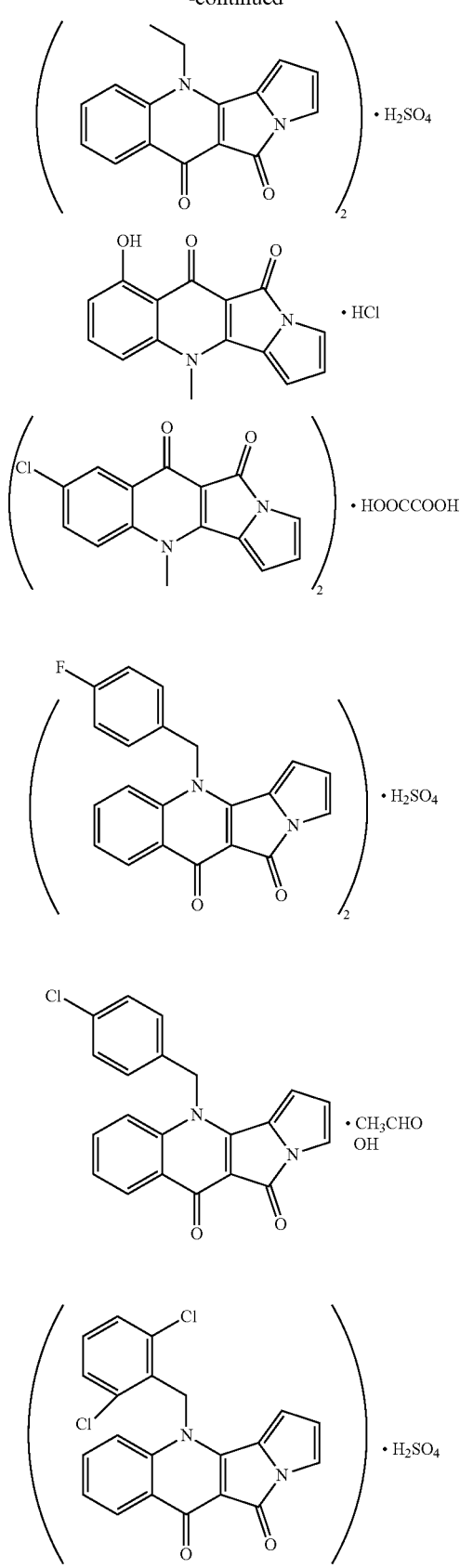

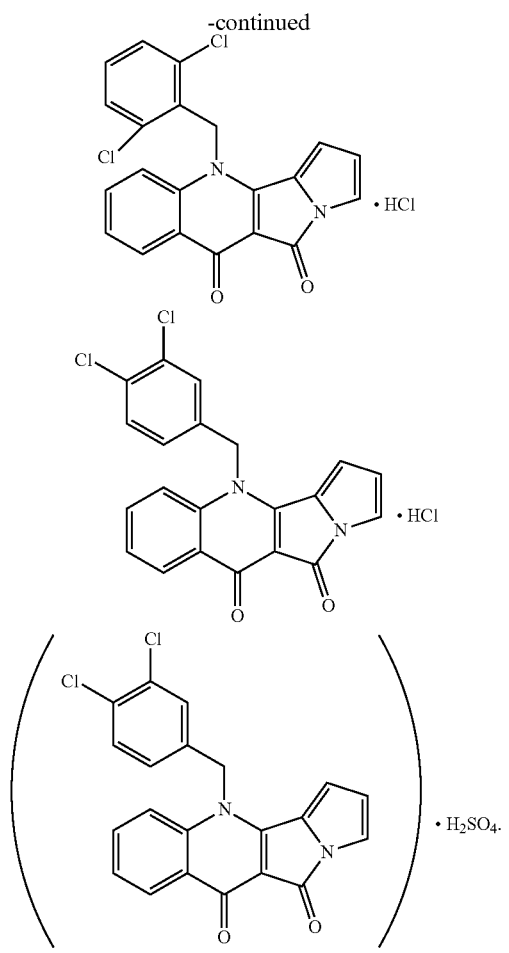

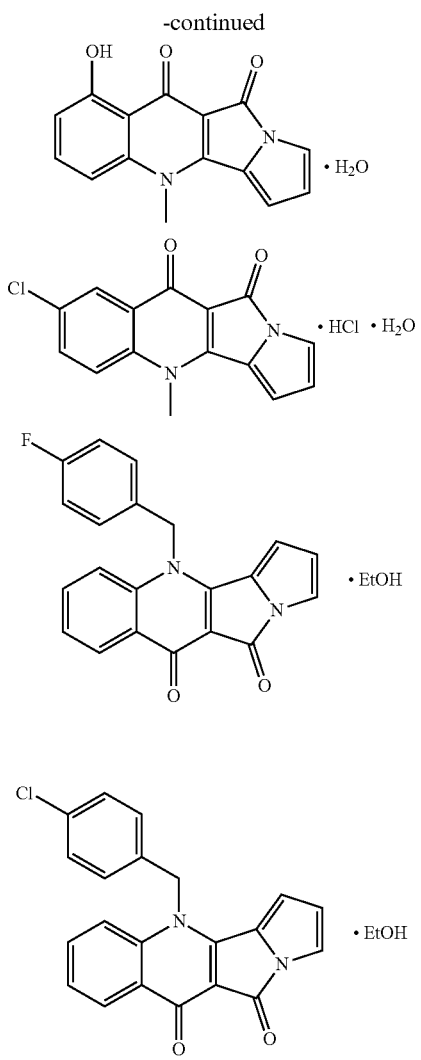

A "solvate" in the present disclosure refers to a complex formed by one or more solvent molecules with a compound disclosed herein. The solvents that form solvates comprise water, isopropanol, ethanol, methanol, DMSO, ethyl acetate, acetic acid, and ethanolamine. The term "hydrate" refers to the complex where the solvent molecule is water.

The solvate of some of the compounds or their salts depicted herein can be illustrated by the specific compounds listed below, but does not limit the present application:

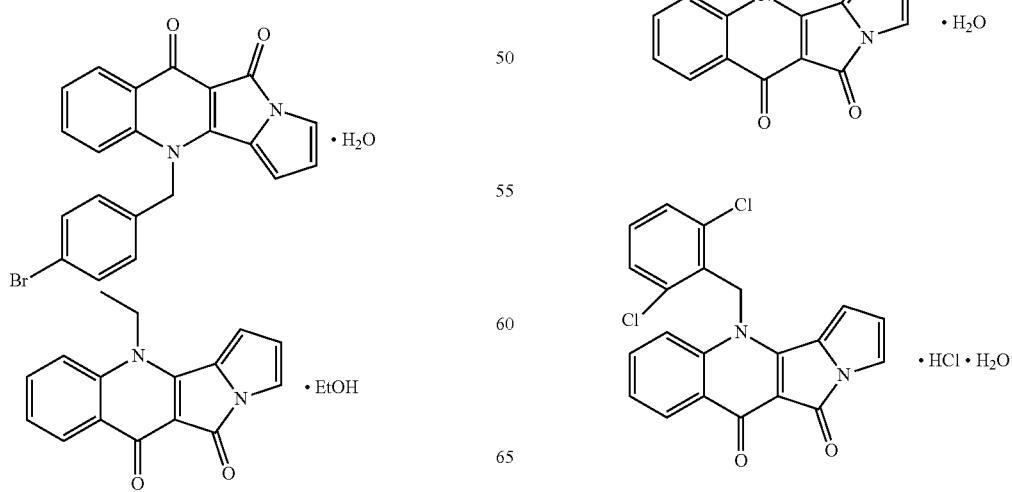

-continued

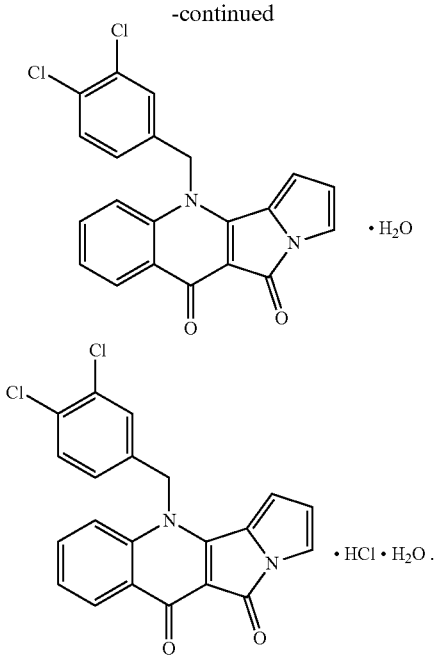

The present disclosure provides a use of a compound disclosed herein, or a pharmaceutically acceptable salt thereof, in the manufacture of a medicament for treating the various diseases caused by inflammation, immune system disorders in a patient, including those described herein. The present disclosure provides a pharmaceutical composition comprising a therapeutically effective amount of a compound of Formula I or II in association with at least one pharmaceutically acceptable carrier, excipient, diluent, adjuvant or vehicle.

The present disclosure also provides a method of treating the various diseases caused by inflammation, immune system disorders in a patient or susceptible to such disease, the method comprising treating the subject with a therapeutically effective amount of the compound of Formula I or II.

Unless otherwise stated, all stereoisomers, geometric isomers, tautomers, nitrogen oxides, hydrates, solvates, metabolites, salts, and pharmaceutically acceptable prodrugs of the compounds disclosed herein are within the scope of the disclosure.

In certain embodiments, the salt is a pharmaceutically acceptable salt. The term "pharmaceutically acceptable" refers to that the substance or composition must be compatible chemically and/or toxicologically, with the other ingredients comprising a Formulation, and/or the mammal being treated therewith.

The compounds disclosed herein also comprise salts of such compounds which are not necessarily pharmaceutically acceptable salts, and which may be useful as intermediates for preparing and/or purifying compounds of Formula I or II and/or for separating enantiomers of compounds of Formula I or II.

If the compound disclosed herein is a base, the desired salt may be prepared by any suitable method available in the art, for example, treatment of the free base with an inorganic acid, such as hydrochloric acid, hydrobromic acid, sulfuric acid, nitric acid, phosphoric acid, and the like. Or with an organic acid, such as acetic acid, maleic acid, succinic acid, mandelic acid, fumaric acid, malonic acid, pyruvic acid, oxalic acid, glycolic acid, salicylic acid; a pyranosidyl acid, such as glucuronic acid or galacturonic acid; an alpha hydroxy acid, such as citric acid or tartaric acid; an amino acid, such as aspartic acid or glutamic acid; an aromatic acid, such as benzoic acid or cinnamic acid, a sulfonic acid, such as p-toluenesulfonic acid or ethanesulfonic acid, and the like.

If the compound disclosed herein is an acid, the desired salt may be prepared by any suitable method, for example, treatment of the free acid with an inorganic or organic base, such as an amine (primary, secondary or tertiary), an alkali metal hydroxide or alkaline earth metal hydroxide, and the like. Some non-limiting examples of suitable salts comprise organic salts derived from amino acids, such as glycine and arginine, ammonia, primary, secondary, and tertiary amines, and cyclic amines, such as piperidine, morpholine and piperazine, and inorganic salts derived from sodium, calcium, potassium, magnesium, manganese, iron, copper, zinc, aluminum, lithium, and the like.

According to another aspect, the disclosure features pharmaceutical compositions that comprise a compound of Formula I or II, a compound listed herein, or a compound named in Examples 1-259, and a pharmaceutically acceptable carrier, adjuvant, or vehicle. The amount of the compound in the compositions disclosed herein is such that is effective to detectably treat or lessen the various diseases caused by inflammation, immune system disorders in a patient.

It will be also appreciated that the compounds disclosed herein can exist in free form for treatment, or where appropriate, as a pharmaceutically acceptable derivative thereof. Some non-limiting examples of the pharmaceutically acceptable derivative comprise pharmaceutically acceptable prodrugs, salts, esters, salts of such esters, or any other adducts or derivatives which upon administration to a patient in need is capable of providing, directly or indirectly, a compound as otherwise described herein, or a metabolite or residue thereof.

As described above, the pharmaceutically acceptable compositions disclosed herein additionally comprise a pharmaceutically acceptable carrier, adjuvant, or vehicle, which, as used herein, comprises any and all solvents, diluents, or other liquid vehicle, dispersion or suspension aids, surface active agents, isotonic agents, thickening or emulsifying agents, preservatives, solid binders, lubricants and the like, as suited to the particular dosage form desired. As described in the reference below: In Remington: The Science and Practice of Pharmacy, 21st edition, 2005, ed. D. B. Troy, Lippincott Williams & Wilkins, Philadelphia, and Encyclopedia of Pharmaceutical Technology, eds. J. Swarbrick and J. C. Boylan, 1988-1999, Marcel Dekker, New York, all of which are herein incorporated by reference in their entireties, are disclosed various carriers used in Formulating pharmaceutically acceptable compositions and known techniques for the preparation thereof. Except insofar as any conventional carrier medium is incompatible with the compounds disclosed herein, such as by producing any undesirable biological effect or otherwise interacting in a deleterious manner with any other component(s) of the pharmaceutically acceptable composition, its use is contemplated to be within the scope of this disclosure.

Some non-limiting examples of materials which can serve as pharmaceutically acceptable carriers comprise ion exchangers, alumina, aluminum stearate, lecithin, serum proteins, such as human serum albumin, buffer substances such as phosphates, glycine, sorbic acid, or potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrolidone, polyacrylates, waxes, polyethylene-polyoxypropylene-block polymers, wool fat, sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil, safflower oil, sesame oil, olive oil, corn oil and soybean oil; glycols such as propylene glycol or polyethylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants.

The compositions disclosed herein may be administered orally, parenterally, by inhalation spray, topically, rectally, nasally, buccally, vaginally or via an implanted reservoir. The compositions comprise orally administered in any orally acceptable dosage form including, but not limited to, capsules, tablets, pills, powders, granules, aqueous suspensions or solutions. The compositions can be orally administered in the following dosage forms: tablets, pellets, capsules, dispensable powders, particles or suspensions, syrup, and elixirs. Alternatively, the compositions disclosed herein can be for external use in the form of ointment, gel, or medicated patch, or they can be administered parenterally in the form of sterile injectable solution or suspension. The compounds disclosed herein may be administered parenterally or intraperitoneal. The compounds disclosed herein (as free bases pharmaceutically acceptable salt) may be formulated into solutions or suspensions in water suitably mixed with surfactant (e.g. hydroxypropyl cellulose, polyvinyl pyrrolidone). Dispersion can be also prepared from a mixture of the active compounds in glycerin, liquid, polyethylene glycol and oil. In the normal condition of storage and usage, these preparations may contain preservatives to prevent the growth of microorganisms.

The pharmaceutical forms suitable for injection comprise sterile water or dispersion and sterile powder (used for the temporary preparation of sterile injectable solutions or dispersions). In all the cases, these forms must be sterile, and they must be fluid to allow their discharge from the injection syringe. These forms must be stable in the condition of production and storage, and they must prevent from the pollution of microorganisms (such as bacteria and fungi). The carriers may be solvents or dispersion media, including, for example, water, alcohols (such as glycerin, propylene glycol and liquid polyethylene glycol), plant oil and combinations thereof.

The compounds disclosed herein can be administered in a local rather than systemic manner, for example, via injection of the compound directly into organ, often in a depot or sustained release formulation. Furthermore, the pharmaceutical composition comprising a compound disclosed herein can be administered in a targeted drug delivery system, for example, in a liposome coated with organ-specific antibody. The liposomes may target to and be taken up selectively by the organ. In addition, the pharmaceutical compositions comprising a compound disclosed herein may be provided in the form of a rapid release formulation, in the form of an extended release formulation, or in the form of an intermediate release formulation For administration by inhalation, the compounds disclosed herein may be in a form as an aerosol, a mist or a powder. The pharmaceutical compound disclosed herein may be conveniently delivered in the form of an aerosol spray presentation from pressurized packs or a nebulizer, with the use of a suitable propellant, e.g., lorodifluoromethane, trichlorofluoromethane, dichlorotetrafluoroethane. carbon dioxide or other suitable gas. In the case of a pressurized aerosol, the dosage unit may be determined by providing a value to deliver a metered amount. Capsules and cartridges, such as, by way of example only, gelatin for use in an inhaler or insufflators maybe formulated containing a powder mix of the compound disclosed herein and a suitable powder base such as lactose or starch.

The compounds disclosed herein may be also formulated in rectal compositions such as enemas, rectal gels, rectal foams, rectal aerosol, suppositories, gel suppositories, or retention enemas, containing conventional suppository bases such as cocoa butter or other glycerides, as well as any synthetic polymers suitable for preparing suppository bases such as polyvinylpyrrolidone, PEG, and the like. In suppository forms of the compositions, a low-melting wax such as, but not limited to, a mixture of fatty acid glycerides, optionally in combination with cocoa butter is first melted.

Additionally, the compound disclosed herein may be used in combination with other agents of treating inflammation, fibrosis, such as, but not limited to, azathioprine, cyclophosphamide, prednisone, prednisolone, aspirin, acetaminophen, indomethacin, naproxen, naproxen, diclofenac, ibuprofen, nimesulide, rofecoxib, celecoxib, levamisole, interleukin, interferon, transfer factor, thymosin, anti-lymphocyte globulin, cyclosporine, mycophenolate mofetil, and the like.

The pharmaceutical compositions disclosed herein may be formulated in conventional manner using one or more physiologically acceptable carriers comprising excipients and auxiliaries which facilitate processing of the active compounds into preparations which may be used pharmaceutically. Proper formulation is dependent upon the route of administration chosen. Any of the well-known techniques, carriers, and excipients may be used as suitable and as understood in the art. The pharmaceutical compositions comprising a compound disclosed herein may be manufactured by a conventional method, such as by means of conventional mixing, dissolving, granulating, dragee-making, levigating, emulsifying, encapsulating, entrapping, or compression processes.

The pharmaceutical compositions disclosed herein comprise at least one pharmaceutically acceptable carrier, diluent or excipient and a compound disclosed herein as an active ingredient in free-acid or free-base form, or in a pharmaceutically acceptable salt form. In addition, the pharmaceutical compositions disclosed herein comprise other medicinal or pharmaceutical agents, carriers, adjuvants, such as preserving, stabilizing, wetting or emulsifying agents, solution promoters, salts for regulating the osmotic pressure, and/or buffers. In addition, the pharmaceutical compositions contain other therapeutically valuable substances.

Methods for the preparation of the pharmaceutical compositions disclosed herein comprise formulating the compounds disclosed herein with one or more inert, pharmaceutically acceptable excipients or carriers to form a solid, semi-solid or liquid. Some non-limiting examples of solid compositions comprise powders, tablets, dispersible granules, capsules, cachets, and suppositories. Some non-limiting examples of liquid compositions comprise solutions in which a compound is dissolved, emulsions comprising a compound, or a solution containing liposomes, micelles, or nanoparticles comprising a compound as disclosed herein. Some non-limiting examples of semi-solid compositions comprise gels, suspensions and creams. The compositions may be in liquid solutions or suspensions, solid forms suitable for solution or suspension in a liquid prior to use, or as emulsions. The pharmaceutical compositions disclosed herein may also contain minor amounts of nontoxic, auxiliary substances, such as wetting or emulsifying agents, pH buffering agents, and so forth.

The compounds disclosed herein are preferably formulated in dosage unit form for ease of administration and uniformity of dosage. The expression "dosage unit form" refers to a physically discrete unit of agent appropriate for the patient to be treated. It will be understood, however, that the total daily usage of the compounds and compositions disclosed herein will be decided by the attending physician within the scope of sound medical judgment. The specific effective dose level for any particular patient or organism will depend upon a variety of factors including the disorder being treated and the severity of the disorder; the activity of the specific compound employed; the specific composition employed; the age, body weight, general health, gender and diet of the patient; the time of administration, route of administration, and rate of excretion of the specific compound employed; the duration of the treatment; drugs used in combination or coincidental with the specific compound employed, and like factors well known in the medical arts.

The selective biological properties of the compounds may be enhanced through being modified by additional appropriate functional groups. Such modification is known in the field herein and comprises the modification of penetrate to biological cavities (such as blood, lymphatic system, central nervous system), improves oral effectiveness and improves the solubility so that it can be administered by injection, alter metabolism and change the excretion.

DETAILED DESCRIPTION OF EMBODIMENTS

The following specific examples are intended to further illustrate the application, but the application is in no way limited to these examples. (All materials used are commercially available unless otherwise stated).

For ethyl 4-oxo-2-(1H-pyrrol-2-yl)-1,4-dihydroquinoline-3-carboxylate

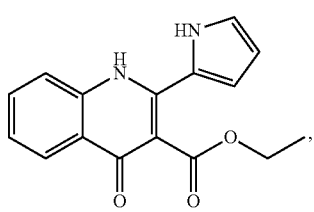

the synthetic route is as follows:

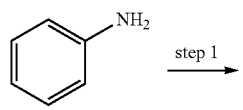

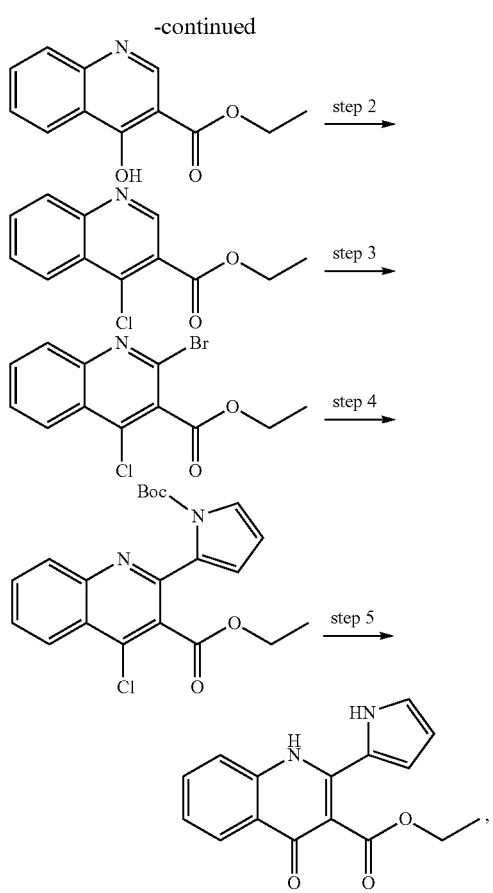

the specific implementation steps are as follows:

Step 1) Ethyl 4-hydroxyquinoline-3-carboxylate

Aniline (1.0 mL) and diethyl ethoxymethanemalonate (2.2 mL) were added to an appropriate amount of ethanol, heated to reflux for three hours, and cooled to room temperature. Then, 40 mL of phenyl ether was added, and the mixture was refluxed for 1 hour. The mixture was cooled to room temperature. After the reaction was completed, ice water was added, the mixture was extracted with ethyl acetate (100 mL×2) and the organic phases were combined. The combined organic phases were washed with brine, dried with anhydrous sodium sulfate, filtered, and concentrated. The residue was purified by silica gel column chromatography to give the product 1.6 g (69% yield).

Step 2) Ethyl 4-chloroquinoline-3-carboxylate

Ethyl 4-hydroxy-2-hydro-quinoline-3-carboxylate (2.0 g) was dissolved in an appropriate amount of dioxane, and then mixed with phosphorus oxychloride (0.68 mL), and heated under reflux for 1 hour. After the reaction was completed, the reaction solution was poured into ice water, extracted with ethyl acetate (100 mL×2) and the organic phases were combined. The combined organic phases were washed with brine, dried with anhydrous sodium sulfate, filtered, and concentrated. The residue was purified by silica gel column chromatography to give a white solid (63% yield).

Step 3) Ethyl 2-bromo-4-chloroquinoline-3-carboxylate

Ethyl 4-chloroquinoline-3-carboxylate (1.0 g) was dissolved in an appropriate amount of chloroform, and benzoic acid (1.4 g) was added at room temperature, followed by stirring at room temperature for four hours. Phosphorus tribromide (2.0 g) was added to the reaction mixture, followed by stirring for 1 hour. After the reaction was completed, the reaction solution was poured into ice water, adjusted to pH=7 with a saturated aqueous solution of potassium carbonate, extracted with ethyl acetate (100 mL×2) and the organic phases were combined. The organic phases were washed with brine, dried with anhydrous sodium sulfate, filtered, and concentrated. The residue was purified by silica gel column chromatography to give a white solid (61% yield).

Step 4) Ethyl 2-(1-(tert-butoxycarbonyl)-1H-pyrrol-2-yl)-4-chloroquinoline-3-carboxylate Ethyl 2-bromo-4-chloroquinoline-3-carboxylate (1.0 g) and (1-(tert-butoxycarbonyl)-1H-pyrrol-2-yl)boronic acid (0.6 g) were dissolved in an appropriate amount of 1,4-dioxane, cesium carbonate (4.0 g) and palladium acetate (360 mg) were added thereto. The reaction solution was stirred at a high temperature for 3 hours. After the reaction was completed, the reaction solution was poured into ice water, extracted with ethyl acetate (100 mL×2) and the organic phases were combined. The combined organic phases were washed with brine, dried with anhydrous sodium sulfate, filtered, and concentrated. The residue was purified by silica gel column chromatography (EtOAc:PET=1:30) to give a colorless oil (64% yield).

Step 5) Ethyl 4-oxo-2-(1H-pyrrol-2-yl)-1,4-dihydro-quinoline-3-carboxylate

Ethyl 2-(1-(tert-butoxycarbonyl)-H-pyrrol-2-yl)-4-chloroquinoline-3-carboxylate (600 mg) is dissolved in an appropriate amount of acetic acid, ethanol and water, and then heated to about 70° C. The reaction was continued for 16 hours. The acetic acid and ethanol were distilled off under reduced pressure, and the obtained residue was diluted with water and adjusted to slightly alkaline with saturated potassium carbonate solution, then extracted with ethyl acetate (100 mL×2) and the organic phases were combined. The combined organic phases were washed with brine, dried with anhydrous sodium sulfate, filtered, and concentrated. The residue was purified by silica gel column chromatography to give a pale yellow solid (58% yield).

Only the original raw material aniline was sequentially changed to 4-fluoroaniline, 4-chloroaniline, 4-bromoaniline, 3-bromoaniline, 3-chloro-4-fluoroaniline, 3,4-dichloroaniline, 4-bromo-3-chloroaniline, according to the same reaction conditions and procedures can be obtained the corresponding intermediate:
ethyl-6-fluoro-4-oxo-2-(1H-pyrrol-2-yl)-1,4-dihydroquinoline-3-carboxylate,
ethyl-6-chloro-4-oxo-2-(1H-pyrrol-2-yl)-1,4-dihydroquinoline-3-carboxylate,
ethyl-6-bromo-4-oxo-2-(1H-pyrrol-2-yl)-1,4-dihydroquinoline-3-carboxylate,
ethyl-7-bromo-4-oxo-2-(1H-pyrrol-2-yl)-1,4-dihydroquinoline-3-carboxylate,
ethyl-7-bromo-6-fluoro-4-oxo-2-(1H-pyrrol-2-yl)-1,4-dihydroquinoline-3-carboxylate,
ethyl-7-bromo-6-chloro-4-oxo-2-(1H-pyrrol-2-yl)-1,4-dihydroquinoline-3-carboxylate,
ethyl-6,7-dibromo-4-oxo-2-(1H-pyrrol-2-yl)-1,4-dihydroquinoline-3-carboxylate.

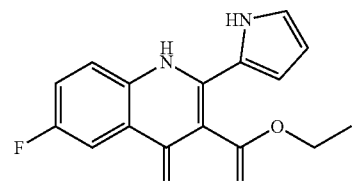

ethyl 6-fluoro-4-oxo-2-(1H-pyrrol-2-yl)-1,4-dihydroquinoline-3-carboxylate

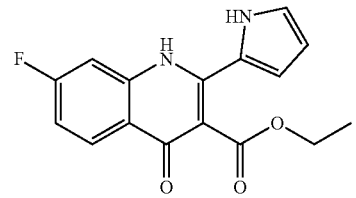

ethyl 7-fluoro-4-oxo-2-(1H-pyrrol-2-yl)-1,4-dihydroquinoline-3-carboxylate

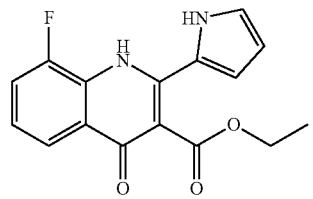

ethyl 8-fluoro-4-oxo-2-(1H-pyrrol-2-yl)-1,4-dihydroquinoline-3-carboxylate

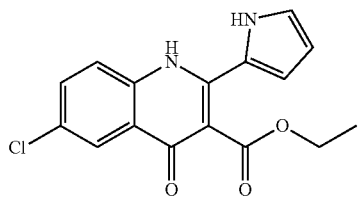

ethyl 6-chloro-4-oxo-2-(1H-pyrrol-2-yl)-1,4-dihydroquinoline-3-carboxylate

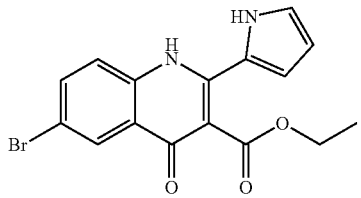

ethyl 6-bromo-4-oxo-2-(1H-pyrrol-2-yl)-1,4-dihydroquinoline-3-carboxylate

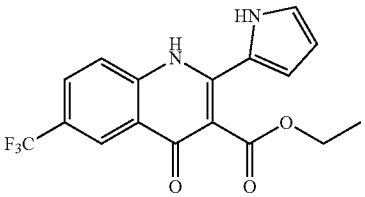

ethyl 4-oxo-2-(1H-pyrrol-2-yl)-7-(trifluoromethyl)-1,4-dihydroquinoline-3-carboxylate

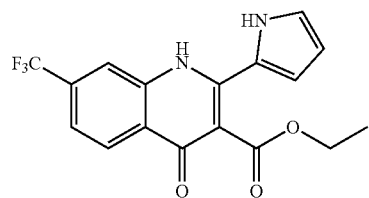

ethyl 4-oxo-2-(1H-pyrrol-2-yl)-6-
(trifluoromethyl)-1,4-
dihydroquinoline-3-carboxylate

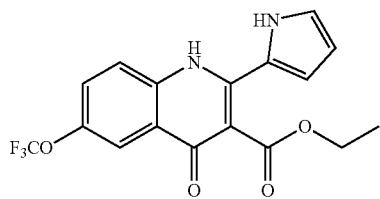

ethyl 4-oxo-2-(1H-pyrrol-2-yl)-6-
(trifluoromethoxy)-1,4-
dihydroquinoline-3-carboxylate

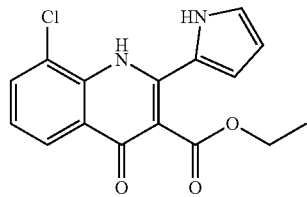

ethyl 8-chloro-4-oxo-2-(1H-pyrrol-2-
yl)-1,4-dihydroquinoline-3-
carboxylate

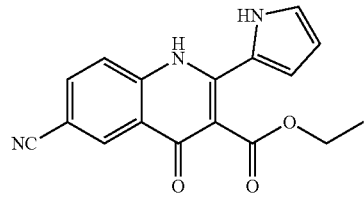

ethyl 6-cyano-4-oxo-2-
(1H-pyrrol-2-yl)-1,4-
dihydroquinoline-3-carboxylate

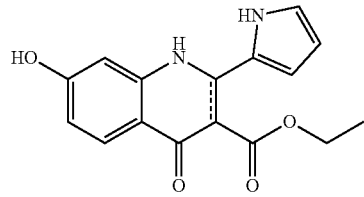

ethyl 7-hydroxyl-4-oxo-2-
(1H-pyrrol-2-yl)-1,4-
dihydroquinoline-3-carboxylate

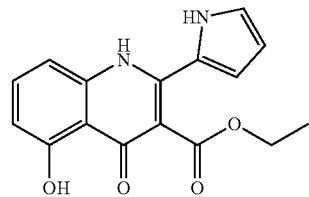

ethyl 5-hydroxyl-4-oxo-2-
(1H-pyrrol-2-yl)-1,4-
dihydroquinoline-3-carboxylate

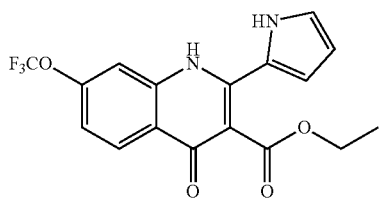

ethyl 4-oxo-2-(1H-pyrrol-2-yl)-7-
(trifluoromethoxy)-1,4-
dihydroquinoline-3-carboxylate

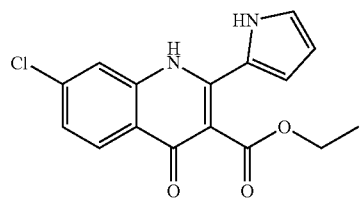

ethyl 7-chloro-4-oxo-2-(1H-pyrrol-
2-yl)-1,4-dihydroquinoline-
3-carboxylate

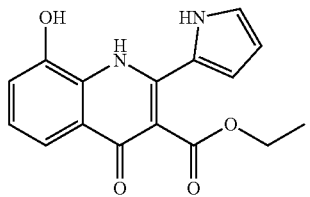

ethyl 8-hydroxy-4-oxo-2-(1H-pyrrol-
2-yl)-1,4-dihydroquinoline-
3-carboxylate

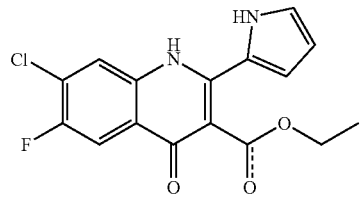

ethyl 7-chloro-6-fluoro-4-oxo-2-
(1H-pyrrol-2-yl)-1,4-dihydroquinoline-
3-carboxylate

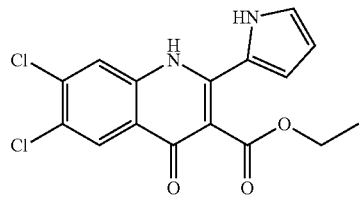

ethyl 6,7-dichloro-4-oxo-2-
(1H-pyrrol-2-yl)-1,4-
dihydroquinoline-3-carboxylate

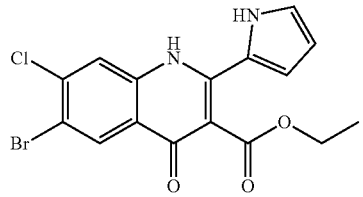

ethyl 6-bromo-7-chloro-4-oxo-2-
(1H-pyrrol-2-yl)-1,4-
dihydroquinoline-3-carboxylate -continued

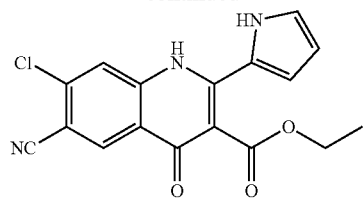

ethyl 7-chloro-6-cyano-4-oxo-2-(1H-
pyrrol-2-yl)-1,4-dihydroquinoline-
3-carboxylate

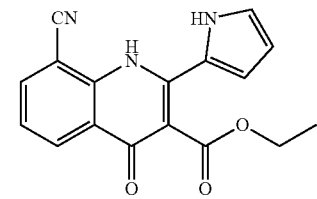

ethyl 8-cyano-4-oxo-2-(1H-
pyrrol-2-yl)-1,4-dihydroquinoline-
3-carboxylate

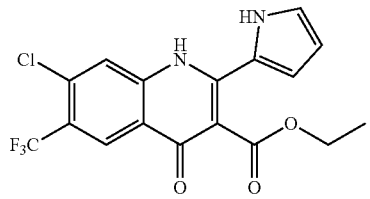

ethyl 7-chloro-4-oxo-2-(1H-
pyrrol-2-yl)-6-(trifluoromethyl)-
1,4-dihydroquinoline-
3-carboxylate

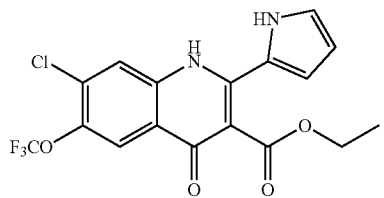

ethyl 7-chloro-4-oxo-2-(1H-
pyrrol-2-yl)-6-(trifluoromethoxy)-
1,4-dihydroquinoline-
3-carboxylate

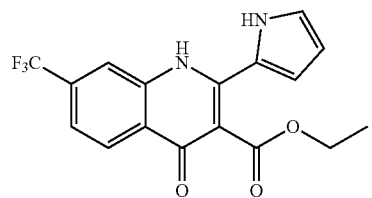

ethyl 4-oxo-2-(1H-pyrrol-2-yl)-7-
(trifluoromethyl)-1,4-dihydroquinoline-
3-carboxylate

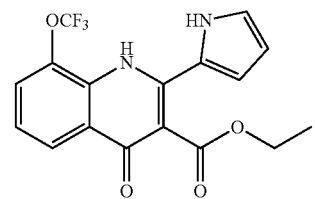

ethyl 4-oxo-2-(1H-pyrrol-2-yl)-
8-(trifluoromethoxy)-1,4-
dihydroquinoline-
3-carboxylate -continued

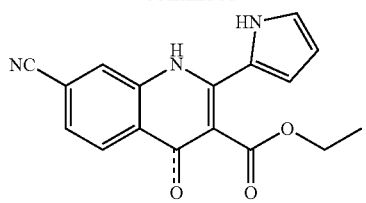

ethyl 7-cyano-4-oxo-2-(1H-pyrrol-
2-yl)-1,4-dihydroquinoline-3-
carboxylate

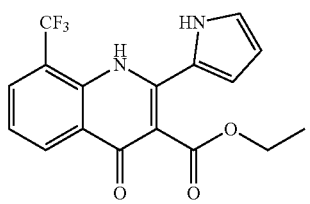

ethyl 4-oxo-2-(1H-pyrrol-
2-yl)-8-(trifluoromethyl)-1,4-
dihydroquinoline-3-
carboxylate

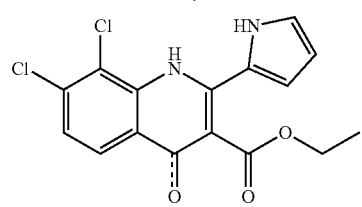

ethyl 7,8-dichloro-4-oxo-2-(1H-pyrrol-
2-yl)-1,4-dihydroquinoline-3-
carboxylate

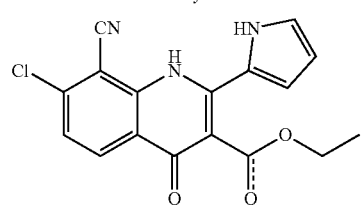

ethyl 7-chloro-8-cyano-4-oxo-2-
(1H-pyrrol-2-yl)-1,4-
dihydroquinoline-3-carboxylate

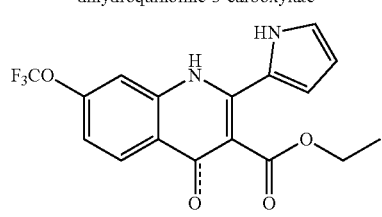

ethyl 4-oxo-2-(1H-pyrrol-2-yl)-7-
(trifluoromethoxy)-1,4-
dihydroquinoline-3-
carboxylate

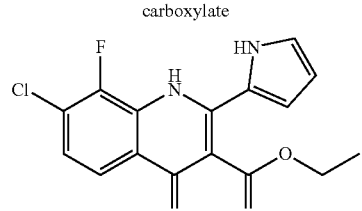

ethyl 7-chloro-8-fluoro-4-oxo-2-
(1H-pyrrol-2-yl)-1,4-
dihydroquinoline-3-carboxylate -continued

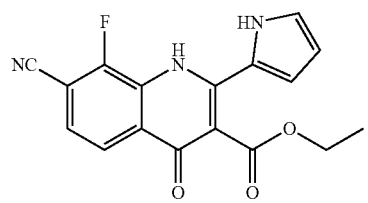

ethyl 7-cyano-8-fluoro-4-oxo-2-
(1H-pyrrol-2-yl)-1,4-
dihydroquinoline-3-carboxylate

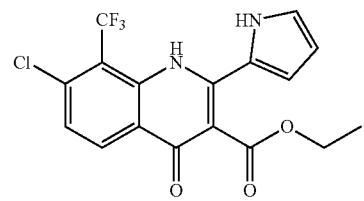

ethyl 7-chloro-4-oxo-2-
(1H-pyrrol-2-yl)-8-(trifluoromethyl)-1,4-
dihydroquinoline-3-carboxylate

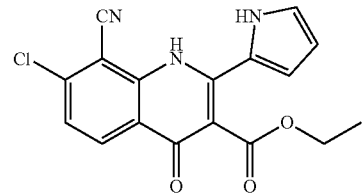

ethyl 7-chloro-8-cyano-4-oxo-2-
(1H-pyrrol-2-yl)-1,4-
dihydroquinoline-3-carboxylate

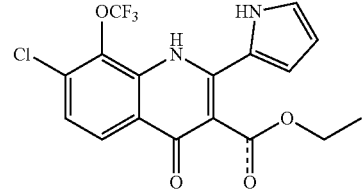

ethyl 7-chloro-4-oxo-2-
(1H-pyrrol-2-yl)-8-(trifluoromethoxy)-
1,4-dihydroquinoline-3-carboxylate

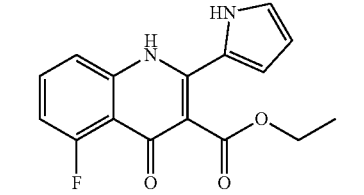

ethyl 5-fluoro-4-oxo-2-
(1H-pyrrol-2-yl)-1,4-
dihydroquinoline-3-carboxylate

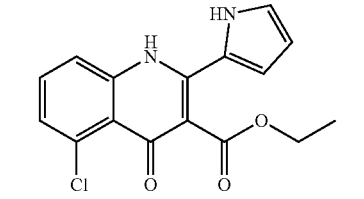

ethyl 5-chloro-4-oxo-2-
(1H-pyrrol-2-yl)-1,4-
dihydroquinoline-3-carboxylate

-continued

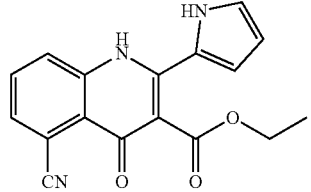

ethyl 5-cyano-4-oxo-2-
(1H-pyrrol-2-yl)-1,4-
dihydroquinoline-3-carboxylate

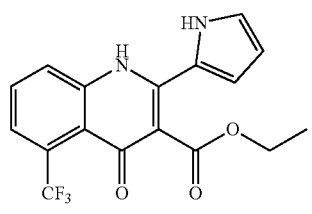

ethyl 4-oxo-2-
(1H-pyrrol-2-yl)-5-(trifluoromethyl)-1,4-
dihydroquinoline-3-carboxylate

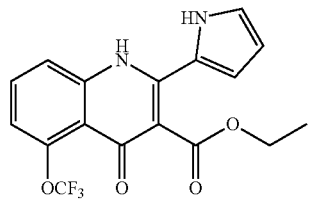

ethyl 4-oxo-2-
(1H-pyrrol-2-yl)-5-(trifluoromethoxy)-
1,4-dihydroquinoline-3-carboxylate

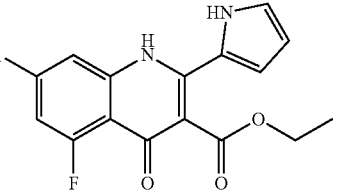

ethyl 7-chloro-5-fluoro-4-oxo-2-
(1H-pyrrol-2-yl)-1,4-
dihydroquinoline-3-carboxylate These intermediates and equivalent bromination reagents are obtained in the presence of potassium carbonate in acetonitrile or acetone at 50° C. to give the tetracyclic quinolinone derivatives and their enol isomer derivatives (the products obtained without bromination reagents are tetracyclic quinolinone derivatives and enol isomer derivatives thereof, in which $R_5$ is hydrogen.)

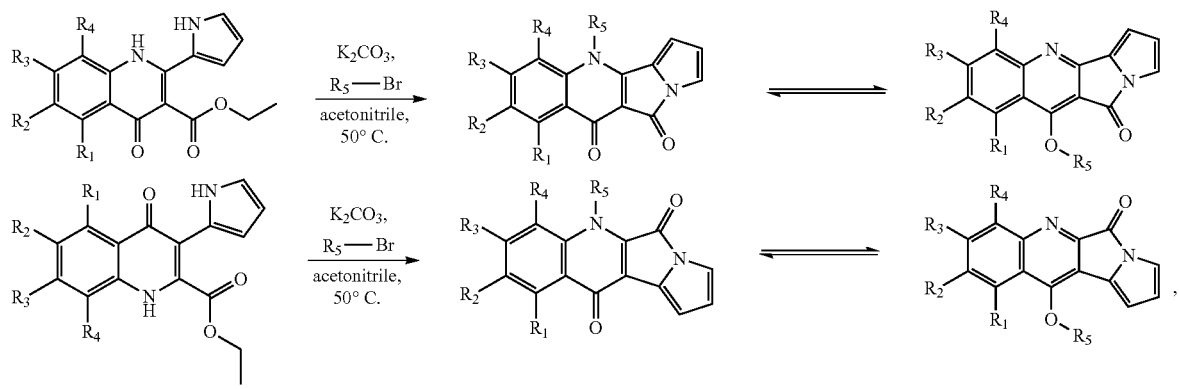

wherein $R_1$, $R_2$, $R_3$, $R_4$, $R_5$ have the same definition with any of the above aspects of $R_1$, $R_2$, $R_3$, $R_4$, $R_5$ in the present disclosure.

Example 1

4-Isopropyl-9H-pyrrolizino[1,2-b]quinoline-9,10(4H)-dione (Compound 5a) and its isomer 9-isopropoxy-10H-pyrrolizino[1,2-b]quinolin-10-one (Compound 5b)

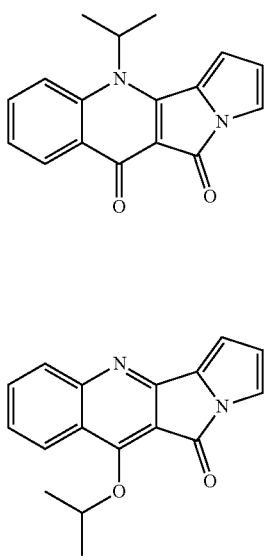

Steps: Ethyl 4-oxo-2-(1H-pyrrol-2-yl)-1,4-dihydroquinoline-3-carboxylate (50 mg) and potassium carbonate (10 mg) were dissolved in an appropriate amount of acetonitrile. The mixture was stirred at a high temperature for 10 h, and then 1-(bromomethyl)-4-methylbenzene (46 mg) was added. After the reaction was completed, the reaction mixture was poured into ice water, and the pH was adjusted to neutral with dilute aqueous hydrochloric acid, extracted with ethyl acetate (50 mL×2), and the organic phases were combined. The combined organic phases were evaporated, washed with brine, dried with anhydrous sodium sulfate, filtered, and concentrated. The residue was purified by silica gel column chromatography to give the products as yellow solids (35% and 30% yields). ESI-MS m/z 279.11 [M+H]$^+$.

Example 2

4-Allyl-9H-pyrrolizino[1,2-b]quinoline-9,10(4H)-dione (Compound 6a) and its isomer 9-(allyloxy)-10H-pyrrolizino[1,2-b]quinolin-10-one (Compound 6b)

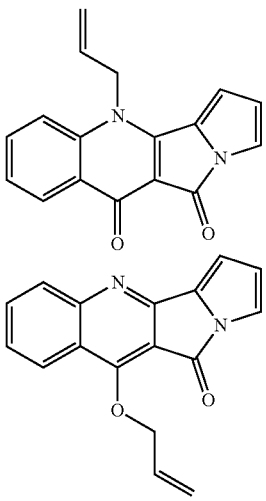

Steps: Following the procedure of Example 1, ethyl 4-oxo-2-(1H-pyrrol-2-yl)-1,4-dihydroquinoline-3-carboxylate (50 mg) and 3-bromopropyl-1-ene (46 mg) were subjected to reaction and post-treatment to give yellow solids (39% and 30% yields). ESI-MS m/z 277.09[M+H]$^+$.

Example 3

4-Isopentyl-9H-pyrrolizino[1,2-b]quinoline-9,10(4H)-dione (Compound 8a) and its isomer 9-(isopentyloxy)-10H-pyrrolizino[1,2-b]quinolin-10-one (Compound 8b)

Steps: Following the procedure of Example 1, ethyl 4-oxo-2-(1H-pyrrol-2-yl)-1,4-dihydroquinoline-3-carboxylate (50 mg) and 1-bromo-3-methylbutane (46 mg) were subjected to reaction and post-treatment to give yellow solids (35% and 30% yields). ESI-MS m/z 379.06 [M+H]$^+$.

Example 4

4-(3-Methylbut-2-en-1-yl)-9H-pyrrolizino[1,2-b]quinoline-9,10(4H)-dione (Compound 9a) and its isomer 9-((3-methylbut-2-en-1-yl)oxy)-10H-pyrrolizino[1,2-b]quinolin-10-one (Compound 9b)

Steps: Following the procedure of Example 1, ethyl 4-oxo-2-(1H-pyrrol-2-yl)-1,4-dihydroquinoline-3-carboxylate (50 mg) and 1-bromo-3-methylbut-2-ene (46 mg) were subjected to reaction and post-treatment to give yellow solids (34% and 30% yields). ESI-MS m/z 305.12 [M+H]$^+$.

Example 5

4-(2-Hydroxyethyl)-9H-pyrrolizino[1,2-b]quinoline-9,10(4H)-dione (Compound 11a) and its isomer 9-(2-hydroxyethoxy)-10H-pyrrolizino[1,2-b]quinolin-10-one (Compound 11b)

Steps: Following the procedure of Example 1, ethyl 4-oxo-2-(1H-pyrrol-2-yl)-1,4-dihydroquinoline-3-carboxylate (50 mg) and 2-bromoethan-1-ol (46 mg) were subjected to reaction and post-treatment to give yellow solids (32% and 30% yields). ESI-MS m/z 280.08 [M+H]$^+$.

Example 6

4-(4-Fluorophenyl)-9H-pyrrolizino[1,2-b]quinoline-9,10(4H)-dione (Compound 18a) and its isomer 9-(4-fluorophenoxy)-10H-pyrrolizino[1,2-b]quinolin-10-one (Compound 18b)

Steps: Following the procedure of Example 1, ethyl 4-oxo-2-(1H-pyrrol-2-yl)-1,4-dihydroquinoline-3-carboxylate (50 mg) and 1-bromo-4-fluorobenzene (46 mg) were subjected to reaction and post-treatment to give yellow solids (32% and 30% yields). ESI-MS m/z 330.08 [M+H]$^+$.

Example 7

4-(4-Chlorophenyl)-9H-pyrrolizino[1,2-b]quinoline-9,10(4H)-dione (Compound 34a) and its isomer 9-(4-chlorophenoxy)-10H-pyrrolizino[1,2-b]quinolin-10-one (Compound 34b)

Steps: Following the procedure of Example 1, ethyl 4-oxo-2-(1H-pyrrol-2-yl)-1,4-dihydroquinoline-3-carboxylate (50 mg) and 1-bromo-4-chlorobenzene (46 mg) were subjected to reaction and post-treatment to give yellow solids (50% and 30% yields). ESI-MS m/z 346.05 [M+H]$^+$, 348.05 [M+2+H]$^+$.

Example 8

4-(2-([1,1'-Biphenyl]-4-yl)-2-oxoethyl)-9H-pyrrolizino[1,2-b]quinoline-9,10(4H)-dione (Compound 50a) and its isomer 9-(2-([1,1'-biphenyl]-4-yl)-2-oxoethoxy)-10H-pyrrolizino[1,2-b]quinolin-10-one (Compound 50b)

Steps: Following the procedure of Example 1, ethyl 4-oxo-2-(1H-pyrrol-2-yl)-1,4-dihydroquinoline-3-carboxylate (50 mg) and 1-([1,1'-biphenyl]-4-yl)-2-bromoethan-1-one (46 mg) were subjected to reaction and post-treatment to give yellow solids (32% and 30% yields). ESI-MS m/z 430.13 [M+H]$^+$.

Example 9

4-(4-Bromophenyl)-9H-pyrrolizino[1,2-b]quinoline-9,10(4H)-dione (Compound 64a) and its isomer 9-(4-bromophenoxy)-10H-pyrrolizino[1,2-b]quinolin-10-one (Compound 64b)

Steps: Following the procedure of Example 1, ethyl 4-oxo-2-(1H-pyrrol-2-yl)-1,4-dihydroquinoline-3-carboxylate (50 mg) and 1-bromo-4-bromobenzene (46 mg) were subjected to reaction and post-treatment to give yellow solids (45% and 32% yields). ESI-MS m/z 390.00 [M+H]$^+$, 392.00 [M+2+H]$^+$.

Example 10

4'-((9,10-Dioxo-9H-pyrrolizino[1,2-b]quinolin-4(10H)-yl)methyl)-[1,1'-biphenyl]-2-carboxylic acid (Compound 81a) and its isomer 4'-(((10-oxo-10H-pyrrolizino[1,2-b]quinolin-9-yl)oxy)methyl)-[1,1'-biphenyl]-2-carboxylic acid (Compound 81b)

Steps: Following the procedure of Example 1, ethyl 4-oxo-2-(1H-pyrrol-2-yl)-1,4-dihydroquinoline-3-carboxylate (50 mg) and 4'-(bromomethyl)-[1,1'-biphenyl]-2-carboxylic acid (15 mg) were subjected to reaction and post-treatment to give yellow solids (27% and 25% yields). ESI-MS m/z 447.13 [M+H]$^+$.

Example 11

4-(2-(4-Chlorophenyl)-2-oxoethyl)-9H-pyrrolizino[1,2-b]quinoline-9,10(4H)-dione (Compound 90a) and its isomer 9-(2-(4-chlorophenyl)-2-oxoethoxy)-10H-pyrrolizino[1,2-b]quinolin-10-one (Compound 90b)

Steps: Following the procedure of Example 1, ethyl 4-oxo-2-(1H-pyrrol-2-yl)-1,4-dihydroquinoline-3-carboxylate (50 mg) and 2-bromo-1-(4-chlorophenyl)ethan-1-one (46 mg) were subjected to reaction and post-treatment to give yellow solids (32% and 27% yields). ESI-MS m/z 388.06 [M+H]$^+$, 390.06 [M+2+H]$^+$.

Example 12

4-(2-Oxo-2-(4-(trifluoromethyl)phenyl)ethyl)-9H-pyrrolizino[1,2-b]quinoline-9,10(4)-dione (Compound 91a) and its isomer 9-(2-oxo-2-(4-(trifluoromethyl)phenyl)ethoxy)-10H-pyrrolizino[1,2-b]quinolin-10-one (Compound 91b)

Steps: Following the procedure of Example 1, ethyl 4-oxo-2-(1H-pyrrol-2-yl)-1,4-dihydroquinoline-3-carboxylate (50 mg) and 2-bromo-1-(4-(trifluoromethyl)phenyl)ethan-1-one (15 mg) were subjected to reaction and post-treatment to give yellow solids (28% and 27% yields). ESI-MS m/z 423.09 [M+H]$^+$.

Example 13

4-(Furan-2-carbonyl)-9H-pyrrolizino[1,2-b]quinoline-9,10(4H)-dione (Compound 95a) and its isomer 10-oxo-10H-pyrrolizino[1,2-b]quinolin-9-yl furan-2-carboxylate (Compound 95b)

Steps: Following the procedure of Example 1, ethyl 4-oxo-2-(1H-pyrrol-2-yl)-1,4-dihydroquinoline-3-carboxylate (50 mg) and furan-2-carbonyl chloride (15 mg) were subjected to reaction and post-treatment to give yellow solids (34% and 35% yields). ESI-MS m/z 331.06 [M+H]⁺.

Example 14

2-(9,10-Dioxo-9H-pyrrolizino[1,2-b]quinolin-4 (10H)-yl)acetic acid (Compound 100a) and its isomer 2-((10-oxo-10H-pyrrolizino[1,2-b]quinolin-9-yl)oxy)acetic acid (Compound 100b)

Steps: Following the procedure of Example 1, ethyl 4-oxo-2-(1H-pyrrol-2-yl)-1,4-dihydroquinoline-3-carboxylate (50 mg) and 2-bromoacetic acid (15 mg) were subjected to reaction and post-treatment to give yellow solids (30% and 35% yields). ESI-MS m/z 295.06[M+H]⁺.

Example 15

4-Benzyl-9H-pyrrolizino[1,2-b]quinoline-9,10(4H)-dione (Compound 103a) and its isomer 9-(benzyloxy)-10H-pyrrolizino[1,2-b]quinolin-10-one (Compound 103b)

Steps: Following the procedure of Example 1, ethyl 4-oxo-2-(1H-pyrrol-2-yl)-1,4-dihydroquinoline-3-carboxylate (50 mg) and benzyl bromide (15 mg) were subjected to reaction and post-treatment to give yellow solids (35% and 35% yields). ESI-MS m/z 326.11 [M+H]⁺.

Example 16

4-Ethyl-7-fluoro-9H-pyrrolizino[1,2-b]quinoline-9,10(4H)-dione (Compound 104a) and its isomer 9-ethoxy-7-fluoro-10H-pyrrolizino[1,2-b]quinolin-10-one (Compound 104b)

Steps: Following the procedure of Example 1, ethyl 6-fluoro-4-oxo-2-(1H-pyrrol-2-yl)-1,4-dihydroquinoline-3-carboxylate (50 mg) and bromoethane (5 mg) were subjected to reaction and post-treatment to give yellow solids (40% and 35% yields). ESI-MS m/z 283.08 [M+H].

Example 17

7-Fluoro-4-isopentyl-9H-pyrrolizino[1,2-b]quinoline-9,10(4H)-dione (Compound 105a) and its isomer 7-fluoro-9-(isopentyloxy)-10H-pyrrolizino[1,2-b]quinolin-10-one (Compound 105b)

Steps: Following the procedure of Example 1, ethyl 6-fluoro-4-oxo-2-(1H-pyrrol-2-yl)-1,4-dihydroquinoline-3-carboxylate (50 mg) and 1-bromo-3-methylbutane (9 mg) were subjected to reaction and post-treatment to give yellow solids (30% and 55% yields). ESI-MS m/z 325.13 [M+H]⁺.

Example 18

7-Fluoro-4-isopropyl-9H-pyrrolizino[1,2-b]quinoline-9,10(4H)-dione (Compound 108a) and its isomer 7-fluoro-9-isopropoxy-10H-pyrrolizino[1,2-b]quinolin-10-one (Compound 108b)

Steps: Following the procedure of Example 1, ethyl 6-fluoro-4-oxo-2-(4H-pyrrol-2-yl)-1,4-dihydroquinoline-3-carboxylate (50 mg) and 2-bromopropane (10 mg) were subjected to reaction and post-treatment to give yellow solids (45% and 35% yields). ESI-MS m/z 297.10 [M+H]⁺.

Example 19

4-Allyl-7-fluoro-9H-pyrrolizino[1,2-b]quinoline-9, 10(4H)-dione (Compound 109a) and its isomer 9-(allyloxy)-7-fluoro-10H-pyrrolizino[1,2-b]quinolin-10-one (Compound 109b)

Steps: Following the procedure of Example 1, ethyl 6-fluoro-4-oxo-2-(1H-pyrrol-2-yl)-1,4-dihydroquinoline-3-carboxylate (50 mg) and 3-bromoprop-1-ene (6 mg) were subjected to reaction and post-treatment to give yellow solids (30% and 45% yields). ESI-MS m/z 295.08 [M+H]⁺.

Example 20

7-Fluoro-4-(3-methylbut-2-en-1-yl)-9H-pyrrolizino [1,2-b]quinoline-9,10(4H)-dione (Compound 112a) and its isomer 7-fluoro-9-((3-methylbut-2-en-1-yl)oxy)-10H-pyrrolizino[1,2-b]quinolin-10-one (Compound 112b)

Steps: Following the procedure of Example 1, ethyl 6-fluoro-4-oxo-2-(1H-pyrrol-2-yl)-1,4-dihydroquinoline-3-carboxylate (50 mg) and 1-bromo-3-methylbut-2-ene (10 mg) were subjected to reaction and post-treatment to give yellow solids (35% and 45% yields). ESI-MS m/z 323.11 [M+H]⁺.

Example 21

7-Fluoro-4-(2-hydroxyethyl)-9H-pyrrolizino[1,2-b] quinoline-9,10(4H)-dione (Compound 114a) and its isomer 7-fluoro-9-(2-hydroxyethoxy)-10H-pyrrolizino[1,2-b]quinolin-10-one (Compound 114b)

Steps: Following the procedure of Example 1, ethyl 6-fluoro-4-oxo-2-(1H-pyrrol-2-yl)-1,4-dihydroquinoline-3-carboxylate (50 mg) and 2-bromoeth-1-ol (10 mg) were subjected to reaction and post-treatment to give yellow solids (30% and 38% yields). ESI-MS m/z 298.08 [M+H]⁺.

Example 22

4-(4-Chlorophenyl)-7-fluoro-3b,9a-dihydro-9H-pyrrolizino[1,2-b]quinoline-9,10(4H)-dione (Compound 133a) and its isomer 9-(4-chlorophenoxy)-7-fluoro-10H-pyrrolizino[1,2-b]quinolin-10-one (Compound 133b)

Steps: Following the procedure of Example 1, ethyl 6-fluoro-4-oxo-2-(1H-pyrrol-2-yl)-1,4-dihydroquinoline-3-carboxylate (50 mg) and 4-chlorobromobenzene (10 mg) were subjected to reaction and post-treatment to give yellow solids (37% and 40% yields). ESI-MS m/z 364.04 [M+H]⁺, 366.04 [M+2+H]⁺.

Example 23

7-Fluoro-4-phenethyl-9H-pyrrolizino[1,2-b]quinoline-9,10(4H)-dione (Compound 141a) and its isomer 7-Fluoro-9-phenethoxy-10H-pyrrolizino[1,2-b] quinolin-10-one (Compound 141b)

Steps: Following the procedure of Example 1, ethyl 6-fluoro-4-oxo-2-(1H-pyrrol-2-yl)-1,4-dihydroquinoline-3- carboxylate (50 mg) and (2-bromoethyl)benzene (15 mg) were subjected to reaction and post-treatment to give yellow solids (35% and 34% yields).

ESI-MS m/z 359.11[M+H]$^+$.

Example 24

4-Cyclopropyl-7-fluoro-9H-pyrrolizino[1,2-b]quinoline-9,10(4H)-dione (Compound 144a) and its isomer 9-cyclopropoxy-7-fluoro-10H-pyrrolizino[1,2-b]quinolin-10-one (Compound 144b)

Steps: Following the procedure of Example 1, ethyl 6-fluoro-4-oxo-2-(1H-pyrrol-2-yl)-1,4-dihydroquinoline-3-carboxylate (50 mg) and bromocyclopropane (7 mg) were subjected to reaction and post-treatment to give yellow solids (25% and 30% yields). ESI-MS m/z 295.08 [M+H]$^+$.

Example 25

7-Fluoro-4-(furan-2-carbonyl)-9H-pyrrolizino[1,2-b]quinoline-9,10(4H)-dione (Compound 150a) and its isomer 7-fluoro-10-oxo-10H-pyrrolizino[1,2-b]quinolin-9-yl furan-2-carboxylate (Compound 150b)

Steps: Following the procedure of Example 1, ethyl 6-fluoro-4-oxo-2-(1H-pyrrol-2-yl)-1,4-dihydroquinoline-3-carboxylate (50 mg) and furan-2-carbonyl chloride (7 mg) were subjected to reaction and post-treatment to give yellow solids (34% and 34% yields).

ESI-MS m/z 349.05 [M+H]$^+$.

Example 26

2-(7-Fluoro-9,10-dioxo-9H-pyrrolizino[1,2-b]quinolin-4(10H)-yl)acetic acid (Compound 153a) and its isomer 2-((7-fluoro-10-oxo-10H-pyrrolizino[1,2-b]quinolin-9-yl)oxy)acetic acid (Compound 153b)

Steps: Following the procedure of Example 1, ethyl 6-fluoro-4-oxo-2-(1H-pyrrol-2-yl)-1,4-dihydroquinoline-3-carboxylate (50 mg) and 2-bromoacetic acid (15 mg) were subjected to reaction and post-treatment to give yellow solids (30% and 34% yields).

ESI-MS m/z 312.05[M+H]$^+$.

Example 27

7-Fluoro-9H-pyrrolizino[1,2-b]quinoline-9,10(4H)-dione (Compound 156a) and its isomer 7-fluoro-9-hydroxy-10H-pyrrolizino[1,2-b]quinolin-10-one (Compound 156b)

Steps: Ethyl 6-fluoro 4-oxo-2-(1H-pyrrol-2-yl)-1,4-dihydroquinoline-3-carboxylate (50 mg) and potassium carbonate (10 mg) were dissolved in an appropriate amount of acetonitrile, the mixture was stirred at a high temperature for 10 h. After the reaction was completed, the reaction mixture was poured into ice water, and the pH was adjusted to neutral with dilute aqueous hydrochloric acid, extracted with ethyl acetate (50 mL×2), and the organic phases were combined. The combined organic phases were evaporated, washed with brine, dried with anhydrous sodium sulfate, filtered, and concentrated. The residue was purified by silica gel column chromatography to give the products as yellow solids (40% and 50% yields). ESI-MS m/z 254.05 [M+H]$^+$.

Example 28

7-Fluoro-4-methyl-9H-pyrrolizino[1,2-b]quinoline-9,10(4H)-dione (Compound 157a) and its isomer 7-fluoro-9-methoxy-10H-pyrrolizino[1,2-b]quinolin-10-one (Compound 157b)

Steps: Following the procedure of Example 1, ethyl 6-fluoro-4-oxo-2-(1H-pyrrol-2-yl)-1,4-dihydroquinoline-3-carboxylate (50 mg) and iodomethane (10 mg) were subjected to reaction and post-treatment to give yellow solids (45% and 50% yields). ESI-MS m/z 269.06 [M+H]$^+$.

Example 29

7-Chloro-9H-pyrrolizino[1,2-b]quinoline-9,10(4H)-dione (Compound 180a) and its isomer 7-chloro-9-hydroxy-10H-pyrrolizino[1,2-b]quinolin-10-one (Compound 180b)

Steps: Following the procedure of Example 27, ethyl 6-chloro-4-oxo-2-(1H-pyrrol-2-yl)-1,4-dihydroquinoline-3-carboxylate (50 mg) was subjected to reaction and post-treatment to give yellow solids (30% and 35% yields). ESI-MS m/z 270.02 [M+H]$^+$, 272.02 [M+2+H]$^+$.

Example 30

4-(4-Fluorophenyl)-9,10-dioxo-4,10-dihydro-9H-pyrrolizino[1,2-b]quinoline-7-carbonitrile (Compound 199a) and its isomer 9-(4-fluorophenoxy)-10-oxo-10H-pyrrolizino[1,2-b]quinoline-7-carbonitrile (Compound 199b)

Steps: Following the procedure of Example 1, ethyl 6-cyano-4-oxo-2-(1H-pyrrol-2-yl)-1,4-dihydroquinoline-3-carboxylate (50 mg) and 4-fluorobromobenzene (10 mg) were subjected to reaction and post-treatment to give yellow solids (35% and 35% yields). ESI-MS m/z 355.08 [M+H]$^+$.

Example 31

4-(4-Chlorophenyl)-9,10-dioxo-4,10-dihydro-9H-pyrrolizino[1,2-b]quinoline-7-carbonitrile (Compound 210a) and its isomer 9-(4-chlorophenoxy)-10-oxo-10H-pyrrolizino[1,2-b]quinoline-7-carbonitrile (Compound 210b)

Steps: Following the procedure of Example 1, ethyl 6-cyano-4-oxo-2-(1H-pyrrol-2-yl)-1,4-dihydroquinoline-3-carboxylate (50 mg) and 4-chlorobromobenzene (10 mg) were subjected to reaction and post-treatment to give yellow solids (30% and 30% yields). ESI-MS m/z 371.05 [M+H]$^+$, 373.04 [M+2+H]$^+$.

Example 32

9,10-Dioxo-4,10-dihydro-9H-pyrrolizino[1,2-b]quinoline-7-carbonitrile (Compound 222a) and its isomer 9-hydroxy-10-oxo-10H-pyrrolizino[1,2-b]quinoline-7-carbonitrile (Compound 222b)

Steps: Following the procedure of Example 27, ethyl 6-cyano-4-oxo-2-(1H-pyrrol-2-yl)-1,4-dihydroquinoline-3-carboxylate (50 mg) was subjected to reaction and post-

Example 33

7-Bromo-9H-pyrrolizino[1,2-b]quinoline-9,10(4H)-dione (Compound 246a) and its isomer 7-bromo-9-hydroxy-10H-pyrrolizino[1,2-b]quinolin-10-one (Compound 246b)

Steps: Following the procedure of Example 27, ethyl 6-bromo-4-oxo-2-(1H-pyrrol-2-yl)-1,4-dihydroquinoline-3-carboxylate (50 mg) was subjected to reaction and post-treatment to give yellow solids (15% and 20% yields). ESI-MS m/z 313.97 [M+H]$^+$, 315.97 [M+2+H]$^+$.

Example 34

4-(4-Fluorophenyl)-7-(trifluoromethyl)-9H-pyrrolizino[1,2-b]quinoline-9,10(4H)-dione (Compound 259a) and its isomer 9-(4-fluorophenoxy)-7-(trifluoromethyl)-10H-pyrrolizino[1,2-b]quinolin-10-one (Compound 259b)

Steps: Following the procedure of Example 1, ethyl 6-trifluoromethyl-4-oxo-2-(1H-pyrrol-2-yl)-1,4-dihydroquinoline-3-carboxylate (50 mg) and 4-fluorobromobenzene (23 mg) were subjected to reaction and post-treatment to give yellow solids (15% and 15% yields). ESI-MS m/z 398.07 [M+H]$^+$.

Example 35

4-(4-Chlorophenyl)-7-(trifluoromethyl)-9H-pyrrolizino[1,2-b]quinoline-9,10(4H)-dione (Compound 276a) and its isomer 9-(4-chlorophenoxy)-7-(trifluoromethyl)-10H-pyrrolizino[1,2-b]quinolin-10-one (Compound 276b)

Steps: Following the procedure of Example 1, ethyl 6-trifluoromethyl-4-oxo-2-(1H-pyrrol-2-yl)-1,4-dihydroquinoline-3-carboxylate (50 mg) and 4-chlorobromobenzene (29 mg) were subjected to reaction and post-treatment to give yellow solids (25% and 25% yields). ESI-MS m/z 414.04 [M+H]$^+$, 416.04 [M+2+H]$^+$.

Example 36

2-((10-Oxo-7-(trifluoromethyl)-10H-pyrrolizino[1,2-b]quinolin-9-yl)oxy)acetic acid (Compound 279b) and its isomer 2-(9,10-dioxo-7-(trifluoromethyl)-9H-pyrrolizino[1,2-b]quinolin-4(10H)-yl)acetic acid (Compound 279a)

Steps: Following the procedure of Example 1, ethyl 6-trifluoromethyl-4-oxo-2-(1H-pyrrol-2-yl)-1,4-dihydroquinoline-3-carboxylate (50 mg) and 2-bromoacetic acid (25 mg) were subjected to reaction and post-treatment to give yellow solids (33% and 35% yields). ESI-MS m/z 363.05 [M+H]$^+$.

Example 37

7-(Trifluoromethyl)-9H-pyrrolizino[1,2-b]quinoline-9,10(4H)-dione (Compound 282a) and its isomer 9-hydroxy-7-(trifluoromethyl)-10H-pyrrolizino[1,2-b]quinolin-10-one (Compound 282b)

Steps: Following the procedure of Example 27, ethyl 6-trifluoromethyl 4-oxo-2-(1H-pyrrol-2-yl)-1,4-dihydroquinoline-3-carboxylate (50 mg) was subjected to reaction and post-treatment to give yellow solids (40% and 55% yields). ESI-MS m/z 304.05 [M+H]$^+$.

Example 38

4-(4-Chlorophenyl)-7-(trifluoromethoxy)-9H-pyrrolizino[1,2-b]quinoline-9,10(4H)-dione (Compound 300a) and its isomer 9-(4-chlorophenoxy)-7-(trifluoromethoxy)-10H-pyrrolizino[1,2-b]quinolin-10-one (Compound 300b)

Steps: Following the procedure of Example 1, ethyl 6-trifluoromethoxy-4-oxo-2-(1H-pyrrol-2-yl)-1,4-dihydroquinoline-3-carboxylate (50 mg) and 4-chlorobromobenzene (20 mg) were subjected to reaction and post-treatment to give yellow solids (25% and 35% yields). ESI-MS m/z 430.03 [M+H]$^+$, 432.03 [M+2+H]$^+$.

Example 39

7-(Trifluoromethoxy)-9H-pyrrolizino[1,2-b]quinoline-9,10(4H)-dione (Compound 300a) and its isomer 9-hydroxy-7-(trifluoromethoxy)-10H-pyrrolizino[1,2-b]quinolin-10-one (Compound 300b)

Steps: Following the procedure of Example 27, ethyl 6-trifluoromethoxy 4-oxo-2-(1H-pyrrol-2-yl)-1,4-dihydroquinoline-3-carboxylate (50 mg) was subjected to reaction and post-treatment to give yellow solids (20% and 45% yields). ESI-MS m/z 320.04 [M+H]$^+$.

Example 40

9-Hydroxy-6-(piperazin-1-yl)-10H-pyrrolizino[1,2-b]quinolin-10-one (Compound 319b) and its isomer 6-(piperazin-1-yl)-9H-pyrrolizino[1,2-b]quinoline-9,10(4H)-dione (Compound 319a)

Steps: 9-Hydroxy-10H-pyrrolizino[1,2-b]quinolin-10-one, anhydrous piperazine (28 mg) and dimethylformamide (55 mL) were stirred and mixed, and the mixture was reacted at 140° C. for 2 h, and the solvent was evaporated under reduced pressure, the residue was suspended in water 30 mL and boiled for a few minutes, and then was subjected to cooling, suction filtration, water washing, and vacuum drying to constant weight to give yellow solids 15.7 mg and 15.8 mg. (48% and 49% yields). ESI-MS m/z 320.13 [M+H]$^+$.

Example 41

4-Methyl-6-(piperazin-1-yl)-9H-pyrrolizino[1,2-b]quinoline-9,10(4H)-dione (Compound 328a) and its isomer 9-methoxy-6-(piperazin-1-yl)-10H-pyrrolizino[1,2-b]quinolin-10-one (Compound 328b)

Steps: Following the procedure of Example 1, ethyl 4-oxo-2-(1H-pyrrol-2-yl)-1,4-dihydroquinoline-3-carboxylate (50 mg) and CH$_3$I (10 mL) were subjected to reaction and post-treatment to give a yellow solid. Then the obtained yellow solid (20 mg) was stirred and mixed with anhydrous piperazine (28 mg) and dimethylformamide (55 mL), and the mixture was reacted at 140° C. for 2 h, and the solvent was evaporated under reduced pressure, the residue was suspended in water 30 mL and boiled for a few minutes, and then was subjected to cooling, suction filtration, water washing, and vacuum drying to constant weight to give yellow solids 15.7 mg and 10.2 mg. (75% and 70% yields). ESI-MS m/z 335.14 [M+H]$^+$.

Example 42

4-Ethyl-7-fluoro-6-(piperazin-1-yl)-9H-pyrrolizino [1,2-b]quinoline-9,10(4H)-dione (Compound 329a) and its isomer 9-ethoxy-7-fluoro-6-(piperazin-1-yl)-10H-pyrrolizino[1,2-b]quinolin-10-one (Compound 329b)

Steps: Following the procedure of Example 1, ethyl 7-chloro-6-fluoro-4-oxo-2-(1H-pyrrol-2-yl)-1,4-dihydroquinoline-3-carboxylate (50 mg) and CH$_3$CH$_2$Br (10 mL) were subjected to reaction and post-treatment to give yellow solid. Then the obtained yellow solid (20 mg) was stirred and mixed with anhydrous piperazine (28 mg) and dimethylformamide (55 mL), and the mixture was reacted at 140° C. for 2 h, and the solvent was evaporated under reduced pressure, the residue was suspended in water 30 mL and boiled for a few minutes, and then was subjected to cooling, suction filtration, water washing, and vacuum drying to constant weight to give yellow solids (50% and 70% yields). ESI-MS m/z 367.15[M+H]$^+$.

Example 43

7-Fluoro-4-isopropyl-6-(piperazin-1-yl)-9H-pyrrolizino[1,2-b]quinoline-9,10(4H)-dione (Compound 331a) and its isomer 7-fluoro-9-isopropoxy-6-(piperazin-1-yl)-10H-pyrrolizino[1,2-b]quinolin-10-one (Compound 331b)

Steps: Following the procedure of Example 1, ethyl 7-chloro-6-fluoro-4-oxo-2-(1H-pyrrol-2-yl)-1,4-dihydroquinoline-3-carboxylate (50 mg) and 2-bromopropane (10 mL) were subjected to reaction and post-treatment to give yellow solid. Then the obtained yellow solid (20 mg) was stirred and mixed with anhydrous piperazine (28 mg) and dimethylformamide (55 mL), and the mixture was reacted at 140° C. for 2 h, and the solvent was evaporated under reduced pressure, the residue was suspended in water 30 mL and boiled for a few minutes, and then was subjected to cooling, suction filtration, water washing, and vacuum drying to constant weight to give yellow solids (78% and 70% yields). ESI-MS m/z 381.16 [M+H]$^+$.

Example 44

4-Cyclopropyl-7-fluoro-6-(piperazin-1-yl)-9H-pyrrolizino[1,2-b]quinoline-9,10(4H)-dione (Compound 340a) and its isomer 9-cyclopropoxy-7-fluoro-6-(piperazin-1-yl)-10H-pyrrolizino[1,2-b]quinolin-10-one (Compound 340b)

Steps: Following the procedure of Example 1, ethyl 7-chloro-6-fluoro-4-oxo-2-(1H-pyrrol-2-yl)-1,4-dihydroquinoline-3-carboxylate (50 mg) and bromocyclopropane (10 mL) were subjected to reaction and post-treatment to give yellow solid. Then the obtained yellow solid (20 mg) was stirred and mixed with anhydrous piperazine (28 mg) and dimethylformamide (55 mL), and the mixture was reacted at 140° C. for 2 h, and the solvent was evaporated under reduced pressure, the residue was suspended in water 30 mL and boiled for a few minutes, and then was subjected to cooling, suction filtration, water washing, and vacuum drying to constant weight to give yellow solids (68% and 70% yields). ESI-MS m/z 379.15[M+H]$^+$.

Example 45

7-Fluoro-4-(furan-2-carbonyl)-6-(piperazin-1-yl)-9H-pyrrolizino[1,2-b]quinoline-9,10(4H)-dione (Compound 343a) and its isomer 7-fluoro-10-oxo-6-(piperazin-1-yl)-10H-pyrrolizino[1,2-b]quinolin-9-ylfuran-2-carboxylate (Compound 343b)

Steps: Following the procedure of Example 1, ethyl 7-chloro-6-fluoro-4-oxo-2-(1H-pyrrol-2-yl)-1,4-dihydroquinoline-3-carboxylate (50 mg) and furan-2-carbonyl chloride (15 μL) were subjected to reaction and post-treatment to give yellow solid. Then the obtained yellow solid (20 mg) was stirred and mixed with anhydrous piperazine (28 mg) and dimethylformamide (55 mL), and the mixture was reacted at 140° C. for 2 h, and the solvent was evaporated under reduced pressure, the residue was suspended in water 30 mL and boiled for a few minutes, and then was subjected to cooling, suction filtration, water washing, and vacuum drying to constant weight to give yellow solids (88% and 70% yields). ESI-MS m/z 433.12 [M+H]$^+$.

Example 46

7-Fluoro-6-(piperazin-1-yl)-9H-pyrrolizino[1,2-b] quinoline-9,10(4H)-dione (Compound 346a) and its isomer 7-fluoro-9-hydroxy-6-(piperazin-1-yl)-10H-pyrrolizino[1,2-b]quinolin-10-one (Compound 346b)

Steps: Following the procedure of Example 27, ethyl 7-chloro-6-fluoro-4-oxo-2-(1H-pyrrol-2-yl)-1,4-dihydroquinoline-3-carboxylate (50 mg) was subjected to reaction and post-treatment to give yellow solid. Then the obtained yellow solid (20 mg) was stirred and mixed with anhydrous piperazine (28 mg) and dimethylformamide (55 mL), and the mixture was reacted at 140° C. for 2 h, and the solvent was evaporated under reduced pressure, the residue was suspended in water 30 mL and boiled for a few minutes, and then was subjected to cooling, suction filtration, water washing, and vacuum drying to constant weight to give yellow solids (79% and 70% yields). ESI-MS m/z 339.12 [M+H]$^+$.

Example 47

7-Fluoro-4-isopentyl-6-(piperazin-1-yl)-9H-pyrrolizino[1,2-b]quinoline-9,10(4H)-dione (Compound 347a) and its isomer 7-fluoro-9-(isopentyloxy)-6-(piperazin-1-yl)-10H-pyrrolizino[1,2-b]quinolin-10-one (Compound 347b)

Steps: Following the procedure of Example 1, ethyl 7-chloro-6-fluoro-4-oxo-2-(1H-pyrrol-2-yl)-1,4-dihydroquinoline-3-carboxylate (50 mg) and 1-bromo-3-methylbutane (15 mL) were subjected to reaction and post-treatment to give yellow solid. Then the obtained yellow solid (20 mg) was stirred and mixed with anhydrous piperazine (28 mg) and dimethylformamide (55 mL), and the mixture was reacted at 140° C. for 2 h, and the solvent was evaporated under reduced pressure, the residue was suspended in water 30 mL and boiled for a few minutes, and then was subjected to cooling, suction filtration, water washing, and vacuum drying to constant weight to give yellow solids (78% and 70% yields). ESI-MS m/z 409.20 [M+H]$^+$.

Example 48

7-Fluoro-4-(2-hydroxyethyl)-6-(piperazin-1-yl)-9H-pyrrolizino[1,2-b]quinoline-9,10(4H)-dione (Compound 348a) and its isomer 7-fluoro-9-(2-hydroxyethoxy)-6-(piperazin-1-yl)-10H-pyrrolizino[1,2-b]quinolin-10-one (Compound 348b)

Steps: Following the procedure of Example 1, ethyl 7-chloro-6-fluoro-4-oxo-2-(1H-pyrrol-2-yl)-1,4-dihydroquinoline-3-carboxylate (50 mg) and 2-bromoeth-1-ol (10 µL) were subjected to reaction and post-treatment to give yellow solid. Then the obtained yellow solid (20 mg) was stirred and mixed with anhydrous piperazine (28 mg) and dimethylformamide (55 mL), and the mixture was reacted at 140° C. for 2 h, and the solvent was evaporated under reduced pressure, the residue was suspended in water 30 mL and boiled for a few minutes, and then was subjected to cooling, suction filtration, water washing, and vacuum drying to constant weight to give yellow solids (78% and 70% yields). ESI-MS m/z 382.14 [M+H]$^+$.

Example 49

4-Allyl-7-fluoro-6-(piperazin-1-yl)-9H-pyrrolizino[1,2-b]quinoline-9,10(4H)-dione (Compound 349a) and its isomer 9-(allyloxy)-7-fluoro-6-(piperazin-1-yl)-10H-pyrrolizino[1,2-b]quinolin-10-one (Compound 349b)

Steps: Following the procedure of Example 1, ethyl 7-chloro-6-fluoro-4-oxo-2-(1H-pyrrol-2-yl)-1,4-dihydroquinoline-3-carboxylate (50 mg) and 3-bromoprop-1-ene (10 mL) were subjected to reaction and post-treatment to give yellow solid. Then the obtained yellow solid (20 mg) was stirred and mixed with anhydrous piperazine (28 mg) and dimethylformamide (55 mL), and the mixture was reacted at 140° C. for 2 h, and the solvent was evaporated under reduced pressure, the residue was suspended in water 30 mL and boiled for a few minutes, and then was subjected to cooling, suction filtration, water washing, and vacuum drying to constant weight to give yellow solids (66% and 70% yields). ESI-MS m/z 379.15[M+H]$^+$.

Example 50

7-Fluoro-4-(3-methylbut-2-en-1-yl)-6-(piperazin-1-yl)-9H-pyrrolizino[1,2-b]quinoline-9,10(4H)-dione (Compound 354a) and its isomer 7-fluoro-9-((3-methylbut-2-en-1-yl)oxy)-6-(piperazin-1-yl)-10H-pyrrolizino[1,2-b]quinolin-10-one (Compound 354b)

Steps: Following the procedure of Example 1, ethyl 7-chloro-6-fluoro-4-oxo-2-(1H-pyrrol-2-yl)-1,4-dihydroquinoline-3-carboxylate (50 mg) and 1-bromo-3-methylbut-2-ene (10 mL) were subjected to reaction and post-treatment to give yellow solid. Then the obtained yellow solid (20 mg) was stirred and mixed with anhydrous piperazine (28 mg) and dimethylformamide (55 mL), and the mixture was reacted at 140° C. for 2 h, and the solvent was evaporated under reduced pressure, the residue was suspended in water 30 mL and boiled for a few minutes, and then was subjected to cooling, suction filtration, water washing, and vacuum drying to constant weight to give yellow solids (78% and 70% yields). ESI-MS m/z 407.18[M+H]$^+$.

Example 51

7-Fluoro-4-methyl-6-(piperazin-1-yl)-9H-pyrrolizino[1,2-b]quinoline-9,10(4H)-dione (Compound 361a) and its isomer 7-fluoro-9-methoxy-6-(piperazin-1-yl)-10H-pyrrolizino[1,2-b]quinolin-10-one (Compound 361b)

Steps: Following the procedure of Example 1, ethyl 7-chloro-6-fluoro-4-oxo-2-(1H-pyrrol-2-yl)-1,4-dihydroquinoline-3-carboxylate (50 mg) and CH$_3$I (10 mL) were subjected to reaction and post-treatment to give yellow solid. Then the obtained yellow solid (20 mg) was stirred and mixed with anhydrous piperazine (28 mg) and dimethylformamide (55 mL), and the mixture was reacted at 140° C. for 2 h, and the solvent was evaporated under reduced pressure, the residue was suspended in water 30 mL and boiled for a few minutes, and then was subjected to cooling, suction filtration, water washing, and vacuum drying to constant weight to give yellow solids (78% and 70% yields). ESI-MS m/z 353.13 [M+H]$^+$.

Example 52

7-Chloro-6-(piperazin-1-yl)-9H-pyrrolizino[1,2-b]quinoline-9,10(4H)-dione (Compound 373a) and its isomer 7-chloro-9-hydroxy-6-(piperazin-1-yl)-10H-pyrrolizino[1,2-b]quinolin-10-one (Compound 373b)

Steps: Following the procedure of Example 27, ethyl 6,7-dichloro-4-oxo-2-(1H-pyrrol-2-yl)-1,4-dihydroquinoline-3-carboxylate (50 mg) was subjected to reaction and post-treatment to give yellow solid. Then the obtained yellow solid (20 mg) was stirred and mixed with anhydrous piperazine (28 mg) and dimethylformamide (55 mL), and the mixture was reacted at 140° C. for 2 h, and the solvent was evaporated under reduced pressure, the residue was suspended in water 30 mL and boiled for a few minutes, and then was subjected to cooling, suction filtration, water washing, and vacuum drying to constant weight to give yellow solids (78% and 70% yields). ESI-MS m/z 354.09 [M+H]$^+$, 356.09 [M+2+H]$^+$.

Example 53

6-(Piperazin-1-yl)-7-(trifluoromethyl)-9H-pyrrolizino[1,2-b]quinoline-9,10(4H)-dione (Compound 397a) and its isomer 9-hydroxy-6-(piperazin-1-yl)-7-(trifluoromethyl)-10H-pyrrolizino[1,2-b]quinolin-10-one (Compound 397b)

Steps: Following the procedure of Example 27, ethyl 7-chloro-6-trifluoromethyl-4-oxo-2-(1H-pyrrol-2-yl)-1,4-dihydroquinoline-3-carboxylate (50 mg) was subjected to reaction and post-treatment to give yellow solid. Then the obtained product was stirred and mixed with anhydrous piperazine (28 mg) and dimethylformamide (55 mL), and the mixture was reacted at 140° C. for 2 h, and the solvent was evaporated under reduced pressure, the residue was suspended in water 30 mL and boiled for a few minutes, and then was subjected to cooling, suction filtration, water washing, and vacuum drying to constant weight to give yellow solids 18.7 mg (78% and 70% yields). ESI-MS m/z 388.11 [M+H]⁺.

Example 54

6-(Piperazin-1-yl)-7-(trifluoromethoxy)-9H-pyrrolizino[1,2-b]quinoline-9,10(4H)-dione (Compound 409a) and its isomer 9-hydroxy-6-(piperazin-1-yl)-7-(trifluoromethoxy)-10H-pyrrolizino[1,2-b]quinolin-10-one (Compound 409b)

Steps: Following the procedure of Example 27, ethyl 7-chloro-6-trifluoromethoxy-4-oxo-2-(1H-pyrrol-2-yl)-1,4-dihydroquinoline-3-carboxylate (50 mg) was subjected to reaction and post-treatment to give yellow solid. Then the obtained product was stirred and mixed with anhydrous piperazine (28 mg) and dimethylformamide (55 mL), and the mixture was reacted at 140° C. for 2 h, and the solvent was evaporated under reduced pressure, the residue was suspended in water 30 mL and boiled for a few minutes, and then was subjected to cooling, suction filtration, water washing, and vacuum drying to constant weight to give yellow solids 18.7 mg (68% and 70% yields). ESI-MS m/z 404.11 [M+H]⁺.

Example 55

5-Chloro-9H-pyrrolizino[1,2-b]quinoline-9,10(4H)-dione (Compound 409a) and its isomer 5-chloro-9-hydroxy-10H-pyrrolizino[1,2-b]quinolin-10-one (Compound 409b)

Steps: Following the procedure of Example 1, ethyl 8-chloro-4-oxo-2-(1H-pyrrol-2-yl)-1,4-dihydroquinoline-3-carboxylate (50 mg) and potassium carbonate (10 mg) were dissolved in an appropriate amount of acetonitrile, the mixture was stirred at a high temperature for 10 h, subjected to reaction and post-treatment to give yellow solids (30% and 30% yields). ESI-MS m/z 271.02 [M+H]⁺, 273.02 [M+2+H]⁺.

Example 56

5-Fluoro-9H-pyrrolizino[1,2-b]quinoline-9,10(4H)-dione (Compound 444a) and its isomer 5-fluoro-9-hydroxy-10H-pyrrolizino[1,2-b]quinolin-10-one (Compound 444b)

Steps: Following the procedure of Example 1, ethyl 8-fluoro-4-oxo-2-1H-pyrrol-2-yl)-1,4-dihydroquinoline-3-carboxylate (50 mg) and potassium carbonate (10 mg) were dissolved in an appropriate amount of acetonitrile, the mixture was stirred at a high temperature for 10 h, subjected to reaction and post-treatment to give yellow solids (35% and 30% yields). ESI-MS m/z 255.05 [M+H]⁺.

Example 57

5-Hydroxy-9H-pyrrolizino[1,2-b]quinoline-9,10 (4H)-dione (Compound 445a) and its isomer 5,9-dihydroxy-10H-pyrrolizino[1,2-b]quinolin-10-one (Compound 445b)

Steps: Following the procedure of Example 1, ethyl 8-hydroxy-4-oxo-2-(1H-pyrrol-2-yl)-1,4-dihydroquinoline-3-carboxylate (50 mg) and potassium carbonate (10 mg) were dissolved in an appropriate amount of acetonitrile, the mixture was stirred at a high temperature for 10 h, subjected to reaction and post-treatment to give yellow solids (41% and 30% yields). ESI-MS m/z 253.05 [M+H]⁺.

Example 58

5-Methoxy-9H-pyrrolizino[1,2-b]quinoline-9,10 (4H)-dione (Compound 446a) and its isomer 9-hydroxy-5-methoxy-10H-pyrrolizino[1,2-b]quinolin-10-one (Compound 446b)

Steps: Following the procedure of Example 1, ethyl 8-methoxy-4-oxo-2-(1H-pyrrol-2-yl)-1,4-dihydroquinoline-3-carboxylate (50 mg) and potassium carbonate (10 mg) were dissolved in an appropriate amount of acetonitrile, the mixture was stirred at a high temperature for 10 h, subjected to reaction and post-treatment to give yellow solids (32% and 30% yields). ESI-MS m/z 267.07 [M+H]⁺.

Example 59

9,10-Dioxo-4,10-dihydro-9H-pyrrolizino[1,2-b]quinoline-5-carbonitrile (Compound 447a) and its isomer 9-hydroxy-10-oxo-10H-pyrrolizino[1,2-b]quinoline-5-carbonitrile (Compound 447b)

Steps: Following the procedure of Example 1, ethyl 8-cyano-4-oxo-2-(1H-pyrrol-2-yl)-1,4-dihydroquinoline-3-carboxylate (50 mg) and potassium carbonate (10 mg) were dissolved in an appropriate amount of acetonitrile, the mixture was stirred at a high temperature for 10 h, subjected to reaction and post-treatment to give yellow solids (45% and 30% yields). ESI-MS m/z 262.05 [M+H]⁺.

Example 60

5-(Trifluoromethyl)-9H-pyrrolizino[1,2-b]quinoline-9,10(4H)-dione (Compound 448a) and its isomer 9-hydroxy-5-(trifluoromethyl)-10H-pyrrolizino[1,2-b]quinolin-10-one (Compound 448b)

Steps: Following the procedure of Example 1, ethyl 8-trifluoromethyl-4-oxo-2-(1H-pyrrol-2-yl)-1,4-dihydroquinoline-3-carboxylate (50 mg) and potassium carbonate (10 mg) were dissolved in an appropriate amount of acetonitrile, the mixture was stirred at a high temperature for 10 h, subjected to reaction and post-treatment to give yellow solids (31% and 30% yields). ESI-MS m/z 305.05 [M+H]⁺.

Example 61

4-(4-Fluorobenzyl)-9,10-dioxo-4,10-dihydro-9H-pyrrolizino[1,2-b]quinoline-5-carbonitrile (Compound 449a) and its isomer 9-((4-fluorobenzyl)oxy)-10-oxo-10H-pyrrolizino[1,2-b]quinoline-5-carbonitrile (Compound 449b)

Steps: Following the procedure of Example 1, ethyl 8-cyano-2-(1H-pyrrol-2-yl)-1,4-dihydroquinoline-3-carboxylate (50 mg) and 4-fluorobenzyl bromide (15 mg) were subjected to reaction and post-treatment to give yellow solids (39% and 30% yields). ESI-MS m/z 370.09 [M+H]⁺.

Example 62

4-(4-Chlorobenzyl)-5-(trifluoromethyl)-9H-pyrrolizino[1,2-b]quinoline-9,10(4H)-dione (Compound 450a) and its isomer 9-((4-chlorobenzyl)oxy)-5-(trifluoromethyl)-10H-pyrrolizino[1,2-b]quinolin-10-one (Compound 450b)

Steps: Following the procedure of Example 1, ethyl 8-trifluoromethyl-2-(1H-pyrrol-2-yl)-1,4-dihydroquinoline-3-carboxylate (50 mg) and 4-chlorobenzyl bromide (15 mg) were subjected to reaction and post-treatment to give yellow solids (30% and 30% yields). ESI-MS m/z 429.05 [M+H]$^+$, 431.05 [M+2+H]$^+$.

Example 63

5-Chloro-4-(4-chlorobenzyl)-9H-pyrrolizino[1,2-b]quinoline-9,10(4H)-dione (Compound 451a) and its isomer 5-chloro-9-((4-chlorobenzyl)oxy)-10H-pyrrolizino[1,2-b]quinolin-10-one (Compound 451b)

Steps: Following the procedure of Example 1, ethyl 8-chloro-2-(1H-pyrrol-2-yl)-1,4-dihydroquinoline-3-carboxylate (50 mg) and 4-chlorobenzyl bromide (15 mg) were subjected to reaction and post-treatment to give yellow solids (31% and 30% yields). ESI-MS m/z 397.03[M+2+H]$^+$, 399.03 [M+2+2+H]$^+$.

Example 64

5-Fluoro-4-(4-fluorobenzyl)-9H-pyrrolizino[1,2-b]quinoline-9,10(4H)-dione (Compound 452a) and its isomer 5-fluoro-9-((4-fluorobenzyl)oxy)-10H-pyrrolizino[1,2-b]quinolin-10-one (Compound 452b)

Steps: Following the procedure of Example 1, ethyl 8-fluoro-2-(1H-pyrrol-2-yl)-1,4-dihydroquinoline-3-carboxylate (50 mg) and 4-fluorobenzyl bromide (15 mg) were subjected to reaction and post-treatment to give yellow solids (38% and 30% yields). ESI-MS m/z 363.09 [M+H]$^+$.

Example 65

4-(4-Chlorobenzyl)-5-fluoro-9H-pyrrolizino[1,2-b]quinoline-9,10(4H)-dione (Compound 453a) and its isomer 9-((4-chlorobenzyl)oxy)-5-fluoro-10H-pyrrolizino[1,2-b]quinolin-10-one (Compound 453b)

Steps: Following the procedure of Example 1, ethyl 8-fluoro-2-(1H-pyrrol-2-yl)-1,4-dihydroquinoline-3-carboxylate (50 mg) and 4-chlorobenzyl bromide (15 mg) were subjected to reaction and post-treatment to give yellow solids (36% and 30% yields). ESI-MS m/z 379.06 [M+H]$^+$, 381.06 [M+2+H]$^+$.

Example 66

4-(3-Fluorobenzyl)-9,10-dioxo-4,10-dihydro-9H-pyrrolizino[1,2-b]quinoline-5-carbonitrile (Compound 454a) and its isomer 9-((3-fluorobenzyl)oxy)-10-oxo-10H-pyrrolizino[1,2-b]quinoline-5-carbonitrile (Compound 454b)

Steps: Following the procedure of Example 1, ethyl 8-cyano-2-(1H-pyrrol-2-yl)-1,4-dihydroquinoline-3-carboxylate (50 mg) and 3-fluorobenzyl bromide (15 mg) were subjected to reaction and post-treatment to give yellow solids (36% and 30% yields). ESI-MS m/z 370.09 [M+H]$^+$.

Example 67

4-(3-Chlorobenzyl)-5-(trifluoromethyl)-9H-pyrrolizino[1,2-b]quinoline-9,10(4H)-dione (Compound 455a) and its isomer 9-((3-chlorobenzyl)oxy)-5-(trifluoromethyl)-10H-pyrrolizino[1,2-b]quinolin-10-one (Compound 455b)

Steps: Following the procedure of Example 1, ethyl 8-trifluoromethyl-2-(1H-pyrrol-2-yl)-1,4-dihydroquinoline-3-carboxylate (50 mg) and 3-chlorobenzyl bromide (15 mg) were subjected to reaction and post-treatment to give yellow solids (33% and 30% yields). ESI-MS m/z 429.05 [M+H]$^+$, 431.05 [M+2+H]$^+$.

Example 68

4-(2-Fluorobenzyl)-9,10-dioxo-4,10-dihydro-9H-pyrrolizino[1,2-b]quinoline-5-carbonitrile (Compound 456a) and its isomer 9-((2-fluorobenzyl)oxy)-10-oxo-10H-pyrrolizino[1,2-b]quinoline-5-carbonitrile (Compound 456b)

Steps: Following the procedure of Example 1, ethyl 8-cyano-2-(1H-pyrrol-2-yl)-1,4-dihydroquinoline-3-carboxylate (50 mg) and 1-(bromomethyl)-2-fluorobenzene (15 mg) were subjected to reaction and post-treatment to give yellow solids (36% and 33% yields). ESI-MS m/z 370.09 [M+H]$^+$.

Example 69

4-(2-Chlorobenzyl)-5-(trifluoromethyl)-9H-pyrrolizino[1,2-b]quinoline-9,10(4H)-dione (Compound 457a) and its isomer 9-((2-chlorobenzyl)oxy)-5-(trifluoromethyl)-10H-pyrrolizino[1,2-b]quinolin-10-one (Compound 457b)

Steps: Following the procedure of Example 1, ethyl 8-trifluoromethyl-2-(1H-pyrrol-2-yl)-1,4-dihydroquinoline-3-carboxylate (50 mg) and 1-(bromomethyl)-2-chlorobenzene (15 mg) were subjected to reaction and post-treatment to give yellow solids (39% and 33% yields). ESI-MS m/z 429.05 [M+H]$^+$, 431.05 [M+2+H]$^+$.

Example 70

5-Fluoro-4-(3-fluorobenzyl)-9H-pyrrolizino[1,2-b]quinoline-9,10(4H)-dione (Compound 458a) and its isomer 5-fluoro-9-((3-fluorobenzyl)oxy)-10H-pyrrolizino[1,2-b]quinolin-10-one (Compound 458b)

Steps: Following the procedure of Example 1, ethyl 8-fluoro-2-(1H-pyrrol-2-yl)-1,4-dihydroquinoline-3-carboxylate (50 mg) and 3-fluorobenzyl bromide (15 mg) were subjected to reaction and post-treatment to give yellow solids (37% and 33% yields). ESI-MS m/z 363.09 [M+H]$^+$.

Example 71

5-Chloro-4-(3-chlorobenzyl)-9H-pyrrolizino[1,2-b]quinoline-9,10(4H)-dione (Compound 459a) and its isomer 5-chloro-9-((3-chlorobenzyl)oxy)-10H-pyrrolizino[1,2-b]quinolin-10-one (Compound 459b)

Steps: Following the procedure of Example 1, Ethyl 8-chloro-2-(1H-pyrrol-2-yl)-1,4-dihydroquinoline-3-carboxylate (50 mg) and 3-chlorobenzyl bromide (15 mg) were subjected to reaction and post-treatment to give yellow solids (36% and 33% yields). ESI-MS m/z 397.03 [M+2+H]$^+$, 399.03 [M+2+2+H]$^+$.

Example 72

5-Chloro-4-(2-fluorobenzyl)-9H-pyrrolizino[1,2-b]quinoline-9,10(4H)-dione (Compound 460a) and its isomer 5-chloro-9-((2-fluorobenzyl)oxy)-10H-pyrrolizino[1,2-b]quinolin-10-one (Compound 460b)

Steps: Following the procedure of Example 1, ethyl 8-chloro-2-(1H-pyrrol-2-yl)-1,4-dihydroquinoline-3-carboxylate (50 mg) and 1-(bromomethyl)-2-fluorobenzene (15 mg) were subjected to reaction and post-treatment to give yellow solids (41% and 36% yields). ESI-MS m/z 379.06 [M+H]$^+$, 381.06 [M+2+H]$^+$.

Example 73

5-Chloro-4-(2-chlorobenzyl)-9H-pyrrolizino[1,2-b]quinoline-9,10(4H)-dione (Compound 461a) and its isomer 5-chloro-9-((2-chlorobenzyl)oxy)-10H-pyrrolizino[1,2-b]quinolin-10-one (Compound 461b)

Steps: Following the procedure of Example 1, ethyl 8-chloro-2-(1H-pyrrol-2-yl)-1,4-dihydroquinoline-3-carboxylate (50 mg) and 1-(bromomethyl)-2-chlorobenzene (15 mg) were subjected to reaction and post-treatment to give yellow solids (44% and 36% yields). ESI-MS m/z 397.03 [M+2+H]$^+$, 400.03 [M+2+2+H]$^+$.

Example 74

4-(4-Fluorobenzyl)-9,10-dioxo-4,10-dihydro-9H-pyrrolizino[1,2-b]quinoline-8-carbonitrile (Compound 462a) and its isomer 9-((4-fluorobenzyl)oxy)-10-oxo-10H-pyrrolizino[1,2-b]quinoline-8-carbonitrile (Compound 462b)

Steps: Following the procedure of Example 1, ethyl 5-cyano-4-oxo-2-(1H-pyrrol-2-yl)-1,4-dihydroquinoline-3-carboxylate (50 mg) and 1-(bromomethyl)-4-fluorobenzene (46 mg) were subjected to reaction and post-treatment to give yellow solids (39% and 36% yields). ESI-MS m/z 370.09 [M+H]$^+$.

Example 75

4-(3-Fluorobenzyl)-9,10-dioxo-4,10-dihydro-9H-pyrrolizino[1,2-b]quinoline-8-carbonitrile (Compound 463a) and its isomer 9-((3-fluorobenzyl)oxy)-10-oxo-10H-pyrrolizino[1,2-b]quinoline-8-carbonitrile (Compound 463b)

Steps: Following the procedure of Example 1, ethyl 5-cyano-4-oxo-2-(1H-pyrrol-2-yl)-1,4-dihydroquinoline-3-carboxylate (50 mg) and 1-(bromomethyl)-3-fluorobenzene (46 mg) were subjected to reaction and post-treatment to give yellow solids (39% and 35% yields). ESI-MS m/z 370.09 [M+H]$^+$.

Example 76

8-Chloro-9H-pyrrolizino[1,2-b]quinoline-9,10(4H)-dione (Compound 464a) and its isomer 8-chloro-9-hydroxy-10H-pyrrolizino[1,2-b]quinolin-10-one (Compound 464b)

Steps: Following the procedure of Example 1, ethyl 5-chloro-4-oxo-2-(1H-pyrrol-2-yl)-1,4-dihydroquinoline-3-carboxylate (50 mg) and potassium carbonate (10 mg) were dissolved in an appropriate amount of acetonitrile, the mixture was stirred at a high temperature for 10 h, subjected to reaction and post-treatment to give yellow solids (32% and 30% yields). ESI-MS m/z 271.02 [M+H]$^+$.

Example 77

4-(4-Chlorobenzyl)-8-(trifluoromethyl)-9H-pyrrolizino[1,2-b]quinoline-9,10(4H)-dione (Compound 465a) and its isomer 9-((4-chlorobenzyl)oxy)-8-(trifluoromethyl)-10H-pyrrolizino[1,2-b]quinolin-10-one (Compound 465b)

Steps: Following the procedure of Example 1, ethyl 5-(trifluoromethyl)-4-oxo-2-(1H-pyrrol-2-yl)-1,4-dihydroquinoline-3-carboxylate (50 mg) and 1-(bromomethyl)-4-chlorobenzene (46 mg) were subjected to reaction and post-treatment to give yellow solids (39% and 35% yields). ESI-MS m/z 329.05 [M+H]$^+$.

Example 78

4-(3-Chlorobenzyl)-8-(trifluoromethyl)-9H-pyrrolizino[1,2-b]quinoline-9,10(4H)-dione (Compound 466a) and its isomer 9-((3-chlorobenzyl)oxy)-8-(trifluoromethyl)-10H-pyrrolizino[1,2-b]quinolin-10-one (Compound 466b)

Steps: Following the procedure of Example 1, ethyl 5-(trifluoromethyl)-4-oxo-2-(1H-pyrrol-2-yl)-1,4-dihydroquinoline-3-carboxylate (50 mg) and 1-(bromomethyl)-3-chlorobenzene (46 mg) were subjected to reaction and post-treatment to give yellow solids (39% and 35% yields). ESI-MS m/z 429.15 [M+H]$^+$.

Example 79

8-Fluoro-9H-pyrrolizino[1,2-b]quinoline-9,10(4H)-dione (Compound 467a) and its isomer 8-fluoro-9-hydroxy-10H-pyrrolizino[1,2-b]quinolin-10-one (Compound 467b)

Steps: Following the procedure of Example 1, ethyl 5-fluoro-4-oxo-2-(1H-pyrrol-2-yl)-1,4-dihydroquinoline-3-carboxylate (50 mg) and potassium carbonate (10 mg) were dissolved in an appropriate amount of acetonitrile, the mixture was stirred at a high temperature for 10 h, subjected to reaction and post-treatment to give yellow solids (32% and 30% yields).

Example 80

8-Fluoro-4-(4-fluorobenzyl)-9H-pyrrolizino[1,2-b]quinoline-9,10(4H)-dione (Compound 468a) and its isomer 8-fluoro-9-((4-fluorobenzyl)oxy)-10H-pyrrolizino[1,2-b]quinolin-10-one (Compound 468b)

Steps: Following the procedure of Example 1, ethyl 5-(trifluoromethyl)-4-oxo-2-(1H-pyrrol-2-yl)-1,4-dihydroquinoline-3-carboxylate (50 mg) and 1-(bromomethyl)-4-fluorobenzene (46 mg) were subjected to reaction and post-treatment to give yellow solids (39% and 35% yields). ESI-MS m/z 363.09 [M+H]$^+$.

Example 81

4-(2-Fluorobenzyl)-9,10-dioxo-4,10-dihydro-9H-pyrrolizino[1,2-b]quinoline-8-carbonitrile (Compound 469a) and its isomer 9-((2-fluorobenzyl)oxy)-10-oxo-10H-pyrrolizino[1,2-b]quinoline-8-carbonitrile (Compound 469b)

Steps: Following the procedure of Example 1, ethyl 5-cyano-4-oxo-2-(1H-pyrrol-2-yl)-1,4-dihydroquinoline-3-carboxylate (50 mg) and 1-(bromomethyl)-2-fluorobenzene (46 mg) were subjected to reaction and post-treatment to give yellow solids (39% and 35% yields). ESI-MS m/z 370.09 [M+H]$^+$ Example 82

8-Hydroxy-9H-pyrrolizino[1,2-b]quinoline-9,10(4H)-dione (Compound 470a) and its isomer 8,9-dihydroxy-10H-pyrrolizino[1,2-b]quinolin-10-one (Compound 470b)

Steps: Following the procedure of Example 1, ethyl 5-hydroxy-4-oxo-2-(1H-pyrrol-2-yl)-1,4-dihydroquinoline-3-carboxylate (50 mg) and potassium carbonate (10 mg) were dissolved in an appropriate amount of acetonitrile, the mixture was stirred at a high temperature for 10 h, subjected to reaction and post-treatment to give yellow solids (32% and 30% yields). ESI-MS m/z 253.05 [M+H]$^+$.

Example 83

4-(4-Chlorobenzyl)-8-fluoro-9H-pyrrolizino[1,2-b]quinoline-9,10(4H)-dione (Compound 471a) and its isomer 9-((4-chlorobenzyl)oxy)-8-fluoro-10H-pyrrolizino[1,2-b]quinolin-10-one (Compound 471b)

Steps: Following the procedure of Example 1, ethyl 5-fluoro-4-oxo-2-(1H-pyrrol-2-yl)-1,4-dihydroquinoline-3-carboxylate (50 mg) and 1-(bromomethyl)-4-chlorobenzene (46 mg) were subjected to reaction and post-treatment to give yellow solids (39% and 35% yields). ESI-MS m/z 379.06 [M+H]$^+$.

Example 84

4-(2-Chlorobenzyl)-8-(trifluoromethyl)-9H-pyrrolizino[1,2-b]quinoline-9,10(4H)-dione (Compound 472a) and its isomer 9-((2-chlorobenzyl)oxy)-8-(trifluoromethyl)-10H-pyrrolizino[1,2-b]quinolin-10-one (Compound 472b)

Steps: Following the procedure of Example 1, ethyl fluoro-4-oxo-2-(1H-pyrrol-2-yl)-1,4-dihydroquinoline-3-carboxylate (50 mg) and 1-(bromomethyl)-2-chlorobenzene (46 mg) were subjected to reaction and post-treatment to give yellow solids (39% and 35% yields). ESI-MS m/z 429.15 [M+H]$^+$.

Example 85

8-Methoxy-9H-pyrrolizino[1,2-b]quinoline-9,10(4H)-dione (Compound 473a) and its isomer 9-hydroxy-8-methoxy-10H-pyrrolizino[1,2-b]quinolin-10-one (Compound 473b)

Steps: Following the procedure of Example 1, ethyl 5-methoxy-4-oxo-2-(1H-pyrrol-2-yl)-1,4-dihydroquinoline-3-carboxylate (50 mg) and potassium carbonate (10 mg) were dissolved in an appropriate amount of acetonitrile, the mixture was stirred at a high temperature for 10 h, subjected to reaction and post-treatment to give yellow solids (32% and 30% yields). ESI-MS m/z 267.07 [M+H]$^+$.

Example 86

8-Chloro-4-(4-fluorobenzyl)-9H-pyrrolizino[1,2-b]quinoline-9,10(4H)-dione (Compound 474a) and its isomer 8-chloro-9-((4-fluorobenzyl)oxy)-10H-pyrrolizino[1,2-b]quinolin-10-one (Compound 474b)

Steps: Following the procedure of Example 1, ethyl 5-chloro-4-oxo-2-(1H-pyrrol-2-yl)-1,4-dihydroquinoline-3-carboxylate (50 mg) and 1-(bromomethyl)-4-fluorobenzene (46 mg) were subjected to reaction and post-treatment to give yellow solids (39% and 35% yields). ESI-MS m/z 379.06 [M+H]$^+$.

Example 87

8-Fluoro-4-(3-fluorobenzyl)-9H-pyrrolizino[1,2-b]quinoline-9,10(4H)-dione (Compound 475a) and its isomer 8-fluoro-9-((3-fluorobenzyl)oxy)-10H-pyrrolizino[1,2-b]quinolin-10-one (Compound 475b)

Steps: Following the procedure of Example 1, ethyl 5-fluoro-4-oxo-2-(1H-pyrrol-2-yl)-1,4-dihydroquinoline-3-carboxylate (50 mg) and 1-(bromomethyl)-3-fluorobenzene (46 mg) were subjected to reaction and post-treatment to give yellow solids (39% and 35% yields). ESI-MS m/z 363.09[M+H]$^+$.

Example 88

9,10-Dioxo-4,10-dihydro-9H-pyrrolizino[1,2-b]quinoline-8-carbonitrile (Compound 476a) and its isomer 9-hydroxy-10-oxo-10H-pyrrolizino[1,2-b]quinoline-8-carbonitrile (Compound 476b)

Steps: Following the procedure of Example 1, ethyl 5-cyano-4-oxo-2-(1H-pyrrol-2-yl)-1,4-dihydroquinoline-3-carboxylate (50 mg) and potassium carbonate (10 mg) were dissolved in an appropriate amount of acetonitrile, the mixture was stirred at a high temperature for 10 h, subjected to reaction and post-treatment to give yellow solids (32% and 30% yields). ESI-MS m/z 262.05 [M+H]$^+$.

Example 89

8-Chloro-4-(4-chlorobenzyl)-9H-pyrrolizino[1,2-b]quinoline-9,10(4H)-dione (Compound 477a) and its isomer 8-chloro-9-((4-chlorobenzyl)oxy)-10H-pyrrolizino[1,2-b]quinolin-10-one (Compound 477b)

Steps: Following the procedure of Example 1, ethyl 5-chloro-4-oxo-2-(1H-pyrrol-2-yl)-1,4-dihydroquinoline-3- carboxylate (50 mg) and 1-(bromomethyl)-4-chlorobenzene (46 mg) were subjected to reaction and post-treatment to give yellow solids (39% and 35% yields). ESI-MS m/z 395.03 [M+H]+.

Example 90

8-Chloro-4-(3-chlorobenzyl)-9H-pyrrolizino[1,2-b]quinoline-9,10(4H)-dione (Compound 478a) and its isomer 8-chloro-9-((3-chlorobenzyl)oxy)-10H-pyrrolizino[1,2-b]quinolin-10-one (Compound 478b)

Steps: Following the procedure of Example 1, ethyl 5-chloro-4-oxo-2-(1H-pyrrol-2-yl)-1,4-dihydroquinoline-3-carboxylate (50 mg) and 1-(bromomethyl)-3-chlorobenzene (46 mg) were subjected to reaction and post-treatment to give yellow solids (39% and 35% yields). ESI-MS m/z 395.03 [M+H]+.

Example 91

8-(Trifluoromethyl)-9H-pyrrolizino[1,2-b]quinoline-9,10(4H)-dione (Compound 479a) and its isomer 9-hydroxy-8-(trifluoromethyl)-10H-pyrrolizino[1,2-b]quinolin-10-one (Compound 479b)

Steps: Following the procedure of Example 1, ethyl 5-(trifluoromethyl) 4-oxo-2-(1H-pyrrol-2-yl)-1,4-dihydroquinoline-3-carboxylate (50 mg) and potassium carbonate (10 mg) were dissolved in an appropriate amount of acetonitrile, the mixture was stirred at a high temperature for 10 h, subjected to reaction and post-treatment to give yellow solids (32% and 30% yields). ESI-MS m/z 305.05 [M+H]+.

Example 92

8-Chloro-4-(2-fluorobenzyl)-9H-pyrrolizino[1,2-b]quinoline-9,10(4H)-dione (Compound 480a) and its isomer 8-chloro-9-((2-fluorobenzyl)oxy)-10H-pyrrolizino[1,2-b]quinolin-10-one (Compound 480a)

Steps: Following the procedure of Example 1, ethyl 5-chloro-4-oxo-2-(1H-pyrrol-2-yl)-1,4-dihydroquinoline-3-carboxylate (50 mg) and 1-(bromomethyl)-2-fluorobenzene (46 mg) were subjected to reaction and post-treatment to give yellow solids (39% and 35% yields). ESI-MS m/z 379.06 [M+H]>.

Example 93

5-Chloro-4-(4-fluorobenzyl)-9H-pyrrolizino[1,2-b]quinoline-9,10(4H)-dione (Compound 481a) and its isomer 5-chloro-9-((4-fluorobenzyl)oxy)-10H-pyrrolizino[1,2-b]quinolin-10-one (Compound 481b)

Steps: Following the procedure of Example 1, ethyl 8-chloro-2-(1H-pyrrol-2-yl)-1,4-dihydroquinoline-3-carboxylate (50 mg) and 1-(bromomethyl)-4-fluorobenzene (15 mg) were subjected to reaction and post-treatment to give yellow solids (43% and 39% yields). ESI-MS m/z 379.06 [M+H]+, 381.06 [M+2+H]+.

Example 94

4-(4-Fluorobenzyl)-9,10-dioxo-6-(piperazin-1-yl)-4,10-dihydro-9H-pyrrolizino[1,2-b]quinoline-5-carbonitrile (Compound 482a) and its isomer 9-((4-fluorobenzyl)oxy)-10-oxo-6-(piperazin-1-yl)-10H-pyrrolizino[1,2-b]quinoline-5-carbonitrile (Compound 482b)

Steps: Following the procedure of Example 1, ethyl 8-cyano-4-oxo-2-(1H-pyrrol-2-yl)-1,4-dihydroquinoline-3-carboxylate (50 mg) and 1-(bromomethyl)-4-fluorobenzene (10 mL) were subjected to reaction and post-treatment to give yellow solid. Then the obtained yellow solid (20 mg) was stirred and mixed with anhydrous piperazine (28 mg) and dimethylformamide (55 mL), and the mixture was reacted at 140° C. for 2 h, and the solvent was evaporated under reduced pressure, the residue was suspended in water 30 mL and boiled for a few minutes, and then was subjected to cooling, suction filtration, water washing, and vacuum drying to constant weight to give yellow solids. (78% and 73% yields). ESI-MS m/z 454.16 [M+H]+.

Example 95

4-(4-Chlorobenzyl)-6-(piperazin-1-yl)-5-(trifluoromethyl)-9H-pyrrolizino[1,2-b]quinoline-9,10(4H)-dione (Compound 483a) and its isomer 9-((4-chlorobenzyl)oxy)-6-(piperazin-1-yl)-5-(trifluoromethyl)-10H-pyrrolizino[1,2-b]quinolin-10-one (Compound 483b)

Steps: Following the procedure of Example 1, ethyl 8-trifluoromethyl-4-oxo-2-(1H-pyrrol-2-yl)-1,4-dihydroquinoline-3-carboxylate (50 mg) and 1-(bromomethyl)-4-chlorobenzene (10 mL) were subjected to reaction and post-treatment to give yellow solid. Then the obtained yellow solid (20 mg) was stirred and mixed with anhydrous piperazine (28 mg) and dimethylformamide (55 mL), and the mixture was reacted at 140° C. for 2 h, and the solvent was evaporated under reduced pressure, the residue was suspended in water 30 mL and boiled for a few minutes, and then was subjected to cooling, suction filtration, water washing, and vacuum drying to constant weight to give yellow solids. (75% and 73% yields)
ESI-MS m/z 513.12 [M+H]+, 515.12 [M+2+H]+.

Example 96

4-(4-Chlorobenzyl)-5-fluoro-6-(piperazin-1-yl)-9H-pyrrolizino[1,2-b]quinoline-9,10(4H)-dione (Compound 484a) and its isomer 9-((4-chlorobenzyl)oxy)-5-fluoro-6-(piperazin-1-yl)-10H-pyrrolizino[1,2-b]quinolin-10-one (Compound 484b)

Steps: Following the procedure of Example 1, ethyl 8-fluoro-4-oxo-2-(1H-pyrrol-2-yl)-1,4-dihydroquinoline-3-carboxylate (50 mg) and 1-(bromomethyl)-4-chlorobenzene (10 mL) were subjected to reaction and post-treatment to give yellow solid. Then the obtained yellow solid (20 mg) was stirred and mixed with anhydrous piperazine (28 mg) and dimethylformamide (55 mL), and the mixture was reacted at 140° C. for 2 h, and the solvent was evaporated under reduced pressure, the residue was suspended in water 30 mL and boiled for a few minutes, and then was subjected to cooling, suction filtration, water washing, and vacuum drying to constant weight to give yellow solids. (76% and 73% yields). ESI-MS m/z 463.13 [M+H]+, 465.13 [M+2+H]+.

Example 97

5-Fluoro-4-(4-fluorobenzyl)-6-(piperazin-1-yl)-9H-pyrrolizino[1,2-b]quinoline-9,10(4H)-dione (Compound 485a) and its isomer 5-fluoro-9-((4-fluorobenzyl)oxy)-6-(piperazin-1-yl)-10H-pyrrolizino[1,2-b]quinolin-10-one (Compound 485b)

Steps: Following the procedure of Example 1, ethyl 8-fluoro-4-oxo-2-(1H-pyrrol-2-yl)-1,4-dihydroquinoline-3- carboxylate (50 mg) and 1-(bromomethyl)-4-fluorobenzene (10 mL) were subjected to reaction and post-treatment to give yellow solid. Then the obtained yellow solid (20 mg) was stirred and mixed with anhydrous piperazine (28 mg) and dimethylformamide (55 mL), and the mixture was reacted at 140° C. for 2 h, and the solvent was evaporated under reduced pressure, the residue was suspended in water 30 mL and boiled for a few minutes, and then was subjected to cooling, suction filtration, water washing, and vacuum drying to constant weight to give yellow solids. (79% and 73% yields). ESI-MS m/z 447.16 $[M+H]^+$.

Example 98

4-(4-Fluorobenzyl)-9,10-dioxo-6-(piperazin-1-yl)-4,10-dihydro-9H-pyrrolizino[1,2-b]quinoline-5-carbonitrile (Compound 486a) and its isomer 9-((4-fluorobenzyl)oxy)-10-oxo-6-(piperazin-1-yl)-10H-pyrrolizino[1,2-b]quinoline-5-carbonitrile (Compound 486b)

Steps: Following the procedure of Example 1, ethyl 8-cyano-4-oxo-2-(1H-pyrrol-2-yl)-1,4-dihydroquinoline-3-carboxylate (50 mg) and 1-(bromomethyl)-4-fluorobenzene (10 mL) were subjected to reaction and post-treatment to give yellow solid. Then the obtained yellow solid (20 mg) was stirred and mixed with anhydrous piperazine (28 mg) and dimethylformamide (55 mL), and the mixture was reacted at 140° C. for 2 h, and the solvent was evaporated under reduced pressure, the residue was suspended in water 30 mL and boiled for a few minutes, and then was subjected to cooling, suction filtration, water washing, and vacuum drying to constant weight to give yellow solids. (71% and 69% yields). ESI-MS m/z 454.16 $[M+H]^+$.

Example 99

4-(4-Chlorobenzyl)-6-(piperazin-1-yl)-5-(trifluoromethyl)-9H-pyrrolizino[1,2-b]quinoline-9,10(4H)-dione (Compound 487a) and its isomer 9-((4-chlorobenzyl)oxy)-6-(piperazin-1-yl)-5-(trifluoromethyl)-10H-pyrrolizino[1,2-b]quinolin-10-one (Compound 487b)

Steps: Following the procedure of Example 1, ethyl 8-trifluoromethyl-4-oxo-2-(1H-pyrrol-2-yl)-1,4-dihydroquinoline-3-carboxylate (50 mg) and 1-(bromomethyl)-4-chlorobenzene (10 mL) were subjected to reaction and post-treatment to give yellow solid. Then the obtained yellow solid (20 mg) was stirred and mixed with anhydrous piperazine (28 mg) and dimethylformamide (55 mL), and the mixture was reacted at 140° C. for 2 h, and the solvent was evaporated under reduced pressure, the residue was suspended in water 30 mL and boiled for a few minutes, and then was subjected to cooling, suction filtration, water washing, and vacuum drying to constant weight to give yellow solids (78% and 72% yields). ESI-MS m/z 513.12 $[M+H]^+$, 515.12 $[M+2+H]^+$.

Example 100

6-Fluoro-9H-pyrrolizino[1,2-b]quinoline-9,10(4H)-dione (Compound 488a) and its isomer 6-fluoro-9-hydroxy-10H-pyrrolizino[1,2-b]quinolin-10-one (Compound 488b)

Steps: Following the procedure of Example 27, ethyl 7-fluoro-4-oxo-2-(1H-pyrrol-2-yl)-1,4-dihydroquinoline-3-carboxylate (50 mg) was subjected to reaction and post-treatment to give solids.
ESI-MS m/z 254.05 $[M+H]^+$.

Example 101

6-Fluoro-4-(4-fluorobenzyl)-9H-pyrrolizino[1,2-b]quinoline-9,10(4H)-dione (Compound 490a) and its isomer 6-fluoro-9-((4-fluorobenzyl)oxy)-10H-pyrrolizino[1,2-b]quinolin-10-one (Compound 490b)

Steps: Following the procedure of Example 1, ethyl 7-fluoro-4-oxo-2-(1H-pyrrol-2-yl)-1,4-dihydroquinoline-3-carboxylate (50 mg) and 1-(bromomethyl)-4-fluorobenzene (10 mg) were subjected to reaction and post-treatment to give solids (45% and 39% yields). ESI-MS m/z 363.09$[M+H]^+$.

Example 102

6-Fluoro-4-(3-fluorobenzyl)-9H-pyrrolizino[1,2-b]quinoline-9,10(4H)-dione (Compound 491a) and its isomer 6-fluoro-9-((3-fluorobenzyl)oxy)-10H-pyrrolizino[1,2-b]quinolin-10-one (Compound 491b)

Steps: Following the procedure of Example 1, ethyl 7-fluoro-4-oxo-2-(1H-pyrrol-2-yl)-1,4-dihydroquinoline-3-carboxylate (50 mg) and 1-(bromomethyl)-3-fluorobenzene (10 mg) were subjected to reaction and post-treatment to give solids (60% and 58% yields). ESI-MS m/z 363.09$[M+H]^+$.

Example 103

4-(4-Chlorobenzyl)-6-fluoro-9H-pyrrolizino[1,2-b]quinoline-9,10(4H)-dione (Compound 496a) and its isomer 9-((4-chlorobenzyl)oxy)-6-fluoro-10H-pyrrolizino[1,2-b]quinolin-10-one (Compound 496b)

Steps: Following the procedure of Example 1, ethyl 7-fluoro-4-oxo-2-(1H-pyrrol-2-yl)-1,4-dihydroquinoline-3-carboxylate (50 mg) and 1-(bromomethyl)-4-chlorobenzene (10 mg) were subjected to reaction and post-treatment to give solids (31% and 28% yields). ESI-MS m/z 378.06$[M+H]^+$, 380.05$[M+H]^+$.

Example 104

4-(3-Chlorobenzyl)-6-fluoro-9H-pyrrolizino[1,2-b]quinoline-9,10(4H)-dione (Compound 497a) and its isomer 9-((3-chlorobenzyl)oxy)-6-fluoro-10H-pyrrolizino[1,2-b]quinolin-10-one (Compound 497b)

Steps: Following the procedure of Example 1, ethyl 7-fluoro-4-oxo-2-(1H-pyrrol-2-yl)-1,4-dihydroquinoline-3-carboxylate (50 mg) and 1-(bromomethyl)-3-chlorobenzene (10 mg) were subjected to reaction and post-treatment to give solids (31% and 28% yields). ESI-MS m/z 378.06$[M+H]^+$, 380.05$[M+H]^+$.

Example 105

6-Chloro-9H-pyrrolizino[1,2-b]quinoline-9,10(4H)-dione (Compound 500a) and its isomer 6-chloro-9-hydroxy-10H-pyrrolizino[1,2-b]quinolin-10-one (Compound 500b)

Steps: Following the procedure of Example 27, ethyl 7-chloro-4-oxo-2-(1H-pyrrol-2-yl)-1,4-dihydroquinoline-3-carboxylate (50 mg) was subjected to reaction and post-treatment to give solids.
ESI-MS m/z 270.02 $[M+H]^+$, 272.02 $[M+2+H]^+$.

Example 106

6-Chloro-4-(4-fluorobenzyl)-9H-pyrrolizino[1,2-b]quinoline-9,10(4H)-dione (Compound 502a) and its isomer 6-chloro-9-((4-fluorobenzyl)oxy)-10H-pyrrolizino[1,2-b]quinolin-10-one (Compound 502b)

Steps: Following the procedure of Example 1, ethyl 7-chloro-4-oxo-2-(1H-pyrrol-2-yl)-1,4-dihydroquinoline-3-carboxylate (50 mg) and 1-(bromomethyl)-4-fluorobenzene (10 mg) were subjected to reaction and post-treatment to give solids (50% and 47% yields). ESI-MS m/z 378.06[M+H]$^+$, 380.05[M+H]$^+$.

Example 107

6-Chloro-4-(2-fluorobenzyl)-9H-pyrrolizino[1,2-b]quinoline-9,10(4H)-dione (Compound 504a) and its isomer 6-chloro-9-((2-fluorobenzyl)oxy)-10H-pyrrolizino[1,2-b]quinolin-10-one (Compound 504b)

Steps: Following the procedure of Example 1, ethyl 7-chloro-4-oxo-2-(1H-pyrrol-2-yl)-1,4-dihydroquinoline-3-carboxylate (50 mg) and 1-(bromomethyl)-2-fluorobenzene (10 mg) were subjected to reaction and post-treatment to give solids (35% and 33% yields). ESI-MS m/z 378.06[M+H]$^+$, 380.05[M+H]$^+$.

Example 108

6-Chloro-4-(4-chlorobenzyl)-9H-pyrrolizino[1,2-b]quinoline-9,10(4H)-dione (Compound 508a) and its isomer 6-chloro-9-((4-chlorobenzyl)oxy)-10H-pyrrolizino[1,2-b]quinolin-10-one (Compound 508b)

Steps: Following the procedure of Example 1, ethyl 7-chloro-4-oxo-2-(1H-pyrrol-2-yl)-1,4-dihydroquinoline-3-carboxylate (50 mg) and 1-(bromomethyl)-4-chlorobenzene (10 mg) were subjected to reaction and post-treatment to give solids (50% and 48% yields). ESI-MS m/z 394.03[M+2+H]$^+$, 396.02[M+2+2+H]$^+$.

Example 109

6-Chloro-4-(2-chlorobenzyl)-9H-pyrrolizino[1,2-b]quinoline-9,10(4H)-dione Compound 510a) and its isomer 6-chloro-9-((2-chlorobenzyl)oxy)-10H-pyrrolizino[1,2-b]quinolin-10-one (Compound 510b)

Steps: Following the procedure of Example 1, ethyl 7-chloro-4-oxo-2-(1H-pyrrol-2-yl)-1,4-dihydroquinoline-3-carboxylate (50 mg) and 1-(bromomethyl)-2-chlorobenzene (10 mg) were subjected to reaction and post-treatment to give solids (40% and 38% yields). ESI-MS m/z 394.03[M+2+H]$^+$, 396.02[M+2+2+H]$^+$.

Example 110

9,10-Dioxo-4,10-dihydro-9H-pyrrolizino[1,2-b]quinoline-6-carbonitrile (Compound 512a) and its isomer 9-hydroxy-10-oxo-10H-pyrrolizino[1,2-b]quinoline-6-carbonitrile (Compound 512b)

Steps: Following the procedure of Example 27, ethyl 4-oxo-2-(1H-pyrrol-2-yl)-1,4-dihydro-7-cyanoquinoline-3-carboxylate (50 mg) was subjected to reaction and post-treatment to give solids.
ESI-MS m/z 261.05 [M+H]$^+$.

Example 111

4-(4-Fluorobenzyl)-9,10-dioxo-4,10-dihydro-9H-pyrrolizino[1,2-b]quinoline-6-carbonitrile (Compound 514a) and its isomer 9-((4-fluorobenzyl)oxy)-10-oxo-10H-pyrrolizino[1,2-b]quinoline-6-carbonitrile (Compound 514b)

Steps: Following the procedure of Example 1, ethyl 4-oxo-2-(1H-pyrrol-2-yl)-1,4-dihydro-7-cyanoquinoline-3-carboxylate (50 mg) and 1-(bromomethyl)-4-fluorobenzene (15 mg) were subjected to reaction and post-treatment to give solids (32% and 29% yields). ESI-MS m/z 370.11 [M+H]$^+$.

Example 112

4-(3-Fluorobenzyl)-9,10-dioxo-4,10-dihydro-9H-pyrrolizino[1,2-b]quinoline-6-carbonitrile (Compound 515a) and its isomer 9-((3-fluorobenzyl)oxy)-10-oxo-10H-pyrrolizino[1,2-b]quinoline-6-carbonitrile (Compound 515b)

Steps: Following the procedure of Example 1, ethyl 4-oxo-2-(1H-pyrrol-2-yl)-1,4-dihydro-7-cyanoquinoline-3-carboxylate (50 mg) and 1-(bromomethyl)-3-fluorobenzene (15 mg) were subjected to reaction and post-treatment to give solids (32% and 29% yields). ESI-MS m/z 370.11 [M+H]$^+$.

Example 113

4-(2-Fluorobenzyl)-9,10-dioxo-4,10-dihydro-9H-pyrrolizino[1,2-b]quinoline-6-carbonitrile (Compound 516a) and its isomer 9-((2-fluorobenzyl)oxy)-10-oxo-10H-pyrrolizino[1,2-b]quinoline-6-carbonitrile (Compound 516b)

Steps: Following the procedure of Example 1, ethyl 4-oxo-2-(1H-pyrrol-2-yl)-1,4-dihydro-7-cyanoquinoline-3-carboxylate (50 mg) and 1-(bromomethyl)-2-fluorobenzene (15 mg) were subjected to reaction and post-treatment to give solids (37% and 35% yields). ESI-MS m/z 370.11 [M+H]$^+$.

Example 114

6-Hydroxy-9H-pyrrolizino[1,2-b]quinoline-9,10(4H)-dione (Compound 524a) and its isomer 6,9-dihydroxy-10H-pyrrolizino[1,2-b]quinolin-10-one (Compound 524b)

Steps: Following the procedure of Example 27, ethyl 7-hydroxy-4-oxo-2-(1H-pyrrol-2-yl)-1,4-dihydroquinoline-3-carboxylate (50 mg) was subjected to reaction and post-treatment to give solids (30% and 30% yields). ESI-MS m/z 252.02 [M+H]$^+$.

Example 115

6-(Trifluoromethyl)-9H-pyrrolizino[1,2-b]quinoline-9,10(4H)-dione (Compound 536a) and its isomer 9-hydroxy-6-(trifluoromethyl)-10H-pyrrolizino[1,2-b]quinolin-10-one (Compound 536b)

Steps: Following the procedure of Example 1, ethyl 7-trifluoromethyl-4-oxo-2-(1H-pyrrol-2-yl)-1,4-dihydroquinoline-3-carboxylate (50 mg) and potassium carbonate (50 mg) were dissolved in an appropriate amount of acetonitrile, the mixture was stirred at a high temperature for 10 h, subjected to reaction and post-treatment to give solids (35% and 35% yields). ESI-MS m/z 304.05 [M+H]$^+$.

Example 116

4-(4-Chlorobenzyl)-6-(trifluoromethyl)-9H-pyrrolizino[1,2-b]quinoline-9,10(4H)-dione (Compound 544a) and it isomer 9-((4-chlorobenzyl)oxy)-6-(trifluoromethyl)-10H-pyrrolizino[1,2-b]quinolin-10-one (Compound 544b)

Steps: Following the procedure of Example 1, ethyl 7-trifluoromethyl-4-oxo-2-(1H-pyrrol-2-yl)-1,4-dihydroquinoline-3-carboxylate (50 mg) and 1-(bromomethyl)-4-chlorobenzene (20 mg) were subjected to reaction and post-treatment to give solids (35% and 45% yields). ESI-MS m/z 428.05 [M+H]$^+$, 430.05 [M+2+H]$^+$.

Example 117

4-(3-Chlorobenzyl)-6-(trifluoromethyl)-9H-pyrrolizino[1,2-b]quinoline-9,10(4H)-dione (Compound 545a) and its isomer 9-((3-chlorobenzyl)oxy)-6-(trifluoromethyl)-10H-pyrrolizino[1,2-b]quinolin-10-one (Compound 545b)

Steps: Following the procedure of Example 1, ethyl 7-trifluoromethyl-4-oxo-2-(1H-pyrrol-2-yl)-1,4-dihydroquinoline-3-carboxylate (50 mg) and 1-(bromomethyl)-3-chlorobenzene (20 mg) were subjected to reaction and post-treatment to give solids (30% and 35% yields). ESI-MS m/z 428.05 [M+H]$^+$, 430.05 [M+2+H]$^+$.

Example 118

4-(2-Chlorobenzyl)-6-(trifluoromethyl)-9H-pyrrolizino[1,2-b]quinoline-9,10(4H)-dione (Compound 546a) and its isomer 9-((2-chlorobenzyl)oxy)-6-(trifluoromethyl)-10H-pyrrolizino[1,2-b]quinolin-10-one (Compound 546b)

Steps: Following the procedure of Example 1, ethyl 7-trifluoromethyl-4-oxo-2-(1H-pyrrol-2-yl)-1,4-dihydroquinoline-3-carboxylate (50 mg) and 1-(bromomethyl)-2-chlorobenzene (20 mg) were subjected to reaction and post-treatment to give solids (35% and 35% yields). ESI-MS m/z 428.05 [M+H]$^+$, 430.05 [M+2+H]$^+$.

Example 119

6-(Trifluoromethoxy)-9H-pyrrolizino[1,2-b]quinoline-9,10(4H)-dione (Compound 548a) and its isomer 9-hydroxy-6-trifluoromethoxy-10H-pyrrolizino[1,2-b]quinolin-10-one (Compound 548b)

Steps: Following the procedure of Example 27, ethyl 7-trifluoromethoxy-4-oxo-2-(1H-pyrrol-2-yl)-1,4-dihydroquinoline-3-carboxylate (50 mg) was subjected to reaction and post-treatment to give solids (30% and 42% yields). ESI-MS m/z 266.07 [M+H]$^+$.

Example 120

6-Methoxy-9H-pyrrolizino[1,2-b]quinoline-9,10(4H)-dione (Compound 560a) and its isomer 9-hydroxy-6-methoxy-10H-pyrrolizino[1,2-b]quinolin-10-one (Compound 560b)

Steps: Following the procedure of Example 27, ethyl 7-methoxy-4-oxo-2-(1H-pyrrol-2-yl)-1,4-dihydroquinoline-3-carboxylate (50 mg) was subjected to reaction and post-treatment to give solids (38% and 38% yields). ESI-MS m/z 266.07 [M+H]$^+$.

Example 121

4-(2-Chloro-4-fluorobenzyl)-9H-pyrrolizino[1,2-b]quinoline-9,10(4H)-dione (Compound 572a) and its isomer 9-((2-chloro-4-fluorobenzyl)oxy)-10H-pyrrolizino[1,2-b]quinolin-10-one (Compound 572b)

Steps: Following the procedure of Example 1, ethyl 4-oxo-2-(1H-pyrrol-2-yl)-1,4-dihydroquinoline-3-carboxylate (50 mg) and 2-chloro-4-fluorobenzyl bromide (15 mg) were subjected to reaction and post-treatment to give yellow solids (38% and 35% yields).

Among them, the nuclear magnetic resonance spectrum data of the N-substituted product: $^1$H NMR (500 MHz, DMSO-d6) δ 8.26 (dd, J=7.9, 1.5 Hz, 1H), 7.73-7.69 (m, 1H), 7.66 (dd, J=8.7, 2.5 Hz, 1H), 7.56 (d, J=8.6 Hz, 1H), 7.53-7.46 (m, 2H), 7.08 (td, J=8.5, 2.6 Hz, 1H), 6.98 (dd, J=8.7, 6.0 Hz, 1H), 6.52 (d, J=3.3 Hz, 1H), 6.34 (t, J=3.2 Hz, 1H), 5.68 (s, 2H); ESI-MS m/z 378.06 [M+H]$^+$, 380.05[M+2+2+H]$^+$.

Example 122

4-(2,5-Difluorobenzyl)-9H-pyrrolizino[1,2-b]quinoline-9,10(4H)-dione (Compound 573a) and its isomer 9-((2,5-difluorobenzyl)oxy)-10H-pyrrolizino[1,2-b]quinolin-10-one (Compound 573b)

Steps: Following the procedure of Example 1, ethyl 4-oxo-2-(1H-pyrrol-2-yl)-1,4-dihydroquinoline-3-carboxylate (50 mg) and 2,5-difluorobenzyl bromide (15 mg) were subjected to reaction and post-treatment to give yellow solids (40% and 38% yields). ESI-MS m/z 362.09 [M+H]$^+$.

Example 123

4-(2-Methylbenzyl)-9H-pyrrolizino[1,2-b]quinoline-9,10(4H)-dione (Compound 574a) and its isomer 9-((2-methylbenzyl)oxy)-10H-pyrrolizino[1,2-b]quinolin-10-one (Compound 574b)

Steps: Following the procedure of Example 1, ethyl 4-oxo-2-(1H-pyrrol-2-yl)-1,4-dihydroquinoline-3-carboxylate (50 mg) and 2-methylbenzyl bromide (15 mg) were subjected to reaction and post-treatment to give yellow solids (38% and 35% yields). Among them, the nuclear magnetic resonance spectrum data of the N-substituted product: $^1$H NMR (500 MHz, CDCl$_3$) δ 8.54 (dd, J=7.9, 1.1 Hz, 1H), 8.00 (d, J=7.9 Hz, 1H), 7.64-7.56 (m, 1H), 7.44 (t, J=7.5 Hz, 1H), 7.31-7.18 (m, 3H), 7.07 (t, J=7.5 Hz, 1H), 6.73 (d, J=7.7 Hz, 1H), 6.25 (d, J=3.2 Hz, 1H), 6.22 (t, J=3.1 Hz, 1H), 5.48 (s, 2H);
ESI-MS m/z 340.12[M+H]$^+$.

Example 124

4-(4-Iodobenzyl)-9H-pyrrolizino[1,2-b]quinoline-9, 10(4H)-dione (Compound 575a) and its isomer 9-((4-iodobenzyl)oxy)-10H-pyrrolizino[1,2-b]quinolin-10-one (Compound 575b)

Steps: Following the procedure of Example 1, ethyl 4-oxo-2-(1H-pyrrol-2-yl)-1,4-dihydroquinoline-3-carboxylate (50 mg) and 1-(bromomethyl)-4-iodobenzene (46 mg) were subjected to reaction and post-treatment to give yellow solids (45% and 40% yields).
ESI-MS m/z 453.00[M+H]$^+$.

Example 125

4-(2-Iodobenzyl)-9H-pyrrolizino[1,2-b]quinoline-9, 10(4H)-dione (Compound 576a) and its isomer 9-((2-iodobenzyl)oxy)-10H-pyrrolizino[1,2-b]quinolin-10-one (Compound 576b)

Steps: Following the procedure of Example 1, ethyl 4-oxo-2-(1H-pyrrol-2-yl)-1,4-dihydroquinoline-3-carboxylate (50 mg) and 1-(bromomethyl)-2-iodobenzene (46 mg) were subjected to reaction and post-treatment to give yellow solids (45% and 40% yields). Among them, the nuclear magnetic resonance spectrum data of the N-substituted product: $^1$H NMR (500 MHz, CDCl$_3$) δ 8.54 (dd, J=7.9, 1.1 Hz, 1H), 8.00 (d, J=7.9 Hz, 1H), 7.64-7.56 (m, 1H), 7.44 (t, J=7.5 Hz, 1H), 7.31-7.18 (m, 3H), 7.07 (t, J=7.5 Hz, 1H), 6.73 (d, J=7.7 Hz, 1H), 6.25 (d, J=3.2 Hz, 1H), 6.22 (t, J=3.1 Hz, 1H), 5.48 (s, 2H);
ESI-MS m/z 453.00[M+H]$^+$.

Example 126

2-((9,10-Dioxo-9H-pyrrolizino[1,2-b]quinolin-4 (10H)-yl)methyl)benzonitrile (Compound 577a) and its isomer 2-(((10-oxo-10H-pyrrolizino[1,2-b]quinolin-9-yl)oxy)methyl)benzonitrile (Compound 577b)

Steps: Following the procedure of Example 1, Ethyl 4-oxo-2-(1H-pyrrol-2-yl)-1,4-dihydroquinoline-3-carboxylate (50 mg) and 2-(bromomethyl)benzonitrile (15 mg) were subjected to reaction and post-treatment to give yellow solids (29% and 25% yields). Among them, the nuclear magnetic resonance spectrum data of the N-substituted product: 1H NMR (500 MHz, CDCl$_3$) δ 8.54 (dd, J=7.9, 1.2 Hz, 1H), 7.86 (d, J=7.6 Hz, 1H), 7.65-7.59 (m, 1H), 7.55 (t, J=7.6 Hz, 1H), 7.48 (m, 2H), 7.31 (d, J=2.9 Hz, 1H), 7.25 (d, J=8.8 Hz, 1H), 7.03 (d, J=7.8 Hz, 1H), 6.34 (d, J=3.4 Hz, 1H), 6.25 (t, J=3.2 Hz, 1H), 5.80 (s, 2H);
ESI-MS m/z 352.10[M+H]$^+$.

Example 127

4-(2,4-Difluorobenzyl)-9H-pyrrolizino[1,2-b]quinoline-9,10(4H)-dione (Compound 578a) and its isomer 9-((2,4-difluorobenzyl)oxy)-10H-pyrrolizino[1,2-b]quinolin-10-one (Compound 578b)

Steps: Following the procedure of Example 1, ethyl 4-oxo-2-(1H-pyrrol-2-yl)-1,4-dihydroquinoline-3-carboxylate (50 mg) and 2,4-difluorobenzyl bromide (15 mg) were subjected to reaction and post-treatment to give yellow solids (49% and 45% yields).
ESI-MS m/z 362.09 [M+H]$^+$.

Example 128

4-(3,5-Difluorobenzyl)-9H-pyrrolizino[1,2-b]quinoline-9,10(4H)-dione (Compound 579a) and its isomer 9-((3,5-difluorobenzyl)oxy)-10H-pyrrolizino[1,2-b]quinolin-10-one (Compound 579b)

Steps: Following the procedure of Example 1, ethyl 4-oxo-2-(1H-pyrrol-2-yl)-1,4-dihydroquinoline-3-carboxylate (50 mg) and 3,5-difluorobenzyl bromide (15 mg) were subjected to reaction and post-treatment to give yellow solids (49% and 45% yields).
ESI-MS m/z 362.09 [M+H]$^+$.

Example 129

4-(3,5-Dimethoxybenzyl)-9H-pyrrolizino[1,2-b]quinoline-9,10(4H)-dione (Compound 580a) and its isomer 9-((3,5-dimethoxybenzyl)oxy)-10H-pyrrolizino[1,2-b]quinolin-10-one (Compound 580b)

Steps: Following the procedure of Example 1, ethyl 4-oxo-2-(1H-pyrrol-2-yl)-1,4-dihydroquinoline-3-carboxylate (50 mg) and 1-(bromomethyl)-3,5-bis(methoxy)benzene (46 mg) were subjected to reaction and post-treatment to give yellow solids (34% and 30% yields).
ESI-MS m/z 386.13 [M+H]$^+$.

Example 130

4-(2-(Trifluoromethyl)benzyl)-9H-pyrrolizino[1,2-b]quinoline-9,10(4H)-dione (Compound 581a) and its isomer 9-((2-(trifluoromethyl)benzyl)oxy)-10H-pyrrolizino[1,2-b]quinolin-10-one (Compound 581b)

Steps: Following the procedure of Example 1, ethyl 4-oxo-2-(1H-pyrrol-2-yl)-1,4-dihydroquinoline-3-carboxylate (50 mg) and 2-(trifluoromethyl)benzyl bromide (15 mg) were subjected to reaction and post-treatment to give yellow solids (35% and 30% yields).
ESI-MS m/z 394.09[M+H]$^+$.

Example 131

4-(3-Chloro-2-fluorobenzyl)-9H-pyrrolizino[1,2-b]quinoline-9,10(4H)-dione (Compound 582a) and its isomer 9-((3-chloro-2-fluorobenzyl)oxy)-10H-pyrrolizino[1,2-b]quinolin-10-one (Compound 582b)

Steps: Following the procedure of Example 1, ethyl 4-oxo-2-(1H-pyrrol-2-yl)-1,4-dihydroquinoline-3-carboxylate (50 mg) and 2-fluoro-3-chlorobenzyl bromide (15 mg) were subjected to reaction and post-treatment to give yellow solids (40% and 35% yields).
ESI-MS m/z 378.06 [M+H]$^+$, 380.05[M+2+H]$^+$.

Example 132

4-(3-Nitrobenzyl)-9H-pyrrolizino[1,2-b]quinoline-9, 10(4H)-dione (Compound 583a) and its isomer 9-((3-nitrobenzyl)oxy)-10H-pyrrolizino[1,2-b]quinolin-10-one (Compound 583b)

Steps: Following the procedure of Example 1, ethyl 4-oxo-2-(1H-pyrrol-2-yl)-1,4-dihydroquinoline-3-carboxylate (50 mg) and 3-nitrobenzyl bromide (15 mg) were subjected to reaction and post-treatment to give yellow solids (30% and 33% yields).

ESI-MS m/z 372.09[M+H]$^+$, 374.09 [M+2+H]$^+$.

Example 133

4-(2,3,4-Trifluorobenzyl)-9H-pyrrolizino[1,2-b]quinoline-9,10(4H)-dione (Compound 584a) and its isomer 9-((2,3,4-trifluorobenzyl)oxy)-10H-pyrrolizino[1,2-b]quinolin-10-one (Compound 584b)

Steps: Following the procedure of Example 1, ethyl 4-oxo-2-(1H-pyrrol-2-yl)-1,4-dihydroquinoline-3-carboxylate (50 mg) and 2,3,4-trifluorobenzyl bromide (15 mg) were subjected to reaction and post-treatment to give yellow solids (49% and 45% yields).

ESI-MS m/z 380.08 [M+H]$^+$.

Example 134

4-(2,4,5-Trifluorobenzyl)-9H-pyrrolizino[,2-b]quinoline-9,10(4H)-dione (Compound 585a) and its isomer 9-((2,4,5-trifluorobenzyl)oxy)-10H-pyrrolizino[1,2-b]quinolin-10-one (Compound 585b)

Steps: Following the procedure of Example 1, ethyl 4-oxo-2-(1H-pyrrol-2-yl)-1,4-dihydroquinoline-3-carboxylate (50 mg) and 2,4,5-trifluorobenzyl bromide (15 mg) were subjected to reaction and post-treatment to give yellow solids (50% and 53% yields).

ESI-MS m/z 380.08 [M+H]$^+$.

Example 135

4-((Perfluorophenyl)methyl)-9H-pyrrolizino[1,2-b]quinoline-9,10(4H)-dione (Compound 586a) and its isomer 9-((perfluorophenyl)methoxy)-10H-pyrrolizino[1,2-b]quinolin-10-one (Compound 586b)

Steps: Following the procedure of Example 1, ethyl 4-oxo-2-(1H-pyrrol-2-yl)-1,4-dihydroquinoline-3-carboxylate (50 mg) and 2,3,4,5,6-pentafluorobenzyl bromide (15 mg) were subjected to reaction and post-treatment to give yellow solids (55% and 51% yields).

ESI-MS m/z 416.06 [M+H]$^+$.

Example 136

4-(2,3,4,5-Tetrafluorobenzyl)-9H-pyrrolizino[1,2-b]quinoline-9,10(4H)-dione (Compound 587a) and its isomer 9-((2,3,4,5-tetrafluorobenzyl)oxy)-10H-pyrrolizino[1,2-b]quinolin-10-one (Compound 587b)

Steps: Following the procedure of Example 1, ethyl 4-oxo-2-(1H-pyrrol-2-yl)-1,4-dihydroquinoline-3-carboxylate (50 mg) and 2,3,4,5-tetrafluorobenzyl bromide (15 mg) were subjected to reaction and post-treatment to give yellow solids (60% and 51% yields).

ESI-MS m/z 398.07 [M+H]$^+$.

Example 137

4-(4-Fluorobenzyl)-9H-pyrrolizino[1,2-b]quinoline-9,10(4H)-dione (Compound 588a) and its isomer 9-((4-fluorobenzyl)oxy)-10H-pyrrolizino[1,2-b]quinolin-10-one (Compound 588b)

Steps: Following the procedure of Example 1, ethyl 4-oxo-2-(1H-pyrrol-2-yl)-1,4-dihydroquinoline-3-carboxylate (50 mg) and 4-fluorobenzyl bromide (15 mg) were subjected to reaction and post-treatment to give yellow solids (31% and 35% yields). Among them, the nuclear magnetic resonance spectrum data of the N-substituted product: $^1$H NMR (500 MHz, DMSO-d$_6$) δ 8.27-8.21 (m, 1H), 7.78-7.65 (m, 2H), 7.47 (m, 2H), 7.35 (dd, J=8.6, 5.4 Hz, 2H), 7.17 (t, J=8.8 Hz, 2H), 6.84 (d, J=3.2 Hz, 1H), 6.35 (t, J=3.2 Hz, 1H), 5.75 (s, 2H); ESI-MS m/z 344.10 [M+H]$^+$.

Example 138

4-(4-Chlorobenzyl)-9H-pyrrolizino[1,2-b]quinoline-9,10(4H)-dione (Compound 589a) and its isomer 9-((4-chlorobenzyl)oxy)-10H-pyrrolizino[1,2-b]quinolin-10-one (Compound 589b)

Steps: Following the procedure of Example 1, ethyl 4-oxo-2-(1H-pyrrol-2-yl)-1,4-dihydroquinoline-3-carboxylate (50 mg) and 4-chlorobenzyl bromide (15 mg) were subjected to reaction and post-treatment to give yellow solids (32% and 34% yields). Among them, the nuclear magnetic resonance spectrum data of the N-substituted product: $^1$H NMR (500 MHz, DMSO-d$_6$) δ 8.23 (d, J=7.8 Hz, 1H), 7.68 (d, J=3.5 Hz, 2H), 7.50-7.45 (m, 2H), 7.40 (d, J=8.5 Hz, 2H), 7.32 (d, J=8.5 Hz, 2H), 6.83 (d, J=3.3 Hz, 1H), 6.35 (t, J=3.2 Hz, 1H), 5.76 (s, 2H); ESI-MS m/z 361.07[M+H]$^+$, 363.07[M+2+H]$^+$.

Example 139

4-((9,10-Dioxo-9H-pyrrolizino[1,2-b]quinolin-4(10H)-yl)methyl)benzonitrile Compound 590a) and its isomer 4-(((10-oxo-10H-pyrrolizino[1,2-b]quinolin-9-yl)oxy)methyl)benzonitrile (Compound 590b)

Steps: Following the procedure of Example 1, ethyl 4-oxo-2-(1H-pyrrol-2-yl)-1,4-dihydroquinoline-3-carboxylate (50 mg) and P-cyanobenzyl bromide (15 mg) were subjected to reaction and post-treatment to give yellow solids (29% and 26% yields). Among them, the nuclear magnetic resonance spectrum data of the N-substituted product: $^1$H NMR (500 MHz, CDCl$_3$) δ 8.43 (d, J=8.0 Hz, 1H), 7.71 (d, J=8.4 Hz, 2H), 7.59-7.52 (m, 1H), 7.40-7.34 (m, 3H), 7.24 (d, J=2.9 Hz, 1H), 7.22 (d, J=8.5 Hz, 1H), 6.28 (d, J=3.0 Hz, 1H), 6.22 (t, J=3.2 Hz, 1H), 5.65 (s, 2H); ESI-MS m/z 352.10[M+H]$^+$.

Example 140

4-(4-(Trifluoromethyl)benzyl)-9H-pyrrolizino[1,2-b]quinoline-9,10(4H)-dione (Compound 591a) and its isomer 9-((4-(trifluoromethyl)benzyl)oxy)-10H-pyrrolizino[1,2-b]quinolin-10-one (Compound 591b)

Steps: Following the procedure of Example 1, ethyl 4-oxo-2-(1H-pyrrol-2-yl)-1,4-dihydroquinoline-3-carboxylate (50 mg) and 4-(trifluoromethyl)benzyl bromide (15 mg) were subjected to reaction and post-treatment to give yellow solids (35% and 29% yields).

ESI-MS m/z 394.09[M+H]$^+$.

Example 141

4-(4-(Trifluoromethoxy)benzyl)-9H-pyrrolizino[1,2-b]quinoline-9,10(4H)-dione (Compound 592a) and its isomer 9-((4-(trifluoromethoxy)benzyl)oxy)-10H-pyrrolizino[1,2-b]quinolin-10-one (Compound 592b)

Steps: Following the procedure of Example 1, ethyl 4-oxo-2-(1H-pyrrol-2-yl)-1,4-dihydroquinoline-3-carboxylate (50 mg) and 4-(trifluoromethoxy)benzyl bromide (15 mg) were subjected to reaction and post-treatment to give yellow solids (31% and 29% yields). Among them, the nuclear magnetic resonance spectrum data of the N-substituted product: $^1$H NMR (500 MHz, CDCl$_3$) δ 8.42 (d, J=7.9 Hz, 1H), 7.61-7.51 (m, 1H), 7.36 (t, J=7.5 Hz, 1H), 7.30 (d, J=8.5 Hz, 1H), 7.28-7.19 (m, 5H), 6.35 (d, J=3.3 Hz, 1H), 6.23 (t, J=3.1 Hz, 1H), 5.60 (s, 2H); ESI-MS m/z 411.09 [M+H]$^+$.

Example 142

4-(4-Nitrobenzyl)-9H-pyrrolizino[1,2-b]quinoline-9,10(4H)-dione (Compound 593a) and its isomer 9-((4-nitrobenzyl)oxy)-10H-pyrrolizino[1,2-b]quinolin-10-one (Compound 593b)

Steps: Following the procedure of Example 1, ethyl 4-oxo-2-(1H-pyrrol-2-yl)-1,4-dihydroquinoline-3-carboxylate (50 mg) and p-nitrobenzyl bromide (15 mg) were subjected to reaction and post-treatment to give yellow solids (28% and 29% yields). Among them, the nuclear magnetic resonance spectrum data of the N-substituted product: $^1$H NMR (500 MHz, CDCl$_3$) δ 8.42 (d, J=7.9 Hz, 1H), 7.61-7.51 (m, 1H), 7.36 (t, J=7.5 Hz, 1H), 7.30 (d, J=8.5 Hz, 1H), 7.28-7.19 (m, 5H), 6.35 (d, J=3.3 Hz, 1H), 6.23 (t, J=3.1 Hz, 1H), 5.60 (s, 2H); ESI-MS m/z 372.09 [M+H]$^+$, 374.09 [M+2+H]$^+$.

Example 143

4-(4-Bromobenzyl)-9H-pyrrolizino[1,2-b]quinoline-9,10(4H)-dione (Compound 594a) and its isomer 9-((4-bromobenzyl)oxy)-10H-pyrrolizino[1,2-b]quinolin-10-one (Compound 594b)

Steps: Following the procedure of Example 1, ethyl 4-oxo-2-(1H-pyrrol-2-yl)-1,4-dihydroquinoline-3-carboxylate (50 mg) and p-bromobenzyl bromide (15 mg) were subjected to reaction and post-treatment to give yellow solids (30% and 31% yields).
ESI-MS m/z 405.02[M+H]$^+$, 407.02 [M+2+H]$^+$.

Example 144

4-(3-Fluorobenzyl)-9H-pyrrolizino[1,2-b]quinoline-9,10(4H)-dione (Compound 595a) and its isomer 9-((3-fluorobenzyl)oxy)-10H-pyrrolizino[1,2-b]quinolin-10-one (Compound 595b)

Steps: Following the procedure of Example 1, ethyl 4-oxo-2-(1H-pyrrol-2-yl)-1,4-dihydroquinoline-3-carboxylate (50 mg) and 3-fluorobenzyl bromide (15 mg) were subjected to reaction and post-treatment to give yellow solids (31% and 35% yields). Among them, the nuclear magnetic resonance spectrum data of the N-substituted product: $^1$H NMR (500 MHz, CDCl$_3$) δ 8.32 (d, J=7.9 Hz, 1H), 7.47 (t, J=7.7 Hz, 1H), 7.35-7.21 (m, 3H), 7.15 (d, J=2.4 Hz, 1H), 6.92 (m, 2H), 6.83 (d, J=9.0 Hz, 1H), 6.28 (d, J=3.1 Hz, 1H), 6.14 (t, J=3.0 Hz, 1H), 5.51 (s, 2H); ESI-MS m/z 344.10 [M+H]$^+$.

Example 145

4-(3-Chlorobenzyl)-9H-pyrrolizino[1,2-b]quinoline-9,10(4H)-dione (Compound 596a) and its isomer 9-((3-chlorobenzyl)oxy)-10H-pyrrolizino[1,2-b]quinolin-10-one (Compound 596b)

Steps: Following the procedure of Example 1, ethyl 4-oxo-2-(1H-pyrrol-2-yl)-1,4-dihydroquinoline-3-carboxylate (50 mg) and 3-chlorobenzyl bromide (15 mg) were subjected to reaction and post-treatment to give yellow solids (32% and 35% yields).
ESI-MS m/z 361.07[M+H]$^+$, 363.07[M+2+H]$^+$.

Example 146

3-((9,10-Dioxo-9H-pyrrolizino[1,2-b]quinolin-4(10H)-yl)methyl)benzonitrile (Compound 597a) and its isomer 3-(((10-oxo-10H-pyrrolizino[1,2-b]quinolin-9-yl)oxy)methyl)benzonitrile (Compound 597b)

Steps: Following the procedure of Example 1, ethyl 4-oxo-2-(1H-pyrrol-2-yl)-1,4-dihydroquinoline-3-carboxylate (50 mg) and 3-cyanobenzyl bromide (15 mg) were subjected to reaction and post-treatment to give yellow solids (29% and 30% yields).
ESI-MS m/z 352.10[M+H]$^+$.

Example 147

4-(3-(Trifluoromethyl)benzyl)-9H-pyrrolizino[1,2-b]quinoline-9,10(4H)-dione (Compound 598a) and its isomer 9-((3-(trifluoromethyl)benzyl)oxy)-10H-pyrrolizino[1,2-b]quinolin-10-one (Compound 598b)

Steps: Following the procedure of Example 1, ethyl 4-oxo-2-(1H-pyrrol-2-yl)-1,4-dihydroquinoline-3-carboxylate (50 mg) and 3-(trifluoromethyl)benzyl bromide (15 mg) were subjected to reaction and post-treatment to give yellow solids (35% and 30% yields). Among them, the nuclear magnetic resonance spectrum data of the N-substituted product: $^1$H NMR (500 MHz, DMSO-d$_6$) δ 8.24 (d, J=7.6 Hz, 1H), 7.89 (s, 1H), 7.76-7.65 (m, 2H), 7.65 (d, J=7.8 Hz, 1H), 7.48 (m, 13.0, 4.8 Hz, 3H), 7.40 (d, J=7.8 Hz, 1H), 6.85 (d, J=3.3 Hz, 1H), 6.34 (t, J=3.1 Hz, 1H), 5.88 (s, 2H); ESI-MS m/z 395.09[M+H]$^+$.

Example 148

4-(2-Fluorobenzyl)-9H-pyrrolizino[1,2-b]quinoline-9,10(4H)-dione (Compound 599a) and its isomer 9-((2-fluorobenzyl)oxy)-10H-pyrrolizino[1,2-b]quinolin-10-one (Compound 599b)

Steps: Following the procedure of Example 1, ethyl 4-oxo-2-(1H-pyrrol-2-yl)-1,4-dihydroquinoline-3-carboxylate (50 mg) and 2-fluorobenzyl bromide (15 mg) were subjected to reaction and post-treatment to give yellow solids (35% and 30% yields). Among them, the nuclear magnetic resonance spectrum data of the N-substituted product: $^1$H NMR (500 MHz, DMSO-d$_6$) δ 8.24 (dd, J=7.9, 1.4 Hz, 1H), 7.73-7.68 (m, 1H), 7.65 (d, J=8.4 Hz, 1H), 7.50 (d, J=3.0 Hz, 1H), 7.47 (d, J=7.7 Hz, 1H), 7.40-7.35 (m, 1H), 7.34-7.28 (m, 1H), 7.09 (t, J=7.4 Hz, 1H), 7.06 (t, J=7.0 Hz, 1H), 6.78 (d, J=3.3 Hz, 1H), 6.35 (t, J=3.2 Hz, 1H), 5.77 (s, 2H); ESI-MS m/z 344.10 [M+H]$^+$; ESI-MS m/z 344.10 [M+H]$^+$.

Example 149

4-(2-Chlorobenzyl)-9H-pyrrolizino[1,2-b]quinoline-9,10(4H)-dione (Compound 600a) and its isomer 9-((2-chlorobenzyl)oxy)-10H-pyrrolizino[1,2-b]quinolin-10-one (Compound 600b)

Steps: Following the procedure of Example 1, ethyl 4-oxo-2-(1H-pyrrol-2-yl)-1,4-dihydroquinoline-3-carboxylate (50 mg) and 2-chlorobenzyl bromide (15 mg) were subjected to reaction and post-treatment to give yellow solids (32% and 30% yields). Among them, the nuclear magnetic resonance spectrum data of the N-substituted product: $^1$H NMR (500 MHz, DMSO-d$_6$) δ 8.26 (dd, J=7.9, 1.5 Hz, 1H), 7.73-7.68 (m, 1H), 7.64-7.61 (m, 1H), 7.58 (d, J=8.5 Hz, 1H), 7.49 (dd, J=9.1, 5.3 Hz, 2H), 7.37-7.32 (m, 1H), 7.20 (dd, J=11.0, 4.2 Hz, 1H), 6.90 (d, J=7.2 Hz, 1H), 6.48 (d, J=3.4 Hz, 1H), 6.33 (t, J=3.2 Hz, 1H), 5.72 (s, 2H); ESI-MS m/z 361.07[M+H]$^+$, 363.07[M+2+H]$^+$.

Example 150

4-(3,4-Difluorobenzyl)-9H-pyrrolizino[1,2-b]quinoline-9,10(4H)-dione (Compound 601a) and its isomer 9-((3,4-difluorobenzyl)oxy)-10H-pyrrolizino[1,2-b]quinolin-10-one (Compound 60b)

Steps: Following the procedure of Example 1, ethyl 4-oxo-2-(1H-pyrrol-2-yl)-1,4-dihydroquinoline-3-carboxylate (50 mg) and 3,4-difluorobenzyl bromide (15 mg) were subjected to reaction and post-treatment to give yellow solids (32% and 30% yields). Among them, the nuclear magnetic resonance spectrum data of the N-substituted product: $^1$H NMR (500 MHz, DMSO-d$_6$) δ 8.24 (dd, J=7.9, 1.3 Hz, 1H), 7.74 (d, J=1.9 Hz, 1H), 7.69 (m, 2H), 7.55 (d, J=8.4 Hz, 1H), 7.51-7.44 (m, 2H), 7.17 (dd, J=8.4, 2.0 Hz, 1H), 6.85 (d, J=3.4 Hz, 1H), 6.35 (t, J=3.2 Hz, 1H), 5.76 (s, 2H); Nuclear magnetic resonance data of O-substituted products: $^1$H NMR (500 MHz, CDCl$_3$) δ 8.17 (d, J=7.6 Hz, 11H), 7.92 (d, J=8.2 Hz, 1H), 7.79-7.68 (m, 1H), 7.44 (t, J=7.6 Hz, 1H), 7.35 (dd, J=13.5, 5.2 Hz, 1H), 7.24-7.14 (m, 3H), 6.72 (d, J=3.1 Hz, 1H), 6.42 (t, J=3.1 Hz, 1H), 5.90 (s, 2H); ESI-MS m/z 363.09[M+H]$^+$.

Example 151

4-(4-Chloro-2-fluorobenzyl)-9H-pyrrolizino[1,2-b]quinoline-9,10(4H)-dione (Compound 602a) and its isomer 9-((4-chloro-2-fluorobenzyl)oxy)-10H-pyrrolizino[1,2-b]quinolin-10-one (Compound 602b)

Steps: Following the procedure of Example 1, ethyl 4-oxo-2-(1H-pyrrol-2-yl)-1,4-dihydroquinoline-3-carboxylate (50 mg) and 4-chloro-2-fluorobenzyl bromide (15 mg) were subjected to reaction and post-treatment to give yellow solids (32% and 30% yields). Among them, the nuclear magnetic resonance spectrum data of the N-substituted product: $^1$H NMR (500 MHz, DMSO-d$_6$) δ 8.26 (dd, J=7.9, 1.5 Hz, 1H), 7.73-7.69 (m, 1H), 7.66 (dd, J=8.7, 2.5 Hz, 1H), 7.56 (d, J=8.6 Hz, 1H), 7.53-7.46 (m, 2H), 7.08 (td, J=8.5, 2.6 Hz, 1H), 6.98 (dd, J=8.7, 6.0 Hz, 1H), 6.52 (d, J=3.3 Hz, 1H), 6.34 (t, J=3.2 Hz, 1H), 5.68 (s, 2H); ESI-MS m/z 379.06[M+H]$^+$, 381.06[M+2+H]$^+$.

Example 152

4-(3-Chloro-4-fluorobenzyl)-9H-pyrrolizino[1,2-b]quinoline-9,10(4H)-dione (Compound 603a) and its isomer 9-((3-chloro-4-fluorobenzyl)oxy)-10H-pyrrolizino[1,2-b]quinolin-10-one (Compound 603b)

Steps: Following the procedure of Example 1, ethyl 4-oxo-2-(1H-pyrrol-2-yl)-1,4-dihydroquinoline-3-carboxylate (50 mg) and 4-(bromomethyl)-2-chloro-1-fluorobenzene (46 mg) were subjected to reaction and post-treatment to give yellow solids (32% and 30% yields).

ESI-MS m/z 379.06 [M+H]$^+$, 381.06 [M+2+H]$^+$.

Example 153

4-(4-Methylbenzyl)-9H-pyrrolizino[1,2-b]quinoline-9,10(4H)-dione (Compound 604a) and its isomer 9-((4-methylbenzyl)oxy)-10H-pyrrolizino[1,2-b]quinolin-10-one (Compound 604b)

Steps: Following the procedure of Example 1, ethyl 4-oxo-2-(1H-pyrrol-2-yl)-1,4-dihydroquinoline-3-carboxylate (50 mg) and 1-(bromomethyl)-4-methylbenzene (46 mg) were subjected to reaction and post-treatment to give yellow solids (35% and 30% yields).

ESI-MS m/z 341.12 [M+H]$^+$.

Example 154

4-(4-(Tert-butyl)benzyl)-9H-pyrrolizino[1,2-b]quinoline-9,10(4H)-dione (Compound 605a) and its isomer 9-((4-(tert-butyl)benzyl)oxy)-10H-pyrrolizino[1,2-b]quinolin-10-one (Compound 605b)

Steps: Following the procedure of Example 1, ethyl 4-oxo-2-(1H-pyrrol-2-yl)-1,4-dihydroquinoline-3-carboxylate (50 mg) and 1-(bromomethyl)-4-(tert-butyl)benzene (46 mg) were subjected to reaction and post-treatment to give yellow solids (37% and 39% yields).

ESI-MS m/z 341.12 [M+H]$^+$.

Example 155

4-(4-Bromo-2-fluorobenzyl)-9H-pyrrolizino[1,2-b]quinoline-9,10(4H)-dione (Compound 606a) and its isomer 9-((4-bromo-2-fluorobenzyl)oxy)-10H-pyrrolizino[1,2-b]quinolin-10-one (Compound 606b)

Steps: Following the procedure of Example 1, ethyl 4-oxo-2-(1H-pyrrol-2-yl)-1,4-dihydroquinoline-3-carboxylate (50 mg) and 4-bromo-1-(bromomethyl)-2-fluorobenzene (46 mg) were subjected to reaction and post-treatment to give yellow solids (40% and 36% yields).

ESI-MS m/z 425.01 [M+2+H]+, 427.01 [M+2+2+H]+.

Example 156

4-(3,5-Bis(trifluoromethyl)benzyl)-9H-pyrrolizino[1,2-b]quinoline-9,10(4H)-dione (Compound 607a) and its isomer 9-((3,5-bis(trifluoromethyl)benzyl)oxy)-10H-pyrrolizino[1,2-b]quinolin-10-one (Compound 607b)

Steps: Following the procedure of Example 1, ethyl 4-oxo-2-(1H-pyrrol-2-yl)-1,4-dihydroquinoline-3-carboxylate (50 mg) and 1-(bromomethyl)-3,5-bis(trifluoromethyl)benzene (46 mg) were subjected to reaction and post-treatment to give yellow solids (34% and 40% yields). Among them, the nuclear magnetic resonance spectrum data of the N-substituted product: 1H NMR (500 MHz, CDCl$_3$) δ 8.44 (d, J=6.7 Hz, 1H), 7.89 (s, 1H), 7.66 (s, 2H), 7.57 (t, J=7.2 Hz, 1H), 7.40 (t, J=7.5 Hz, 1H), 7.25 (m, 1H), 7.18 (t, J=12.3 Hz, 1H), 6.29 (d, J=3.3 Hz, 1H), 6.24 (t, J=3.2 Hz, 1H), 5.71 (s, 2H); Among them, the nuclear magnetic resonance spectrum data of the O-substituted product: 1H NMR (500 MHz, CDCl$_3$) δ 8.18-8.14 (m, 1H), 8.01 (s, 2H), 7.96-7.90 (m, 2H), 7.76-7.70 (m, 1H), 7.47 (dd, J=11.2, 4.0 Hz, 1H), 7.23-7.18 (m, 1H), 6.76-6.72 (m, 1H), 6.43 (t, J=3.1 Hz, 1H), 6.05 (s, 2H); ESI-MS m/z 463.08 [M+H]$^+$.

Example 157

4-(3-Iodobenzyl)-9H-pyrrolizino[1,2-b]quinoline-9,10(4H)-dione (Compound 608a) and its isomer 9-((3-iodobenzyl)oxy)-10H-pyrrolizino[1,2-b]quinolin-10-one (Compound 608b)

Steps: Following the procedure of Example 1, ethyl 4-oxo-2-(1H-pyrrol-2-yl)-1,4-dihydroquinoline-3-carboxylate (50 mg) and 1-(bromomethyl)-3-iodobenzene (46 mg) were subjected to reaction and post-treatment to give yellow solids (45% and 42% yields).
ESI-MS m/z 453.00[M+H]$^+$.

Example 158

4-(3-Methylbenzyl)-9H-pyrrolizino[1,2-b]quinoline-9,10(4H)-dione (Compound 609a) and its isomer 9-((3-methylbenzyl)oxy)-10H-pyrrolizino[1,2-b]quinolin-10-one (Compound 609b)

Steps: Following the procedure of Example 1, ethyl 4-oxo-2-(1H-pyrrol-2-yl)-1,4-dihydroquinoline-3-carboxylate (50 mg) and 1-(bromomethyl)-3-methylbenzene (46 mg) were subjected to reaction and post-treatment to give yellow solids (44% and 48% yields).
ESI-MS m/z 341.12 [M+H]+.

Example 159

4-(3-Methoxybenzyl)-9H-pyrrolizino[1,2-b]quinoline-9,10(4H)-dione (Compound 610a) and its isomer 9-((3-methoxybenzyl)oxy)-10H-pyrrolizino[1,2-b]quinolin-10-one (Compound 610b)

Steps: Following the procedure of Example 1, ethyl 4-oxo-2-(1H-pyrrol-2-yl)-1,4-dihydroquinoline-3-carboxylate (50 mg) and 1-(bromomethyl)-3-methoxybenzene (46 mg) were subjected to reaction and post-treatment to give yellow solids (48% and 42% yields).
ESI-MS m/z 357.12 [M+H]$^+$.

Example 160

4-(2-Chloro-5-(trifluoromethyl)benzyl)-9H-pyrrolizino[1,2-b]quinoline-9,10(4H)-dione (Compound 611a) and its isomer 9-((2-chloro-5-(trifluoromethyl)benzyl)oxy)-10H-pyrrolizino[1,2-b]quinolin-10-one (Compound 611b)

Steps: Following the procedure of Example 1, ethyl 4-oxo-2-(1H-pyrrol-2-yl)-1,4-dihydroquinoline-3-carboxylate (50 mg) and 2-(bromomethyl)-1-chloro-4-(trifluoromethyl)benzene (46 mg) were subjected to reaction and post-treatment to give yellow solids (33% and 32% yields).
ESI-MS m/z 428.05[M+H]+, 430.05[M+H]+.

Example 161

4-(2-Bromobenzyl)-9H-pyrrolizino[1,2-b]quinoline-9,10(4H)-dione (Compound 612a) and its isomer 9-((2-bromobenzyl)oxy)-10H-pyrrolizino[1,2-b]quinolin-10-one (Compound 612b)

Steps: Following the procedure of Example 1, ethyl 4-oxo-2-(1H-pyrrol-2-yl)-1,4-dihydroquinoline-3-carboxylate (50 mg) and 1-bromo-2-(bromomethyl)benzene (46 mg) were subjected to reaction and post-treatment to give yellow solids (39% and 36% yields).
ESI-MS m/z 407.02 [M+2+H]+, 409.02[M+2+2+H]+.

Example 162

4-(3,4-Dichlorobenzyl)-9H-pyrrolizino[1,2-b]quinoline-9,10(4H)-dione (Compound 613a) and its isomer 9-((3,4-dichlorobenzyl)oxy)-10H-pyrrolizino[1,2-b]quinolin-10-one (Compound 613b)

Steps: Following the procedure of Example 1, ethyl 4-oxo-2-(1H-pyrrol-2-yl)-1,4-dihydroquinoline-3-carboxylate (50 mg) and 4-(bromomethyl)-1,2-dichlorobenzene (46 mg) were subjected to reaction and post-treatment to give yellow solids (41% and 42% yields).
Among them, the nuclear magnetic resonance spectrum data of the O-substituted product: $^1$H NMR (500 MHz, CDCl$_3$) δ 8.17 (dd, J=8.3, 0.8 Hz, 1H), 7.94-7.87 (m, 1H), 7.74-7.69 (m, 1H), 7.61 (d, J=1.7 Hz, 1H), 7.49 (d, J=8.2 Hz, 1H), 7.47-7.41 (m, 1H), 7.34 (dd, J=8.2, 1.9 Hz, 1H), 7.19 (d, J=2.3 Hz, 1H), 6.73 (s, 1H), 6.42 (t, J=3.1 Hz, 1H), 5.90 (s, 2H); ESI-MS m/z 399.02 [M+2+H]$^+$, 401.02 [M+2+2+H]$^+$.

Example 163

4-(2,6-Dichlorobenzyl)-9H-pyrrolizino[1,2-b]quinoline-9,10(4H)-dione (Compound 614a) and its isomer 9-((2,6-dichlorobenzyl)oxy)-10H-pyrrolizino[1,2-b]quinolin-10-one (Compound 614b)

Steps: Following the procedure of Example 1, ethyl 4-oxo-2-(1H-pyrrol-2-yl)-1,4-dihydroquinoline-3-carboxylate (50 mg) and 2-(bromomethyl)-1,3-dichlorobenzene (46 mg) were subjected to reaction and post-treatment to give yellow solids (44% and 45% yields). Among them, the nuclear magnetic resonance spectrum data of the N-substituted product: $^1$H NMR (500 MHz, CDCl$_3$) δ 8.44 (d, J=6.7 Hz, 1H), 7.89 (s, 1H), 7.66 (s, 2H), 7.57 (t, J=7.2 Hz, 1H), 7.40 (t, J=7.5 Hz, 1H), 7.25 (m, 1H), 7.18 (t, J=12.3 Hz, 1H), 6.29 (d, J=3.3 Hz, 1H), 6.24 (t, J=3.2 Hz, 1H), 5.71 (s, 2H); ESI-MS m/z 399.02 [M+2+H]$^+$, 401.02 [M+2+2+H]$^+$.

Example 164

4-(2,6-Difluorobenzyl)-9H-pyrrolizino[1,2-b]quinoline-9,10(4H)-dione (Compound 615a) and its isomer 9-((2,6-difluorobenzyl)oxy)-10H-pyrrolizino[1,2-b]quinolin-10-one (Compound 615b)

Steps: Following the procedure of Example 1, ethyl 4-oxo-2-(1H-pyrrol-2-yl)-1,4-dihydroquinoline-3-carboxylate (50 mg) and 2-(bromomethyl)-1,3-difluorobenzene (46 mg) were subjected to reaction and post-treatment to give yellow solids (32% and 34% yields).
ESI-MS m/z 363.09 [M+H]$^+$.

Example 165

2-((9,10-Dioxo-9H-pyrrolizino[1,2-b]quinolin-4(10H)-yl)methyl)-4-fluorobenzonitrile (Compound 616a) and its isomer 4-fluoro-2-(((10-oxo-10H-pyrrolizino[1,2-b]quinolin-9-yl)oxy)methyl)benzonitrile (Compound 616b)

Steps: Following the procedure of Example 1, ethyl 4-oxo-2-(1H-pyrrol-2-yl)-1,4-dihydroquinoline-3-carboxylate (50 mg) and 2-(bromomethyl)-4-fluorobenzonitrile (46 mg) were subjected to reaction and post-treatment to give yellow solids (46% and 48% yields).
ESI-MS m/z 370.09[M+H]$^+$.

Example 166

7-Fluoro-4-(4-fluorobenzyl)-9H-pyrrolizino[1,2-b]quinoline-9,10(4H)-dione (Compound 617a) and its isomer 7-fluoro-9-((4-fluorobenzyl)oxy)-10H-pyrrolizino[1,2-b]quinolin-10-one (Compound 617b)

Steps: Following the procedure of Example 1, ethyl 6-fluoro-4-oxo-2-(1H-pyrrol-2-yl)-1,4-dihydroquinoline-3-carboxylate (50 mg) and 4-fluorobenzyl bromide (10 mg) were subjected to reaction and post-treatment to give production (31% and 35% yields).
ESI-MS m/z 363.09[M+H]$^+$.

Example 167

4-(4-Chlorobenzyl)-7-fluoro-9H-pyrrolizino[1,2-b]quinoline-9,10(4H)-dione (Compound 618a) and its isomer 9-((4-chlorobenzyl)oxy)-7-fluoro-10H-pyrrolizino[1,2-b]quinolin-10-one (Compound 618b)

Steps: Following the procedure of Example 1, ethyl 6-fluoro-4-oxo-2-(1H-pyrrol-2-yl)-1,4-dihydroquinoline-3-carboxylate (50 mg) and 4-chlorobenzyl bromide (15 mg) were subjected to reaction and post-treatment to give yellow solids (34% and 35% yields).
ESI-MS m/z 379.06[M+H]$^+$, 381.06 [M+2+H]$^+$.

Example 168

4-((7-Fluoro-9,10-dioxo-9H-pyrrolizino[1,2-b]quinolin-4(10H)-yl)methyl)benzonitrile (Compound 619a) and its isomer 4-(((7-fluoro-10-oxo-10H-pyrrolizino[1,2-b]quinolin-9-yl)oxy)methyl)benzonitrile (Compound 619b)

Steps: Following the procedure of Example 1, ethyl 6-fluoro-4-oxo-2-(1H-pyrrol-2-yl)-1,4-dihydroquinoline-3-carboxylate (50 mg) and p-cyanobenzyl bromide (15 mg) were subjected to reaction and post-treatment to give yellow solids (32% and 34% yields).
ESI-MS m/z 370.09[M+H]$^+$.

Example 169

7-Fluoro-4-(4-(trifluoromethyl)benzyl)-9H-pyrrolizino[1,2-b]quinoline-9,10(4H)-dione (Compound 620a) and its isomer 7-Fluoro-9-((4-(trifluoromethyl)benzyl)oxy)-10H-pyrrolizino[1,2-b]quinolin-10-one (Compound 620b)

Steps: Following the procedure of Example 1, ethyl 6-fluoro-4-oxo-2-(1H-pyrrol-2-yl)-1,4-dihydroquinoline-3-carboxylate (50 mg) and p-trifluoromethylbenzyl bromide (15 mg) were subjected to reaction and post-treatment to give yellow solids (29% and 33% yields).
ESI-MS m/z 413.08[M+H]$^+$.

Example 170

4-(4-Chloro-2-fluorobenzyl)-7-fluoro-9H-pyrrolizino[1,2-b]quinoline-9,10(4H)-dione (Compound 621a) and its isomer 9-((4-chloro-2-fluorobenzyl)oxy)-7-fluoro-10H-pyrrolizino[1,2-b]quinolin-10-one (Compound 621b)

Steps: Following the procedure of Example 1, ethyl 6-fluoro-4-oxo-2-(1H-pyrrol-2-yl)-1,4-dihydroquinoline-3-carboxylate (50 mg) and 4-chloro-2-fluorobenzyl bromide (15 mg) were subjected to reaction and post-treatment to give yellow solids (31% and 30% yields).
ESI-MS m/z 397.05[M+H]+,399.05[M+2+H]+.

Example 171

4-(2,4-Difluorobenzyl)-6-(piperazin-1-yl)-9H-pyrrolizino[1,2-b]quinoline-9,10(4H)-dione (Compound 622a) and its isomer 9-((2,4-difluorobenzyl)oxy)-6-(piperazin-1-yl)-10H-pyrrolizino[1,2-b]quinolin-10-one (Compound 622b)

Steps: Following the procedure of Example 1, ethyl 6-fluoro-4-oxo-2-(1H-pyrrol-2-yl)-1,4-dihydroquinoline-3-carboxylate (50 mg) and 2,4-difluorobenzyl bromide (15 mg) were subjected to reaction and post-treatment to give yellow solids. Then the obtained yellow solid (20 mg) was stirred and mixed with anhydrous piperazine (28 mg) and dimethylformamide (55 mL), and the mixture was reacted at 140° C. for 2 h, and the solvent was evaporated under reduced pressure, the residue was suspended in water 30 mL and boiled for a few minutes, cooling, suction filtration, water washing, vacuum drying to constant weigh to give yellow solids. (78% and 73% yields).
ESI-MS m/z 447.16[M+H]+.

Example 172

4-(3,5-Bis(trifluoromethyl)benzyl)-7-fluoro-9H-pyrrolizino[1,2-b]quinoline-9,10(4H)-dione (Compound 623a) and its isomer 9-((3,5-bis(trifluoromethyl)benzyl)oxy)-7-fluoro-10H-pyrrolizino[1,2-b]quinolin-10-one (Compound 623b)

Steps: Following the procedure of Example 1, ethyl 6-fluoro-4-oxo-2-(1H-pyrrol-2-yl)-1,4-dihydroquinoline-3- carboxylate (50 mg) and 1-(bromomethyl)-3,5-bis(trifluoromethyl)benzene (10 mg) were subjected to reaction and post-treatment to give yellow solids (30% and 30% yields). ESI-MS m/z 481.07 [M+H]$^+$.

Example 173

4-(4-Fluorobenzyl)-9,10-dioxo-4,10-dihydro-9H-pyrrolizino[1,2-b]quinoline-7-carbonitrile (Compound 624a) and its isomer 9-((4-fluorobenzyl)oxy)-10-oxo-10H-pyrrolizino[1,2-b]quinoline-7-carbonitrile (Compound 624b)

Steps: Following the procedure of Example 1, Ethyl 4-oxo-2-(1H-pyrrol-2-yl)-1,4-dihydro-6-cyanoquinoline-3-carboxylate (50 mg) and 4-fluorobenzyl bromide (15 mg) were subjected to reaction and post-treatment to give yellow solids (32% and 33% yields).
ESI-MS m/z 370.11 [M+H]+.

Example 174

4-(4-Chlorobenzyl)-9,10-dioxo-4,10-dihydro-9H-pyrrolizino[1,2-b]quinoline-7-carbonitrile (Compound 625a) and its isomer 9-((4-chlorobenzyl)oxy)-10-oxo-10H-pyrrolizino[1,2-b]quinoline-7-carbonitrile (Compound 625b)

Steps: Following the procedure of Example 1, Ethyl 4-oxo-2-(1H-pyrrol-2-yl)-1,4-dihydro-6-cyanoquinoline-3-carboxylate (50 mg) and 4-chlorobenzyl bromide (15 mg) were subjected to reaction and post-treatment to give yellow solids (33% and 36% yields).
ESI-MS m/z 386.08 [M+H]$^+$, 388.08 [M+2+H]$^+$.

Example 175

4-(4-Cyanobenzyl)-9,10-dioxo-4,10-dihydro-9H-pyrrolizino[1,2-b]quinoline-7-carbonitrile (Compound 626a) and its isomer 9-((4-cyanobenzyl)oxy)-10-oxo-10H-pyrrolizino[1,2-b]quinoline-7-carbonitrile (Compound 626b)

Steps: Following the procedure of Example 1, Ethyl 4-oxo-2-(1H-pyrrol-2-yl)-1,4-dihydro-6-cyanoquinoline-3-carboxylate (50 mg) and p-cyanobenzyl bromide (15 mg) were subjected to reaction and post-treatment to give yellow solids (31% and 34% yields).
ESI-MS m/z 377.10 [M+H]$^+$.

Example 176

9,10-Dioxo-4-(4-(trifluoromethyl)benzyl)-4,10-dihydro-9H-pyrrolizino[1,2-b]quinoline-7-carbonitrile (Compound 627a) and its isomer 10-oxo-9-((4-(trifluoromethyl)benzyl)oxy)-10H-pyrrolizino[1,2-b]quinoline-7-carbonitrile (Compound 627b)

Steps: Following the procedure of Example 1, Ethyl 4-oxo-2-(1H-pyrrol-2-yl)-1,4-dihydro-6-cyanoquinoline-3-carboxylate (50 mg) and 4-(trifluoromethyl)benzyl bromide (15 mg) were subjected to reaction and post-treatment to give yellow solids (29% and 30% yields).
ESI-MS m/z 420.09 [M+H]$^+$.

Example 177

4-([1,1'-Biphenyl]-4-ylmethyl)-9,10-dioxo-4,10-dihydro-9H-pyrrolizino[1,2-b]quinoline-7-carbonitrile (Compound 628a) and its isomer 9-([1,1'-biphenyl]-4-ylmethoxy)-10-oxo-10H-pyrrolizino[1,2-b]quinoline-7-carbonitrile (Compound 628b)

Steps: Following the procedure of Example 1, Ethyl 4-oxo-2-(1H-pyrrol-2-yl)-1,4-dihydro-6-cyanoquinoline-3-carboxylate (50 mg) and 4-(bromomethyl)-11-biphenyl (15 mg) were subjected to reaction and post-treatment to give yellow solids (30% and 26% yields).
ESI-MS m/z 430.15 [M+H]$^+$.

Example 178

4-((2'-Cyano-[1,1'-biphenyl]-4-yl)methyl)-9,10-dioxo-4,10-dihydro-9H-pyrrolizino[1,2-b]quinoline-7-carbonitrile (Compound 629a) and its isomer 9-((2'-cyano-[1,1'-biphenyl]-4-yl)methoxy)-10-oxo-10H-pyrrolizino[,2-b]quinoline-7-carbonitrile (Compound 629b)

Steps: Following the procedure of Example 1, ethyl 4-oxo-2-(1H-pyrrol-2-yl)-1,4-dihydro-6-cyanoquinoline-3-carboxylate (50 mg) and 4'-(bromomethyl)-[1,1'-biphenyl]-2-carbonitrile (15 mg) were subjected to reaction and post-treatment to give yellow solids (28% and 27% yields).
ESI-MS m/z 455.14 [M+H]$^+$.

Example 179

4-(2,4-Difluorobenzyl)-6-(piperazin-1-yl)-9H-pyrrolizino[1,2-b]quinoline-9,10(4H)-dione (Compound 630a) and its isomer 9-((2,4-difluorobenzyl)oxy)-6-(piperazin-1-yl)-10H-pyrrolizino[1,2-b]quinolin-10-one (Compound 630b)

Steps: Following the procedure of Example 1, ethyl 7-chloro-4-oxo-2-(1H-pyrrol-2-yl)-1,4-dihydroquinoline-3-carboxylate (50 mg) and 2,4-difluorobenzyl bromide (15 μL) were subjected to reaction and post-treatment to give yellow solids. Then the obtained yellow solid (20 mg) was stirred and mixed with anhydrous piperazine (28 mg) and dimethylformamide (55 mL), and the mixture was reacted at 140° C. for 2 h, and the solvent was evaporated under reduced pressure, the residue was suspended in water 30 mL and boiled for a few minutes, cooling, suction filtration, water washing, vacuum drying to constant weigh to give yellow solids 15.7 mg and 14.8 mg (48% and 43% yields).
ESI-MS m/z 447.16[M+H]$^+$.

Example 180

4-(3,5-Bis(trifluoromethyl)benzyl)-6-(piperazin-1-yl)-9H-pyrrolizino[1,2-b]quinoline-9,10(4H)-dione (Compound 631a) and its isomer 9-((3,5-bis(trifluoromethyl)benzyl)oxy)-6-(piperazin-1-yl)-10H-pyrrolizino[,2-b]quinolin-10-one (Compound 631b)

Steps: Following the procedure of Example 1, ethyl 4-oxo-2-(1H-pyrrol-2-yl)-1,4-dihydroquinoline-3-carboxylate (50 mg) and 1-(bromomethyl)-3,5-bis(trifluoromethyl)benzene (10 mg) were subjected to reaction and post-treatment to give the production. Then the obtained yellow solid (20 mg) was stirred and mixed with anhydrous piperazine (28 mg) and DMF (55 mL), and the mixture was reacted at 140° C. for 2 h, and the solvent was evaporated under reduced pressure, the residue was suspended in water 30 mL and boiled for a few minutes, and then was subjected to cooling, suction filtration, water washing, and vacuum drying to constant weight to give yellow solids 15.7 and 14.5 mg (38% and 45% yields).

ESI-MS m/z 547.15 [M+H]$^+$.

Example 181

4-(4-Chlorobenzyl)-7-fluoro-6-(piperazin-1-yl)-9H-pyrrolizino[1,2-b]quinoline-9,10(4H)-dione (Compound 632a) and its isomer 9-((4-chlorobenzyl)oxy)-7-fluoro-6-(piperazin-1-yl)-10H-pyrrolizino[1,2-b]quinolin-10-one (Compound 632b)

Steps: Following the procedure of Example 1, ethyl 7-chloro-6-fluoro-4-oxo-2-(1H-pyrrol-2-yl)-1,4-dihydroquinoline-3-carboxylate (50 mg) and 4-chlorobenzyl bromide (15 mg) were subjected to reaction and post-treatment to give yellow solids. Then the obtained yellow solid (20 mg) was stirred and mixed with anhydrous piperazine (28 mg) and dimethylformamide (55 mL), and the mixture was reacted at 140° C. for 2 h, and the solvent was evaporated under reduced pressure, the residue was suspended in water 30 mL and boiled for a few minutes, and then was subjected to cooling, suction filtration, water washing, and vacuum drying to constant weight to give yellow solids (48% and 43% yields).

ESI-MS m/z 463.13[M+H]$^+$, 465.13 [M+2+H].

Example 182

4-(4-Bromobenzyl)-7-fluoro-6-(piperazin-1-yl)-9H-pyrrolizino[1,2-b]quinoline-9,10(4H)-dione (Compound 633a) and its isomer 9-((4-bromobenzyl)oxy)-7-fluoro-6-(piperazin-1-yl)-10H-pyrrolizino[1,2-b]quinolin-10-one (Compound 633b)

Steps: Following the procedure of Example 1, ethyl 7-chloro-6-fluoro-4-oxo-2-(1H-pyrrol-2-yl)-1,4-dihydroquinoline-3-carboxylate (50 mg) and p-bromobenzyl bromide (15 mg) were subjected to reaction and post-treatment to give yellow solids. Then the obtained yellow solid (20 mg) was stirred and mixed with anhydrous piperazine (28 mg) and dimethylformamide (55 mL), and the mixture was reacted at 140° C. for 2 h, and the solvent was evaporated under reduced pressure, the residue was suspended in water 30 mL and boiled for a few minutes, and then was subjected to cooling, suction filtration, water washing, and vacuum drying to constant weight to give yellow solids (38% and 36% yields).

ESI-MS m/z 507.08[M+H]$^+$, 509.08 [M+2+H].

Example 183

7-Fluoro-4-(4-fluorobenzyl)-6-(piperazin-1-yl)-9H-pyrrolizino[1,2-b]quinoline-9,10(4H)-dione (Compound 634a) and its isomer 7-fluoro-9-((4-fluorobenzyl)oxy)-6-(piperazin-1-yl)-10H-pyrrolizino[1,2-b]quinolin-10-one (Compound 634b)

Steps: Following the procedure of Example 1, ethyl 7-chloro-6-fluoro-4-oxo-2-(1H-pyrrol-2-yl)-1,4-dihydroquinoline-3-carboxylate (50 mg) and 4-fluorobenzyl bromide (15 μL) were subjected to reaction and post-treatment to give yellow solids. Then the obtained yellow solid (20 mg) was stirred and mixed with anhydrous piperazine (28 mg) and dimethylformamide (55 mL), and the mixture was reacted at 140° C. for 2 h, and the solvent was evaporated under reduced pressure, the residue was suspended in water 30 mL and boiled for a few minutes, and then was subjected to cooling, suction filtration, water washing, and vacuum drying to constant weight to give yellow solids (35% and 39% yields).

ESI-MS m/z 447.16[M+H]$^+$.

Example 184

4-((7-Fluoro-9,10-dioxo-6-(piperazin-1-yl)-9H-pyrrolizino[1,2-b]quinolin-4(10H)-yl)methyl)benzonitrile (Compound 635a) and its isomer 4-(((7-fluoro-10-oxo-6-(piperazin-1-yl)-10H-pyrrolizino[1,2-b]quinolin-9-yl)oxy)methyl)benzonitrile (Compound 635b)

Steps: Following the procedure of Example 1, ethyl 7-chloro-6-fluoro-4-oxo-2-(1H-pyrrol-2-yl)-1,4-dihydroquinoline-3-carboxylate (50 mg) and 4-cyanobenzyl bromide (15 mg) were subjected to reaction and post-treatment to give yellow solids. Then the obtained yellow solid (20 mg) was stirred and mixed with anhydrous piperazine (28 mg) and dimethylformamide (55 mL), and the mixture was reacted at 140° C. for 2 h, and the solvent was evaporated under reduced pressure, the residue was suspended in water 30 mL and boiled for a few minutes, and then was subjected to cooling, suction filtration, water washing, and vacuum drying to constant weight to give yellow solids (38% and 39% yields).

ESI-MS m/z 454.16[M+H]$^+$.

Example 185

7-Fluoro-6-(piperazin-1-yl)-4-(4-(trifluoromethyl)benzyl)-9H-pyrrolizino[1,2-b]quinoline-9,10(4H)-dione (Compound 636a) and its isomer 7-fluoro-6-(piperazin-1-yl)-9-((4-(trifluoromethyl)benzyl)oxy)-10H-pyrrolizino[1,2-b]quinolin-10-one (Compound 636b)

Steps: Following the procedure of Example 1, ethyl 7-chloro-6-fluoro-4-oxo-2-(1H-pyrrol-2-yl)-1,4-dihydroquinoline-3-carboxylate (50 mg) and 4-(trifluoromethyl)benzylbromide (15 mg) were subjected to reaction and post-treatment to give yellow solids. Then the obtained yellow solid (20 mg) was stirred and mixed with anhydrous piperazine (28 mg) and dimethylformamide (55 mL), and the mixture was reacted at 140° C. for 2 h, and the solvent was evaporated under reduced pressure, the residue was suspended in water 30 mL and boiled for a few minutes, and then was subjected to cooling, suction filtration, water washing, and vacuum drying to constant weight to give yellow solids (42% and 39% yields).

ESI-MS m/z 497.15[M+H]$^+$.

Example 186

4-([1,1'-Biphenyl]-4-ylmethyl)-7-fluoro-6-(piperazin-1-yl)-9H-pyrrolizino[1,2-b]quinoline-9,10(4H)-dione (Compound 637a) and its isomer 9-([1,1'-biphenyl]-4-ylmethoxy)-7-fluoro-6-(piperazin-1-yl)-10H-pyrrolizino[1,2-b]quinolin-10-one (Compound 637b)

Steps: Following the procedure of Example 1, ethyl 7-chloro-6-fluoro-4-oxo-2-(1H-pyrrol-2-yl)-1,4-dihydroquinoline-3-carboxylate (50 mg) and 4-(bromomethyl)-1,1'-biphenyl (15 mg) were subjected to reaction and post-treatment to give yellow solids. Then the obtained yellow solid (20 mg) was stirred and mixed with anhydrous piperazine (28 mg) and dimethylformamide (55 mL), and the mixture was reacted at 140° C. for 2 h, and the solvent was evaporated under reduced pressure, the residue was suspended in water 30 mL and boiled for a few minutes, and then was subjected to cooling, suction filtration, water washing, and vacuum drying to constant weight to give yellow solids (47% and 39% yields).

ESI-MS m/z 505.20[M+H]$^+$.

Example 187

4'-((7-Fluoro-9,10-dioxo-6-(piperazin-1-yl)-9H-pyrrolizino[1,2-b]quinolin-4(10H)-yl)methyl)-[1,1'-biphenyl]-2-carbonitrile (Compound 638a) and its isomer 4'-(((7-fluoro-10-oxo-6-(piperazin-1-yl)-10H-pyrrolizino[1,2-b]quinolin-9-yl)oxy)methyl)-[1,1'-biphenyl]-2-carbonitrile (Compound 638b)

Steps: Following the procedure of Example 1, ethyl 7-chloro-6-fluoro-4-oxo-2-(1H-pyrrol-2-yl)-1,4-dihydroquinoline-3-carboxylate (50 mg) and 4'-(bromomethyl)-2cyano-1,1'-biphenyl (15 mg) were subjected to reaction and post-treatment to give yellow solids. Then the obtained yellow solid (20 mg) was stirred and mixed with anhydrous piperazine (28 mg) and dimethylformamide (55 mL), and the mixture was reacted at 140° C. for 2 h, and the solvent was evaporated under reduced pressure, the residue was suspended in water 30 mL and boiled for a few minutes, and then was subjected to cooling, suction filtration, water washing, and vacuum drying to constant weight to give yellow solids (41% and 55% yields).

ESI-MS m/z 520.19[M+H]$^+$.

Example 188

4-(3,5-Bis(trifluoromethyl)benzyl)-7-fluoro-6-(piperazin-1-yl)-9H-pyrrolizino[,2-b]quinoline-9,10(4H)-dione (Compound 639a) and its isomer 9-((3,5-bis (trifluoromethyl)benzyl)oxy)-7-fluoro-6-(piperazin-1-yl)-10H-pyrrolizino[1,2-b]quinolin-10-one (Compound 639b)

Steps: Following the procedure of Example 1, ethyl 7-chloro-6-fluoro-4-oxo-2-(1H-pyrrol-2-yl)-1,4-dihydroquinoline-3-carboxylate (50 mg) and 1-(bromomethyl)-3,5-bis(trifluoromethyl)benzene (10 mg) were subjected to reaction and post-treatment to give yellow solids. Then the obtained yellow solid (20 mg) was stirred and mixed with anhydrous piperazine (28 mg) and dimethylformamide (55 mL), and the mixture was reacted at 140° C. for 2 h, and the solvent was evaporated under reduced pressure, the residue was suspended in water 30 mL and boiled for a few minutes, and then was subjected to cooling, suction filtration, water washing, and vacuum drying to constant weight to give yellow solids (43% and 51% yields).

ESI-MS m/z 565.14 [M+H]$^+$.

Example 189

4-(4-Chlorobenzyl)-9,10-dioxo-6-(piperazin-1-yl)-4,10-dihydro-9H-pyrrolizino[1,2-b]quinoline-7-carbonitrile (Compound 640a) and its isomer 9-((4-chlorobenzyl)oxy)-10-oxo-6-(piperazin-1-yl)-10H-pyrrolizino[1,2-b]quinoline-7-carbonitrile (Compound 640b)

Steps: Following the procedure of Example 1, ethyl 7-chloro-6-cyano-4-oxo-2-(1H-pyrrol-2-yl)-1,4-dihydroquinoline-3-carboxylate (50 mg) and 4-chlorobenzyl bromide (15 mg) were subjected to reaction and post-treatment to give yellow solids. Then the obtained yellow solid (20 mg) was stirred and mixed with anhydrous piperazine (28 mg) and dimethylformamide (55 mL), and the mixture was reacted at 140° C. for 2 h, and the solvent was evaporated under reduced pressure, the residue was suspended in water 30 mL and boiled for a few minutes, and then was subjected to cooling, suction filtration, water washing, and vacuum drying to constant weight to give yellow solids (45% and 51% yields).

ESI-MS m/z 470.13 [M+H]$^+$, 472.13[M+2H]$^+$.

Example 190

4-(4-Cyanobenzyl)-9,10-dioxo-6-(piperazin-1-yl)-4,10-dihydro-9H-pyrrolizino[1,2-b]quinoline-7-carbonitrile (Compound 641a) and its isomer 9-((4-cyanobenzyl)oxy)-10-oxo-6-(piperazin-1-yl)-10H-pyrrolizino[1,2-b]quinoline-7-carbonitrile (Compound 641b)

Steps: Following the procedure of Example 1, ethyl 7-chloro-6-cyano-4-oxo-2-(1H-pyrrol-2-yl)-1,4-dihydroquinoline-3-carboxylate (50 mg) and p-cyanobenzyl bromide (15 mg) were subjected to reaction and post-treatment to give yellow solids. Then the obtained yellow solid (20 mg) was stirred and mixed with anhydrous piperazine (28 mg) and dimethylformamide (55 mL), and the mixture was reacted at 140° C. for 2 h, and the solvent was evaporated under reduced pressure, the residue was suspended in water 30 mL and boiled for a few minutes, and then was subjected to cooling, suction filtration, water washing, and vacuum drying to constant weight to give yellow solids (40% and 41% yields).

ESI-MS m/z 461.16 [M+H]$^+$.

Example 191

9,10-Dioxo-6-(piperazin-1-yl)-4-(4-(trifluoromethyl) benzyl)-4,10-dihydro-9H-pyrrolizino[1,2-b]quinoline-7-carbonitrile (Compound 642a) and its isomer 10-oxo-6-(piperazin-1-yl)-9-((4-(trifluoromethyl) benzyl)oxy)-10H-pyrrolizino[1,2-b]quinoline-7-carbonitrile (Compound 642b)

Steps: Following the procedure of Example 1, ethyl 7-chloro-6-cyano-4-oxo-2-(1H-pyrrol-2-yl)-1,4-dihydroquinoline-3-carboxylate (50 mg) and 4-(trifluoromethyl) benzylbromide (15 mg) were subjected to reaction and post-treatment to give yellow solids. Then the obtained yellow solid (20 mg) was stirred and mixed with anhydrous piperazine (28 mg) and dimethylformamide (55 mL), and the mixture was reacted at 140° C. for 2 h, and the solvent was evaporated under reduced pressure, the residue was suspended in water 30 mL and boiled for a few minutes, and then was subjected to cooling, suction filtration, water washing, and vacuum drying to constant weight to give yellow solids (40% and 51% yields).

ESI-MS m/z 504.16 [M+H]$^+$.

Example 192

4-([1,1'-Biphenyl]-4-ylmethyl)-9,10-dioxo-6-(piperazin-1-yl)-4,10-dihydro-9H-pyrrolizino[1,2-b]quinoline-7-carbonitrile (Compound 643a) and its isomer 9-([1,1'-biphenyl]-4-ylmethoxy)-10-oxo-6-(piperazin-1-yl)-10H-pyrrolizino[1,2-b]quinoline-7-carbonitrile (Compound 643b)

Steps: Following the procedure of Example 1, ethyl 7-chloro-6-cyano-4-oxo-2-(1H-pyrrol-2-yl)-1,4-dihydroquinoline-3-carboxylate (50 mg) and 4-(bromomethyl)-1,1'-biphenyl (15 mg) were subjected to reaction and post-treatment to give yellow solids. Then the obtained yellow solid (20 mg) was stirred and mixed with anhydrous piperazine (28 mg) and dimethylformamide (55 mL), and the mixture was reacted at 140° C. for 2 h, and the solvent was evaporated under reduced pressure, the residue was suspended in water 30 mL and boiled for a few minutes, and then was subjected to cooling, suction filtration, water washing, and vacuum drying to constant weight to give yellow solids (42% and 41% yields).
ESI-MS m/z 514.22 [M+H]$^+$.

Example 193

4-((2'-Cyano-[1,1'-biphenyl]-4-yl)methyl)-9,10-dioxo-6-(piperazin-1-yl)-4,10-dihydro-9H-pyrrolizino[1,2-b]quinoline-7-carbonitrile (Compound 644a) and its isomer 9-((2'-cyano-[1,1'-biphenyl]-4-yl)methoxy)-10-oxo-6-(piperazin-1-yl)-10H-pyrrolizino[1,2-b]quinoline-7-carbonitrile (Compound 644b)

Steps: Following the procedure of Example 1, ethyl 7-chloro-6-cyano-4-oxo-2-(1H-pyrrol-2-yl)-1,4-dihydroquinoline-3-carboxylate (50 mg) and 4'-(Bromomethyl)-[1,1'-biphenyl]-2-carbonitrile (15 mg) were subjected to reaction and post-treatment to give yellow solids. Then the obtained yellow solid (20 mg) was stirred and mixed with anhydrous piperazine (28 mg) and dimethylformamide (55 mL), and the mixture was reacted at 140° C. for 2 h, and the solvent was evaporated under reduced pressure, the residue was suspended in water 30 mL and boiled for a few minutes, and then was subjected to cooling, suction filtration, water washing, and vacuum drying to constant weight to give yellow solids (48% and 43% yields).
ESI-MS m/z 539.21 [M+H]$^+$.

Example 194

8-Chloro-4-(2-chlorobenzyl)-9H-pyrrolizino[1,2-b]quinoline-9,10(4H)-dione (Compound 645a) and its isomer 8-chloro-9-((2-chlorobenzyl)oxy)-10H-pyrrolizino[1,2-b]quinolin-10-one (Compound 645b)

Steps: Following the procedure of Example 1, ethyl 5-chloro-4-oxo-2-(1H-pyrrol-2-yl)-1,4-dihydroquinoline-3-carboxylate (50 mg) and 2-chlorobenzyl bromide (15 mg) were subjected to reaction and post-treatment to give yellow solids (39% and 40% yields).
ESI-MS m/z 395.03 [M+H]$^+$, 397.03 [M+2+H]$^+$.

Example 195

8-Fluoro-4-(4-fluorobenzyl)-6-(piperazin-1-yl)-9H-pyrrolizino[1,2-b]quinoline-9,10(4H)-dione (Compound 646a) and its isomer 8-fluoro-9-((4-fluorobenzyl)oxy)-6-(piperazin-1-yl)-10H-pyrrolizino[1,2-b]quinolin-10-one (Compound 646b)

Steps: Following the procedure of Example 1, ethyl 7-chloro-5-fluoro-4-oxo-2-(1H-pyrrol-2-yl)-1,4-dihydroquinoline-3-carboxylate (50 mg) and 4-fluorobenzyl bromide (15 mg) were subjected to reaction and post-treatment to give yellow solids. Then the obtained yellow solid (20 mg) was stirred and mixed with anhydrous piperazine (28 mg) and dimethylformamide (55 mL), and the mixture was reacted at 140° C. for 2 h, and the solvent was evaporated under reduced pressure, the residue was suspended in water 30 mL and boiled for a few minutes, and then was subjected to cooling, suction filtration, water washing, and vacuum drying to constant weight to give product (45% and 49% yields).
ESI-MS m/z 447.16[M+H]$^+$.

Example 196

4-(4-Chlorobenzyl)-8-fluoro-6-(piperazin-1-yl)-9H-pyrrolizino[1,2-b]quinoline-9,10(4H)-dione (Compound 647a) and its isomer 9-((4-chlorobenzyl)oxy)-8-fluoro-6-(piperazin-1-yl)-10H-pyrrolizino[1,2-b]quinolin-10-one (Compound 647b)

Steps: Following the procedure of Example 1, ethyl 7-chloro-5-fluoro-4-oxo-2-(1H-pyrrol-2-yl)-1,4-dihydroquinoline-3-carboxylate (50 mg) and 4-chlorobenzyl bromide (15 mg) were subjected to reaction and post-treatment to give yellow solids. Then the obtained yellow solid (20 mg) was stirred and mixed with anhydrous piperazine (28 mg) and dimethylformamide (55 mL), and the mixture was reacted at 140° C. for 2 h, and the solvent was evaporated under reduced pressure, the residue was suspended in water 30 mL and boiled for a few minutes, and then was subjected to cooling, suction filtration, water washing, and vacuum drying to constant weight to give yellow solids (35% and 40% yields).
ESI-MS m/z 463.13[M+H]$^+$.

Example 197

4'-((9,10-Dioxo-9H-pyrrolizino[1,2-b]quinolin-4(10H)-yl)methyl)-[1,1'-biphenyl]-2-carbonitrile (Compound 648a) and its isomer 4'-(((10-oxo-10H-pyrrolizino[1,2-b]quinolin-9-yl)oxy)methyl)-[1,1'-biphenyl]-2-carbonitrile (Compound 648b)

Steps: Following the procedure of Example 1, ethyl 4-oxo-2-(1H-pyrrol-2-yl)-1,4-dihydroquinoline-3-carboxylate (50 mg) and 2'-cyano-4bromomethyl-biphenyl (15 mg) were subjected to reaction and post-treatment to give yellow solids (31% and 37% yields). Among them, the nuclear magnetic resonance spectrum data of the N-substituted product: $^1$H NMR (500 MHz, CDCl$_3$) δ 8.54 (dd, J=7.9, 1.2 Hz, 1H), 7.86 (d, J=7.6 Hz, 1H), 7.65-7.59 (m, 1H), 7.55 (t, J=7.6 Hz, 1H), 7.48 (m, 2H), 7.31 (d, J=2.9 Hz, 1H), 7.25 (d, J=8.8 Hz, 1H), 7.03 (d, J=7.8 Hz, 1H), 6.34 (d, J=3.4 Hz, 1H), 6.25 (t, J=3.2 Hz, 1H), 5.80 (s, 2H); ESI-MS m/z 428.13 [M+H]$^+$.

Example 198

4-([1,1'-Biphenyl]-4-ylmethyl)-9H-pyrrolizino[1,2-b]quinoline-9,10(4H)-dione (Compound 649a) and its isomer 9-([1,1'-biphenyl]-4-ylmethoxy)-10H-pyrrolizino[1,2-b]quinolin-10-one (Compound 649b)

Steps: Following the procedure of Example 1, ethyl 4-oxo-2-(1H-pyrrol-2-yl)-1,4-dihydroquinoline-3-carboxylate (50 mg) and 4-bromomethylbiphenyl (15 mg) were subjected to reaction and post-treatment to give yellow solids (31% and 36% yields). Among them, the nuclear magnetic resonance spectrum data of the N-substituted product: $^1$H NMR (500 MHz, CDCb$_3$) δ 8.43 (d, J=7.7 Hz, 1H), 7.57 (m, 5H), 7.39 (m, 5H), 7.26 (m, 3H), 6.41 (s, 1H), 6.23 (s, 1H), 5.65 (s, 2H); ESI-MS m/z 403.14 [M+H]⁺.

Example 199

4-(Methylsulfonyl)-9H-pyrrolizino[1,2-b]quinoline-9,10(4H)-dione (Compound 650a) and its isomer 10-oxo-10H-pyrrolizino[1,2-b]quinolin-9-yl methanesulfonate (Compound 650b)

Steps: Following the procedure of Example 1, ethyl 4-oxo-2-(1H-pyrrol-2-yl)-1,4-dihydroquinoline-3-carboxylate (50 mg) and methanesulfonyl chloride (15 mg) were subjected to reaction and post-treatment to give yellow solids (26% and 30% yields).
ESI-MS m/z 315.04 [M+H]⁺.

Example 200

4-(3-Hydroxypropyl)-9H-pyrrolizino[1,2-b]quinoline-9,10(4H)-dione (Compound 16a) and its isomer 9-(3-hydroxypropoxy)-10H-pyrrolizino[1,2-b]quinolin-10-one (Compound 16b)

Steps: Following the procedure of Example 1, ethyl 4-oxo-2-(1H-pyrrol-2-yl)-1,4-dihydroquinoline-3-carboxylate (50 mg) and 3-bromopropan-1-ol (60 mg) were subjected to reaction and post-treatment to give yellow solids (44% and 45% yields).
ESI-MS m/z 295.10 [M+H]⁺.

Example 201

4-(2-Methoxyethyl)-9H-pyrrolizino[1,2-b]quinoline-9,10(4H)-dione (Compound 652a) and its isomer 9-(2-methoxyethoxy)-10H-pyrrolizino[1,2-b]quinolin-10-one (Compound 652b)

Steps: Following the procedure of Example 1, ethyl 4-oxo-2-(1H-pyrrol-2-yl)-1,4-dihydroquinoline-3-carboxylate (50 mg) and 1-bromo-2-methoxyethane (50 mg) were subjected to reaction and post-treatment to give yellow solids (45% and 45% yields).
ESI-MS m/z 295.10 [M+H]+.

Example 202

4-(2-Fluoroethyl)-9H-pyrrolizino[1,2-b]quinoline-9,10(4H)-dione (Compound 653a) and its isomer 9-(2-fluoroethoxy)-10H-pyrrolizino[1,2-b]quinolin-10-one (Compound 653b)

Steps: Following the procedure of Example 1, ethyl 4-oxo-2-(1H-pyrrol-2-yl)-1,4-dihydroquinoline-3-carboxylate (50 mg) and I-bromo-2-fluoroethane (70 mg) were subjected to reaction and post-treatment to give yellow solids (26% and 22% yields).
ESI-MS m/z 283.08 [M+H]+.

Example 203

Ethyl 2-(9,10-dioxo-9H-pyrrolizino[1,2-b]quinolin-4(10H)-yl)acetate (Compound 654a) and its isomer ethyl 2-((10-oxo-10H-pyrrolizino[1,2-b]quinolin-9-yl)oxy)acetate (Compound 654b)

Steps: Following the procedure of Example 1, ethyl 4-oxo-2-(1H-pyrrol-2-yl)-1,4-dihydroquinoline-3-carboxylate (50 mg) and ethyl 2-bromoacetate (60 mg) were subjected to reaction and post-treatment to give yellow solids (35% and 40% yields).
ESI-MS m/z 323.10 [M+H]+.

Example 204

4-Neopentyl-9H-pyrrolizino[1,2-b]quinoline-9,10(4H)-dione (Compound 656a) and its isomer 9-(neopentyloxy)-10H-pyrrolizino[1,2-b]quinolin-10-one (Compound 656b)

Steps: Following the procedure of Example 1, ethyl 4-oxo-2-(1H-pyrrol-2-yl)-1,4-dihydroquinoline-3-carboxylate (50 mg) and 1-bromo-2,2-dimethylpropane (50 mg) were subjected to reaction and post-treatment to give yellow solids (36% and 40% yields).
ESI-MS m/z 307.14 [M+H]⁺.

Example 205

4-(2,2,2-Trifluoroethyl)-9H-pyrrolizino[1,2-b]quinoline-9,10(4H)-dione (Compound 657a) and its isomer 9-(2,2,2-trifluoroethoxy)-10H-pyrrolizino[1,2-b]quinolin-10-one (Compound 657b)

Steps: Following the procedure of Example 1, ethyl 4-oxo-2-(1H-pyrrol-2-yl)-1,4-dihydroquinoline-3-carboxylate (50 mg) and 2-bromo-trifluoroethane (50 mg) were subjected to reaction and post-treatment to give yellow solids (37% and 44% yields).
ESI-MS m/z 319.06 [M+H]⁺.

Example 206

4-(2-(Dimethylamino)ethyl)-9H-pyrrolizino[1,2-b]quinoline-9,10(4H)-dione (Compound 12a) and its isomer 9-(2-(dimethylamino)ethoxy)-10H-pyrrolizino[1,2-b]quinolin-10-one (Compound 12b)

Steps: Following the procedure of Example 1, ethyl 4-oxo-2-(1H-pyrrol-2-yl)-1,4-dihydroquinoline-3-carboxylate (50 mg) and 2-bromo-N,N-dimethylethane-1-amine (50 mg) were subjected to reaction and post-treatment to give yellow solids (30% and 41% yields).
ESI-MS m/z 308.14 [M+H]⁺.

Example 207

4-(3-(Dimethylamino)propyl)-9H-pyrrolizino[1,2-b]quinoline-9,10(4H)-dione (Compound 658a) and its isomer 9-(3-(dimethylamino)propoxy)-10H-pyrrolizino[1,2-b]quinolin-10-one (Compound 658b)

Steps: Following the procedure of Example 1, ethyl 4-oxo-2-(1H-pyrrol-2-yl)-1,4-dihydroquinoline-3-carboxylate (50 mg) and 3-bromo-N,N-dimethylpropan-1-amine (50 mg) were subjected to reaction and post-treatment to give yellow solids (30% and 39% yields).
ESI-MS m/z 322.15[M+H]+.

Example 208

4-(3-(Methylsulfonyl)propyl)-9H-pyrrolizino[1,2-b]quinoline-9,10(4H)-dione (Compound 659a) and its isomer 9-(3-(methylsulfonyl)propoxy)-10H-pyrrolizino[1,2-b]quinolin-10-one (Compound 659b)

Steps: Following the procedure of Example 1, ethyl 4-oxo-2-(1H-pyrrol-2-yl)-1,4-dihydroquinoline-3-carboxylate (50 mg) and 1-bromo-3-(methylsulfonyl) propane (50 mg) were subjected to reaction and post-treatment to give yellow solids (37% and 45% yields).

ESI-MS m/z 357.09[M+H]$^+$.

Example 209

4-(2-Hydroxy-2-methylpropyl)-9H-pyrrolizino[1,2-b]quinoline-9,10(4H)-dione (Compound 660a) and its isomer 9-(2-hydroxy-2-methylpropoxy)-10H-pyrrolizino[1,2-b]quinolin-10-one (Compound 660b)

Steps: Following the procedure of Example 1, ethyl 4-oxo-2-(1H-pyrrol-2-yl)-1,4-dihydroquinoline-3-carboxylate (50 mg) and I-bromo-2-methylpropan-2-ol (43 mg) were subjected to reaction and post-treatment to give yellow solids (35% and 39% yields).

ESI-MS m/z 309.12[M+H]$^+$.

Example 210

4-(Prop-2-yn-1-yl)-9H-pyrrolizino[1,2-b]quinoline-9,10(4H)-dione (Compound 7a) and its isomer 9-(prop-2-yn-1-yloxy)-10H-pyrrolizino[1,2-b]quinolin-10-one (Compound 7b)

Steps: Following the procedure of Example 1, ethyl 4-oxo-2-(1H-pyrrol-2-yl)-1,4-dihydroquinoline-3-carboxylate (50 mg) and 3-bromopropyne (70 mg) were subjected to reaction and post-treatment to give yellow solids (30% and 42% yields).

ESI-MS m/z 275.08[M+H]$^+$.

Example 211

4-Cyclopropyl-9H-pyrrolizino[1,2-b]quinoline-9,10(4H)-dione (Compound 673a) and its isomer 9-cyclopropoxy-10H-pyrrolizino[1,2-b]quinolin-10-one (Compound 673b)

Steps: Following the procedure of Example 1, ethyl 4-oxo-2-(1H-pyrrol-2-yl)-1,4-dihydroquinoline-3-carboxylate (50 mg) and bromocyclopropane (60 mg) were subjected to reaction and post-treatment to give yellow solids (35% and 45% yields).

ESI-MS m/z 277.09[M+H]$^+$.

Example 212

Ethyl (E)-4-(9,10-dioxo-9H-pyrrolizino[1,2-b]quinolin-4(10H)-yl)but-2-enoate (Compound 661a) and its isomer ethyl (E)-4-((10-oxo-10H-pyrrolizino[1,2-b]quinolin-9-yl)oxy)but-2-enoate (Compound 661b)

Steps: Following the procedure of Example 1, ethyl 4-oxo-2-(1H-pyrrol-2-yl)-1,4-dihydroquinoline-3-carboxylate (50 mg) and (E)-4-bromobut-2-enoic acid ethyl ester (45 mg) were subjected to reaction and post-treatment to give yellow solids (36% and 44% yields).

ESI-MS m/z 349.11[M+H]+.

Example 213

4-(2-Morpholinoethyl)-9H-pyrrolizino[1,2-b]quinoline-9,10(4H)-dione (Compound 662a) and its isomer 9-(2-morpholinoethoxy)-10H-pyrrolizino[1,2-b]quinolin-10-one (Compound 662b)

Steps: Following the procedure of Example 1, ethyl 4-oxo-2-(1H-pyrrol-2-yl)-1,4-dihydroquinoline-3-carboxylate (50 mg) and 4-(2-bromoethyl) morpholine (45 mg) were subjected to reaction and post-treatment to give yellow solids (35% and 36% yields).

ESI-MS m/z 350.15[M+H]+.

Example 214

4-(3-Morpholinopropyl)-9H-pyrrolizino[1,2-b]quinoline-9,10(4H)-dione (Compound 663a) and its isomer 9-(3-morpholinopropoxy)-10H-pyrrolizino[1,2-b]quinolin-10-one (Compound 663b)

Steps: Following the procedure of Example 1, ethyl 4-oxo-2-(1H-pyrrol-2-yl)-1,4-dihydroquinoline-3-carboxylate (50 mg) and 4-(3-bromopropyl)morpholine (50 mg) were subjected to reaction and post-treatment to give yellow solids (35% and 37% yields).

ESI-MS m/z 364.16[M+H]+.

Example 215

4-(2-(Piperidin-1-yl)ethyl)-9H-pyrrolizino[1,2-b]quinoline-9,10(4H)-dione (Compound 665a) and its isomer 9-(2-(piperidin-1-yl)ethoxy)-10H-pyrrolizino[1,2-b]quinolin-10-one (Compound 665b)

Steps: Following the procedure of Example 1, ethyl 4-oxo-2-(1H-pyrrol-2-yl)-1,4-dihydroquinoline-3-carboxylate (50 mg) and 1-(2-bromoethyl) piperidine (50 mg) were subjected to reaction and post-treatment to give yellow solids (35% and 39% yields).

ESI-MS m/z 348.17[M+H]$^+$.

Example 216

4-(3-(Piperidin-1-yl)propyl)-9H-pyrrolizino[1,2-b]quinoline-9,10(4H)-dione (Compound 666a) and its isomer 9-(3-(piperidin-1-yl)propoxy)-10H-pyrrolizino[1,2-b]quinolin-10-one (Compound 666b)

Steps: Following the procedure of Example 1, ethyl 4-oxo-2-(1H-pyrrol-2-yl)-1,4-dihydroquinoline-3-carboxylate (50 mg) and 1-(3-bromoethyl) piperidine (50 mg) were subjected to reaction and post-treatment to give yellow solids (38% and 39% yields).

ESI-MS m/z 362.18[M+H]$^+$.

Example 217

4-(4-(Piperidin-1-yl)butyl)-9H-pyrrolizino[1,2-b]quinoline-9,10(4H)-dione (Compound 667a) and its isomer 9-(4-(piperidin-1-yl)butoxy)-10H-pyrrolizino[1,2-b]quinolin-10-one (Compound 667b)

Steps: Following the procedure of Example 1, ethyl 4-oxo-2-(1H-pyrrol-2-yl)-1,4-dihydroquinoline-3-carboxylate (50 mg) and 1-(4-bromobutyl) piperidine (50 mg) were subjected to reaction and post-treatment to give yellow solids (39% and 39% yields).
ESI-MS m/z 376.20[M+H]$^+$.

Example 218

4-(4-Morpholinobutyl)-9H-pyrrolizino[1,2-b]quinoline-9,10(4H)-dione and (Compound 664a) its isomer 9-(4-morpholinobutoxy)-10H-pyrrolizino[1,2-b]quinolin-10-one (Compound 664b)

Steps: Following the procedure of Example 1, ethyl 4-oxo-2-(1H-pyrrol-2-yl)-1,4-dihydroquinoline-3-carboxylate (50 mg) and 4-(4-bromobutyl) morpholine (46 mg) were subjected to reaction and post-treatment to give yellow solids (35% and 39% yields).
ESI-MS m/z 378.18[M+H]$^+$.

Example 219

4-(2-Propoxyethyl)-9H-pyrrolizino[1,2-b]quinoline-9,10(4H)-dione (Compound 671a) and its isomer 9-(2-propoxyethoxy)-10H-pyrrolizino[1,2-b]quinolin-10-one (Compound 671b)

Steps: Following the procedure of Example 1, ethyl 4-oxo-2-(1H-pyrrol-2-yl)-1,4-dihydroquinoline-3-carboxylate (50 mg) and 1-(2-bromoethoxy) propane (50 mg) were subjected to reaction and post-treatment to give yellow solids (38% and 40% yields).
ESI-MS m/z 323.14 [M+H]$^+$.

Example 220

4-(3-Ethoxypropyl)-9H-pyrrolizino[1,2-b]quinoline-9,10(4H)-dione (Compound 672a) and its isomer 9-(3-ethoxypropoxy)-10H-pyrrolizino[1,2-b]quinolin-10-one (Compound 672b)

Steps: Following the procedure of Example 1, ethyl 4-oxo-2-(1H-pyrrol-2-yl)-1,4-dihydroquinoline-3-carboxylate (50 mg) and I-bromo-3-ethoxypropane (50 mg) were subjected to reaction and post-treatment to give yellow solids (39% and 40% yields).
ESI-MS m/z 323.14 [M+H]$^+$.

Example 221

4-(2-(Piperazin-1-yl)ethyl)-9H-pyrrolizino[1,2-b]quinoline-9,10(4H)-dione (Compound 98a) and its isomer 9-(2-(piperazin-1-yl)ethoxy)-10H-pyrrolizino[1,2-b]quinolin-10-one (Compound 98b)

Steps: Following the procedure of Example 1, ethyl 4-oxo-2-(1H-pyrrol-2-yl)-1,4-dihydroquinoline-3-carboxylate (50 mg) and 1-(2-bromoethyl)piperazine (50 mg) were subjected to reaction and post-treatment to give yellow solids (35% and 40% yields).
ESI-MS m/z 349.16[M+H]$^+$.

Example 222

4-(3-(Piperazin-1-yl)propyl)-9H-pyrrolizino[1,2-b]quinoline-9,10(4H)-dione (Compound 669a) and its isomer 9-(3-(piperazin-1-yl)propoxy)-10H-pyrrolizino[1,2-b]quinolin-10-one (Compound 669b)

Steps: Following the procedure of Example 1, ethyl 4-oxo-2-(1H-pyrrol-2-yl)-1,4-dihydroquinoline-3-carboxylate (50 mg) and 1-(3-bromopropyl)piperazine (50 mg) were subjected to reaction and post-treatment to give yellow solids (35% and 30% yields).
ESI-MS m/z 363.18[M+H]$^+$.

Example 223

4-(4-(Piperazin-1-yl)butyl)-9H-pyrrolizino[1,2-b]quinoline-9,10(4H)-dione (Compound 670a) and its isomer 9-(4-(piperazin-1-yl)butoxy)-10H-pyrrolizino[1,2-b]quinolin-10-one (Compound 670b)

Steps: Following the procedure of Example 1, ethyl 4-oxo-2-(1H-pyrrol-2-yl)-1,4-dihydroquinoline-3-carboxylate (50 mg) and 1-(4-bromobutyl)piperazine (50 mg) were subjected to reaction and post-treatment to give yellow solids (38% and 35% yields).
ESI-MS m/z 377.19[M+H]$^+$.

Example 224

4-(2-Nitrobenzyl)-9H-pyrrolizino[1,2-b]quinoline-9,10(4H)-dione (Compound 668a) and its isomer 9-((2-nitrobenzyl)oxy)-10H-pyrrolizino[1,2-b]quinolin-10-one (Compound 668b)

Steps: Following the procedure of Example 1, ethyl 4-oxo-2-(1H-pyrrol-2-yl)-1,4-dihydroquinoline-3-carboxylate (50 mg) and 2-nitrobenzyl bromide (20 mg) were subjected to reaction and post-treatment to give yellow solids (45% and 40% yields).
ESI-MS m/z 372.09 [M+H]$^+$.

Example 225

8-Methyl-9H-pyrrolizino[1,2-b]quinoline-9,10(4H)-dione (Compound 678a) and its isomer 9-hydroxy-8-methyl-10H-pyrrolizino[1,2-b]quinolin-10-one (Compound 678b)

Steps: Following the procedure of Example 27, ethyl 5-methyl-4-oxo-2-(1H-pyrrol-2-yl)-1,4-dihydroquinoline-3-carboxylate (50 mg) was subjected to reaction and post-treatment to give yellow solids (35% and 35% yields).
ESI-MS m/z 251.08 [M+H]$^+$.

Example 226

7-Methyl-9H-pyrrolizino[1,2-b]quinoline-9,10(4H)-dione (Compound 696a) and its isomer 9-hydroxy-7-methyl-10H-pyrrolizino[1,2-b]quinolin-10-one (Compound 696b)

Steps: Following the procedure of Example 27, ethyl 6-methyl-4-oxo-2-(1H-pyrrol-2-yl)-1,4-dihydroquinoline-3-carboxylate (50 mg) was subjected to reaction and post-treatment to give yellow solids (25% and 35% yields).
ESI-MS m/z 251.08 [M+H]$^+$.

Example 227

6-Methyl-9H-pyrrolizino[1,2-b]quinoline-9,10(4H)-dione (Compound 714a) and its isomer 9-hydroxy-6-methyl-10H-pyrrolizino[1,2-b]quinolin-10-one (Compound 714b)

Steps: Following the procedure of Example 27, ethyl 7-methyl-4-oxo-2-(1H-pyrrol-2-yl)-1,4-dihydroquinoline- 3-carboxylate (50 mg) was subjected to reaction and post-treatment to give yellow solids (30% and 35% yields). ESI-MS m/z 251.08 [M+H]+.

Example 228

5-Methyl-9H-pyrrolizino[1,2-b]quinoline-9,10(4H)-dione (Compound 732a) and its isomer 9-hydroxy-5-methyl-10H-pyrrolizino[1,2-b]quinolin-10-one (Compound 732b)

Steps: Following the procedure of Example 27, ethyl 8-methyl-4-oxo-2-(1H-pyrrol-2-yl)-1,4-dihydroquinoline-3-carboxylate (50 mg) was subjected to reaction and post-treatment to give yellow solids (30% and 30% yields). ESI-MS m/z 251.08 [M+H]+.

Example 229

5,7-Dimethyl-9H-pyrrolizino[1,2-b]quinoline-9,10(4H)-dione (Compound 750a) and its isomer 9-hydroxy-5,7-dimethyl-10H-pyrrolizino[1,2-b]quinolin-10-one (Compound 750b)

Steps: Following the procedure of Example 27, ethyl 6,8-dimethyl-4-oxo-2-(1H-pyrrol-2-yl)-1,4-dihydroquinoline-3-carboxylate (50 mg) was subjected to reaction and post-treatment to give yellow solids (30% and 35% yields). ESI-MS m/z 265.09 [M+H]+.

Example 230

6,7-Dimethyl-9H-pyrrolizino[1,2-b]quinoline-9,10(4H)-dione (Compound 756a) and its isomer 9-hydroxy-6,7-dimethyl-10H-pyrrolizino[1,2-b]quinolin-10-one (Compound 756b)

Steps: Following the procedure of Example 27, ethyl 6,7-dimethyl-4-oxo-2-(1H-pyrrol-2-yl)-1,4-dihydroquinoline-3-carboxylate (50 mg) was subjected to reaction and post-treatment to give yellow solids (25% and 25% yields). ESI-MS m/z 265.09 [M+H]+.

Example 231

6,8-Dimethyl-9H-pyrrolizino[1,2-b]quinoline-9,10(4H)-dione (Compound 768a) and its isomer 9-hydroxy-6,8-dimethyl-10H-pyrrolizino[1,2-b]quinolin-10-one (Compound 768b)

Steps: Following the procedure of Example 27, ethyl 5,7-dimethyl-4-oxo-2-(1H-pyrrol-2-yl)-1,4-dihydroquinoline-3-carboxylate (50 mg) was subjected to reaction and post-treatment to give yellow solids (35% and 35% yields). ESI-MS m/z 265.09 [M+H]+.

Example 232

5,8-Dimethyl-9H-pyrrolizino[1,2-b]quinoline-9,10(4H)-dione (Compound 772a) and its isomer 9-hydroxy-5,8-dimethyl-10H-pyrrolizino[1,2-b]quinolin-10-one (Compound 772b)

Steps: Following the procedure of Example 27, ethyl 5,8-dimethyl-4-oxo-2-(1H-pyrrol-2-yl)-1,4-dihydroquinoline-3-carboxylate (50 mg) was subjected to reaction and post-treatment to give yellow solids (25% and 35% yields). ESI-MS m/z 265.09 [M+H]+.

Example 233

10-Methyl-5H-pyrrolizino[2,1-b]quinoline-5,11(6H)-dione (Compound 776a) and its isomer 11-hydroxy-10-methyl-5H-pyrrolizino[2,1-b]quinolin-5-one (Compound 776b)

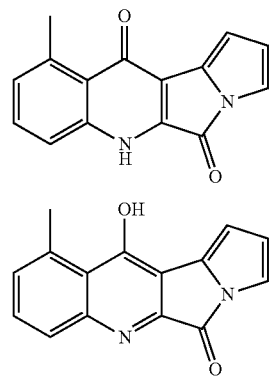

Steps: Following the procedure of Example 27, ethyl 5-methyl-4-oxo-3-(1H-pyrrol-2-yl)-1,4-dihydroquinoline-2-carboxylate (50 mg) was subjected to reaction and post-treatment to give yellow solids (30% and 33% yields). ESI-MS m/z 251.08 [M+H]+.

Example 234

9-Methyl-5H-pyrrolizino[2,1-b]quinoline-5,11(6H)-dione and (Compound 777a) its isomer 11-hydroxy-9-methyl-5H-pyrrolizino[2,1-b]quinolin-5-one (Compound 777b)

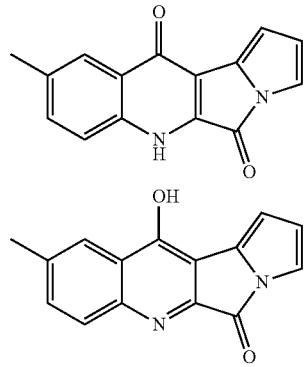

Steps: Following the procedure of Example 27, ethyl 6-methyl-4-oxo-3-(1H-pyrrol-2-yl)-1,4-dihydroquinoline-2-carboxylate (50 mg) was subjected to reaction and post-treatment to give yellow solids (35% and 36% yields). ESI-MS m/z 251.08 [M+H]+.

Example 235

8-Methyl-5H-pyrrolizino[2,1-b]quinoline-5,11(6H)-dione (Compound 778a) and its isomer 11-hydroxy-8-methyl-5H-pyrrolizino[2,1-b]quinolin-5-one (Compound 778b)

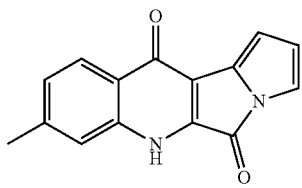

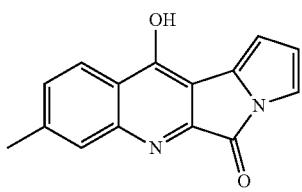

Steps: Following the procedure of Example 27, ethyl 7-methyl-4-oxo-3-(1H-pyrrol-2-yl)-1,4-dihydroquinoline-2-carboxylate (50 mg) was subjected to reaction and post-treatment to give yellow solids (35% and 35% yields). ESI-MS m/z 251.08 [M+H]+.

Example 236

7-Methyl-5H-pyrrolizino[2,1-b]quinoline-5,11(6H)-dione (Compound 779a) and its isomer 11-hydroxy-7-methyl-5H-pyrrolizino[2,1-b]quinolin-5-one (Compound 779b)

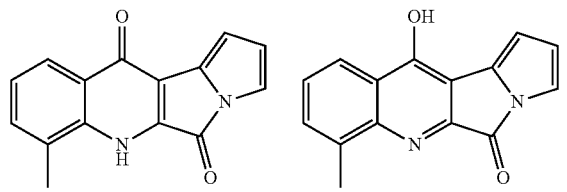

Steps: Following the procedure of Example 27, ethyl 8-methyl-4-oxo-3-(1H-pyrrol-2-yl)-1,4-dihydroquinoline-2-carboxylate (50 mg) was subjected to reaction and post-treatment to give yellow solids (35% and 37% yields). ESI-MS m/z 251.08 [M+H]+.

Example 237

7,9-Dimethyl-5H-pyrrolizino[2,1-b]quinoline-5,11(6H)-dione (Compound 780a) and its isomer 11-hydroxy-7,9-dimethyl-5H-pyrrolizino[2,1-b]quinolin-5-one (Compound 780b)

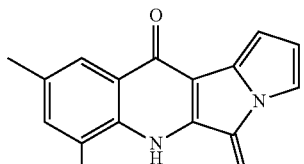

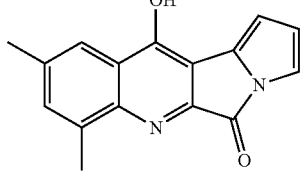

Steps: Following the procedure of Example 27, ethyl 6,8-dimethyl-4-oxo-3-(1H-pyrrol-2-yl)-1,4-dihydroquinoline-2-carboxylate (50 mg) was subjected to reaction and post-treatment to give yellow solids (25% and 25% yields). ESI-MS m/z 265.09 [M+H]+.

Example 238

8,9-Dimethyl-5H-pyrrolizino[2,1-b]quinoline-5,11(6H)-dione (Compound 781a) and its isomer 11-hydroxy-8,9-dimethyl-5H-pyrrolizino[2,1-b]quinolin-5-one (Compound 781b)

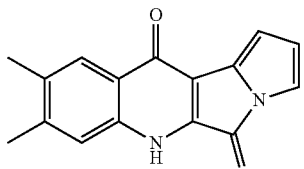

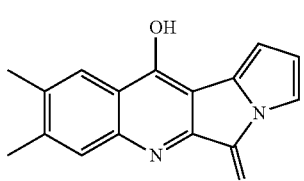

Steps: Following the procedure of Example 27, ethyl 6,7-dimethyl-4-oxo-3-(1H-pyrrol-2-yl)-1,4-dihydroquinoline-2-carboxylate (50 mg) was subjected to reaction and post-treatment to give yellow solids (30% and 35% yields). ESI-MS m/z 265.09 [M+H]+.

Example 239

8,10-Dimethyl-5H-pyrrolizino[2,1-b]quinoline-5,11 (6H)-dione (Compound 782a) and its isomer 11-hydroxy-8,10-dimethyl-5H-pyrrolizino[2,1-b]quinolin-5-one (Compound 782b)

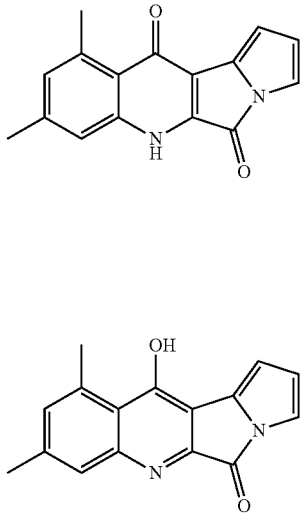

Steps: Following the procedure of Example 27, ethyl 5,7-dimethyl-4-oxo-3-(1H-pyrrol-2-yl)-1,4-dihydroquinoline-2-carboxylate (50 mg) was subjected to reaction and post-treatment to give yellow solids (35% and 35% yields). ESI-MS m/z 265.09 [M+H]⁺.

Example 240

7,10-Dimethyl-5H-pyrrolizino[2,1-b]quinoline-5,11 (6H)-dione (Compound 783a) and its isomer 11-hydroxy-7,10-dimethyl-5H-pyrrolizino[2,1-b]quinolin-5-one (Compound 783b)

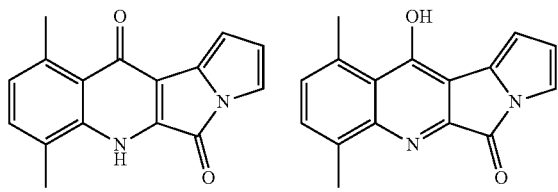

Steps: Following the procedure of Example 27, ethyl 5,8-dimethyl-4-oxo-3-(1H-pyrrol-2-yl)-1,4-dihydroquinoline-2-carboxylate (50 mg) was subjected to reaction and post-treatment to give yellow solids (30% and 35% yields). ESI-MS m/z 265.09 [M+H]⁺.

Example 241

6-(2-(Piperidin-1-yl)ethyl)-5H-pyrrolizino[2,1-b] quinoline-5,11(6H)-dione (Compound 784a) and its isomer 11-(2-(piperidin-1-yl)ethoxy)-5H-pyrrolizino [2,1-b]quinolin-5-one (Compound 784b)

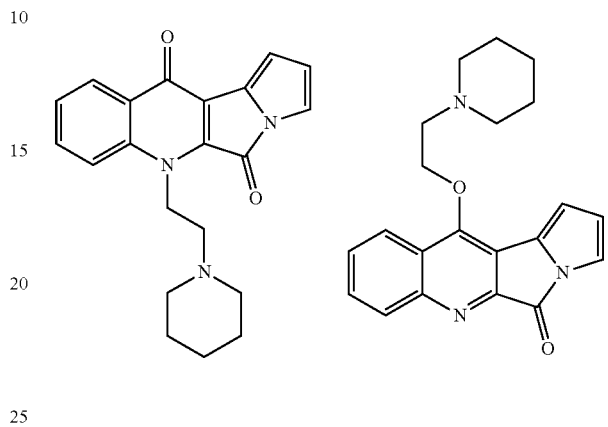

Steps: Following the procedure of Example 1, ethyl 4-oxo-3-(1H-pyrrol-2-yl)-1,4-dihydroquinoline-2-carboxylate (50 mg) and 1-(2-bromoethyl)piperazine (50 mg) were subjected to reaction and post-treatment to give yellow solids (35% and 36% yields).

ESI-MS m/z 348.17[M+H]⁺.

Example 242

6-(2-Morpholinoethyl)-5H-pyrrolizino[2,1-b]quinoline-5,11(6H)-dione (Compound 785a) and its isomer 11-(2-morpholinoethoxy)-5H-pyrrolizino[2,1-b] quinolin-5-one (Compound 785b)

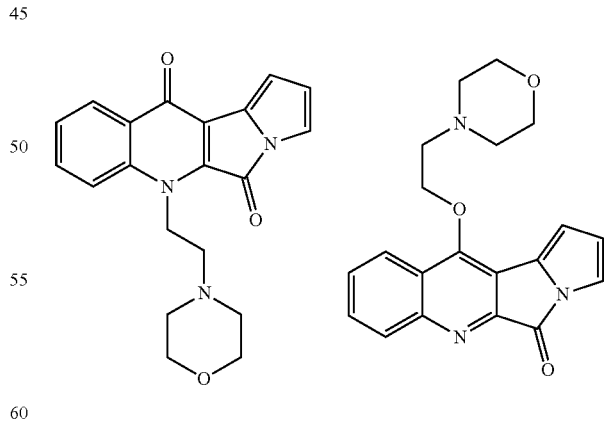

Steps: Following the procedure of Example 1, ethyl 4-oxo-3-(1H-pyrrol-2-yl)-1,4-dihydroquinoline-2-carboxylate (50 mg) and 4-(2-bromoethyl)morpholine (50 mg) were subjected to reaction and post-treatment to give yellow solids (35% and 36% yields).

ESI-MS m/z 350.15[M+H]⁺.

Example 243

6-(3-(Piperidin-1-yl)propyl)-5H-pyrrolizino[2,1-b]quinoline-5,11(6H)-dione (Compound 786a) and its isomer 11-(3-(piperidin-1-yl)propoxy)-5H-pyrrolizino[2,1-b]quinolin-5-one (Compound 786b)

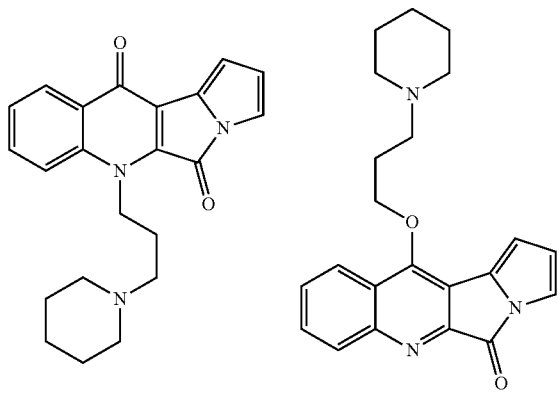

Steps: Following the procedure of Example 1, ethyl 4-oxo-3-(1H-pyrrol-2-yl)-1,4-dihydroquinoline-2-carboxylate (50 mg) and 1-(3-bromopropyl)piperidine (50 mg) were subjected to reaction and post-treatment to give yellow solids (38% and 36% yields).

ESI-MS m/z 362.18[M+H]$^+$.

Example 244

6-(3-Morpholinopropyl)-5H-pyrrolizino[2,1-b]quinoline-5,11(6H)-dione (Compound 787a) and its isomer 11-(3-morpholinopropoxy)-5H-pyrrolizino[2,1-b]quinolin-5-one (Compound 787b)

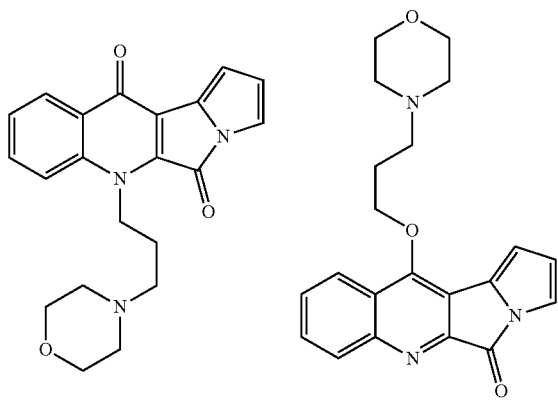

Steps: Following the procedure of Example 1, ethyl 4-oxo-3-(1H-pyrrol-2-yl)-1,4-dihydroquinoline-2-carboxylate (50 mg) and 4-(3-bromopropyl)morpholine (50 mg) were subjected to reaction and post-treatment to give yellow solids (35% and 38% yields).

ESI-MS m/z 364.16[M+H]$^+$.

Example 245

6-(4-(Piperidin-1-yl)butyl)-5H-pyrrolizino[2,1-b]quinoline-5,11(6H)-dione (Compound 788a) and its isomer 11-(4-(piperidin-1-yl)butoxy)-5H-pyrrolizino[2,1-b]quinolin-5-one (Compound 788b)

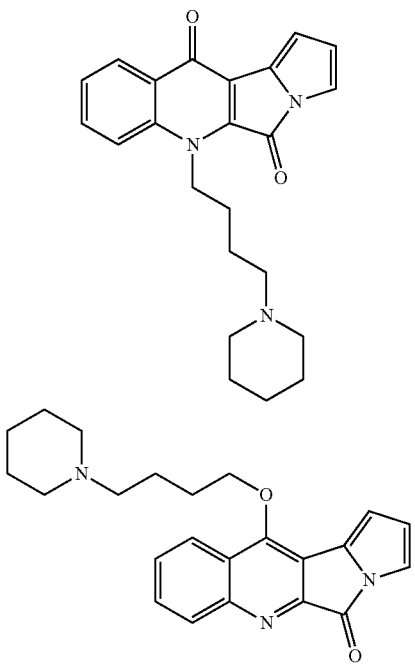

Steps: Following the procedure of Example 1, ethyl 4-oxo-3-(1H-pyrrol-2-yl)-1,4-dihydroquinoline-2-carboxylate (50 mg) and 1-(4-bromobutyl)piperidine (50 mg) were subjected to reaction and post-treatment to give yellow solids (39% and 38% yields).

ESI-MS m/z 376.20[M+H]$^+$.

Example 246

6-(4-Morpholinobutyl)-5H-pyrrolizino[2,1-b]quinoline-5,11(6H)-dione (Compound 789a) and its isomer 11-(4-morpholinobutoxy)-5H-pyrrolizino[2,1-b]quinolin-5-one (Compound 789b)

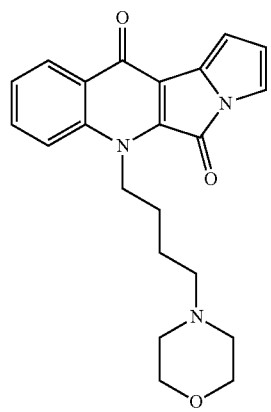

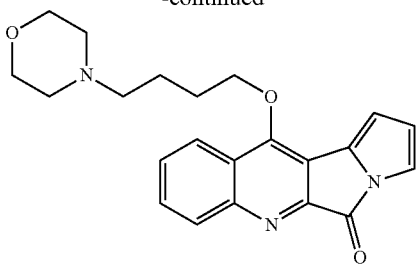

Steps: Following the procedure of Example 1, ethyl 4-oxo-3-(1H-pyrrol-2-yl)-1,4-dihydroquinoline-2-carboxylate (50 mg) and 4-(4-bromobutyl)morpholine (46 mg) were subjected to reaction and post-treatment to give yellow solids (35% and 38% yields).

ESI-MS m/z 378.18[M+H]$^+$.

Example 247

6-(2-Propoxyethyl)-5H-pyrrolizino[2,1-b]quinoline-5,11(6H)-dione (Compound 790a) and its isomer 11-(2-propoxyethoxy)-5H-pyrrolizino[2,1-b]quinolin-5-one (Compound 790b)

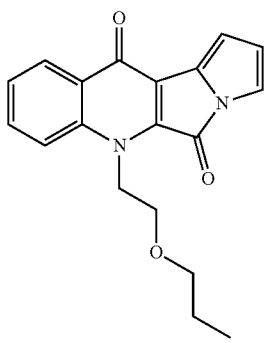

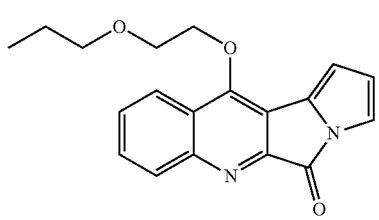

Steps: Following the procedure of Example 1, ethyl 4-oxo-3-(1H-pyrrol-2-yl)-1,4-dihydroquinoline-2-carboxylate (50 mg) and 1-(2-bromoethoxy)propane (50 mg) were subjected to reaction and post-treatment to give yellow solids (38% and 35% yields).

ESI-MS m/z 323.14 [M+H]$^+$.

Example 248

6-(3-Ethoxypropyl)-5H-pyrrolizino[2,1-b]quinoline-5,11(6H)-dione (Compound 791a) and its isomer 11-(3-ethoxypropoxy)-5H-pyrrolizino[2,1-b]quinolin-5-one (Compound 791b)

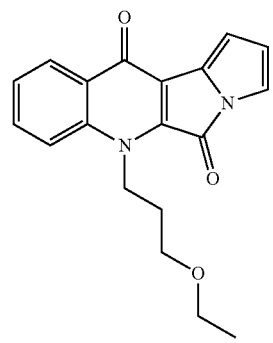

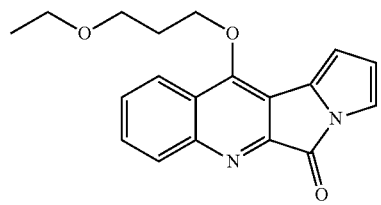

Steps: Following the procedure of Example 1, ethyl 4-oxo-3-(1H-pyrrol-2-yl)-1,4-dihydroquinoline-2-carboxylate (50 mg) and 1-bromo-3-ethoxypropane (50 mg) were subjected to reaction and post-treatment to give yellow solids (39% and 35% yields).

ESI-MS m/z 323.14 [M+H]$^+$.

Example 249

6-(2-(Piperazin-1-yl)ethyl)-5H-pyrrolizino[2,1-b]quinoline-5,11(6H)-dione (Compound 792a) and its isomer 11-(2-(piperazin-1-yl)ethoxy)-5H-pyrrolizino[2,1-b]quinolin-5-one (Compound 792b)

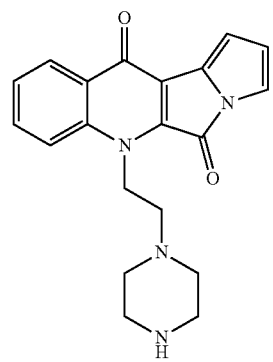

-continued

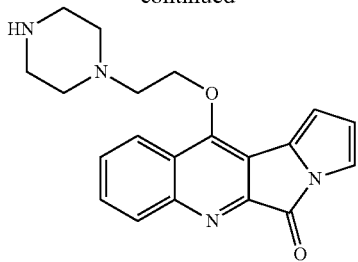

Steps: Following the procedure of Example 1, ethyl 4-oxo-3-(1H-pyrrol-2-yl)-1,4-dihydroquinoline-2-carboxylate (50 mg) and 1-(2-bromoethyl)piperazine (50 mg) were subjected to reaction and post-treatment to give yellow solids (35% and 39% yields).

ESI-MS m/z 349.16[M+H]$^+$.

Example 250

6-(3-(Piperazin-1-yl)propyl)-5H-pyrrolizino[2,1-b]quinoline-5,11(6H)-dione (Compound 793a) and its isomer 11-(3-(piperazin-1-yl)propoxy)-5H-pyrrolizino[2,1-b]quinolin-5-one (Compound 793b)

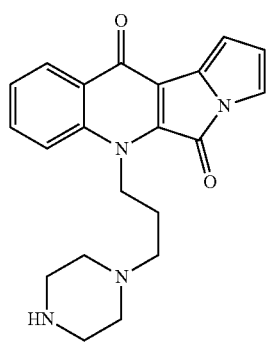

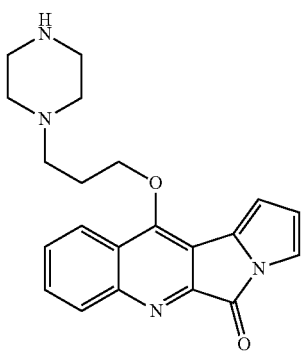

Steps: Following the procedure of Example 1, ethyl 4-oxo-3-(1H-pyrrol-2-yl)-1,4-dihydroquinoline-2-carboxylate (50 mg) and 1-(3-bromopropyl)piperazine (50 mg) were subjected to reaction and post-treatment to give yellow solids (35% and 36% yields).

ESI-MS m/z 363.18[M+H]$^+$.

Example 251

6-(4-(Piperazin-1-yl)butyl)-5H-pyrrolizino[2,1-b]quinoline-5,11(6H)-dione (Compound 794a) and its isomer 11-(4-(piperazin-1-yl)butoxy)-5H-pyrrolizino[2,1-b]quinolin-5-one (Compound 794b)

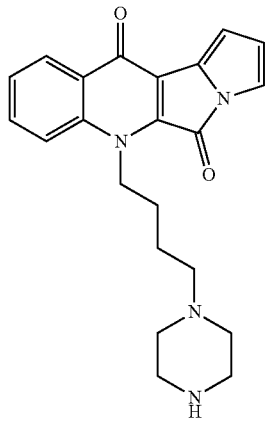

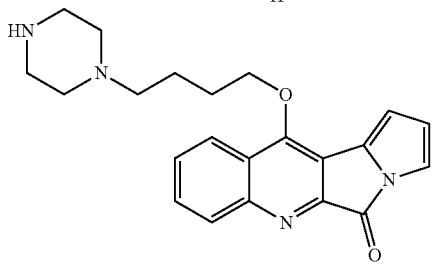

Steps: Following the procedure of Example 1, ethyl 4-oxo-3-(1H-pyrrol-2-yl)-1,4-dihydroquinoline-2-carboxylate (50 mg) and 1-(4-bromobutyl)piperazine (50 mg) were subjected to reaction and post-treatment to give yellow solids (38% and 36% yields).

ESI-MS m/z 377.19[M+H]$^+$.

Example 252

4'-((5,11-Dioxo-5,11-dihydro-6H-pyrrolizino[2,1-b]quinolin-6-yl)methyl)-[1,1'-biphenyl]-2-carbonitrile (Compound 795a) and its isomer 4'-(((5-oxo-5H-pyrrolizino[2,1-b]quinolin-11-yl)oxy)methyl)-[1,1'-biphenyl]-2-carbonitrile (Compound 795b)

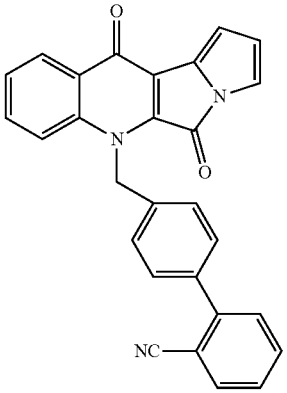

-continued

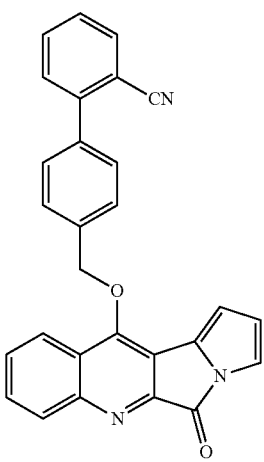

Steps: Following the procedure of Example 1, ethyl 4-oxo-3-(1H-pyrrol-2-yl)-1,4-dihydroquinoline-2-carboxylate (50 mg) and 2-cyano-4-bromomethyl-biphenyl (15 mg) were subjected to reaction and post-treatment to give yellow solids (38% and 36% yields).

ESI-MS m/z 428.14[M+H]$^+$.

Example 253

6-([1,1'-Biphenyl]-4-ylmethyl)-5H-pyrrolizino[2,1-b]quinoline-5,11(6H)-dione (Compound 796a) and its isomer 11-([1,1'-biphenyl]-4-ylmethoxy)-5H-pyrrolizino[2,1-b]quinolin-5-one (Compound 796b)

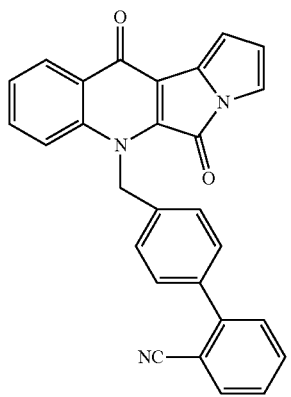

-continued

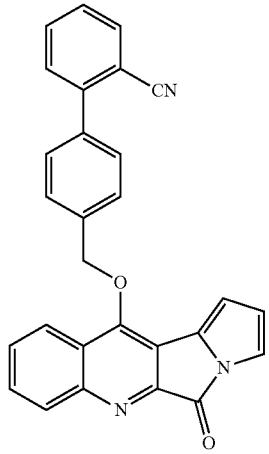

Steps: Following the procedure of Example 1, ethyl 4-oxo-3-(1H-pyrrol-2-yl)-1,4-dihydroquinoline-2-carboxylate (50 mg) and 4-bromomethyl-biphenyl (25 mg) were subjected to reaction and post-treatment to give yellow solids (38% and 36% yields).

ESI-MS m/z 403.14[M+H]$^+$.

Example 254

1-Methyl-5H-pyrrolizino[2,1-b]quinoline-5,11(6H)-dione (Compound 797a) and its isomer 11-hydroxy-1-methyl-5H-pyrrolizino[2,1-b]quinolin-5-one (Compound 797b)

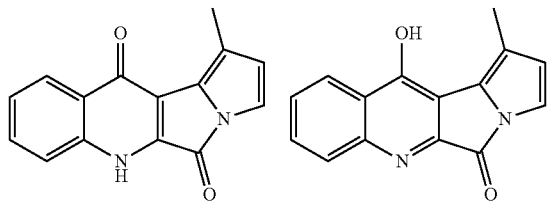

Steps: Following the procedure of Example 1, ethyl 3-(3-methyl-H-pyrrol-2-yl)-4-oxo-1,4-dihydroquinoline-2-carboxylate (50 mg) was subjected to reaction and post-treatment to give yellow solids (35% and 35% yields).

ESI-MS m/z 251.08 [M+H]$^+$.

Example 255

2-Methyl-5H-pyrrolizino[2,1-b]quinoline-5,11(6H)-dione (Compound 798a) and its isomer 11-hydroxy-2-methyl-5H-pyrrolizino[2,1-b]quinolin-5-one (Compound 798b)

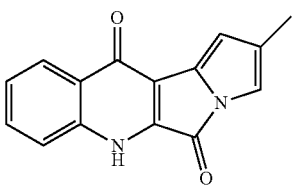

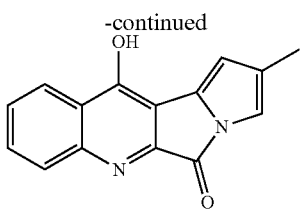

Steps: Following the procedure of Example 1, ethyl 3-(4-methyl-H-pyrrol-2-yl)-4-oxo-1,4-dihydroquinoline-2-carboxylate (50 mg) was subjected to reaction and post-treatment to give yellow solids (35% and 35% yields). ESI-MS m/z 251.08 [M+H]$^+$.

Example 256

3-Methyl-5H-pyrrolizino[2,1-b]quinoline-5,11(6H)-dione (Compound 799a) and its isomer 11-hydroxy-3-methyl-5H-pyrrolizino[2,1-b]quinolin-5-one (Compound 799b)

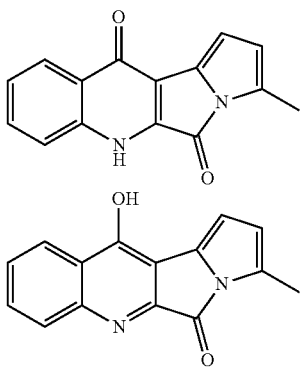

Steps: Following the procedure of Example 1, ethyl 3-(5-methyl-1H-pyrrol-2-yl)-4-oxo-1,4-dihydroquinoline-2-carboxylate (50 mg) was subjected to reaction and post-treatment to give yellow solids (30% and 35% yields). ESI-MS m/z 251.08 [M+H]$^+$.

Example 257

1-Methyl-9H-pyrrolizino[1,2-b]quinoline-9,10(4H)-dione (Compound 800a) and its isomer 9-hydroxy-1-methyl-10H-pyrrolizino[1,2-b]quinolin-10-one (Compound 800b)

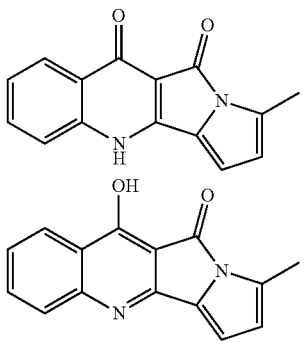

Steps: Following the procedure of Example 1, ethyl 2-(5-methyl-H-pyrrol-2-yl)-4-oxo-1,4-dihydroquinoline-3-carboxylate (50 mg) was subjected to reaction and post-treatment to give yellow solids (25% and 35% yields). ESI-MS m/z 251.08 [M+H]$^+$.

Example 258

2-Methyl-9H-pyrrolizino[1,2-b]quinoline-9,10(4H)-dione (Compound 801a) and its isomer 9-hydroxy-2-methyl-0H-pyrrolizino[1,2-b]quinolin-10-one (Compound 801b)

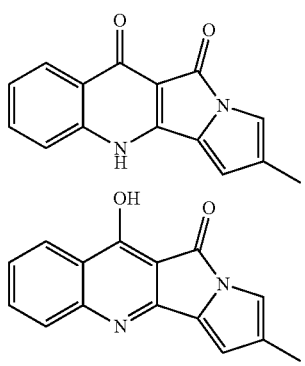

Steps: Following the procedure of Example 1, ethyl 2-(4-methyl-H-pyrrol-2-yl)-4-oxo-1,4-dihydroquinoline-3-carboxylate (50 mg) was subjected to reaction and post-treatment to give yellow solids (35% and 35% yields). ESI-MS m/z 251.08 [M+H]$^+$.

Example 259

3-Methyl-5H-pyrrolizino[2,1-b]quinoline-5,11(6H)-dione (Compound 802a) and its isomer 11-hydroxy-3-methyl-5H-pyrrolizino[2,1-b]quinolin-5-one (Compound 802b)

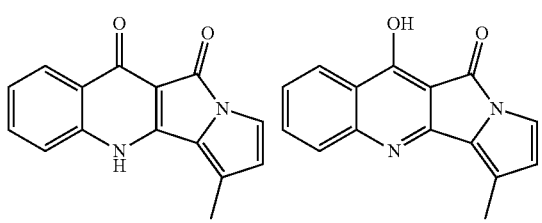

Steps: Following the procedure of Example 1, ethyl 3-(3-methyl-1H-pyrrol-2-yl)-4-oxo-1,4-dihydroquinoline-2-carboxylate (50 mg) was subjected to reaction and post-treatment to give yellow solids (30% and 35% yields). ESI-MS m/z 251.08 [M+H]$^+$.

Test Example 1

Anti-Fibrosis Activity Test
The Protocol for the Cell Experiments
1. Cell Seeding
BHK-21 cells in exponential growth phase were selected. After the fusion growth reached 85-95%, normal passage method was utilized to digest and collect the cells, followed by cell counting and adjusting the cell density to 2×10⁴ cells/mL. The cells were seeded into 96-well plates, 100 μL/well, and were incubated under the condition of 5% $CO_2$ at 37° C.

2. Administration to the Cells

The supernatant was removed after the cells had adhered to the wall for 24 hours. The culture solution containing the prepared compounds at different concentrations were added to the wells, 100 μL/well, each concentration in triplicate. The cells were subcultured for 48 hours after administration. Commercially available pirfenidone was employed as the positive control.

3. Assay for the Absorbance

10 μL of CCK-8 solution (1/10 of the volume of the culture solution) was added to each well 48 hours after the administration, and incubated for 2 hours. The absorbance (A) of each well was determined by a microplate reader at 450 nm wavelength. The inhibition rate against cell proliferation for each compound was calculated based on A, wherein inhibition rate against cell proliferation (inhibition ratio, IR)= (1−value of experimental group $(A_i)$/value of blank control group $(A_o)$)×100% and the $IC_{50}$ value of each compound was calculated by the data processing software.

Using the same protocol for the cell experiments, the inhibitory activity of the test compounds against the proliferation of human lung fibroblasts HFL1, human hepatic stellate cells LX-2, human fibrosarcoma cells HT-1080, human dermal fibroblasts CCC-ESF-1, human embryonic lung fibroblast IMR-90, cardiac fibroblast RAT-iCell-C002 was assayed.

The anti-fibrosis activity data are shown as follows:

| Compound number | BHK-21 | HFL1 | LX-2 | HT-1080 | CCC-ESF-1 | IMR-90 | RAT-iCell-C002 |
|---|---|---|---|---|---|---|---|
| Pirfenidone | D | C | D | D | D | D | D |
| 5a/b | C/B | B/B | B/C | C/C | B/B | B/B | A/B |
| 6a/b | B/B | B/B | B/B | A/B | B/C | B/B | B/B |
| 7a/b | A/B | B/B | B/B | B/B | A/A | B/B | B/B |
| 8a/b | C/B | B/B | B/B | B/B | B/B | C/B | B/B |
| 9a/b | D/C | B/B | B/B | B/B | C/C | B/B | B/B |
| 11a/b | B/B | B/B | B/B | B/B | B/B | B/B | B/B |
| 12a/b | B/B | B/B | B/B | B/B | B/B | B/B | B/B |
| 16a/b | B/B | B/B | B/B | B/B | B/B | B/B | B/B |
| 18a/b | A/B | B/B | C/B | B/B | B/B | B/B | B/B |
| 34a/b | A/B | B/B | B/B | B/B | C/A | B/B | B/B |
| 50a/b | B/B | B/B | C/C | B/B | B/A | C/C | C/C |
| 64a/b | B/B | B/B | B/B | B/B | B/B | B/B | B/B |
| 81a/b | A/B | B/B | A/A | B/B | B/B | A/B | B/B |
| 90a/b | B/B | B/B | A/B | B/C | B/B | B/B | B/B |
| 91a/b | B/B | A/A | B/C | C/B | B/B | B/B | B/B |
| 95a/b | B/B | B/B | A/A | A/B | B/B | A/B | B/B |
| 98a/b | A/B | B/B | A/B | B/B | A/B | A/B | B/B |
| 100a/b | B/B | A/B | B/B | B/B | B/B | B/B | B/B |
| 103a/b | B/B | B/B | B/B | B/B | B/B | A/A | B/B |
| 104a/b | A/B | B/B | B/B | A/B | B/B | B/B | B/B |
| 105a/b | B/B | B/B | B/B | B/B | B/B | B/B | B/B |
| 108a/b | B/B | B/B | B/B | C/C | B/B | B/B | B/B |
| 109a/b | B/B | B/B | B/B | B/B | B/B | A/B | B/B |
| 112a/b | C/B | B/B | B/B | B/B | B/B | B/B | B/B |
| 114a/b | A/B | B/B | B/B | B/B | B/B | B/B | B/B |
| 133a/b | B/B | B/B | B/B | B/B | B/B | C/B | B/B |
| 141a/b | B/B | B/B | B/B | B/B | A/C | B/B | B/B |
| 144a/b | B/B | B/B | A/B | B/B | B/B | B/B | B/B |
| 150a/b | B/B | B/B | B/A | B/B | B/B | A/B | B/B |
| 153a/b | A/B | B/B | A/B | B/B | B/B | B/B | B/B |
| 156a/b | B/B | A/A | A/B | B/B | B/B | B/B | B/B |
| 157a/b | C/B | B/B | B/B | B/B | B/B | B/B | B/B |
| 180a/b | D/B | B/B | B/B | B/B | B/B | B/B | B/B |
| 199a/b | A/B | B/B | B/B | B/B | B/B | B/B | B/B |
| 210a/b | B/B | B/B | B/B | B/B | B/B | B/B | B/B |
| 222a/b | B/B | B/B | B/B | B/B | B/B | B/B | B/B |
| 246a/b | C/B | B/B | B/B | B/B | B/B | B/B | B/B |
| 259a/b | B/B | B/B | B/B | B/B | C/C | B/A | B/B |
| 276a/b | A/B | B/B | B/B | B/B | B/B | B/B | C/B |
| 279a/b | B/B | B/B | B/B | B/B | B/B | B/B | B/B |
| 282a/b | B/B | B/B | B/B | B/B | B/B | B/B | B/B |
| 300a/b | C/B | B/B | B/B | B/B | B/B | B/B | B/B |
| 306a/b | B/B | B/B | B/B | B/B | B/B | B/B | B/B |
| 319a/b | B/B | B/B | B/B | B/B | A/A | B/B | B/B |
| 328a/b | A/B | B/B | B/B | B/B | B/B | B/B | B/B |
| 329a/b | B/B | B/B | B/B | B/B | B/B | B/B | C/A |
| 331a/b | B/B | B/B | B/B | B/A | B/B | B/B | B/B |
| 340a/b | B/B | B/B | B/B | C/B | B/B | B/B | B/B |
| 343a/b | B/B | B/B | B/B | A/B | B/B | B/B | B/B |
| 346a/b | B/B | B/B | B/B | B/B | B/B | B/B | B/B |
| 347a/b | B/B | B/B | C/B | B/B | B/B | B/B | B/B |
| 348a/b | D/B | B/B | B/A | B/B | B/B | B/B | B/B |
| 349a/b | B/B | B/B | B/B | B/B | B/B | B/B | B/B |
| 354a/b | B/B | B/B | C/C | B/B | B/B | B/B | A/B |
| 361a/b | B/B | B/B | B/C | A/B | B/B | B/B | B/B |
| 373a/b | B/B | B/B | B/B | B/B | B/B | B/B | B/B |
| 397a/b | B/B | B/B | B/B | B/B | B/B | B/B | B/B |
| 409a/b | B/B | B/B | B/B | B/B | B/B | B/B | B/B |
| 443a/b | B/B | B/B | B/B | B/B | B/B | B/B | B/B |
| 444a/b | B/B | B/B | B/B | B/B | B/B | B/B | B/B |
| 445a/b | B/B | B/B | B/B | B/B | B/B | B/B | B/B |
| 446a/b | B/B | B/B | B/B | B/B | B/B | B/B | B/B |
| 447a/b | B/B | B/B | B/B | A/B | B/B | B/B | B/B |
| 448a/b | B/B | B/B | B/B | B/A | B/B | B/B | B/B |
| 449a/b | B/B | B/B | B/B | B/B | B/B | B/B | B/B |
| 450a/b | B/B | B/B | B/B | C/C | B/B | B/B | B/B |
| 451a/b | B/B | A/A | B/B | B/B | B/B | B/B | B/B |
| 452a/b | B/B | B/B | A/B | B/B | B/B | B/B | B/B |
| 453a/b | B/B | B/B | B/B | B/B | B/B | B/B | B/B |
| 454a/b | B/B | B/B | B/B | B/B | B/B | B/B | B/B |
| 455a/b | B/B | C/C | B/B | B/B | B/B | C/B | B/B |
| 456a/b | B/B | B/B | A/B | B/B | B/B | B/B | B/B |
| 457a/b | B/B | B/B | A/B | B/B | B/B | B/B | B/B |
| 458a/b | A/B | B/B | B/B | B/B | B/B | B/B | B/B |
| 459a/b | B/B | B/B | B/B | C/C | B/B | B/B | B/B |
| 460a/b | A/B | A/B | B/B | B/B | B/B | B/B | B/B |
| 461a/b | A/B | B/B | A/B | B/B | B/B | B/B | B/B |
| 462a/b | A/B | B/B | B/B | B/B | B/B | B/B | B/B |
| 463a/b | B/B | B/B | B/B | C/B | B/B | B/B | B/B |
| 464a/b | A/B | A/A | B/B | B/B | B/B | B/B | B/B |
| 465a/b | B/B | B/B | B/B | B/B | B/B | B/B | B/B |
| 466a/b | B/B | B/B | A/B | B/B | B/B | B/B | B/B |
| 467a/b | A/B | B/B | B/B | B/B | B/B | B/B | B/B |
| 468a/b | A/B | B/B | B/B | B/B | B/B | B/B | B/B |
| 469a/b | A/B | B/B | B/B | C/B | B/B | B/B | B/B |
| 470a/b | B/B | B/B | B/B | B/B | B/B | B/B | B/B |
| 471a/b | B/B | B/B | A/B | B/B | B/B | B/B | B/B |
| 472a/b | A/B | B/B | B/B | B/B | B/B | B/B | B/B |
| 473a/b | B/B | B/B | B/B | B/B | B/B | B/B | A/B |
| 474a/b | A/B | B/B | B/B | B/B | B/B | B/B | B/C |
| 475a/b | B/B | B/B | B/B | C/A | B/B | B/B | B/B |
| 476a/b | A/B | B/B | B/B | B/B | B/B | B/B | B/B |
| 477a/b | B/B | B/B | B/B | B/B | B/B | B/B | B/B |
| 478a/b | B/B | B/B | B/B | B/B | B/B | B/B | B/B |
| 479a/b | B/B | B/B | B/B | B/B | B/B | B/B | B/B |
| 480a/b | B/B | B/B | B/B | B/B | B/B | B/B | A/B |
| 481a/b | A/B | B/B | B/B | B/B | B/B | B/B | B/B |
| 482a/b | B/B | B/B | B/B | C/A | B/B | B/B | B/B |
| 483a/b | A/B | B/B | B/B | B/C | B/B | B/B | B/B |
| 484a/b | B/B | B/B | B/B | B/B | B/B | B/B | B/B |
| 485a/b | B/B | B/B | B/B | B/B | B/B | B/B | B/B |
| 486a/b | B/B | B/B | B/B | B/B | B/B | B/B | B/B |
| 487a/b | B/B | B/B | B/B | B/B | B/B | B/B | A/B |
| 488a/b | B/B | B/B | A/B | B/B | B/B | B/B | B/B |
| 490a/b | B/B | B/B | B/B | B/B | B/B | B/B | A/B |
| 491a/b | A/B | B/B | B/B | B/B | B/B | B/B | B/B |

| | | | IC$_{50}$ (mM) | | | | |
|---|---|---|---|---|---|---|---|
| Compound number | BHK-21 | HFL1 | LX-2 | HT-1080 | CCC-ESF-1 | IMR-90 | RAT-iCell-C002 |
| 496a/b | B/B | B/B | B/B | B/B | B/B | B/B | B/B |
| 497a/b | B/B | B/B | B/B | B/B | B/B | B/B | A/B |
| 500a/b | B/B | B/B | A/B | B/B | B/B | B/B | B/B |
| 502a/b | B/B | B/B | B/B | B/B | B/B | B/B | A/B |
| 504a/b | A/B | B/B | B/B | B/B | B/B | B/B | B/B |
| 508a/b | B/B | B/B | B/B | C/A | B/B | B/B | B/B |
| 510a/b | A/B | B/B | B/B | B/B | B/B | B/B | B/B |
| 512a/b | B/B | B/B | A/A | B/B | B/B | B/B | B/B |
| 514a/b | A/B | B/B | B/B | B/B | B/B | B/B | B/B |
| 515a/b | B/B | B/B | B/B | C/C | B/B | B/C | B/A |
| 516a/b | A/B | B/B | B/B | B/B | B/B | B/B | B/B |
| 524a/b | B/B | B/B | B/B | B/B | B/B | B/B | B/B |
| 536a/b | B/B | B/B | B/B | B/B | B/B | B/B | B/B |
| 544a/b | A/B | B/B | B/B | B/B | B/B | B/B | B/B |
| 545a/b | B/B | B/B | B/B | C/B | B/B | B/B | B/B |
| 546a/b | A/B | B/B | B/B | B/B | B/B | B/B | B/B |
| 548a/b | B/B | B/B | A/B | B/B | B/B | B/B | B/B |
| 560a/b | B/B | B/B | B/B | B/B | B/B | B/B | B/B |
| 572a/b | B/B | B/B | B/B | B/B | B/B | B/B | B/B |
| 573a/b | B/B | B/B | B/B | B/B | B/B | A/B | B/A |
| 574a/b | B/B | B/B | B/B | B/B | B/B | B/B | B/B |
| 575a/b | A/B | B/B | B/B | B/B | B/B | B/B | B/B |
| 576a/b | B/B | B/B | B/B | B/B | B/B | B/B | B/B |
| 577a/b | B/B | B/B | A/B | B/B | B/B | B/B | B/B |
| 578a/b | B/B | B/B | B/B | A/B | B/B | B/B | B/B |
| 579a/b | B/B | B/B | B/B | B/B | B/B | B/B | B/B |
| 580a/b | B/B | B/B | B/B | B/B | B/B | B/B | B/B |
| 581a/b | B/B | B/B | B/B | B/B | B/B | B/B | B/B |
| 582a/b | B/B | B/B | B/B | B/B | B/B | B/B | B/B |
| 583a/b | B/B | B/B | B/B | B/B | B/B | B/B | B/B |
| 584a/b | A/B | B/B | B/B | A/A | B/B | B/C | B/B |
| 585a/b | B/B | B/B | B/B | B/B | B/B | B/B | B/B |
| 586a/b | B/B | B/B | B/B | B/B | B/B | B/B | B/B |
| 587a/b | B/B | B/B | B/B | B/B | B/B | B/B | B/B |
| 588a/b | B/B | B/B | B/B | B/B | B/B | B/B | B/B |
| 589a/b | A/B | B/B | A/A | B/A | B/B | B/B | B/B |
| 590a/b | B/B | B/B | B/B | B/B | B/B | B/B | B/B |
| 591a/b | B/B | B/B | B/B | B/B | B/B | B/B | B/B |
| 592a/b | B/B | B/B | B/B | B/B | B/B | B/B | B/B |
| 593a/b | B/B | B/B | B/B | B/B | B/B | B/B | B/B |
| 594a/b | A/B | B/B | B/B | B/B | B/B | B/B | B/B |
| 595a/b | B/B | B/B | B/B | B/B | A/B | B/B | B/B |
| 596a/b | B/B | B/B | B/B | B/B | B/B | B/B | B/B |
| 597a/b | B/B | B/B | B/B | B/B | B/B | B/B | B/B |
| 598a/b | B/B | B/B | B/B | B/B | B/B | B/B | B/B |
| 599a/b | B/B | B/B | B/B | B/B | B/B | B/B | B/B |
| 600a/b | B/B | B/B | B/B | B/B | B/B | B/B | B/B |
| 601a/b | B/B | B/B | B/B | B/B | B/B | B/B | B/B |
| 602a/b | B/B | B/B | B/B | B/B | B/B | B/B | B/B |
| 603a/b | A/B | B/B | B/B | B/B | B/B | B/B | B/B |
| 604a/b | B/B | B/B | B/B | A/B | B/B | B/B | B/B |
| 605a/b | B/B | B/B | B/B | B/B | B/B | B/B | B/B |
| 606a/b | A/B | B/B | B/B | A/B | B/B | B/B | B/B |
| 607a/b | B/B | B/B | B/B | B/B | B/B | B/B | B/B |
| 608a/b | A/B | B/B | B/B | B/B | A/B | B/B | B/B |
| 609a/b | B/B | B/B | B/B | B/B | B/B | B/B | B/B |
| 610a/b | B/B | B/B | B/B | B/B | B/B | B/B | B/B |
| 611a/b | B/B | B/B | B/B | B/B | B/B | B/B | B/B |
| 612a/b | B/B | B/B | B/B | B/B | B/B | B/B | B/B |
| 613a/b | A/B | B/B | B/B | B/B | B/B | B/B | B/B |
| 614a/b | B/B | B/B | B/B | A/B | B/B | B/B | B/B |
| 615a/b | B/B | B/B | B/B | B/B | B/B | B/B | B/B |
| 616a/b | B/B | B/B | B/B | B/B | B/B | B/B | B/B |
| 617a/b | A/B | B/B | B/B | B/B | B/B | B/B | B/B |
| 618a/b | B/B | B/B | B/B | B/B | B/B | B/B | B/B |
| 619a/b | B/B | B/B | B/B | B/B | A/A | B/B | B/B |
| 620a/b | A/B | B/B | B/B | B/B | C/C | B/B | B/B |
| 621a/b | B/B | B/B | B/B | B/B | B/B | B/B | B/B |
| 622a/b | B/B | B/B | B/B | B/B | B/B | B/B | B/B |
| 623a/b | A/B | B/B | B/B | B/B | A/B | B/B | B/B |
| 624a/b | A/B | A/A | C/C | B/B | B/B | B/B | B/B |
| 625a/b | B/B | B/B | B/B | B/B | B/B | B/B | B/B |
| 626a/b | B/B | B/B | B/B | B/B | A/A | B/B | B/B |
| 627a/b | A/B | B/B | B/B | B/B | B/B | B/B | B/B |
| 628a/b | B/B | C/B | B/B | B/B | B/B | B/B | B/B |
| 629a/b | A/B | B/B | B/B | B/B | A/B | B/B | B/B |
| 630a/b | A/B | A/C | C/C | B/B | B/B | B/B | B/B |
| 631a/b | B/B | B/B | B/B | B/B | B/B | B/B | B/B |
| 632a/b | B/B | B/B | B/B | B/B | A/B | B/B | B/B |
| 633a/b | A/B | B/B | B/B | B/B | B/B | B/B | B/B |
| 634a/b | B/B | B/B | B/B | B/B | B/B | B/B | B/B |
| 635a/b | B/B | B/B | B/B | B/B | B/B | B/B | B/B |
| 636a/b | B/B | B/B | B/B | B/B | A/B | B/B | B/B |
| 637a/b | A/B | B/B | B/B | B/B | C/C | B/B | B/B |
| 638a/b | B/B | B/B | B/B | B/B | B/B | B/B | B/B |
| 639a/b | B/B | B/B | B/B | B/B | A/B | B/B | B/B |
| 640a/b | B/B | B/B | B/B | B/B | B/B | B/B | B/B |
| 641a/b | B/B | B/B | B/B | B/B | B/B | B/B | B/B |
| 642a/b | B/B | B/B | B/B | B/B | B/B | A/B | B/B |
| 643a/b | A/B | B/B | B/B | C/A | B/B | B/B | B/B |
| 644a/b | B/B | B/B | B/B | B/B | B/B | B/B | B/B |
| 645a/b | B/B | B/B | B/B | B/B | A/B | B/B | B/B |
| 646a/b | B/B | B/B | B/B | B/B | B/B | B/B | B/B |
| 647a/b | B/B | B/B | B/B | B/B | B/B | B/B | B/B |
| 648a/b | B/B | B/B | B/B | B/B | B/B | B/B | B/B |
| 649a/b | B/B | B/B | B/B | B/B | B/B | B/B | B/B |
| 650a/b | A/B | B/B | B/B | B/B | B/B | B/B | B/B |
| 652a/b | B/B | B/B | B/B | B/B | B/B | B/B | B/B |
| 653a/b | B/B | B/B | B/B | B/B | B/B | B/B | B/B |
| 654a/b | C/B | B/B | B/B | B/B | A/A | B/B | B/B |
| 656a/b | B/B | B/B | B/B | B/B | B/B | B/B | B/B |
| 657a/b | B/B | B/B | B/B | B/B | B/B | B/B | B/B |
| 658a/b | B/B | B/B | B/B | B/B | B/B | B/B | B/B |
| 659a/b | B/B | B/B | B/B | B/B | B/B | B/B | B/B |
| 660a/b | B/B | B/B | B/B | B/B | B/B | B/B | B/B |
| 661a/b | A/B | B/B | B/B | B/B | B/B | B/B | B/B |
| 662a/b | B/B | B/B | B/B | B/B | B/B | B/B | B/B |
| 663a/b | A/B | B/B | B/B | B/B | B/B | B/B | B/B |
| 664a/b | B/B | B/B | B/B | B/B | B/B | B/B | B/B |
| 665a/b | B/B | B/B | A/B | B/B | B/B | B/B | B/B |
| 666a/b | B/B | B/B | B/B | B/B | B/B | B/B | B/B |
| 667a/b | B/B | B/B | B/B | B/B | B/B | B/B | B/B |
| 668a/b | B/B | B/B | B/B | B/B | B/B | B/B | B/B |
| 669a/b | B/B | B/B | B/B | B/B | B/B | B/B | B/B |
| 670a/b | A/B | B/B | B/B | B/B | B/B | A/B | B/B |
| 671a/b | B/B | B/B | B/B | B/B | B/B | B/B | B/B |
| 672a/b | B/B | B/B | B/B | B/B | B/B | B/B | B/B |
| 673a/b | A/B | B/B | B/B | B/B | B/B | B/B | B/B |
| 674a/b | B/B | B/B | B/B | B/B | B/B | B/B | B/B |
| 675a/b | B/B | B/B | B/B | B/B | B/B | B/B | B/B |
| 676a/b | B/B | B/B | B/B | B/B | B/B | B/B | B/B |
| 677a/b | B/B | B/B | B/B | B/B | B/B | B/B | B/B |
| 678a/b | B/B | B/B | B/B | B/B | B/B | B/B | B/B |
| 696a/b | B/B | B/B | B/B | B/B | B/B | B/B | B/B |
| 714a/b | B/B | B/B | B/B | B/B | B/B | B/B | B/B |
| 732a/b | A/B | B/B | B/B | B/B | A/B | B/B | B/B |
| 750a/b | B/B | B/B | B/B | B/B | B/B | B/B | B/B |
| 756a/b | B/B | B/B | B/B | B/B | B/B | B/B | B/B |
| 768a/b | B/B | B/B | B/B | B/B | B/B | B/B | B/B |
| 772a/b | A/B | B/B | B/B | B/B | B/B | B/B | B/B |
| 776a/b | A/B | B/B | B/B | B/B | B/B | B/B | B/B |
| 777a/b | A/B | B/B | B/B | B/B | B/B | B/B | B/B |
| 778a/b | B/B | B/B | B/B | B/B | B/B | B/B | B/B |
| 779a/b | B/B | B/B | B/B | B/B | B/B | B/B | B/B |
| 780a/b | B/B | B/B | B/B | B/B | B/B | B/B | B/B |
| 781a/b | B/B | B/B | B/B | B/B | B/B | B/B | B/B |
| 782a/b | B/B | B/B | B/B | B/B | B/B | B/B | B/B |
| 783a/b | A/B | B/B | B/B | B/B | B/B | B/B | B/B |
| 784a/b | A/B | B/B | B/B | B/B | B/B | B/B | B/B |
| 785a/b | B/B | B/B | B/B | B/B | A/B | B/B | B/B |
| 786a/b | B/B | B/B | B/B | B/B | B/B | B/B | B/B |
| 787a/b | B/B | B/B | B/B | B/B | B/B | B/B | B/B |
| 788a/b | B/B | B/B | B/B | B/B | B/B | B/B | B/B |
| 789a/b | B/B | B/B | B/B | B/B | B/B | B/B | B/B |
| 790a/b | B/B | B/B | B/B | B/B | B/B | B/B | B/B |
| 791a/b | A/B | B/B | B/B | B/B | B/B | B/B | B/B |

| Compound number | BHK-21 | HFL1 | LX-2 | HT-1080 | CCC-ESF-1 | IMR-90 | RAT-iCell-C002 |
|---|---|---|---|---|---|---|---|
| 792a/b | B/B | B/B | B/B | B/B | A/A | B/B | B/B |
| 793a/b | B/B | B/B | B/B | B/B | B/B | B/B | B/B |
| 794a/b | B/B | B/B | B/B | B/B | B/B | B/B | B/B |
| 795a/b | B/B | B/B | B/B | B/B | B/B | B/B | B/B |
| 796a/b | B/B | B/B | B/B | B/B | B/B | B/B | B/B |
| 797a/b | B/B | B/B | B/B | B/B | B/B | B/B | B/B |
| 798a/b | A/B | B/B | B/B | B/B | B/B | B/B | B/B |
| 799a/b | B/B | B/B | B/B | A/B | B/B | B/B | B/B |
| 800a/b | B/B | B/B | B/B | B/B | B/B | B/B | B/B |
| 801a/b | A/B | B/B | B/B | B/B | B/B | B/B | B/B |
| 802a/b | B/B | B/B | B/B | A/B | B/B | B/B | B/B |

Note:
"A" in the table represents an $IC_{50}$ value less than 0.05 mM,
"B" represents an $IC_{50}$ value in the range of 0.05-5.0 mM,
"C" represents an $IC_{50}$ value in the range of 5-20 mM, and
"D" represents an $IC_{50}$ value in the range of 20-100 mM;

Common characteristic of organic fibrosis is excessive deposition of extracellular matrix (ECM) and structural remodeling of organs and tissues, in which a good number of cytokines (CK) participate. It has been shown in the experimental screening in vitro that most of the compounds of the present application have higher anti-fibrosis activity than the positive control pirfenidone. In addition, the compounds of the present application do not cause phototxic reactions, which are produced by pirfenidone. Therefore, the compounds of the present application are safer, which have excellent prospects in anti-fibrosis use. Moreover, the biological activity studies of the present application have revealed that the introduction of halogen into the compound significantly enhances the anti-fibrosis activity.

Test Example 2

Main references for immunological activity test of the compounds of the present application includes: Vogl, S.; Atanasov, A. G.; Binder, M.; Bulusu, M.; Zehl, M.; Fakhrudin, N.; Heiss, E. H.; Picker, P.; Wawrosch, C.; Saukel, J.; Reznicek, G.; Urban, E.; Bochkov, V.; Dirsch, V. M.; Kopp, B. J. *Evid-Based Complementary Alern. Med.* 2013, ID 395316. Commercially available parthenolide was utilized as a positive control.

The ability of the compounds of the present application to inhibit NF-κB activity was tested at an initial concentration of 30 μM.

The assay data for the compounds of the present application were further analyzed to determine their $IC_{50}$ values.

$IC_{50}$ values for the inhibitory activity of the compounds herein against NF-κB are shown in the table below.

| Compound number | $IC_{50}$ (μM) | Compound number | $IC_{50}$ (μM) | Compound number | $IC_{50}$ (μM) | Compound number | $IC_{50}$ (μM) |
|---|---|---|---|---|---|---|---|
| Parthenolide | +++ | 468a/b | ++++/+++ | 591a/b | +++/++++ | 630a/b | +++/+++ |
| 5a/b | ++/++ | 473a/b | +++/+++ | 592a/b | +++/+++ | 631a/b | +++/++++ |
| 6a/b | +++/+++ | 476a/b | ++/++ | 593a/b | ++++/+++ | 648a/b | +++/+++ |
| 7a/b | +++/+++ | 477a/b | ++/++ | 594a/b | ++++/+++ | 649a/b | ++++/++ |
| 8a/b | ++/++ | 478a/b | ++/++ | 595a/b | +++/+++ | 650a/b | +++/+++ |
| 9a/b | +++/+++ | 479a/b | ++/+++ | 596a/b | +++/+++ | 652a/b | +++/+++ |
| 11a/b | +++/+++ | 486a/b | ++/+++ | 597a/b | +++/+++ | 653a/b | +++/+++ |
| 12a/b | +++/+++ | 488a/b | +++/++ | 598a/b | +++/+++ | 654a/b | +++/+++ |
| 16a/b | +++/+++ | 496a/b | ++/++ | 599a/b | ++++/+++ | 656a/b | +++/+++ |
| 18a/b | ++++/+++ | 512a/b | +++/++ | 600a/b | ++++/+++ | 657a/b | ++++/++ |
| 34a/b | ++++/+++ | 514a/b | +++/+++ | 601a/b | +++/+++ | 658a/b | +++++/+++ |
| 50a/b | +++/+++ | 515a/b | +++/+++ | 602a/b | +++/+++ | 659a/b | +++/+++ |
| 64a/b | +++/+++ | 516a/b | ++++/++++ | 603a/b | +++/+++ | 660a/b | +++/+++ |
| 81a/b | +++/+++ | 524a/b | ++++/++ | 604a/b | +++/+++ | 661a/b | ++++/+++ |
| 90a/b | +++/+++ | 536a/b | +++/+++ | 605a/b | +++/+++ | 662a/b | ++++/+++ |
| 91a/b | +++/+++ | 544a/b | ++/+++ | 606a/b | ++++/+++ | 663a/b | +++/+++ |
| 95a/b | +++/+++ | 545a/b | +++/+++ | 607a/b | +++/+++ | 664a/b | +++/+++ |
| 98a/b | +++/+++ | 546a/b | +++/++++ | 608a/b | +++/+++ | 665a/b | ++++/+++ |
| 100a/b | +++/+++ | 548a/b | ++++/+++ | 609a/b | +++/+++ | 666a/b | +++/+++ |
| 103a/b | +++/+++ | 560a/b | +++/+++ | 610a/b | +++/+++ | 667a/b | +++/+++ |
| 112a/b | ++/+++ | 572a/b | +++++/+++ | 611a/b | ++++/+++ | 668a/b | ++++/+++ |
| 141a/b | +++/++++ | 573a/b | +++/+++ | 612a/b | +++/+++ | 669a/b | ++++/+++ |
| 157a/b | ++/++++ | 574a/b | +++/+++ | 613a/b | +++/+++ | 670a/b | ++++/+++ |
| 222a/b | +++/+++ | 575a/b | ++++/+++ | 614a/b | +++/+++ | 671a/b | +++/++++ |
| 246a/b | +++/+++ | 576a/b | +++/+++ | 615a/b | ++++/++ | 672a/b | +++/+++ |
| 279a/b | +++/+++ | 577a/b | +++/+++ | 616a/b | ++++/++ | 673a/b | +++/+++ |
| 282a/b | +++/+++ | 578a/b | +++/+++ | 617a/b | ++++/+++ | 674a/b | ++++/+++ |
| 306a/b | +++/+++ | 579a/b | ++++/++++ | 618a/b | +++/+++ | 675a/b | +++/+++ |
| 319a/b | +++/+++ | 580a/b | +++/+++ | 619a/b | +++/+++ | 676a/b | +++/+++ |
| 328a/b | ++++/+++ | 581a/b | +++/+++ | 620a/b | +++/+++ | 677a/b | +++/+++ |
| 443a/b | +++/+++ | 582a/b | +++/+++ | 621a/b | +++/+++ | 678a/b | +++/+++ |
| 444a/b | +++/+++ | 583a/b | +++/+++ | 622a/b | +++/+++ | 696a/b | +++/+++ |
| 445a/b | +++/+++ | 584a/b | ++++/++++ | 623a/b | +++/+++ | 714a/b | +++/+++++ |
| 446a/b | ++++/+++++ | 585a/b | +++/+++ | 624a/b | ++++/+++ | 732a/b | ++++/+++ |
| 447a/b | ++++/++++ | 586a/b | +++/+++ | 625a/b | +++/+++ | 750a/b | +++/+++ |
| 448a/b | +++/+++ | 587a/b | +++/+++ | 626a/b | +++/+++ | 756a/b | +++/+++ |
| 458a/b | ++++/+++ | 588a/b | +++/+++ | 627a/b | +++/+++ | 768a/b | ++++/+++ |

-continued

| Compound number | IC$_{50}$ (μM) | Compound number | IC$_{50}$ (μM) | Compound number | IC$_{50}$ (μM) | Compound number | IC$_{50}$ (μM) |
|---|---|---|---|---|---|---|---|
| 462a/b | ++++/++++ | 589a/b | +++/+++ | 628a/b | +++/+++ | 772a/b | +++/++++ |
| 464a/b | +++/+++ | 590a/b | +++/+++ | 629a/b | +++/+++ | 776a/b | +++/++++ |
| 787a/b | +++/++++ | 797a/b | +++/++++ | 798a/b | +++/+++ | 799a/b | +++/+++ |

Note:
"+++++" represents an IC$_{50}$ value in the range of 0.001-0.1 μM;
"++++" represents an IC$_{50}$ value in the range of 0.1-1.0 μM;
"+++" represents an IC$_{50}$ value in the range of 1.0-10 μM;
"++" represents an IC$_{50}$ value in the range of 10-50 μM; and
"+" represents an IC$_{50}$ value in the range of 50-100 μM.

Most of the compounds herein exhibit higher or similar inhibitory activity compared with the positive control. The excellent inhibitory activity against NF-κB imparts outstanding use prospects in immunomodulation to the compounds of the present application.

Test Example 3

The effects of the compounds of the present application on the lipopolysaccharide-induced NO secretion in macrophage was tested Principle: Anti-inflammatory drug activity screening is to detect the inhibitory effect of compounds on NO production in the mouse macrophages (RAW264.7). When immune cells are stimulated by microbial endotoxin, inflammatory mediators, etc., a large amount of induced NO synthase (iNOS) is produced, and thus NO is generated for immune response. Accordingly, the inhibition of NO production can serve as a direct indicator of the anti-inflammatory activity of the compound. The activity of the compound to inhibit NO production at the cellular level is directly evaluated in the abovementioned test model, thereby reflecting the anti-inflammatory activity of the compound.

In this experiment, the content of NO in the medium was detected by Gris kit (Molecular probes, G-7921).

Cell Culture and Preparation of the Test Samples

Macrophages (Raw264.7) were cultured in DMEM medium containing 10% fetal bovine serum, with the cell concentration adjusted. The cells were seeded in 24-well cell culture plates, cultured in an incubator, and the test samples in different concentrations were added every other day. The blank medium was used as a blank control, and commercially available indomethacin and resveratrol were employed as positive controls. After the addition of lipopolysaccharide (LPS, 1 μg/ml), incubation was performed for 24 hours. Then the supernatant culture solution was taken, to which Griss reagent was added, and the absorbance value was measured by a microplate reader at 548 nm.

Inhibition rate=(OD$_{LPS}$−OD$_{sample}$)/(OD$_{LPS}$−OD$_{bank}$)× 100%.

The anti-inflammatory activity data is shown as follows:

| Compound number | IC$_{50}$ ((μM) | Compound number | IC$_{50}$ (μM) | Compound number | IC$_{50}$ (μM) | Compound number | IC$_{50}$ (μM) |
|---|---|---|---|---|---|---|---|
| Indomethacin | ++ | 445a/b | +++/+++ | 524a/b | ++++/+++ | 653a/b | +++/+++ |
| Resveratrol | +++ | 446a/b | +++/+++ | 536a/b | +++/+++ | 654a/b | +++/+++ |
| 6a/b | +++/+++ | 447a/b | ++++/+++ | 548a/b | ++/+++ | 656a/b | +++/+++ |
| 7a/b | ++++/++++ | 448a/b | ++++/+++ | 560a/b | ++/+++ | 657a/b | +++/+++ |
| 11a/b | +++/+++ | 449a/b | +++/+++ | 572a/b | ++++/+++ | 658a/b | +++/+++ |
| 12a/b | +++/+++ | 450a/b | +++/+++ | 573a/b | +++/++++ | 659a/b | +++/+++ |
| 16a/b | +++/+++ | 451a/b | +++/+++ | 574a/b | +++/++ | 660a/b | +++/+++ |
| 50a/b | +++/+++ | 452a/b | +++/+++ | 575a/b | +++/+++ | 661a/b | +++/+++ |
| 81a/b | +++/+++ | 453a/b | ++++/++ | 576a/b | +++/+++ | 662a/b | +++/+++ |
| 90a/b | ++++/++++ | 454a/b | ++++/+++ | 577a/b | +++/+++ | 663a/b | ++++/++++ |
| 91a/b | ++++/++++ | 455a/b | +++/+++ | 578a/b | +++/+++ | 664a/b | ++++/++ |
| 95a/b | +++/+++ | 456a/b | +++/+++ | 579a/b | +++/+++ | 665a/b | +++/+++ |
| 98a/b | +++/+++ | 457a/b | +++/+++ | 580a/b | ++++/+++ | 666a/b | +++/+++ |
| 100a/b | ++++/+++ | 458a/b | +++/+++ | 581a/b | ++++/+++ | 667a/b | +++/+++ |
| 103a/b | ++++/+++ | 459a/b | +++/+++ | 582a/b | +++/+++ | 668a/b | +++/+++ |
| 104a/b | +++/+++ | 460a/b | ++++/++ | 583a/b | +++/+++ | 669a/b | +++/+++ |
| 108a/b | +++/+++ | 461a/b | +++/+++ | 584a/b | +++/+++ | 670a/b | +++/+++ |
| 109a/b | ++++/++++ | 462a/b | +++/+++ | 585a/b | +++/+++ | 671a/b | +++/+++ |
| 112a/b | +++/+++ | 463a/b | +++/+++ | 586a/b | ++++/+++ | 672a/b | +++/+++ |
| 114a/b | +++/+++ | 464a/b | +++/+++ | 587a/b | +++/+++ | 673a/b | +++/+++ |
| 133a/b | ++/+++ | 465a/b | ++++/++ | 588a/b | +++/+++ | 674a/b | ++/+++ |
| 141a/b | +++/+++ | 466a/b | +++/+++ | 589a/b | +++/+++ | 675a/b | +++/+++ |
| 144a/b | +++/+++ | 467a/b | +++/+++ | 590a/b | +++/+++ | 676a/b | ++/++ |
| 150a/b | +++/+++ | 468a/b | +++/+++ | 591a/b | ++++/+++ | 677a/b | +++/+++ |
| 153a/b | +++/+++ | 469a/b | ++++/++ | 592a/b | +++/+++ | 678a/b | +++/+++ |
| 156a/b | +++/++++ | 470a/b | ++++/+++ | 593a/b | +++/+++ | 696a/b | +++/+++ |
| 157a/b | ++++/+++ | 471a/b | ++++/+++ | 594a/b | +++/+++ | 710a/b | +++/+++ |
| 180a/b | +++/+++ | 472a/b | +++/+++ | 595a/b | ++++/++++ | 732a/b | +++/+++ |
| 199a/b | +++/+++ | 473a/b | +++/+++ | 596a/b | +++/+++ | 750a/b | +++/+++ |
| 210a/b | +++/+++ | 474a/b | +++/+++ | 597a/b | +++/+++ | 756a/b | ++++/++ |
| 222a/b | +++/+++ | 475a/b | +++/+++ | 598a/b | +++/+++ | 768a/b | +++/+++ |
| 246a/b | +++/+++ | 476a/b | +++/+++ | 599a/b | +++/+++ | 772a/b | +++/+++ |
| 259a/b | +++/+++ | 477a/b | +++/+++ | 600a/b | ++++/+++ | 773a/b | ++/+++ |

-continued

| Compound number | IC$_{50}$ (μM) | Compound number | IC$_{50}$ (μM) | Compound number | IC$_{50}$ (μM) | Compound number | IC$_{50}$ (μM) |
|---|---|---|---|---|---|---|---|
| 276a/b | ++++/+++ | 478a/b | ++++/+++ | 601a/b | +++/+++ | 776a/b | ++/+++ |
| 279a/b | +++/++++ | 479a/b | ++/+++ | 602a/b | +++/+++ | 777a/b | ++/+++ |
| 282a/b | +++/++ | 480a/b | ++/+++ | 603a/b | +++/+++ | 778a/b | ++/+++ |
| 300a/b | ++++/+++ | 481a/b | ++/+++ | 604a/b | +++/+++ | 779a/b | ++/+++ |
| 306a/b | +++/++++ | 482a/b | ++/+++ | 605a/b | +++/+++ | 780a/b | ++/+++ |
| 319a/b | +++/+++ | 483a/b | ++/+++ | 606a/b | +++/+++ | 781a/b | ++/+++ |
| 328a/b | +++/+++ | 484a/b | ++/+++ | 607a/b | ++++/+++ | 782a/b | ++/+++ |
| 329a/b | +++/+++ | 485a/b | ++/+++ | 608a/b | +++/+++ | 783a/b | +++/+++ |
| 331a/b | +++/+++ | 486a/b | ++++/+++ | 609a/b | ++++/+++ | 784a/b | ++/+++ |
| 340a/b | ++++/+++ | 487a/b | ++++/++ | 610a/b | +++/+++ | 785a/b | +++/+++ |
| 343a/b | +++/+++ | 488a/b | ++/+++ | 611a/b | ++/++ | 786a/b | +++/+++ |
| 348a/b | +++/+++ | 490a/b | ++/+++ | 612a/b | ++/++ | 787a/b | ++/++ |
| 349a/b | +++/+++ | 491a/b | ++/+++ | 613a/b | ++/++ | 788a/b | +++/+++ |
| 354a/b | +++/+++ | 496a/b | ++/+++ | 614a/b | ++/++ | 789a/b | +++/+++ |
| 361a/b | +++/+++ | 497a/b | ++++/+++ | 615a/b | ++/++ | 790a/b | +++/+++ |
| 373a/b | ++++/+++ | 500a/b | ++++/+++ | 616a/b | ++/+++ | 791a/b | +++/+++ |
| 397a/b | ++++/++++ | 502a/b | +++/+++ | 648a/b | ++/++ | 792a/b | ++++/++++ |
| 409a/b | +++/+++ | 504a/b | +++/+++ | 649a/b | ++/++ | 793a/b | ++++/++++ |
| 443a/b | +++/+++ | 508a/b | +++/+++ | 650a/b | +++/+++ | 794a/b | +++/+++ |
| 444a/b | ++++/+++ | 512a/b | +++/+++ | 652a/b | +++/+++ | 795a/b | +++/+++ |
| 796a/b | +++/+++ | 797a/b | +++/+++ | 798a/b | +++/+++ | 799a/b | +++/+++ |

Note:
"+++++" represents an IC$_{50}$ value in the range of 0.001-0.1 μM;
"++++" represents an IC$_{50}$ value in the range of 0.1-1.0 μM;
"+++" represents an IC$_{50}$ value in the range of 1.0-10 μM;
"++" represents an IC$_{50}$ value in the range of 10-50 μM;
"+" represents an IC$_{50}$ value in the range of 50-100 μM.

Most of the compounds herein have possess higher or similar inhibition rate compared with the positive controls of indomethacin and resveratrol, which demonstrates that the compounds of the present application can effectively inhibit the secretion of NO by macrophages and possess excellent anti-inflammatory activity.

The invention claimed is:

1. A compound, or a tautomer thereof, or a stereoisomer thereof, or a racemate thereof, or a nonequal mixture of enantiomers thereof, or a geometric isomer thereof, or a solvate thereof, or a pharmaceutically acceptable salt thereof, or a solvate of the salt of the compound, wherein the compound has a structure of Formula I or II

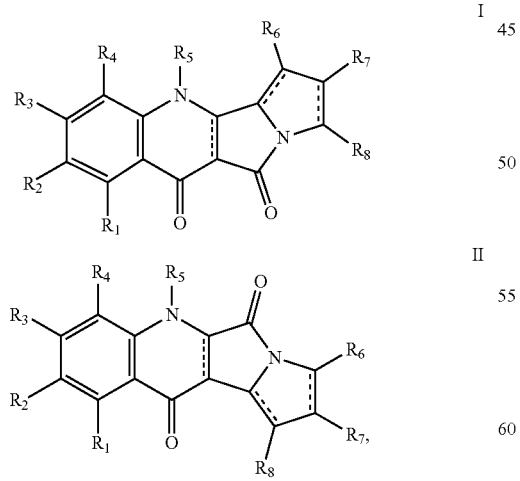

wherein "- - -" is a single bond or absent;
R$_1$, R$_2$, R$_3$ and R$_4$ are each independently selected from the group consisting of hydrogen, deuterium, halogen, hydroxy, amino, nitro, cyano, alkyl, haloalkyl, alkoxy, alkylamino, alkanoyl, hydroxyalkoxy, hydroxyalkylamino, hydroxyalkanoyl, haloalkoxy, haloalkylamino, haloalkanoyl, aminoalkoxy, cycloalkyl, cycloalkyloxy, cycloalkylamino, cycloalkanoyl, alkenyl, alkenylalkoxy, alkenylalkylamino, alkenylalkanoyl, alkynyl, alkynylalkoxy, alkynylalkylamino, alkynylalkanoyl, aryl, aryloxy, aroyl, arylamino, arylalkoxy, arylalkylamino, heteroaryl, heteroaryloxy, heteroaroyl, heteroarylamino, heteroarylalkoxy, heteroarylalkylamino, heteroarylalkanoyl, heterocycloalkyl, heterocyclyloxy, heterocyclylamino, heterocyclylanoyl, heterocyclylalkoxy, heterocyclylalkylamino, heterocyclylalkanoyl, azidoalkoxy, fused bicyclyl, fused heterobicyclyl, fused bicyclyl aliphatic, fused heterobicyclyl aliphatic, fused bicycloxy, fused heterobicycloxy, fused bicyclylamino, fused heterobicyclylamino, fused bicyclylalkoxy, fused heterobicyclylalkoxy, fused bicyclylalkylamino, fused heterobicyclylalkylamino, fused bicycloxyalkoxy, fused heterobicycloxyalkoxy, fused bicyclylaminoalkoxy, fused heterobicyclylaminoalkoxy, fused bicyclyl-C(=O)—, fused bicyclyl-C(=O)O—, fused heterobicyclyl-C(=O)—, fused heterobicyclyl-C(=O)O—, fused bicyclylamino-C(=O)—, fused heterobicyclylamino-C(=O)—, fused bicyclyl-C(=O)N(R$_9$)—, fused heterobicyclyl-C(=O)N(R$_9$)—, spiro bicyclyl, spiro heterobicyclyl, spiro bicyclyl aliphatic, spiro heterobicyclyl aliphatic, spiro bicycloxy, spiro heterobicycloxy, spiro bicyclylamino, spiro heterobicyclylamino, spiro bicyclylalkoxy, spiro heterobicyclylalkoxy, spiro bicyclylalkylamino, spiro heterobicyclylalkylamino, spiro bicycloxyalkoxy, spiro heterobicycloxyalkoxy, spiro bicyclylaminoalkoxy, spiro heterobicyclylaminoalkoxy, spiro bicyclyl-C(=O)—, spiro bicyclyl-C(=O)O—, spiro heterobicyclyl-C(=O)—, spiro heterobicyclyl-C(=O)O—, spiro bicyclylamino-C(=O)—, spiro heterobicyclylamino-C(=O)—, spiro bicyclyl-C(=O)N(R$_9$)—, spiro heterobicyclyl-C(=O)N(R$_9$)—, R$_{10}$R$_9$N—, —C(=O)

$NR_9R_{10}$, —OC(=O)$NR_9R_{10}$, —OC(=O)$OR_9$, —N($R_9$)C(=O)$NR_9R_{10}$, —N($R_9$)C(=O)$OR_{10}$, —N($R_9$)C(=O)—$R_{10}$, $R_9R_{10}$N—S(=O)$_t$—, $R_9$S(=O)$_t$—, $R_9$S(=O)$_t$N($R_{10}$)—, $R_{10}R_9$N-alkyl, $R_9$S(=O)$_t$-alkyl, $R_{10}R_9$N—C(=O)-alkyl, $R_{10}R_9$N-alkoxy, $R_9$S(=O)$_t$-alkoxy, $R_9R_{10}$N—C(=O)-alkoxy, aryl-$(CH_2)_p$-G-$(CH_2)_m$—, heteroaryl-$(CH_2)_p$-G-$(CH_2)_m$—, heterocyclyl-$(CH_2)_p$-G-$(CH_2)_m$—, and cycloalkyl-$(CH_2)_p$-G-$(CH_2)_m$—, wherein G is selected from the group consisting of O, S, $NR_{11}$, S(=O), S(=O)$_2$, C(=O), —C(=O)N($R_9$)—, —OC(=O)N($R_9$)—, —OC(=O)—, —N($R_9$)C(=O)N($R_9$)—, —($R_9$)N—S(=O)—, —OS(=O)$_t$—, and —OS(=O)$_t$N($R_9$)—, wherein each t is 1 or 2, p and m are each independently 0, 1, 2, 3 or 4, wherein each of the aryl-$(CH_2)_p$-G-$(CH_2)_m$—, heteroaryl-$(CH_2)_p$-G-$(CH_2)_m$—, heterocyclyl-$(CH_2)_p$-G-$(CH_2)_m$—, and cycloalkyl-$(CH_2)_p$-G-$(CH_2)_m$— is optionally substituted by one or more substituents selected from the group consisting of F, Cl, Br, I, alkyl, alkenyl, alkynyl, alkoxy and cyano;

$R_5$ is selected from the group consisting of hydrogen, alkyl, haloalkyl, alkanoyl, hydroxyalkanoyl, haloalkanoyl, cycloalkyl, cycloalkanoyl, alkenyl, alkenylalkanoyl, alkynyl, alkynylalkanoyl, aryl, aroyl, heteroaryl, heteroaroyl, heteroarylalkanoyl, heterocycloalkyl, heterocyclylanoyl, heterocyclylalkanoyl, azidoalkyl, fused bicyclyl, fused heterobicyclyl, fused bicyclyl-C(=O)—, fused heterobicyclyl-C(=O)—, fused bicyclylamino-C(=O)—, fused heterobicyclylamino-C(=O)—, spiro bicyclyl, spiro heterobicyclyl, spiro bicyclyl aliphatic, spiro heterobicyclyl aliphatic, spiro bicyclyl-C(=O)—, spiro heterobicyclyl-C(=O)—, spiro bicyclylamino-C(=O)—, spiro heterobicyclylamino-C(=O)—, —C(=O)$NR_9R_{10}$, —OC(=O)$NR_9R_{10}$, —OC(=O)$OR_9$, $R_9R_{10}$N—S(=O)$_t$—, $R_9$S(=O)$_t$—, $R_9$S(=O)$_t$N($R_{10}$)—, $R_{10}R_9$N-alkyl, $R_9$S(=O)$_t$-alkyl, $R_9R_{10}$N—C(=O)-alkyl, $R_{10}R_9$N-alkoxy, $R_9$S(=O)$_t$-alkoxy, $R_9R_{10}$N—C(=O)-alkoxy, aryl-$(CH_2)_p$-G-$(CH_2)_m$—, heteroaryl-$(CH_2)_p$-G-$(CH_2)_m$—, heterocyclyl-$(CH_2)_p$-G-$(CH_2)_m$—, and cycloalkyl-$(CH_2)_p$-G-$(CH_2)_m$—, wherein G is O, S, $NR_{11}$, S(=O), S(=O)$_2$, C(=O), —C(=O)N($R_9$)—, —OC(=O)N($R_9$)—, —OC(=O)—, —($R_9$)N—S(=O)$_t$—, —OS(=O)$_t$—, or —OS(=O)$_t$N($R_9$)—, each t is 1 or 2, p and m are each independently 0, 1, 2, 3 or 4, wherein each of the aryl-$(CH_2)_p$-G-$(CH_2)_m$—, heteroaryl-$(CH_2)_p$-G-$(CH_2)_m$—, heterocyclyl-$(CH_2)_p$-G-$(CH_2)_m$—, and cycloalkyl-$(CH_2)_p$-G-$(CH_2)_m$— is optionally substituted by one or more substituents selected from the group consisting of F, Cl, Br, I, alkyl, alkenyl, alkynyl, alkoxy and cyano;

$R_6$, $R_7$ and $R_8$ are each independently selected from the group consisting of hydrogen, deuterium, halogen, hydroxy, amino, nitro, cyano, alkyl, haloalkyl, alkoxy, alkylamino, alkanoyl, hydroxyalkoxy, hydroxyalkylamino, hydroxyalkanoyl, haloalkoxy, haloalkylamino, haloalkanoyl, aminoalkoxy, cycloalkyl, cycloalkyloxy, cycloalkylamino, cycloalkanoyl, alkenyl, alkenylalkoxy, alkenylalkylamino, alkenylalkanoyl, alkynyl, alkynylalkoxy, alkynylalkylamino, alkynylalkanoyl, aryl, aryloxy, aroyl, arylamino, arylalkoxy, arylalkylamino, heteroaryl, heteroaryloxy, heteroaroyl, heteroarylamino, heteroarylalkoxy, heteroarylalkylamino, heteroarylalkanoyl, heterocycloalkyl, heterocyclyloxy, heterocyclylamino, heterocyclylanoyl, heterocyclylalkoxy, heterocyclylalkylamino, heterocyclylalkanoyl, azidoalkoxy, fused bicyclyl, fused heterobicyclyl, fused bicyclyl aliphatic, fused heterobicyclyl aliphatic, fused bicycloxy, fused heterobicycloxy, fused bicyclylamino, fused heterobicyclylamino, fused bicyclylalkoxy, fused heterobicyclylalkoxy, fused bicyclylalkylamino, fused heterobicyclylalkylamino, fused bicycloxyalkoxy, fused heterobicycloxyalkoxy, fused bicyclylaminoalkoxy, fused heterobicyclylaminoalkoxy, fused bicyclyl-C(=O)—, fused bicyclyl-C(=O)O—, fused heterobicyclyl-C(=O)—, fused heterobicyclyl-C(=O)O—, fused bicyclylamino-C(=O)—, fused heterobicyclylamino-C(=O)—, fused bicyclyl-C(=O)N($R_9$)—, fused heterobicyclyl-C(=O)N($R_9$)—, spiro bicyclyl, spiro heterobicyclyl, spiro bicyclyl aliphatic, spiro heterobicyclyl aliphatic, spiro bicycloxy, spiro heterobicycloxy, spiro bicyclylamino, spiro heterobicyclylamino, spiro bicyclylalkoxy, spiro heterobicyclylalkoxy, spiro bicyclylalkylamino, spiro heterobicyclylalkylamino, spiro bicycloxyalkoxy, spiro heterobicycloxyalkoxy, spiro bicyclylaminoalkoxy, spiro heterobicyclylaminoalkoxy, spiro bicyclyl-C(=O)—, spiro bicyclyl-C(=O)O—, spiro heterobicyclyl-C(=O)—, spiro heterobicyclyl-C(=O)O—, spiro bicyclylamino-C(=O)—, spiro heterobicyclylamino-C(=O)—, spiro bicyclyl-C(=O)N($R_9$)—, spiro heterobicyclyl-C(=O)N($R_9$)—, $R_{10}R_9$N—, —C(=O)$NR_9R_{10}$, —OC(=O)$NR_9R_{10}$, —OC(=O)$OR_9$, —N($R_9$)C(=O)$NR_9R_{10}$, —N($R_9$)C(=O)$OR_{10}$, —N($R_9$)C(=O)—$R_{10}$, $R_9R_{10}$N—S(=O)$_t$—, $R_9$S(=O)$_t$—, $R_9$S(=O)$_t$N($R_{10}$)—, $R_{10}R_9$N-alkyl, $R_9$S(=O)$_t$-alkyl, $R_{10}R_9$N—C(=O)-alkyl, $R_{10}R_9$N-alkoxy, $R_9$S(=O)$_t$-alkoxy, $R_9R_{10}$N—C(=O)-alkoxy, aryl-$(CH_2)_p$-G-$(CH_2)_m$—, heteroaryl-$(CH_2)_p$-G-$(CH_2)_m$—, heterocyclyl-$(CH_2)_p$-G-$(CH_2)_m$—, and cycloalkyl-$(CH_2)_p$-G-$(CH_2)_m$—, wherein G is selected from the group consisting of O, S, $NR_{11}$, S(=O), S(=O)$_2$, C(=O), —C(=O)N($R_9$)—, —OC(=O)N($R_9$)—, —OC(=O)—, —N($R_9$)C(=O)N($R_9$)—, —($R_9$)N—S(=O)—, —OS(=O)$_t$—, and —OS(=O)$_t$N($R_9$)—, wherein each t is 1 or 2, p and m are each independently 0, 1, 2, 3 or 4, wherein each of the aryl-$(CH_2)_p$-G-$(CH_2)_m$—, heteroaryl-$(CH_2)_p$-G-$(CH_2)_m$—, heterocyclyl-$(CH_2)_p$-G-$(CH_2)_m$—, and cycloalkyl-$(CH_2)_p$-G-$(CH_2)_m$— is optionally substituted by one or more substituents selected from the group consisting of F, Cl, Br, I, alkyl, alkenyl, alkynyl, alkoxy and cyano;

$R_{10}$ and $R_9$ are each independently selected from the group consisting of hydrogen, aliphatic, haloaliphatic, hydroxyaliphatic, aminoaliphatic, alkoxyaliphatic, alkylaminoaliphatic, alkylthioaliphatic, arylaliphatic, heteroarylaliphatic, heterocyclylaliphatic, cycloalkylaliphatic, aryloxyaliphatic, heterocyclyloxyaliphatic, cycloalkyloxyaliphatic, arylaminoaliphatic, heterocyclylaminoaliphatic, cycloalkylaminoaliphatic, aryl, heteroaryl, heterocyclyl and cycloalkyl;

with the proviso that where $R_{10}$ and $R_9$ are bonded to a same nitrogen atom, $R_{10}$ and $R_9$ together with the nitrogen atom they are attached to, optionally form a substituted or unsubstituted 3-8 membered ring, a substituted or unsubstituted fused bicyclic ring or a substituted or unsubstituted spiro bicyclic ring, wherein hetero atoms in the heterocyclyl, heteroaryl, fused heterobicyclyl or spiro heterocyclyl are independently selected from the group consisting of N, O, S, and Se, and the number of the hetero atoms is 1-5;

$R_{11}$ is selected from the group consisting of hydrogen, $R_{10}R_9$NC(=O)—, $R_{10}$OC(=O)—, $R_{10}$C(=O)—, $R_{10}R_9NS(=O)$—, $R_{10}OS(=O)$—, $R_{10}S(=O)$—, $R_{10}R_9NS(=O)_2$—, $R_{10}OS(=O)_2$—, $R_{10}S(=O)_2$—, aliphatic, haloaliphatic, hydroxyaliphatic, aminoaliphatic, alkoxyaliphatic, alkylaminoaliphatic, alkylthioaliphatic, arylaliphatic, heteroarylaliphatic, heterocyclylaliphatic, cycloalkylaliphatic, aryloxyaliphatic, heterocyclyloxyaliphatic, cycloalkyloxyaliphatic, arylaminoaliphatic, heterocyclylaminoaliphatic, cycloalkylaminoaliphatic, aryl, heteroaryl, heterocyclyl and carbocyclyl;

$R_1, R_2, R_3, R_4, R_5, R_6, R_7, R_8, R_9, R_{10}, R_{11}$ are optionally substituted by one or more substituents selected from the group consisting of hydroxyl, hydroxymethyl, carboxyl, acetylamino, alkyl, alkoxy, alkylamino, cycloalkyl, alkenyl, alkynyl, trifluoromethyl, trifluoroacetyl, thiol, halogen, nitro, amino, azido (—$N_3$), guanidyl, cyano, tert-butoxycarbonyl (-Boc), carbonyl (—C=O), oxo (=O), thio (=S), sulfonyl, aryl, heteroaryl, and heterocyclyl; wherein in Formula I, when $R_1, R_2, R_3, R_4, R_6, R_7, R_8$ are H, $R_5$ is not H or $CH_3$; and in Formula I, when $R_1, R_2, R_3, R_4, R_5, R_6$ and $R_7$ are H, $R_8$ is not

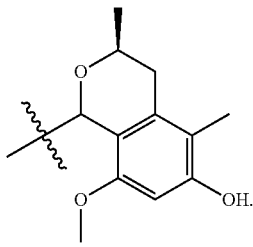

2. The compound, or the tautomer, or the stereoisomer, or the racemate, or the nonequal mixture of enantiomers, or the geometric isomer, or the solvate, or the pharmaceutically acceptable salt, or the solvate of the salt of the compound according to claim 1, wherein $R_1$, $R_2$, $R_3$ and $R_4$ are each independently selected from the group consisting of H, D, F, Cl, Br, I, hydroxy, amino, nitro, cyano, C1-C20 alkyl, C1-C20 haloalkyl, C1-C20 alkoxy, C1-C20 alkylamino, C1-C20 alkanoyl, hydroxy-substituted C1-C20 alkoxy, hydroxy-substituted C1-C20 alkylamino, hydroxy-substituted C1-C20 alkanoyl, C1-C20 haloalkoxy, C1-C20 haloalkylamino, C1-C20 haloalkanoyl, C1-C20 aminoalkoxy, C3-C10 cycloalkyl, C3-C10 cycloalkyloxy, C3-C10 cycloalkylamino, C3-C10 cycloalkanoyl, C2-C8 alkenyl, C2-C8 alkynyl, C6-C10 aryl, C6-C10 aryloxy, C6-C10 aroyl, C6-C10 arylamino, C6-C10 aryl C1-C6 alkoxy, C6-C10 arylalkylamino, C5-C12 heteroaryl, C5-C12 heteroaryloxy, C5-C12 heteroaroyl, C5-C12 heteroarylamino, C5-C12 heteroaryl C1-C6 alkoxy, C5-C12 heteroaryl C1-C6 alkylamino, C4-C12 heterocyclyl C1-C6 alkanoyl, C4-C12 heterocycloalkyl, C4-C12 heterocyclyloxy, C4-C12 heterocyclylamino, C4-C12 heterocyclylanoyl, C4-C12 heterocyclyl C1-C6 alkoxy, C4-C12 heterocyclyl C1-C6 alkylamino, C4-C12 heterocyclyl C1-C6 alkanoyl, $R_{10}R_9N$—, —C(=O)$NR_9R_{10}$, —OC(=O)$NR_9R_{10}$, —OC(=O)$OR_9$, —N($R_9$)C(=O)$NR_9R_{10}$, —N($R_9$)C(=O)$OR_{10}$, —N($R_9$)C(=O)—$R_{10}$, $R_9R_{10}N$—S(=O)$_t$—, $R_9S(=O)_t$—, $R_9S(=O)_t$—$NR_{10}$—, $R_{10}R_9N$—C1-C6 alkyl, $R_9S(=O)_t$—C1-C6 alkyl, $R_9R_{10}N$—C(=O)—C1-C6 alkyl, $R_{10}R_9N$—C1-C6 alkoxy, $R_9S(=O)_t$—C1-C6 alkoxy, $R_9R_{10}N$—C(=O)—C1-C6 alkoxy, C6-C10 aryl-$(CH_2)_p$-G-$(CH_2)_m$—, C5-C12 heteroaryl-$(CH_2)_p$-G-$(CH_2)_m$—, C4-C12 heterocyclyl-$(CH_2)_p$-G-$(CH_2)_m$—, or C3-C10 cycloalkyl-$(CH_2)_p$-$(CH_2)_m$—, wherein G is selected from the group consisting of O, S, $NR_{11}$, S(=O), $S(=O)_2$, C(=O), —C(=O)N($R_9$)—, —OC(=O)N($R_9$)—, —OC(=O)—, —N($R_9$)C(=O)N($R_9$)—, —($R_9$)N—S(=O)$_t$—, —OS(=O)$_t$—, and —OS(=O)$_t$N($R_9$)—, wherein each t is 1 or 2, p and m are each independently 0, 1, 2, 3 or 4, wherein the C6-C10 aryl-$(CH_2)_p$-G-$(CH_2)_m$—, C5-C12 heteroaryl-$(CH_2)_p$-G-$(CH_2)_m$—, C4-C12 heterocyclyl-$(CH_2)_p$-G-$(CH_2)_m$—, and C3-C10 cycloalkyl-$(CH_2)_p$-G-$(CH_2)_m$— are each optionally substituted by one or more substituents selected from the group consisting of F, Cl, Br, I, alkyl, alkenyl, alkynyl, alkoxy and cyano;

$R_5$ is selected from the group consisting of H, C1-C20 alkyl, C1-C20 haloalkyl, C1-C20 alkanoyl, C1-C20 hydroxyalkanoyl, C1-C20 haloalkanoyl, C3-C10 cycloalkyl, C3-C10 cycloalkanoyl, C2-C8 alkenyl, C2-C8 alkenylalkanoyl, C2-C8 alkynyl, C2-C8 alkynylalkanoyl, C6-C10 aryl, C6-C10 aroyl, C5-C12 heteroaryl, C5-C12 heteroaroyl, C4-C12 heterocyclylalkanoyl, C4-C12 heterocycloalkyl, C4-C12 heterocyclylanoyl, C4-C12 heterocyclyl C1-C6 alkanoyl, C5-C12 fused bicyclyl, C5-C12 fused heterobicyclyl, —C(=O)$NR_9R_{10}$, $R_9R_{10}N$—S(=O)$_t$—, $R_9S(=O)_t$—, $R_9S(=O)_t$—$NR_{10}$—, $R_{10}R_9N$—C1-C6 alkyl, $R_9S(=O)_t$—C1-C6 alkyl, $R_9R_{10}N$—C(=O)—C1-C6 alkyl, $R_{10}R_9N$—C1-C6 alkoxy, $R_9S(=O)_t$—C1-C6 alkoxy, $R_9R_{10}N$—C(=O)—C1-C6 alkoxy, C6-C10 aryl-$(CH_2)_p$-G-$(CH_2)_m$—, C5-C12 heteroaryl-$(CH_2)_p$-G-$(CH_2)_m$—, C4-C12 heterocyclyl-$(CH_2)_p$-G-$(CH_2)_m$—, and C3-C10 cycloalkyl-$(CH_2)_p$-G-$(CH_2)_m$—, wherein G is selected from the group consisting of O, S, $NR_{11}$, S(=O), $S(=O)_2$, C(=O), —C(=O)N($R_9$)—, —OC(=O)N($R_9$)—, —OC(=O)—, —($R_9$)N—S(=O)$_t$—, —OS(=O)$_t$—, and —OS(=O)$_t$N($R_9$)—, wherein each t is 1 or 2, p and m are each independently 0, 1, 2, 3 or 4, wherein the C6-C10 aryl-$(CH_2)_p$-G-$(CH_2)_m$—, C5-C12 heteroaryl-$(CH_2)_p$-G-$(CH_2)_m$—, C4-C12 heterocyclyl-$(CH_2)_p$-G-$(CH_2)_m$—, and C3-C10 cycloalkyl-$(CH_2)_p$-G-$(CH_2)_m$— are each optionally substituted by one or more substituents selected from the group consisting of F, Cl, Br, I, alkyl, alkenyl, alkynyl, alkoxy and cyano;

$R_6$, $R_7$ and $R_8$ are each independently selected from the group consisting of H, D, F, Cl, Br, I, hydroxy, amino, nitro, cyano, C1-C20 alkyl, C1-C20 haloalkyl, C1-C20 alkoxy, C1-C20 alkylamino, C1-C20 alkanoyl, hydroxy-substituted C1-C20 alkoxy, hydroxy-substituted C1-C20 alkylamino, hydroxy-substituted C1-C20 alkanoyl, C1-C20 haloalkoxy, C1-C20 haloalkylamino, C1-C20 haloalkanoyl, C1-C20 aminoalkoxy, C3-C10 cycloalkyl, C3-C10 cycloalkyloxy, C3-C10 cycloalkylamino, C3-C10 cycloalkanoyl, C2-C8 alkenyl, C2-C8 alkynyl, C6-C10 aryl, C6-C10 aryloxy, C6-C10 aroyl, C6-C10 arylamino, C6-C10 aryl C1-C6 alkoxy, C6-C10 arylalkylamino, C5-C12 heteroaryl, C5-C12 heteroaryloxy, C5-C12 heteroaroyl, C5-C12 heteroarylamino, C5-C12 heteroaryl C1-C6 alkoxy, C5-C12 heteroaryl C1-C6 alkylamino, C4-C12 heterocyclyl C1-C6 alkanoyl, C4-C12 heterocycloalkyl, C4-C12 heterocyclyloxy, C4-C12 heterocyclylamino, C4-C12 heterocyclylanoyl, C4-C12 heterocyclyl C1-C6 alkoxy, C4-C12 heterocyclyl C1-C6 alkylamino, C4-C12 heterocyclyl C1-C6 alkanoyl, $R_{10}R_9N$—, —C(=O)$NR_9R_{10}$, —OC(=O)$NR_9R_{10}$, —OC(=O)$OR_9$, —N($R_9$)C(=O)$NR_9R_{10}$, —N($R_9$)C(=O)$OR_{10}$, —N($R_9$)C(=O)—$R_{10}$, $R_9R_{10}N$—S(=O)$_t$—, $R_9S$ (=O)$_t$—, R$_9$S(=O)$_t$—NR$_{10}$—, R$_{10}$R$_9$N—C1-C6 alkyl, R$_9$S(=O)$_t$—C1-C6 alkyl, R$_9$R$_{10}$N—C(=O)—C1-C6 alkyl, R$_{10}$R$_9$N—C1-C6 alkoxy, R$_9$S(=O)$_t$—C1-C6 alkoxy, R$_9$R$_{10}$N—C(=O)—C1-C6 alkoxy, C6-C10 aryl-(CH$_2$)$_p$-G-(CH$_2$)$_m$—, C5-C12 heteroaryl-(CH$_2$)$_p$-G-(CH$_2$)$_m$—, C4-C12 heterocyclyl-(CH$_2$)$_p$-G-(CH$_2$)$_m$—, and C3-C10 cycloalkyl-(CH$_2$)$_p$-G-(CH$_2$)$_m$—, wherein G is selected from the group consisting of O, S, NR$_{11}$, S(=O), S(=O)$_2$, C(=O), —C(=O)N(R$_9$)—, —OC(=O)N(R$_9$)—, —OC(=O)—, —N(R$_9$)C(=O)N(R$_9$)—, —(R$_9$)N—S(=O)$_t$—, —OS(=O)$_t$—, and —OS(=O)$_t$N(R$_9$)—, wherein each t is 1 or 2, p and m are each independently 0, 1, 2, 3 or 4, wherein the C6-C10 aryl-(CH$_2$)$_p$-G-(CH$_2$)$_m$—, C5-C12 heteroaryl-(CH$_2$)$_p$-G-(CH$_2$)$_m$—, C4-C12 heterocyclyl-(CH$_2$)$_p$-G-(CH$_2$)$_m$—, and C3-C10 cycloalkyl-(CH$_2$)$_p$-G-(CH$_2$)$_m$— are each optionally substituted by one or more substituents selected from the group consisting of F, Cl, Br, I, alkyl, alkenyl, alkynyl, alkoxy and cyano;

R$_{10}$ and R$_9$ are each independently selected from the group consisting of H, D, C1-C3 aliphatic, C1-C3 haloaliphatic, C1-C3 hydroxyaliphatic, C1-C3 aminoaliphatic, C1-C3 alkoxy C1-C3 aliphatic, C1-C3 alkylamino C1-C3 aliphatic, C1-C3 alkylthio C1-C3 aliphatic, C6-C10 aryl C1-C3 aliphatic, C5-C9 heteroaryl C1-C3 aliphatic, C4-C10 heterocyclyl C1-C3 aliphatic, C3-C10 cycloalkyl C1-C3 aliphatic, C6-C10 aryloxy C1-C3 aliphatic, C4-C10 heterocyclyloxy C1-C3 aliphatic, C3-C10 cycloalkyloxy C1-C3 aliphatic, C6-C10 arylamino C1-C3 aliphatic, C4-C10 heterocyclylamino C1-C3 aliphatic, C3-C10 cycloalkylamino C1-C3 aliphatic, C6-C10 aryl, C5-C10 heteroaryl, C4-C10 heterocyclyl and C3-C10 cycloalkyl; with the proviso that where R$_{10}$ and R$_9$ are bonded to a same nitrogen atom, R$_{10}$ and R$_9$, together with the nitrogen atom they are attached to, optionally form a substituted or unsubstituted 3-8 membered ring, a substituted or unsubstituted fused bicyclic ring or a substituted or unsubstituted spiro bicyclic ring, wherein hetero atoms in the heterocyclyl, heteroaryl, fused heterobicyclyl or spiro heterocyclyl are independently selected from the group consisting of N, O, S, and Se, and the number of the hetero atoms is 1-5;

R$_{11}$ is selected from the group consisting of H, D, R$_{10}$R$_9$NC(=O)—, R$_{10}$OC(=O)—, R$_{10}$C(=O)—, R$_{10}$R$_9$NS(=O)—, R$_{10}$OS(=O)—, R$_{10}$S(=O)—, R$_{10}$R$_9$NS(=O)$_2$—, R$_{10}$OS(=O)$_2$—, R$_{10}$S(=O)$_2$—, C1-C3 aliphatic, C1-C3 haloaliphatic, C1-C3 hydroxyaliphatic, C1-C3 aminoaliphatic, C1-C3 alkoxy C1-C3 aliphatic, C1-C3 alkylamino C1-C3 aliphatic, C1-C3 alkylthio C1-C3 aliphatic, C6-C10 aryl C1-C3 aliphatic, C5-C9 heteroaryl C1-C3 aliphatic, C4-C10 heterocyclyl C1-C3 aliphatic, C3-C10 cycloalkyl C1-C3 aliphatic, C6-C10 aryloxy C1-C3 aliphatic, C4-C10 heterocyclyloxy C1-C3 aliphatic, C3-C10 cycloalkyloxy C1-C3 aliphatic, C6-C10 arylamino C1-C3 aliphatic, C4-C10 heterocyclylamino C1-C3 aliphatic, C3-C10 cycloalkylamino C1-C3 aliphatic, C6-C10 aryl, C5-C10 heteroaryl, C4-C10 heterocyclyl and C3-C10 cycloalkyl;

wherein R$_1$, R$_2$, R$_3$, R$_4$, R$_5$, R$_6$, R$_7$, R$_8$, R$_9$, R$_{10}$, R$_{11}$ are optionally substituted by one or more substituents selected from the group consisting of hydroxyl, hydroxymethyl, carboxyl, acetylamino, alkyl, alkoxy, alkylamino, cycloalkyl, alkenyl, alkynyl, trifluoromethyl, trifluoroacetyl, thiol, halogen, nitro, amino, azido (—N$_3$), guanidyl, cyano, tert-butoxycarbonyl (-Boc), carbonyl (—C=O), oxo (=O), thio (=S), sulfonyl, aryl, heteroaryl, and heterocyclyl; and in Formula I, when R$_1$, R$_2$, R$_3$, R$_4$, R$_5$, R$_6$ and R$_7$ are H, R$_8$ is not

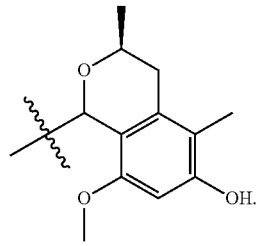

3. The compound, or the tautomer, or the stereoisomer, or the racemate, or the nonequal mixture of enantiomers, or the geometric isomer, or the solvate, or the pharmaceutically acceptable salt, or the solvate of the salt of the compound according to claim 1, wherein R$_1$, R$_2$, R$_3$ and R$_4$ are each independently selected from the group consisting of H, D, F, Cl, Br, I, hydroxy, amino, nitro, cyano, methyl, ethyl, propyl, isopropyl, butyl, tert-butyl, C$_5$H$_{11}$, C$_6$H$_{13}$, C$_8$H$_{17}$, trifluoromethyl, hydroxymethyl, aminomethyl, methoxy, ethoxy, tert-butoxy, methylamino, ethylamino, isopropylamino, 3-hydroxy-propyl, acetyl, trifluoroacetyl, cyanoacetyl, methylaminoacetyl, propionyl, isopropionyl, 2-hydroxypropanoyl, 2-aminopropanoyl, 2-chloropropanoyl, 2-bromopropanoyl, pentanoyl, hexanoyl, heptanoyl, methacryloyl, phenyl, benzoyl, p-nitrophenyl, p-methylbenzoyl, m-fluorobenzoyl, p-aminobenzoyl, p-methoxybenzoyl, 2,4-dimethylbenzoyl, m-azidobenzoyl, benzyl, p-chlorobenzyl, vinyl, propenyl, allyl, n-butenyl, isobutenyl, n-pentenyl, isopentenyl, cyclopropyl, cyclopropanoyl, cyclopentanoyl, cyclohexanoyl, 3-pyridinecarbonyl, naphthyl, phenethylimidazolyl, pyridyl, pyrrolyl, oxazolyl, isoxazolyl, triazolyl, tetrazolyl, furyl, thienyl, thiazolyl, piperidinyl, piperazinyl, indolyl, carbazolyl, benzofuranyl, tetrahydrofuranyl, tetrahydropyranyl, pyrimidine, purine, —N(CH$_3$)$_2$, —C(C=O)NH—C1-C4 alkyl, —OC(C=O)—NH—C1-C4 alkyl, —OC(O=O)O—C1-C4 alkyl, —NHC(=O)NH—C1-C4 alkyl, —NHC(=O)O—C1-C4 alkyl, —NHC(=O)—C1-C4 alkyl, C1-C4 alkyl-NH—S(=O)$_2$—, C1-C4 alkyl-S(=O)$_2$—, C1-C4 alkyl-S(=O)$_2$NH—, phenyl-(CH$_2$)$_P$-G-(CH$_2$)$_m$—, fluorophenyl-(CH$_2$)$_P$-G-(CH$_2$)$_m$—, thiazolyl-(CH$_2$)$_p$-G-(CH$_2$)$_m$—, pyridyl-(CH$_2$)$_p$-G-(CH$_2$)$_m$—, phenylethyl, and cyclohexyl-(CH$_2$)$_p$-G-(CH$_2$)$_m$—, wherein G is selected from the group consisting of O, S, S(=O), S(=O)$_2$, and C(=O), p and m are each independently 0, 1, 2 or 3, wherein the C6-C10 aryl-(CH$_2$)$_P$-G-(CH$_2$)$_m$— is optionally substituted by one or more substituents selected from the group consisting of F, Cl, Br, I, methyl, ethyl, propyl, ethynyl, propynyl, butynyl, methoxy, ethoxy and cyano, wherein R$_1$, R$_2$, R$_3$, R$_4$ are each optionally substituted by one or more substituents selected from the group consisting of F, Cl, Br, I, hydroxy, hydroxymethyl, carboxy, acetylamino, C1-C6 alkyl, C1-C6 alkoxy, C1-C6 alkylamino, trifluoromethyl, trifluoroacetyl, thiol, nitro, amino, azido (—N3), guanidyl, cyano, tert-butoxycarbonyl (-Boc), carbonyl (—C=O), oxo (=O), thio (=S), sulfonyl and phenyl;

R$_5$ is selected from the group consisting of H, methyl, ethyl, propyl, isopropyl, butyl, tert-butyl, C$_5$H$_{11}$, C$_6$H$_{13}$, C$_8$H$_{17}$, trifluoromethyl, hydroxymethyl, aminomethyl, 3-hydroxy-propyl, acetyl, trifluoroacetyl, cyanoacetyl, methylaminoacetyl, propionyl, isopropionyl, 2-hydroxypropanoyl, 2-aminopropanoyl, 2-chloropropanoyl, 2-bromopropanoyl, pentanoyl, hexanoyl, heptanoyl, methacryloyl, phenyl, benzoyl, p-nitrophenyl, p-methylbenzoyl, m-fluorobenzoyl, p-aminobenzoyl, p-methoxybenzoyl, 2,4-dimethylbenzoyl, m-azidobenzoyl, benzyl, p-chlorobenzyl, vinyl, propenyl, allyl, n-butenyl, isobutenyl, n-pentenyl, isopentenyl, cyclopropyl, cyclopropanoyl, cyclopentanoyl, cyclohexanoyl, 3-pyridinecarbonyl, naphthyl, phenethylimidazolyl, pyridyl, pyrrolyl, oxazolyl, isoxazolyl, triazolyl, tetrazolyl, furyl, pyranyl, thienyl, thiazolyl, piperidinyl, piperazinyl, indolyl, carbazolyl, benzofuranyl, tetrahydrofuranyl, tetrahydropyranyl, pyrimidine, purine, pentose, hexose, —(C=O)NH—C1-C4 alkyl, C1-C4 alkyl-NH—S(=O)$_2$—, C1-C4 alkyl-S(=O)$_2$—, phenyl-(CH$_2$)$_P$-G-(CH$_2$)$_m$—, fluorophenyl-(CH$_2$)$_P$-G-(CH$_2$)$_m$—, thiazolyl-(CH$_2$)$_P$-G-(CH$_2$)$_m$—, pyridyl-(CH$_2$)$_P$-G-(CH$_2$)$_m$—, phenylethyl, and cyclohexyl-(CH$_2$)$_P$-G-(CH$_2$)$_m$—, wherein G is selected from the group consisting of O, S, S(=O), S(=O)$_2$, and C(=O), p and m are each independently 0, 1, 2 or 3, wherein the C6-C10 aryl-(CH$_2$)$_P$-G-(CH$_2$)$_m$— is optionally substituted by one or more substituents selected from the group consisting of F, Cl, Br, I, methyl, ethyl, propyl, ethynyl, propynyl, butynyl, methoxy, ethoxy and cyano, wherein R$_5$ is optionally substituted by one or more substituents selected from the group consisting of D, F, Cl, Br, I, hydroxy, hydroxymethyl, carboxy, acetylamino, C1-C6 alkyl, C1-C6 alkoxy, C1-C6 alkylamino, trifluoromethyl, trifluoroacetyl, thiol, nitro, amino, azido (—N3), guanidyl, cyano, tert-butoxycarbonyl (-Boc), carbonyl (—C=O), oxo (=O), thio (=S), sulfonyl and phenyl;

R$_6$, R$_7$ and R$_8$ are each independently selected from the group consisting of H, D, F, Cl, Br, I, hydroxy, amino, nitro, cyano, methyl, ethyl, propyl, isopropyl, butyl, tert-butyl, C$_5$H$_{11}$, C$_6$H$_{13}$, C$_8$H$_{17}$, trifluoromethyl, hydroxymethyl, aminomethyl, methoxy, ethoxy, tert-butoxy, methylamino, ethylamino, isopropylamino, 3-hydroxy-propyl, acetyl, trifluoroacetyl, cyanoacetyl, methylaminoacetyl, propionyl, isopropionyl, 2-hydroxypropanoyl, 2-aminopropanoyl, 2-chloropropanoyl, 2-bromopropanoyl, pentanoyl, hexanoyl, heptanoyl, methacryloyl, phenyl, benzoyl, p-nitrophenyl, p-methylbenzoyl, m-fluorobenzoyl, p-aminobenzoyl, p-methoxybenzoyl, 2,4-dimethylbenzoyl, m-azidobenzoyl, benzyl, p-chlorobenzyl, vinyl, propenyl, allyl, n-butenyl, isobutenyl, n-pentenyl, isopentenyl, cyclopropyl, cyclopropanoyl, cyclopentanoyl, cyclohexanoyl, 3-pyridinecarbonyl, naphthyl, phenethylimidazolyl, pyridyl, pyrrolyl, oxazolyl, isoxazolyl, triazolyl, tetrazolyl, furyl, thienyl, thiazolyl, piperidinyl, piperazinyl, indolyl, carbazolyl, benzofuranyl, tetrahydrofuranyl, tetrahydropyranyl, pyrimidine, purine, —N(CH$_3$)$_2$, —C(C=O)NH—C1-C4 alkyl, —OC(C=O)—NH—C1-C4 alkyl, —OC(O=O)O—C1-C4 alkyl, —NHC(=O)NH—C1-C4 alkyl, —NHC(=O)O—C1-C4 alkyl, —NHC(=O)—C1-C4 alkyl, C1-C4 alkyl-NH—S(=O)$_2$—, C1-C4 alkyl-S(=O)$_2$—, C1-C4 alkyl-S(=O)$_2$NH—, phenyl-(CH$_2$)$_P$-G-(CH$_2$)$_m$—, fluorophenyl-(CH$_2$)$_P$-G-(CH$_2$)$_m$—, thiazolyl-(CH$_2$)$_P$-G-(CH$_2$)$_m$—, pyridyl-(CH$_2$)$_P$-G-(CH$_2$)$_m$—, phenylethyl, and cyclohexyl-(CH$_2$)$_P$-G-(CH$_2$)$_m$—, wherein G is selected from the group consisting of O, S, S(=O), S(=O)$_2$, and C(=O), p and m are each independently 0, 1, 2 or 3, wherein the C6-C10 aryl-(CH$_2$)$_P$-G-(CH$_2$)$_m$— is optionally substituted by one or more substituents selected from the group consisting of F, Cl, Br, I, methyl, ethyl, propyl, ethynyl, propynyl, butynyl, methoxy, ethoxy and cyano, wherein R$_6$, R$_7$, R$_8$ are each optionally substituted by one or more substituents selected from the group consisting of F, Cl, Br, I, hydroxy, hydroxymethyl, carboxy, acetylamino, C1-C6 alkyl, C1-C6 alkoxy, C1-C6 alkylamino, trifluoromethyl, trifluoroacetyl, thiol, nitro, amino, azido (—N3), guanidyl, cyano, tert-butoxycarbonyl (-Boc), carbonyl (—C=O), oxo (=O), thio (=S), sulfonyl and phenyl.

4. The compound, or the tautomer, or the stereoisomer, or the racemate, or the nonequal mixture of enantiomers, or the geometric isomer, or the solvate, or the pharmaceutically acceptable salt, or the solvate of the salt of the compound according to claim 1, wherein the compound has a structure of Formula III or IV,

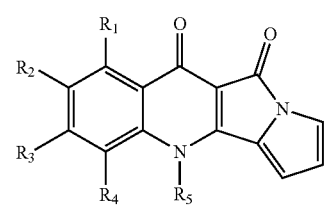

III

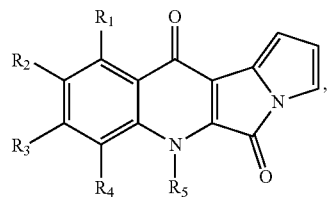

IV wherein R$_1$, R$_2$, R$_3$, R$_4$, R$_6$, R$_7$ and R$_8$ are each independently selected from following substituents:

H
F
Cl
Br
I
OCH$_3$
OH
C$_3$H$_7$
C$_2$H$_5$
CH$_3$
CN
CF$_3$
OCF$_3$
CHF$_2$
NO$_2$
SO$_2$CH$_3$
NH$_2$
COOH
NHOCH$_3$
COOCH$_3$
COOC$_2$H$_5$
NHOC$_2$H$_5$
CONH$_2$
CONHCH$_3$
CONH(CH$_3$)$_2$
SCH$_3$
CH(CH$_3$)OH
CH$_2$CH$_2$OH
CH$_2$CH$_2$NH
CH(CH$_2$NH)OH

219
-continued
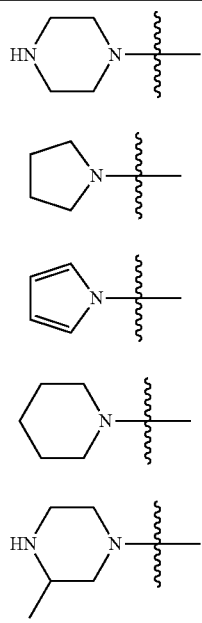
R<sub>5</sub> is selected from:
C$_2$H$_5$
n-C$_3$H$_7$
n-C$_4$H$_9$
n-C$_5$H$_{11}$
CH(CH$_3$)$_2$
H$_2$CHC=CH$_2$
H$_2$CCCH
CH$_2$CH$_2$CH(CH$_3$)$_2$
H$_2$CHC=C(CH$_3$)$_2$
CH$_2$OH
C$_2$H$_4$OH
C$_2$H$_4$N(CH$_3$)$_2$
CH$_2$NH$_2$
C$_2$H$_4$NH$_2$
C$_2$H$_4$N(C$_2$H$_5$)$_2$
C$_3$H$_6$OH
CH$_2$N(CH$_3$)$_2$
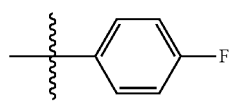
+get,1508
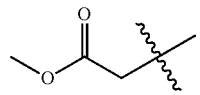
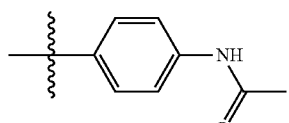
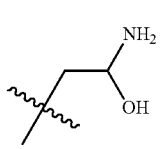
220
-continued
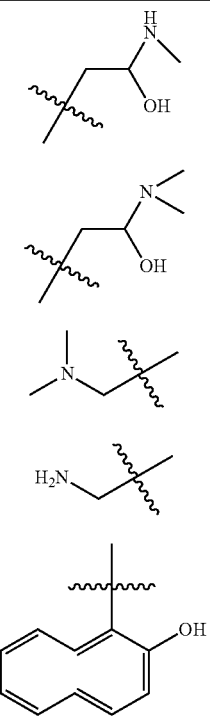
H
CH$_3$
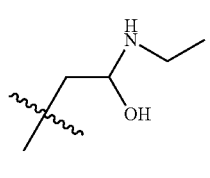
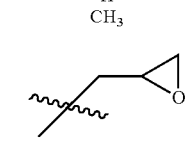
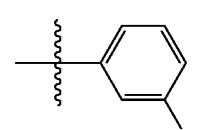
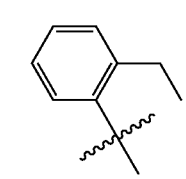
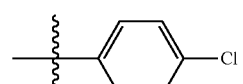
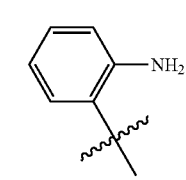

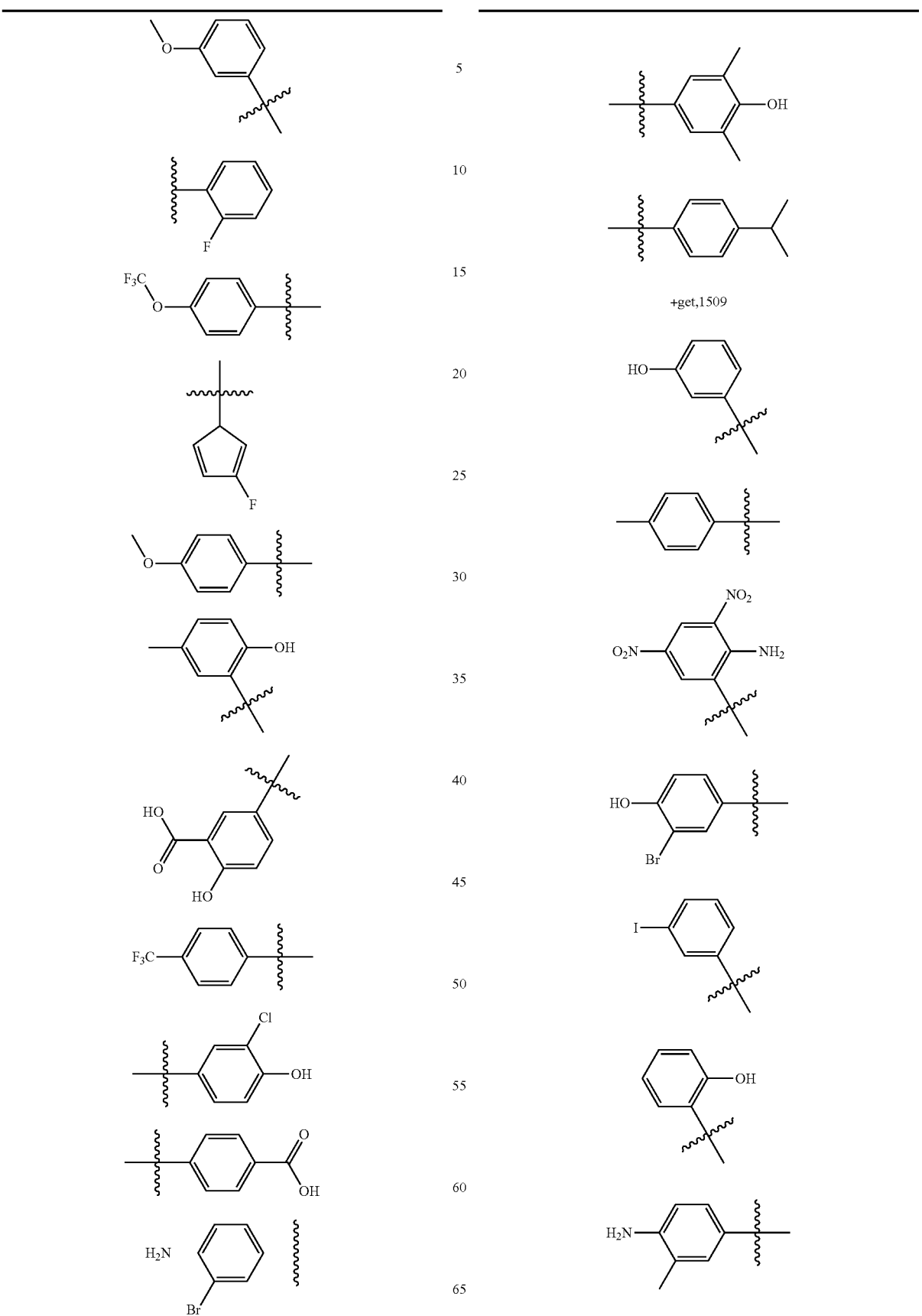

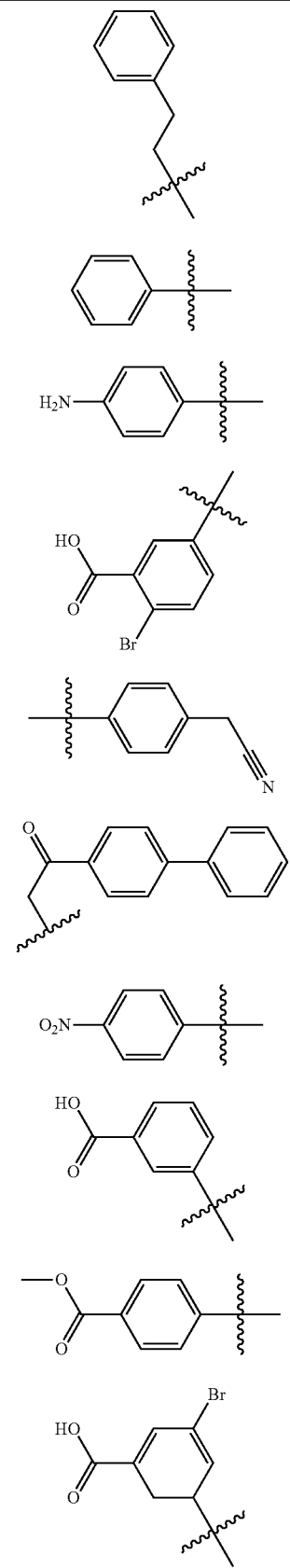
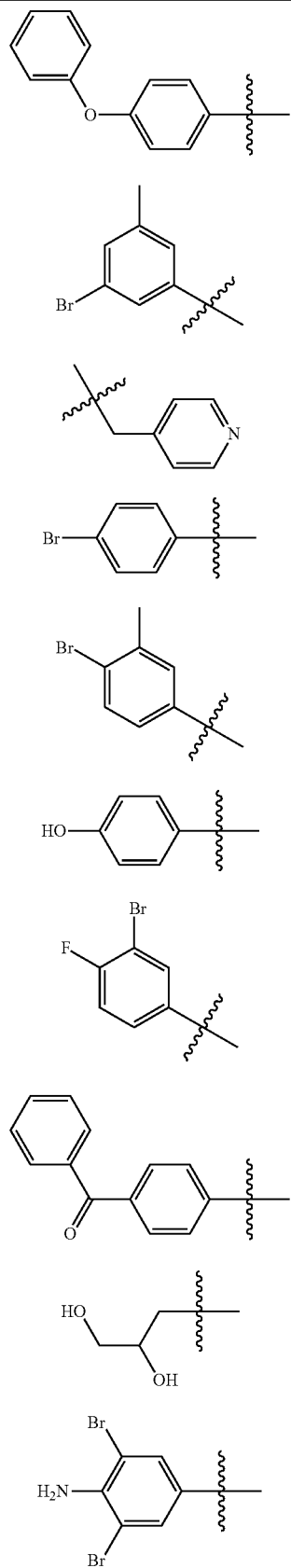

225
-continued
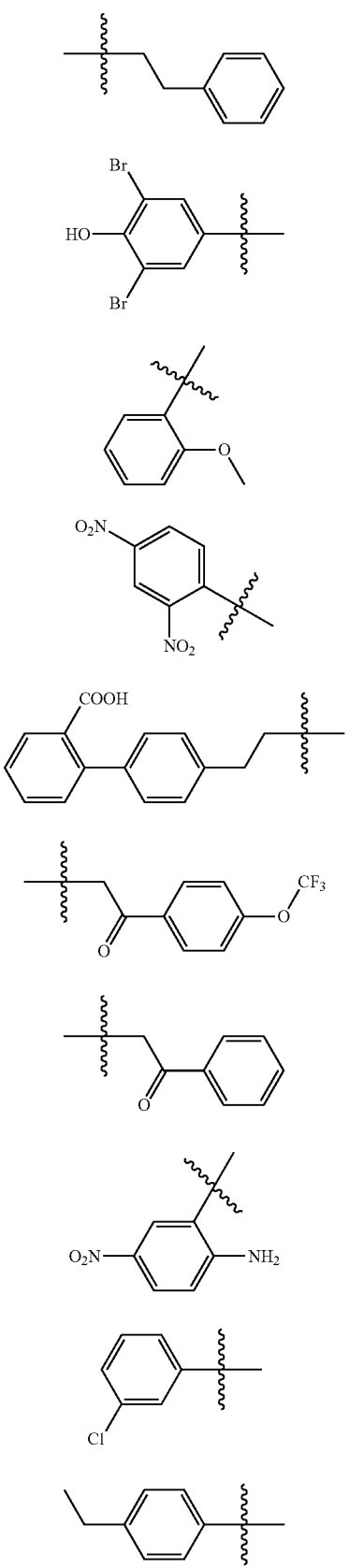
226
-continued
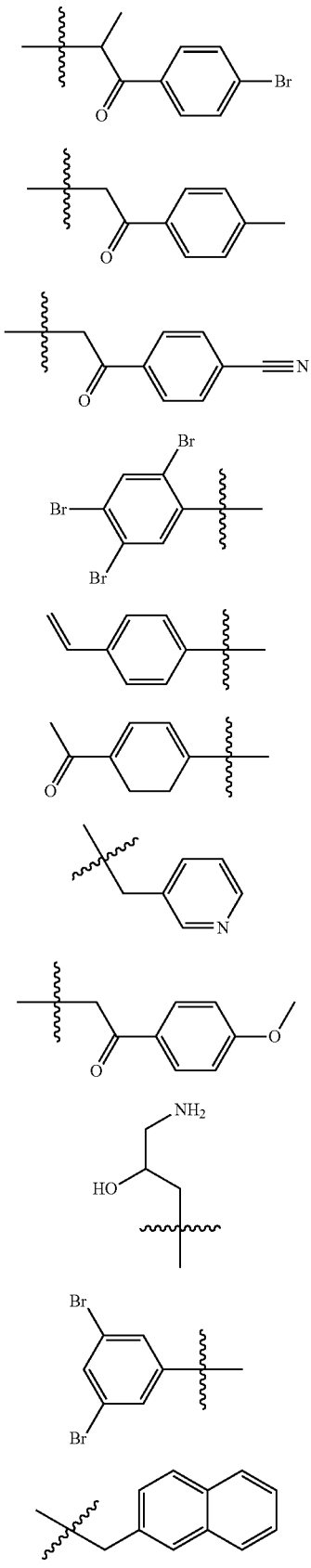

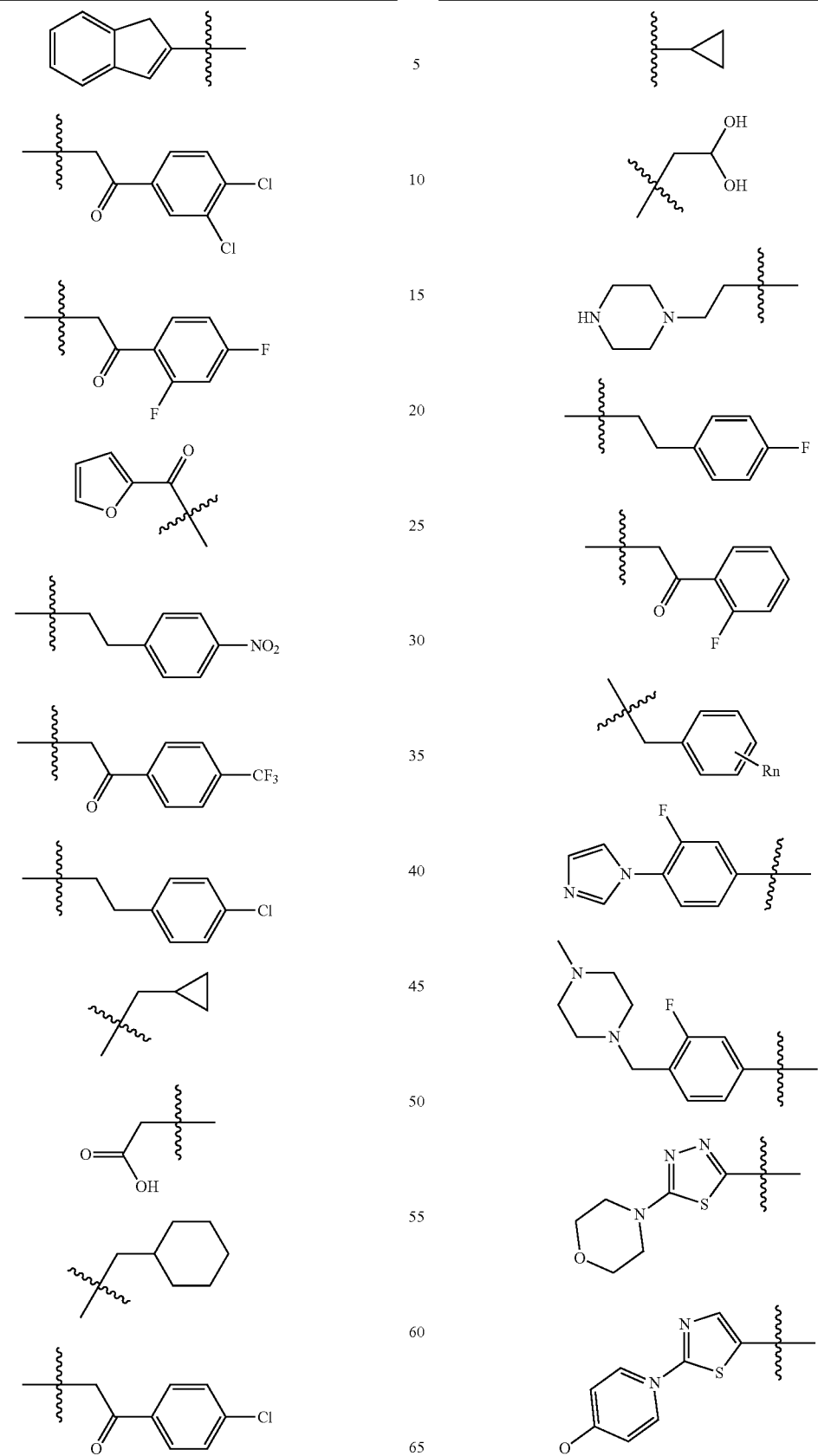

229
-continued
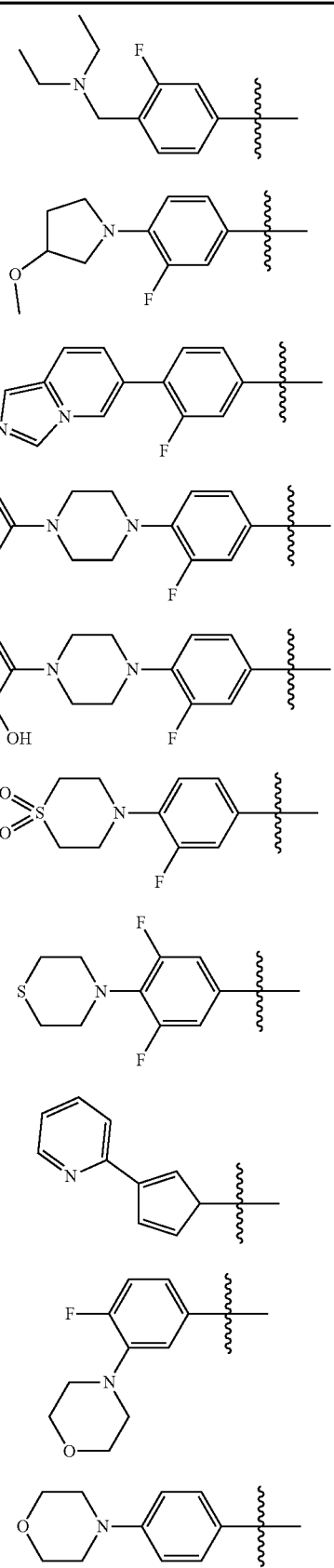
230
-continued
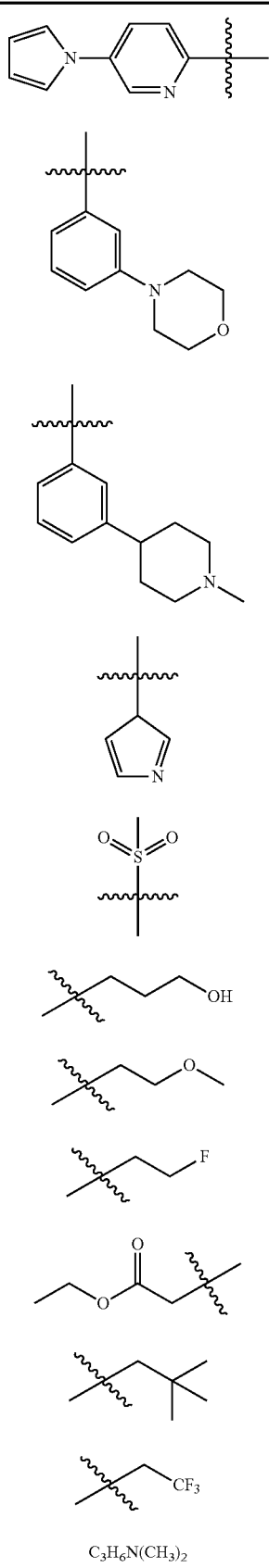
C₃H₆N(CH₃)₂

231
-continued

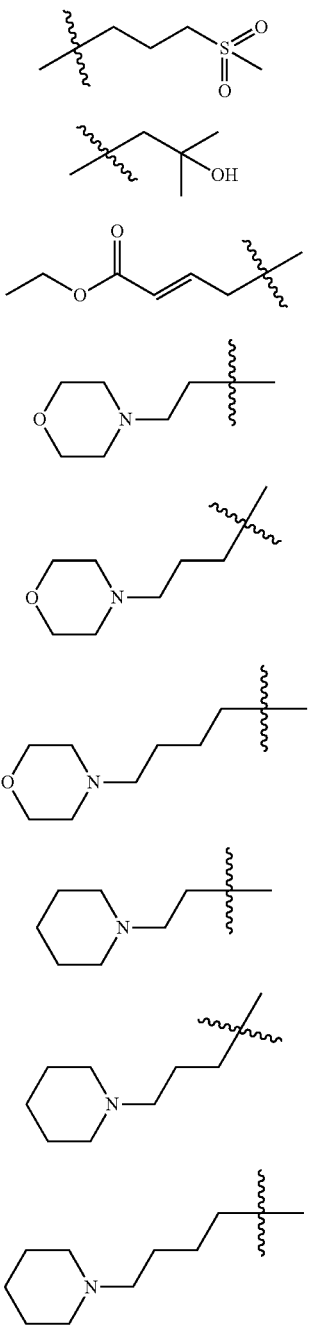

232
-continued

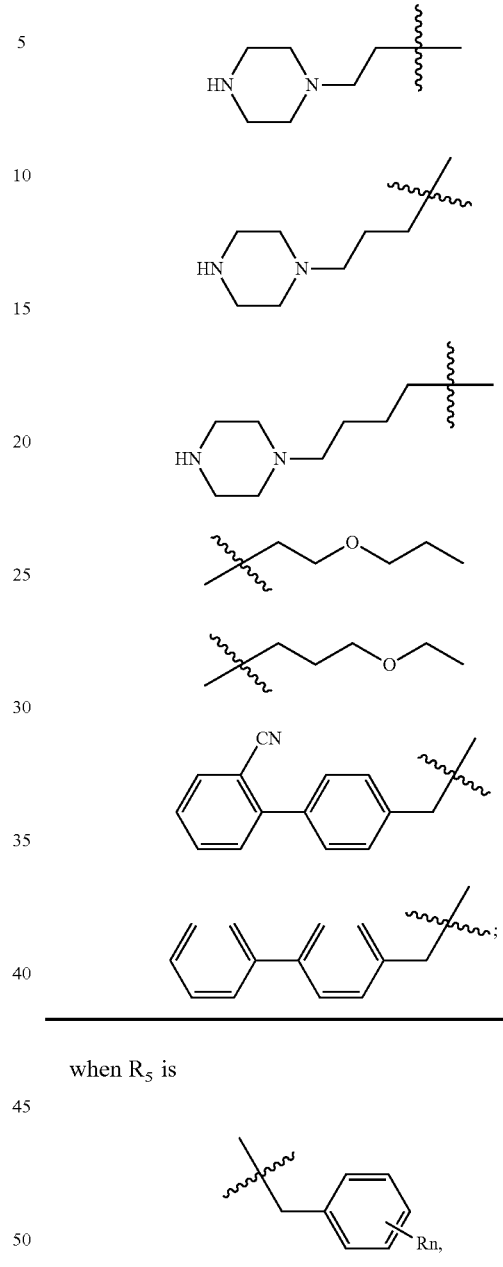

when $R_5$ is

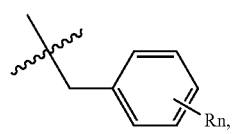

$R_n$ is selected from:

| | | | | | |
|---|---|---|---|---|---|
| H | 3-OCF$_3$ | 2,3-2F | 2,3-2OCH$_3$ | 2-OCF$_3$ | 3-C(CH$_3$)$_3$ |
| 2-CH$_3$ | 3-NO$_2$ | 2,4-2F | 2,4-2OCH$_3$ | 2,3-2F | 2,5-2OCH$_3$ |
| 2-F | 3-COOH | 2,4-2F | 2,6-2OCH$_3$ | 3-CH$_3$ | 4-OCF$_3$ |
| 2-Cl | 3-COOCH$_3$ | 2,5-2F | 3,4-2CH$_3$ | 3-OCF$_3$ | 4-NO$_2$ |
| 2-Br | 3-COOC$_3$H$_5$ | 2,6-2F | 3,5-2CH$_3$ | 3-F | 4-C(CH$_3$)$_3$ |
| 2-I | 3-SO$_2$CH$_3$ | 3,4-2F | 2,3-2Cl | 3-Cl | 4-COOH |
| 2-CN | 3-CH$_2$Br | 3,5-2F | 2,4-2Cl | 3-Br | 4-COOCH$_3$ |
| 2-CF$_3$ | 4-CH$_3$ | 2,3,4-3F | 2,5-2Cl | 3-I | 4-COOC$_2$H$_3$ |
| 2-OCF$_3$ | 4-OCF$_3$ | 2,4,5-3F | 2,6-2Cl | 3-CN | 4-SO$_2$CH$_3$ |
| 2-NO$_2$ | 4-F | 2,3,5-3F | 3,4-2Cl | 3-CF$_3$ | 4-CH$_2$Br |
| 2-C(CH$_3$)$_3$ | 4-Cl | 2,3,6-3F | 3,5-2Cl | 2,3,5,6-4F | 2-F-3-Cl |
| 2-COOH | 4-Br | 2,4,6-3F | 2-F-3-Cl | 2,3,4,5,6-5F | 2-Cl-4-F |
| 2-COOCH$_3$ | 4-I | 2,3,4,5-4F | 2-F-3-Br | 2,3-2CF$_3$ | 3-F-4-OCH$_3$ |
| 2-COOC$_2$H$_5$ | 4-CN | 3,4,5-3F | 3-CF$_3$-5-CF$_3$ | 2,4-2CF$_3$ | 3-Cl-5-F |

-continued

| 2-SO₂CH₃ | 4-CF₃ | 2,4,5,6-4F | 3-Cl-4-F | 2,5-2CF₃ | 2-Br-5-F |
| 2,6-2CF₃ | 2-CN-5-F | 3,4-2CF₃ | 2-Cl-5-CF₃ | 3,5-2CF₃ | 2-OCH₃ |
| 3-OCH₃ | 4-OCH₃, | | | | | wherein in the Formula I, when $R_1=R_2=R_3=R_4=H$, $R_5$ is not H or $CH_3$.

5. The compound, or the tautomer, or the stereoisomer, or the racemate, or the nonequal mixture of enantiomers, or the geometric isomer, or the solvate, or the pharmaceutically acceptable salt, or the solvate of the salt of the compound according to claim 1, wherein the pharmaceutically acceptable salt is selected from the group consisting of hydrochloride, sulfate, phosphate, oxalate, maleate, methanesulfonate, succinate, citrate, fumarate, glucuronide, formate, and acetate; wherein the solvate of the salt of the compound is selected from the group consisting of monohydrate, dihydrate, trihydrate, monomethanol, dimethanol, monoacetonitrile, diacetonitrile, monoacetone, diacetone, hemi-fumarate monohydrate, fumarate dihydrate, and fumarate monoethanol.

6. The compound, or the tautomer, or the stereoisomer, or the racemate, or the nonequal mixture of enantiomers, or the geometric isomer, or the solvate, or the pharmaceutically acceptable salt, or the solvate of the salt of the compound according to claim 1, wherein the compound, or the tautomer, or the stereoisomer, or the racemate, or the nonequal mixture of enantiomers, or the geometric isomer, or the solvate, or the pharmaceutically acceptable salt, or the solvate of the salt of the compound possesses immunomodulatory activity, anti-inflammatory activity, or anti-fibrotic activity.

7. The compound, or the tautomer, or the stereoisomer, or the racemate, or the nonequal mixture of enantiomers, or the geometric isomer, or the solvate, or the pharmaceutically acceptable salt, or the solvate of the salt of the compound according to claim 1, wherein the compound, or the tautomer, or the stereoisomer, or the racemate, or the nonequal mixture of enantiomers, or the geometric isomer, or the solvate, or the pharmaceutically acceptable salt, or the solvate of the salt of the compound possesses inhibitory activity against NF-κB.

8. A pharmaceutical composition, comprising the compound, or the tautomer, or the stereoisomer, or the racemate, or the nonequal mixture of enantiomers, or the geometric isomer, or the solvate, or the pharmaceutically acceptable salt, or the solvate of the salt of the compound according to claim 1 and a pharmaceutically acceptable carrier, diluent, excipient, adjuvant, vehicle or a combination thereof.

9. The pharmaceutical composition according to claim 8, wherein the pharmaceutical composition further comprises at least one drug having immunomodulatory activity, anti-inflammatory activity or anti-fibrosis activity, comprising azathioprine, cyclophosphamide, prednisone, prednisolone, aspirin, acetaminophen, indomethacin, naproxen, nabumetone, diclofenac, ibuprofen, nimesulide, rofecoxib, celecoxib, levamisole, interleukin, interferon, transfer factor, thymosin, anti-lymphocyte globulin, cyclosporine, mycophenolate mofetil.

10. The pharmaceutical composition according to claim 8, wherein the pharmaceutical composition possesses immunomodulatory activity, anti-inflammatory activity, or anti-fibrotic activity.

11. The pharmaceutical composition according to claim 8, wherein the pharmaceutical composition possesses inhibitory activity against NF-κB.

12. A method for treating diseases caused by inflammation, immune system disorders, comprising administering to a subject a therapeutically effective amount of the compound, or the tautomer, or the stereoisomer, or the racemate, or the nonequal mixture of enantiomers, or the geometric isomer, or the solvate, or the pharmaceutically acceptable salt, or the solvate of the salt of the compound according to claim 1.

13. The method according to claim 12, wherein the disease is organ or tissue fibrosis.

14. The method according to claim 12, wherein the disease is selected from the group consisting of renal interstitial fibrosis, glomerulosclerosis, liver fibrosis, pulmonary fibrosis, peritoneum fibrosis, myocardial fibrosis, dermatofibrosis, post-surgery adhesions, benign prostatic hypertrophy, skeletal muscle fibrosis, dermatosclerosis, multiple sclerosis, pancreatic fibrosis, liver cirrhosis, myosarcoma, neurofibroma, pulmonary interstitial fibrosis, diabetic nephropathy, alzheimer disease, vascular fibrosis, serous inflammation, fibrinitis, suppurative inflammation, hemorrhagic inflammation, necrotizing inflammation, catarrhal inflammation, tuberculosis, syphilis, leprosy, lymphogranuloma, allergies, rheumatoid arthritis, rheumatoid heart disease, AIDS, delayed-type immune disease, cytotoxic immune disease, and neurodegenerative diseases.

15. The method according to claim 12, wherein the disease is an immune disorder disease caused by activating NF-κB reactive gene.

16. The method according to claim 12, wherein the disease is an immune disorder disease caused by activating NF-κB reactive gene by factors comprising tumor necrosis factor-α (TNF-α), interleukin-β, lipopolysaccharide (LPS), oxidant, radiation, ultraviolet light, virus or metabolites thereof.

* * * * *

UNITED STATES PATENT AND TRADEMARK OFFICE
CERTIFICATE OF CORRECTION

PATENT NO. : 11,040,028 B2
APPLICATION NO. : 16/580521
DATED : June 22, 2021
INVENTOR(S) : Changlun Shao et al.

It is certified that error appears in the above-identified patent and that said Letters Patent is hereby corrected as shown below:

In the Specification

In the Title, delete first word "PANICINOTAM" and insert --PENICINOTAM--

Signed and Sealed this
Twenty-sixth Day of October, 2021

Drew Hirshfeld
*Performing the Functions and Duties of the*
*Under Secretary of Commerce for Intellectual Property and*
*Director of the United States Patent and Trademark Office*